United States Patent
Chalifoux et al.

(10) Patent No.: US 10,550,056 B2
(45) Date of Patent: Feb. 4, 2020

(54) ARYL COMPOUNDS AND POLYMERS AND METHODS OF MAKING AND USING THE SAME

(71) Applicant: Board of Regents of the Nevada System of Higher Education, on Behalf of the University of Nevada, Reno, Reno, NV (US)

(72) Inventors: Wesley A. Chalifoux, Reno, NV (US); Kyle C. Sproul, Newcastle, CA (US); Wenlong Yang, Reno, NV (US)

(73) Assignee: Board of Regents of the Nevada System of Higher Education, on behalf of the University of Nevada, Reno, Reno, NV (US)

( * ) Notice: Subject to any disclaimer, the term of this patent is extended or adjusted under 35 U.S.C. 154(b) by 0 days.

(21) Appl. No.: 15/558,978

(22) PCT Filed: Mar. 18, 2016

(86) PCT No.: PCT/US2016/023179
§ 371 (c)(1),
(2) Date: Sep. 15, 2017

(87) PCT Pub. No.: WO2016/149633
PCT Pub. Date: Sep. 22, 2016

(65) Prior Publication Data
US 2018/0244596 A1   Aug. 30, 2018

Related U.S. Application Data

(60) Provisional application No. 62/135,692, filed on Mar. 19, 2015, provisional application No. 62/182,351, filed on Jun. 19, 2015.

(51) Int. Cl.
*C07C 43/205*   (2006.01)
*C07C 22/08*   (2006.01)
(Continued)

(52) U.S. Cl.
CPC ............ *C07C 43/2055* (2013.01); *C07C 5/09* (2013.01); *C07C 15/38* (2013.01); *C07C 17/354* (2013.01);
(Continued)

(58) Field of Classification Search
CPC . C07C 43/2055; C07C 15/38; C07C 2603/54; C07C 2603/50; C08G 2261/228; C08G 2261/314; C08G 2261/148
See application file for complete search history.

(56) References Cited

U.S. PATENT DOCUMENTS

2004/0076853 A1   4/2004   Jarikov
2005/0202281 A1   9/2005   Wataru et al.

FOREIGN PATENT DOCUMENTS

EP   2 730 554         5/2014
JP   2009234928 A  *  10/2009
(Continued)

OTHER PUBLICATIONS

English-language machine translation of JP2009234928, performed on Espacenet on Dec. 11, 2018.*
(Continued)

*Primary Examiner* — Nicholas E Hill
(74) *Attorney, Agent, or Firm* — Klarquist Sparkman, LLP

(57) ABSTRACT

Disclosed herein are embodiments of aryl compounds and polymers thereof that are made using methods that do not require harsh conditions or expensive reagents. The methods disclosed herein utilize precursor compounds that can be polymerized to form polycyclic aromatic hydrocarbons and polymers, such as carbon-based polymers like nanostructures (e.g., graphene or graphene-like nanoribbons).

20 Claims, 45 Drawing Sheets

(51) Int. Cl.

| | |
|---|---|
| *C07C 25/24* | (2006.01) |
| *C07C 15/38* | (2006.01) |
| *C07C 201/12* | (2006.01) |
| *C07C 205/06* | (2006.01) |
| *C07C 209/68* | (2006.01) |
| *C07C 211/50* | (2006.01) |
| *C07C 5/09* | (2006.01) |
| *C07C 17/354* | (2006.01) |
| *C07C 25/22* | (2006.01) |
| *C07C 41/20* | (2006.01) |
| *C07C 303/30* | (2006.01) |
| *C07C 309/68* | (2006.01) |
| *C07D 333/08* | (2006.01) |
| *C07F 7/08* | (2006.01) |
| *C08G 61/10* | (2006.01) |

(52) U.S. Cl.
CPC .............. *C07C 22/08* (2013.01); *C07C 25/22* (2013.01); *C07C 25/24* (2013.01); *C07C 41/20* (2013.01); *C07C 201/12* (2013.01); *C07C 205/06* (2013.01); *C07C 209/68* (2013.01); *C07C 211/50* (2013.01); *C07C 303/30* (2013.01); *C07C 309/68* (2013.01); *C07D 333/08* (2013.01); *C07F 7/0805* (2013.01); *C08G 61/10* (2013.01); *C07C 2601/14* (2017.05); *C07C 2603/50* (2017.05); *C07C 2603/54* (2017.05); *C08G 2261/148* (2013.01); *C08G 2261/1414* (2013.01); *C08G 2261/228* (2013.01); *C08G 2261/312* (2013.01)

(56) References Cited

FOREIGN PATENT DOCUMENTS

| | | | | |
|---|---|---|---|---|
| WO | WO-2011138935 A1 | * | 11/2011 | ............. B82Y 10/00 |
| WO | WO 2019/173243 A1 | * | 9/2019 | ........... C07C 323/21 |

OTHER PUBLICATIONS

Takanori Matsuda, et al., "Synthesis of Pyrenes by Twofold Hydroarylation of 2,6-Dialkynylbiphenyls," 40 Chemistry Letters 40-41 (2011).*

Felix Plasser, et al., "The Multiradical Character of One- and Two-Dimensional Graphene Nanoribbons," 52 Angewante Chemie International Edition 2581-84 (2013).*

International Search Report and Written Opinion issued for International Application No. PCT/US2016/023179 dated May 27, 2016.

Machuy et al., "2,6-Bis(phenylethynyl)biphenyls and Their Cyclization to Pyrenes," *Synthesis*, 44(9): 1405-1409, May 1, 2012.

Lorbach et al., "The right way to self-fuse bi- and terpyrenyls to afford graphenic cutouts," *Chemical Communications*, 49(90): 10578, Jan. 1, 2013.

Mochida et al., "Direct Arylation of Polycyclic Aromatic Hydrocarbons through Palladium Catalysis," *Journal of the American Chemical Society*, 133(28): 10716-10719, Jul. 20, 2011.

Chalifoux, "Exploring the Cyclization Reaction of Alkynes to Efficiently Construct Complex Molecules," $3^{rd}$ Year Evaluation Presentation Slides, no earlier than Feb. 2015.

Chalifoux and Sproul, "Pyrene synthesis as a model for a bottom up approach towards graphene nanoribbons," ACS Poster and Poster Abstract, Mar. 19, 2014.

Feng et al., "Blue-Emitting Butterfly-Shaped 1,3,5,9-Tetraarylpyrenes: Synthesis, Crystal Structures, and Photophysical Properties," *Organic Letters*, 15(6): Mar. 15, 2013.

Feng et al., "Synthesis and photophysical properties of novel butterfly-shaped blue emitters based on pyrene," *Organic & Biomolecular Chemistry*, 11(48): 8366, Jan. 1, 2013.

Yamaguchi et al., "Oxidative Cyclization of Bis(biaryl)acetylenes: Synthesis and Photophysics of Dibenzo[g,p]chrysene-Based Fluorescent Polymers," *J. Am. Chem. Soc.*, vol. 123, pp. 12087-12088, Nov. 8, 2001.

Yang et al., "Two-Dimensional Graphene Nanoribbons," *J. Am. Chem. Soc.*, vol. 130, pp. 4216-4217, Mar. 7, 2007.

Yao et al., "Synthesis of Polycyclic Aromatics and Heteroaromatics via Electrophilic Cyclization," *J. Org. Chem.*, vol. 70, pp. 3511-3517, Mar. 23, 2005.

Shaibu et al., "$Ph_2N$-Substituted Ethylene-Bridged p-Phenylene Oligomers: Synthesis and Photophysical and Redox Properties," *J. Org. Chem.*, vol. 76, pp. 1054-1061, Jan. 14, 2011.

International Search Report and Written Opinion issued for International Application No. PCT/US2019/020609 dated Jun. 17, 2019.

Zhu et al. "Synthesis of Pyrene-based Planar Conjugated Polymers and the Regioisomers by Intramolecular Cyclization," Chin. J. Chem. 2015, 33, 431-440, Feb. 3, 2015.

* cited by examiner

ARYL COMPOUNDS AND POLYMERS AND METHODS OF MAKING AND USING THE SAME

CROSS REFERENCE TO RELATED APPLICATION

This application is the U.S. National Stage of International Application No. PCT/US2016/023179, filed Mar. 18, 2016, which was published in English under PCT Article 21(2), which claims the benefit of, and priority to, the earlier filing date of U.S. Provisional Patent Application No. 62/135,692, filed on Mar. 19, 2015, and U.S. Provisional Patent Application No. 62/182,351, filed on Jun. 19, 2015, each of which is herein incorporated by reference in its entirety.

FIELD

The present disclosure concerns aryl compounds and polymeric aryl compounds and methods of making and using the same.

BACKGROUND

Peropyrene compounds, as large polycyclic aromatic hydrocarbons (LPAH), comprise structural features that convey unique photophysical properties to such compounds. However, due to difficult preparation and derivatization of such compounds, their utility has yet to be utilized in various applications. Perylenediimide derivatives, which comprise a similar core as peropyrene compounds, have been prepared and analyzed. Chiral conjugated molecules are a class of interesting research as these molecules have utility in areas such as polarized photoluminescence, enantioselective sensing, etc. Methods exist to introduce chirality into conjugated materials, including appending a chiral auxiliary, or synthesizing an LPAH that is twisted giving rise to axial chirality, such as seen in helicenes. For example, axial chirality in twisted perylenediimide derivatives has been observed where substituents on the cove positions cause twisting of the PAH to relieve steric strain. This is seen even if the substituent is a hydrogen, albeit, with a low barrier to inversion of enantiomers. There is a need in the art, however, for methods to introduce chirality into peropyrene molecules.

Other aromatic ring systems comprising peropyrene cores also are of interest, such as graphene, an organic material comprised of a 2-dimensional monolayer of sp2-hybridized carbon atoms. Graphene has been shown to have interesting electronic, thermal, mechanical, and optical properties. The properties of graphene materials can be altered by varying the size and shape of the graphene sheets. These materials are of interest for device applications such as thin-film transistors (TFTs) and field-effect transistors (FETs) due to their interesting electronic properties. Specifically, graphene is a zero band-gap semiconductor whereas graphene nanoribbons have a persistent band-gap making them useful material in thin-film transistors (TFTs). One particular area of interest is the scission of graphene sheets into thin strips known as graphene nanoribbons that have different properties than graphene. The approach of exfoliation of graphite to produce graphene, followed by scission of graphene is known as a "top-down" approach. These methods result in mixtures of different sizes and shapes of graphene nanoribbons and the products typically have poor solubility, making processing of the material for device applications difficult. Also, the harsh conditions used to produce graphene nanoribbons using a "top-down" approach (lithographic patterning of graphene or unzipping of carbon nanotubes) can result in oxidized graphene nanoribbons, which significantly affects the electronic properties of the material. Thus, there is a need in the art for methods of making graphene nanoribbons that can address these drawbacks.

BRIEF DESCRIPTION OF THE DRAWINGS

FIG. 39A is a TEM image of a polymer embodiment; FIG. 39B is a TEM image using RuO₄ staining that shows curved regions of a polymer embodiment; FIG. 39C is a zoomed TEM image of a polymer sheet illustrating long linear strands of nanoribbons aggregated together; FIG. 39D is an XRD image of a polymer embodiment illustrating the crystallinity of a polymer embodiment; FIG. 39E is a high resolution TEM image of a polymer embodiment on a copper grid coated with lacey carbon; FIG. 39F is a TEM image obtained using RuO₄ staining for high contrast and illustrating a thin sheet of aggregated nanoribbons; and FIG. 39G is a TEM image showing a bundle of short nanoribbons that are approximately 30 nm in length.

FIG. 49A is a combined normalized UV-vis absorption spectrum and FIG. 49B is a combined normalized fluorescence emission spectrum.

DETAILED DESCRIPTION

I. Explanation of Terms

Figure 1:
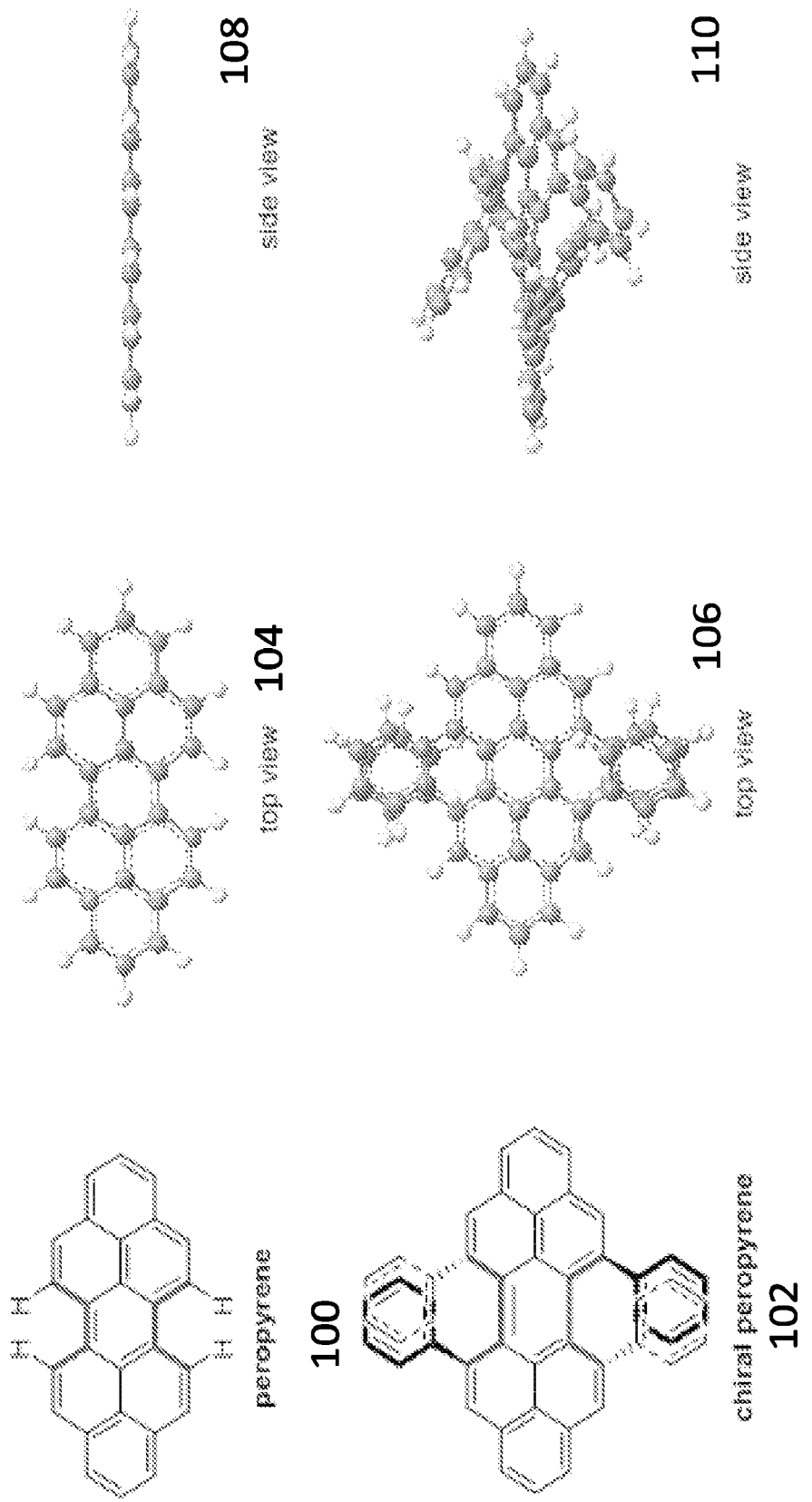
FIG. 1 illustrates a peropyrene core (100), a chiral peropyrene core (102) and top (104 and 106, respectively) and side views (108 and 110, respectively) of these cores.

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Although the steps of some of the disclosed methods are described in a particular, sequential order for convenient presentation, it should be understood that this manner of description encompasses rearrangement, unless a particular ordering is required by specific language set forth below. For example, steps described sequentially may in some cases be rearranged or performed concurrently. Additionally, the description sometimes uses terms like "produce" and "provide" to describe the disclosed methods. These terms are high-level abstractions of the actual steps that are performed. The actual steps that correspond to these terms will vary depending on the particular implementation and are readily discernible by one of ordinary skill in the art.

Unless explained otherwise, all technical and scientific terms used herein have the same meaning as commonly understood to one of ordinary skill in the art to which this disclosure belongs. Although methods and compounds similar or equivalent to those described herein can be used in the practice or testing of the present disclosure, suitable methods and compounds are described below. The compounds, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited.

Furthermore, not all alternatives recited herein are equivalents. The following terms and definitions are provided. Certain functional group terms include an $R^a$ group that, though not part of the defined functional group, indicates how the functional group attaches to the compound to which it is bound.

Aliphatic: A hydrocarbon, or a radical thereof, having at least one carbon atom to 50 carbon atoms, such as one to 25 carbon atoms, or one to ten carbon atoms, and which includes alkanes (or alkyl), alkenes (or alkenyl), alkynes (or alkynyl), including cyclic versions thereof, and further including straight- and branched-chain arrangements, and all stereo and position isomers as well.

Alkyl: A saturated monovalent hydrocarbon having at least one carbon atom to 50 carbon atoms, such as one to 25 carbon atoms, or one to ten carbon atoms, wherein the saturated monovalent hydrocarbon can be derived from removing one hydrogen atom from one carbon atom of a parent compound (e.g., alkane). An alkyl group can be branched, straight-chain, or cyclic (e.g., cycloalkyl).

Alkenyl: An unsaturated monovalent hydrocarbon having at least two carbon atoms 50 carbon atoms, such as two to 25 carbon atoms, or two to ten carbon atoms, and at least one carbon-carbon double bond, wherein the unsaturated monovalent hydrocarbon can be derived from removing one hydrogen atom from one carbon atom of a parent alkene. An alkenyl group can be branched, straight-chain, cyclic (e.g., cylcoalkenyl), cis, or trans (e.g., E or Z).

Alkynyl: An unsaturated monovalent hydrocarbon having at least two carbon atoms 50 carbon atoms, such as two to 25 carbon atoms, or two to ten carbon atoms and at least one carbon-carbon triple bond, wherein the unsaturated monovalent hydrocarbon can be derived from removing one hydrogen atom from one carbon atom of a parent alkyne. An alkynyl group can be branched, straight-chain, or cyclic (e.g., cycloalkynyl).

Alkoxy: —O-alkyl, —O-alkenyl, or —O-alkynyl, with exemplary embodiments including, but not limited to, methoxy, ethoxy, n-propoxy, isopropoxy, n-butoxy, t-butoxy, sec-butoxy, n-pentoxy.

Ambient Temperature: A temperature ranging from 16° C. to 26° C., such as 19° C. to 25° C., or 20° C. to 25° C.

Amine: —$NR^bR^c$, wherein each of $R^b$ and $R^c$ independently is selected from hydrogen, alkyl, alkenyl, alkynyl, aryl, heteroalkyl, heteroalkenyl, heteroalkynyl, heteroaryl, and any combination thereof.

Aryl: An aromatic carbocyclic group comprising at least five carbon atoms to 15 carbon atoms, such as five to ten carbon atoms, having a single ring or multiple condensed rings, which condensed rings can or may not be aromatic provided that the point of attachment is through an atom of the aromatic carbocyclic group.

Diyne: An aryl compound comprising two alkyne groups, typically wherein the alkyne groups are positioned on the aryl ring such that there is at least one carbon atom of the aryl compound located between the two alkyne groups.

Electron-Accepting Group: A functional group capable of accepting electron density from the ring to which it is directly attached, such as by inductive electron withdrawal.

Electron-Donating Group: A functional group capable of donating at least a portion of its electron density into the ring to which it is directly attached, such as by resonance.

Haloaliphatic: An aliphatic group wherein one or more hydrogen atoms, such as one to 10 hydrogen atoms, independently is replaced with a halogen atom, such as fluoro, bromo, chloro, or iodo.

Haloalkyl: An alkyl group wherein one or more hydrogen atoms, such as one to 10 hydrogen atoms, independently is replaced with a halogen atom, such as fluoro, bromo, chloro, or iodo. In an independent embodiment, haloalkyl can be a $CX_3$ group, wherein each X independently can be selected from fluoro, bromo, chloro, or iodo.

Halogen-Metal Exchange: A reaction wherein a bond between a halogen atom and a carbon atom is converted into a bond between a metal atom and the carbon atom using a metal-containing compound as described herein.

Heteroaliphatic: An aliphatic group comprising at least one heteroatom to 20 heteroatoms, such as one to 15 heteroatoms, or one to 5 heteroatoms, which can be selected from, but not limited to oxygen, nitrogen, sulfur, selenium, phosphorous, and oxidized forms thereof within the group.

Heteroalkyl/Heteroalkenyl/Heteroalkynyl: An alkyl, alkenyl, or alkynyl group (which can be branched, straight-chain, or cyclic) comprising at least one heteroatom to 20 heteroatoms, such as one to 15 heteroatoms, or one to 5 heteroatoms, which can be selected from, but not limited to oxygen, nitrogen, sulfur, selenium, phosphorous, and oxidized forms thereof within the group.

Heteroaryl: An aryl group comprising at least one heteroatom to six heteroatoms, such as one to four heteroatoms, which can be selected from, but not limited to oxygen, nitrogen, sulfur, selenium, phosphorous, and oxidized forms thereof within the ring. Such heteroaryl groups can have a single ring or multiple condensed rings, wherein the condensed rings may or may not be aromatic and/or contain a heteroatom, provided that the point of attachment is through an atom of the aromatic heteroaryl group.

Metal-Containing Compound: A metal-containing compound can be any compound comprising a metal and that is capable of undergoing a halogen-metal exchange reaction with a compound or compound precursor disclosed herein. Suitable metal-containing compounds include, but are not limited to, Mg, Li, and the like.

A person of ordinary skill in the art would recognize that the definitions provided above are not intended to include impermissible substitution patterns (e.g., methyl substituted with 5 different groups, and the like). Such impermissible substitution patterns are easily recognized by a person of ordinary skill in the art. Any functional group disclosed herein and/or defined above can be substituted or unsubstituted, unless otherwise indicated herein.

II. Introduction

Methods disclosed herein address the short-comings of conventional methods for making benzene-containing compounds, such as pyrene compounds, peropyrene-based compounds, and polymeric structures, such as nanostructures (e.g., nanoribbons). In particular, a high yielding alkyne benzannulation method is used that provides polycyclic aromatic hydrocarbons (PAHs) such as pyrenes and peropyrenes. In contrast to conventional peropyrene synthesis, the methods disclosed herein are efficient, high-yielding, and do not require harsh reaction conditions. In some embodiments, 4,10-disubstituted pyrene derivatives can be prepared using an efficient Brønsted acid catalyzed double cyclization of 2,6-dialkynylbiphenyl derivatives. Exemplary peropyrenes are illustrated in FIG. 1, which provides different view of the compounds.

Since the discovery of graphene, research has been done on related materials, namely, graphene nanoribbons. The harsh conditions used to produce graphene nanoribbons using a "top-down" approach (lithographic patterning of graphene or unzipping of carbon nanotubes) can result in oxidized graphene nanoribbons, which significantly affects the electronic properties of the material. Also, these top-down methods commonly produce impure graphene nanoribbons as a mixture of different sizes and shapes with poor solubility, which complicates processing of the materials for device applications. In other conventional methods, solution-mediated or surface-assisted polymerization of molecular precursors into linear polyphenylenes followed by their subsequent cyclodehydrogenation can be used to generate nanoribbons. Some "bottom-up" approaches towards graphene nanoribbons have been reported, which rely on oxidative aryl-aryl bond formation (e.g., the Scholl reaction) for key C—C bond forming reactions; however, the harsh conditions required for these methods significantly limit the functionality that can be incorporated into the graphene nanoribbons and thus limit the ability to tune the properties via substitution. Also, only limited quantities of material can be produced with conventional bottom-up methods.

Figure 25:
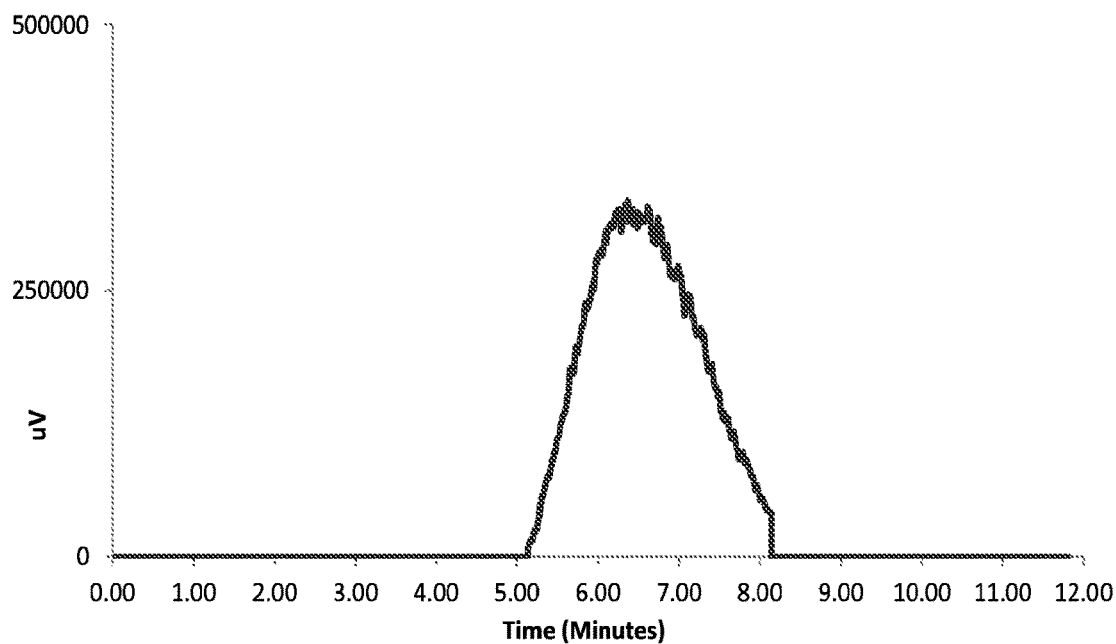
FIG. 25 is a gel permeation chromatogram of an exemplary compound embodiment.
Figure 37:
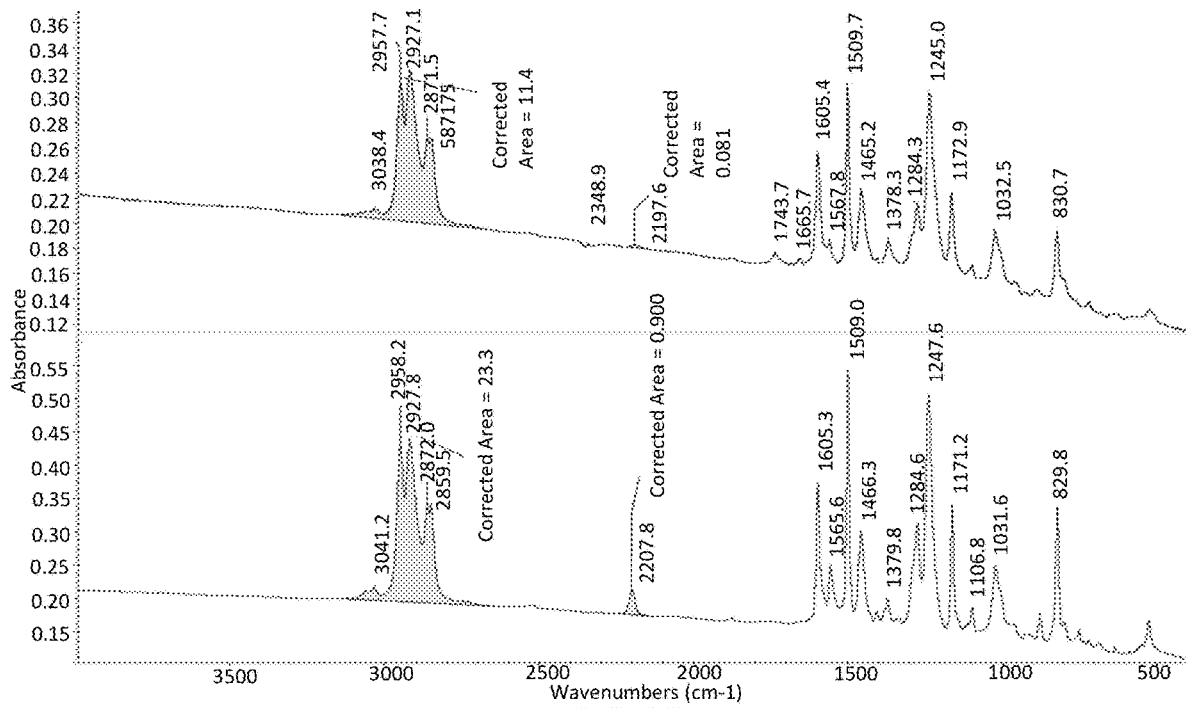
FIG. 37 is a combined FTIR full spectrum illustrating spectra obtained from IR analysis of a polymer embodiment and a polymer embodiment formed using methyl sulfonic acid (MSA).
Figure 38:
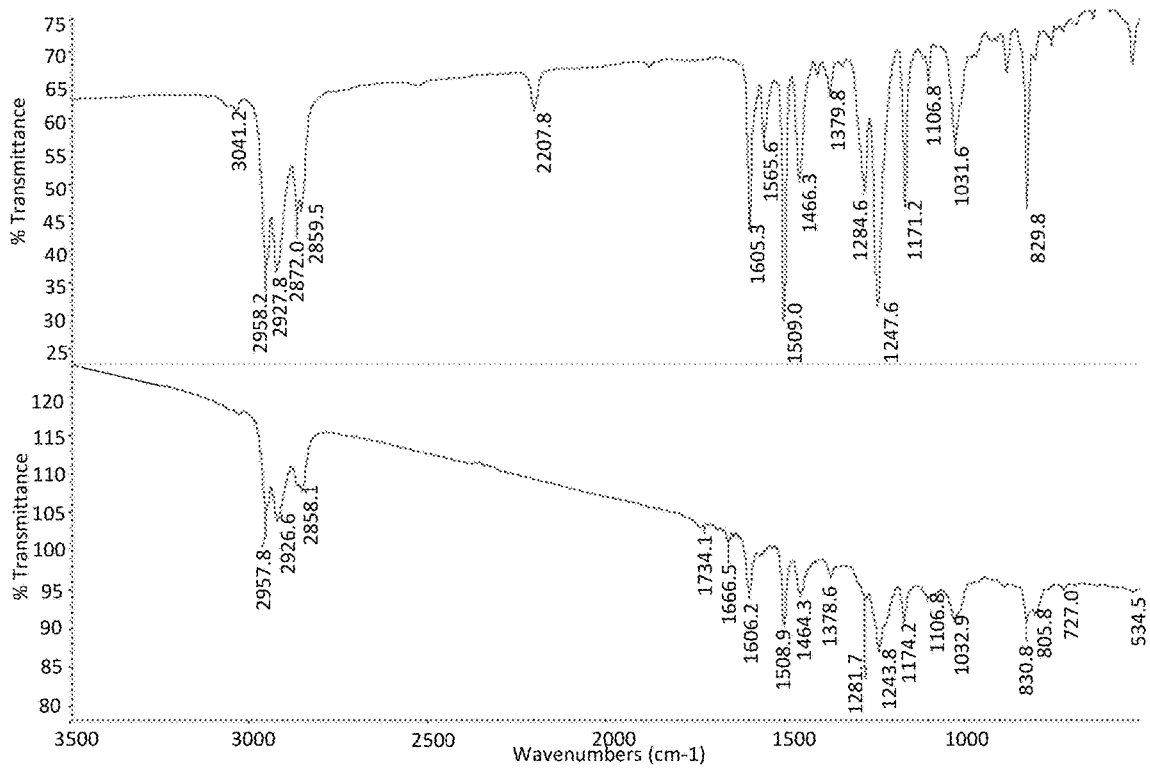
FIG. 38 is a combined FTIR full spectrum illustrating spectra obtained from IR analysis of a polymer embodiment and a polymer embodiment formed using TFA-TfOH.
Figure 50A:
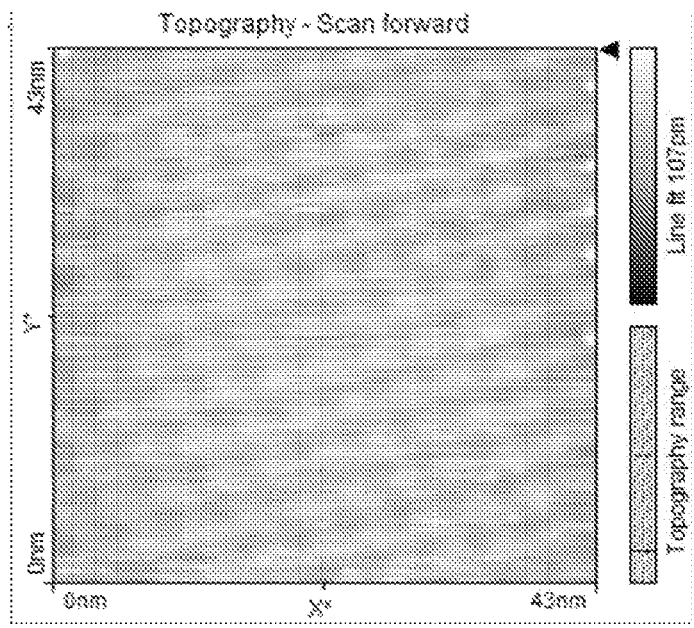
FIGS. 50A and 50B are STM images of a representative compound at the HOPG/TCB interface wherein I=0.4 nA, V=300 mV (FIG. 50A) and I=0.3 nA, V=250 mV (FIG. 50B).
Figure 50B:
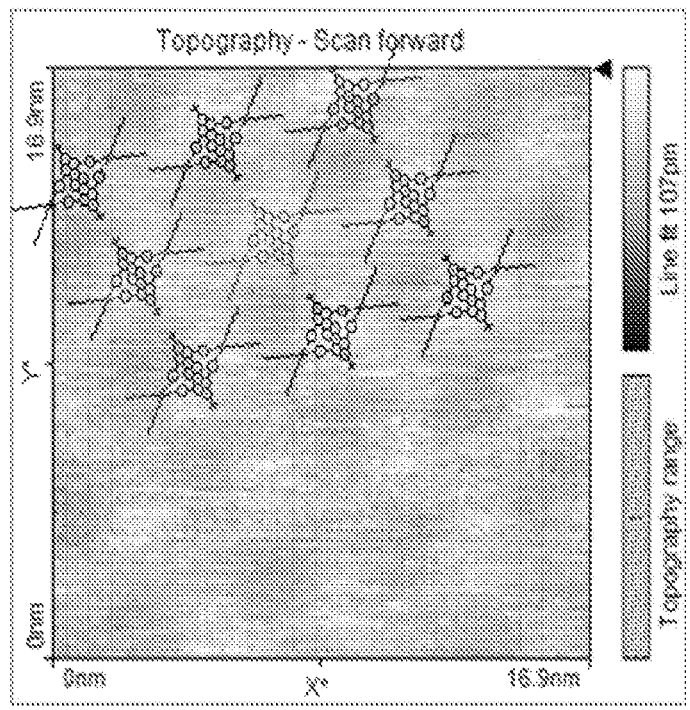

In some embodiments, twisted and axially chiral peropyrene derivatives can be made using the methods disclosed herein. These methods also can be modified to make narrow polymeric nanostructures, such as nanoribbons (ca. 0.5 nm wide) that are highly soluble in a number of common organic solvents. The methods disclosed herein allow for better control of the size, shape, and functionalization of the nanostructures (e.g., nanoribbons), leading to improved solubility and material properties. In embodiments disclosed herein, highly soluble and very narrow armchair edge polymeric structures (e.g., nanoribbons) can be made using an alkyne benzannulation strategy caused by Brønsted acid, which does not require a cyclodehydrogenation reaction step. These soluble and narrow polymeric structures may have significant value in many nano-based semiconductor applications (e.g., FET applications) in view of their metallic to semiconducting properties. In some embodiments, the polymeric compounds (e.g., nanoribbons, such as graphene nanoribbons) are characterized by gel permeation chromatography (GPC) (e.g., FIG. 25), high performance liquid chromatography (HPLC) (e.g., FIG. 6), nuclear magnetic resonance (NMR), infrared spectroscopy (e.g., FIGS. 37 and 38), Raman spectroscopy (e.g., FIGS. 26 and 27), and ultraviolet-visible (UV-vis) and fluorescence spectroscopy (e.g., FIGS. 4, 5, 9, 49A and 49B), as well as transmission electron microscopy (TEM) (e.g., FIGS. 39A-39G), and scanning tunneling microscopy (STM) (e.g., FIG. 40 and FIGS. 50A and 50B).

III. Compounds

In particular disclosed embodiments, compounds having the following formulas can be made according to the methods disclosed herein.

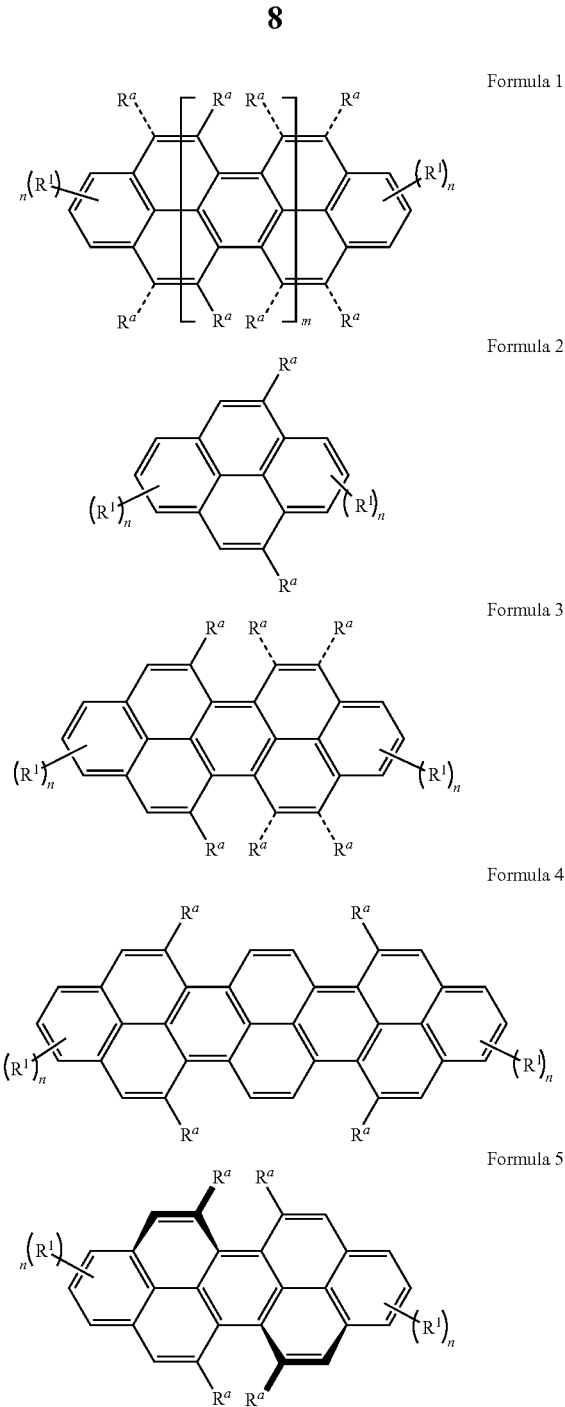

Formula 1

Formula 2

Formula 3

Formula 4

Formula 5

With reference to Formulas 1-5, each $R^1$ moiety can be chosen to promote solubility and/or to control the chemical and/or electrochemical properties of the compound. In some embodiments, each $R^1$ independently can be selected from hydrogen, aliphatic, aryl, heteroaliphatic, or heteroaryl; each $R^a$ independently can be selected from aryl; aryl substituted with one or more functional groups selected from aliphatic, alkoxy, amide, amine, thioether, haloalkyl, nitro, halo, silyl, cycloaliphatic, aryl, and the like; or an electron-donating group; each n independently can be 1, 2, or 3; and m can be 0 to 1000, or higher. Exemplary electron-donating groups include, but are not limited to, alkoxy, thioether, amide, amine, hydroxyl, thiol, acyloxy, silyloxy, heteroaryl (e.g., thiophene), and the like. Aryl rings substituted with one or more functional groups can have such groups positioned meta, ortho, para, or combinations thereof, relative to the position at which the Ra group is attached. In yet additional embodiments wherein $R^1$ is a moiety that can be exchanged or modified to control the chemical and/or electrochemical properties of the compound, each $R^1$ can be selected from electron-donating groups, such as those described above for $R^a$; and $R^1$ also can be selected from electron-withdrawing groups (e.g., CN, halogen, nitro, ester, etc.).

Exemplary compounds meeting Formulas 1-3 are provided below:

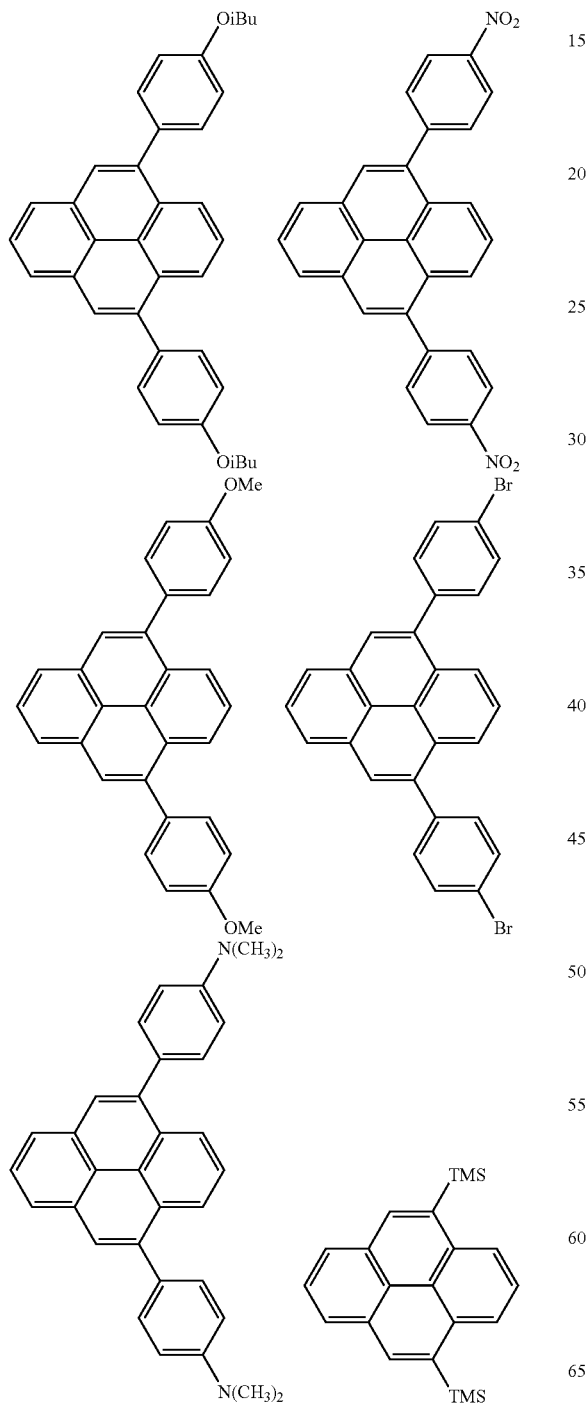

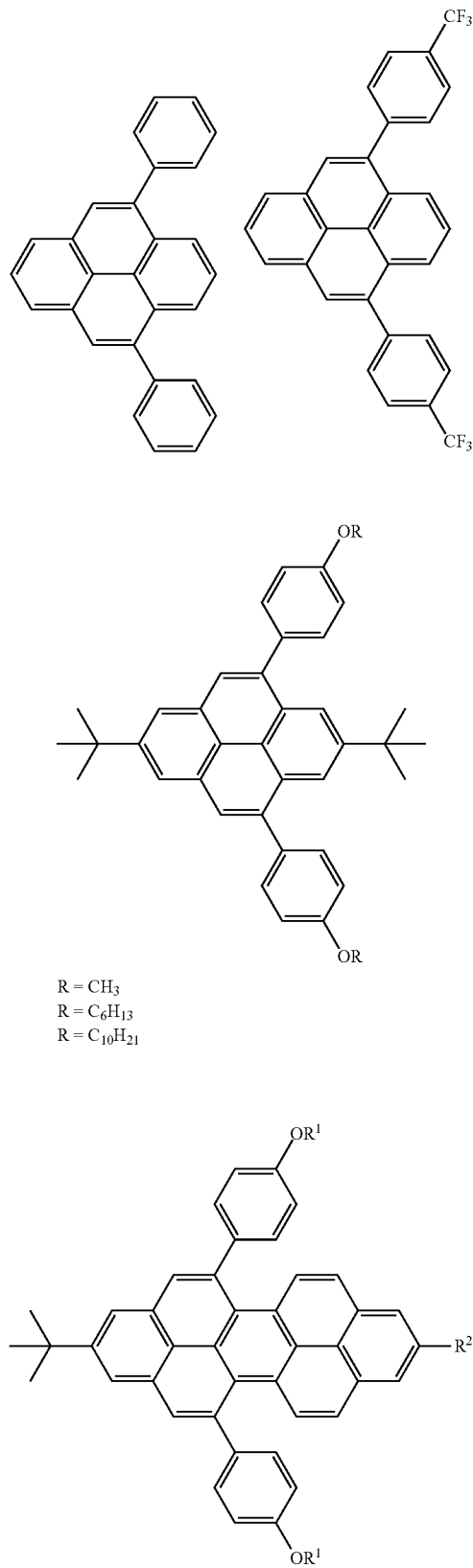

$R = CH_3$
$R = C_6H_{13}$
$R = C_{10}H_{21}$ $R^1 = CH_3, R^2 = $ tert-butyl
$R^1 = C_6H_{13}, R^2 = $ tert-butyl
$R^1 = C_{10}H_{21}, R^2 = H$ 11
-continued
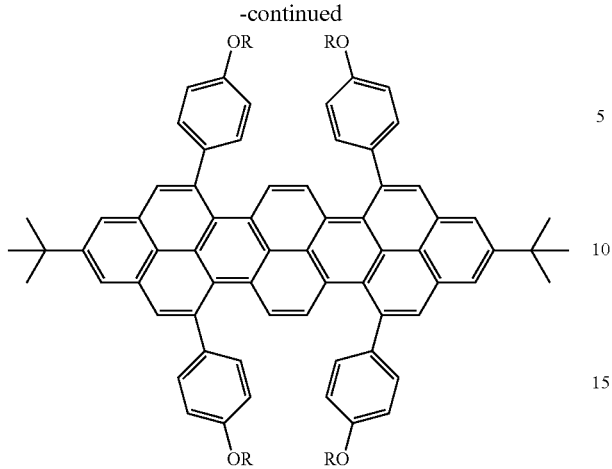
R = CH₃
R = C₆H₁₃
R = C₁₀H₂₁
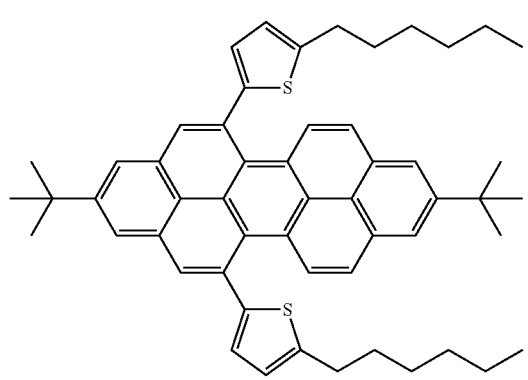
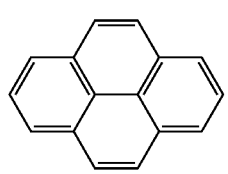
12
-continued
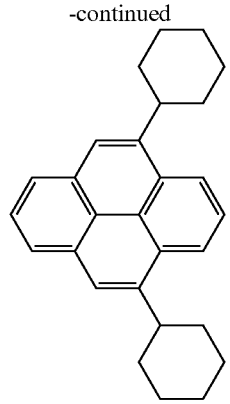
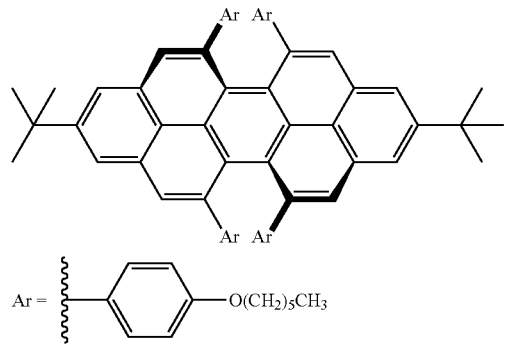
Ar = 
$\begin{smallmatrix}\\\end{smallmatrix}$ —⟨phenyl⟩—O(CH₂)₅CH₃
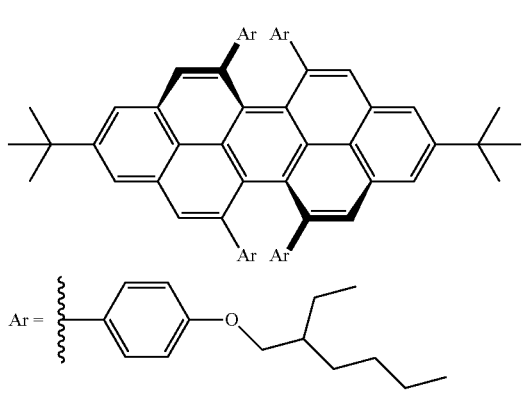
Ar = —⟨phenyl⟩—O—CH₂CH(C₂H₅)C₄H₉
Ar = —⟨phenyl⟩—O—CH₂CH(C₂H₅)C₄H₉

US 10,550,056 B2
13
-continued
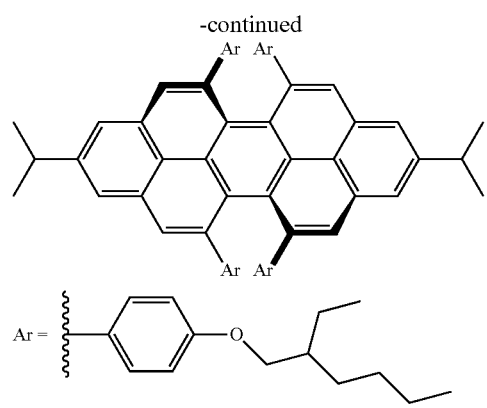
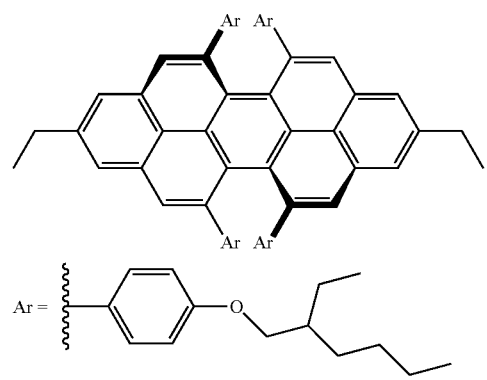
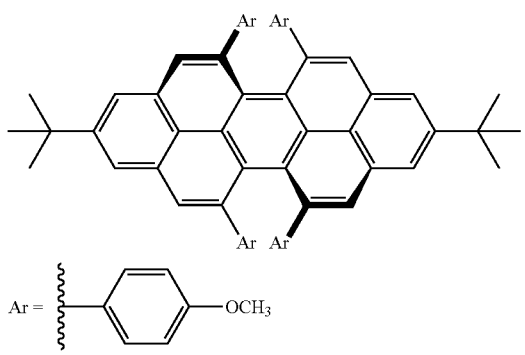
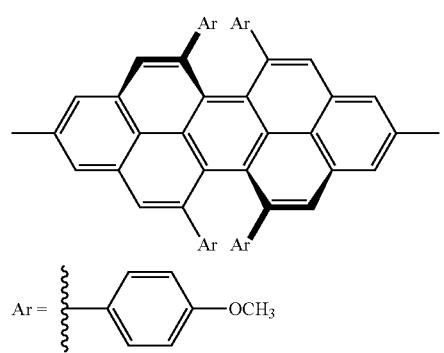
14
-continued
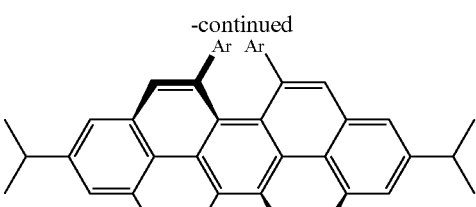
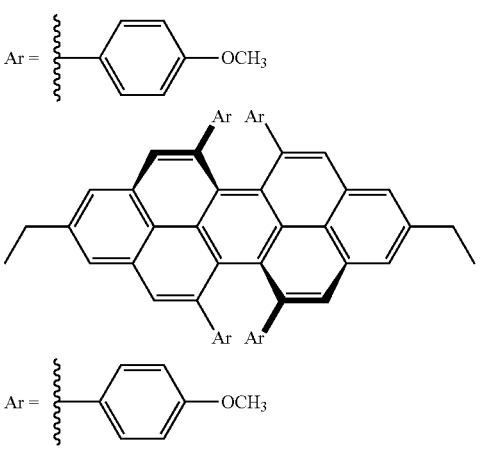
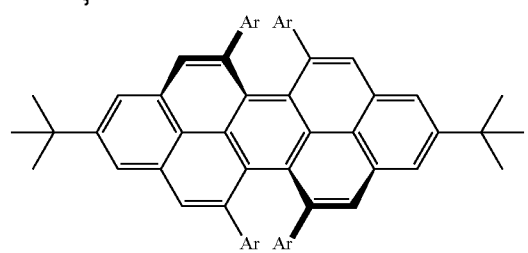
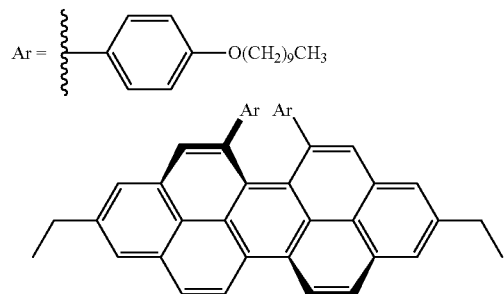
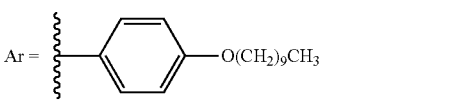
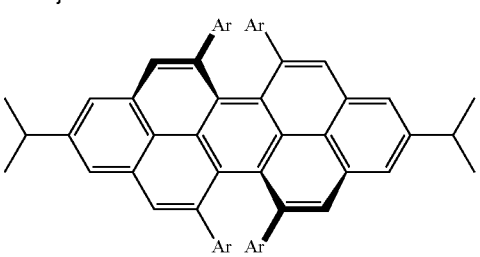
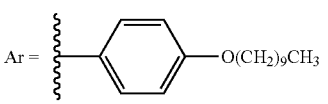

-continued

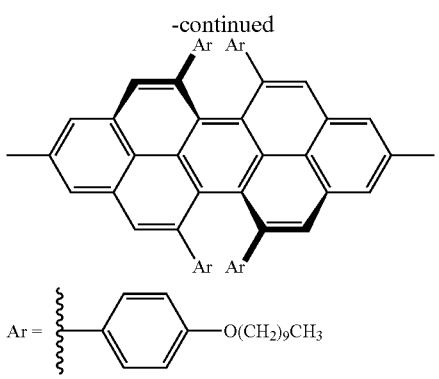

In some embodiments, the methods disclosed herein can be used to produce nanostructures, such as nanoribbons having a Formulas 6 or 7.

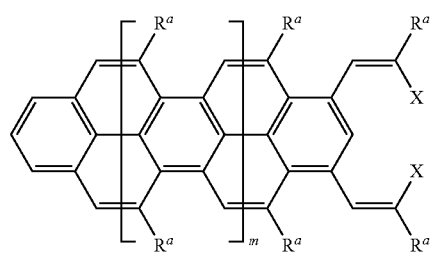

Formula 6

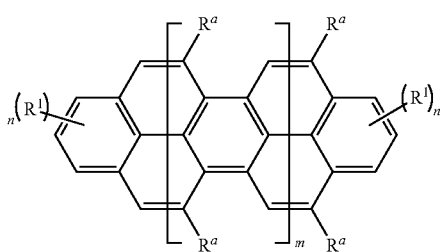

Formula 7

With reference to Formulas 6 and 7, each X independently can be selected from hydrogen or a terminal functional group and m can range from 1 to 1,000 or higher. Each or $R^1$, $R^a$, and n can be as recited above. In some embodiments, each $R^1$ independently can be selected from hydrogen, aliphatic, aryl, heteroaliphatic, or heteroaryl; each $R^a$ independently can be selected from aryl; aryl substituted with one or more functional groups selected from aliphatic, alkoxy, amide, amine, thioether, haloalkyl, nitro, halo, silyl, cycloaliphatic, aryl, and the like; or an electron-donating group; and each n independently can be 1, 2, or 3. Suitable terminal functional groups can be selected from functional groups, such as —$SO_3CH_3$, —$SO_3CF_3$, halogen, or the like. In some embodiments, where $R^a$ is aryl substituted with one or more functional groups, the one or more functional groups can be positioned meta, ortho, para, or combinations thereof, relative to the position at which the $R^a$ group is attached. In some embodiments, m can range from 2 to 500 or higher, or from 3 to 100 or higher, or from 4 to 50 or higher. In exemplary embodiments, m ranges from 10 to 80. Exemplary compounds satisfying Formulas 6 and 7 are illustrated below.

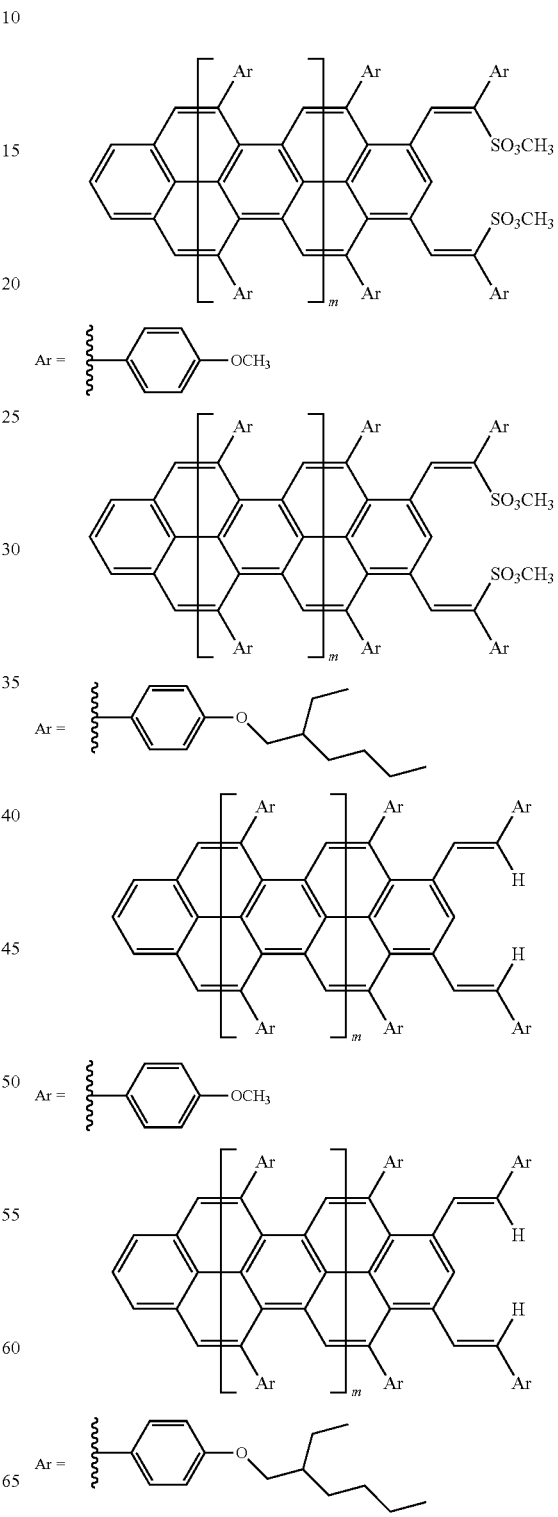

-continued

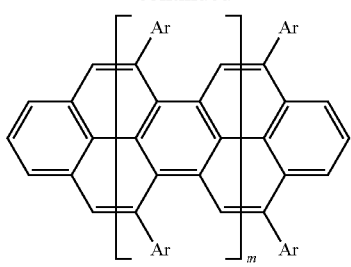

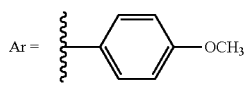
Ar = —⟨phenyl⟩—OCH₃

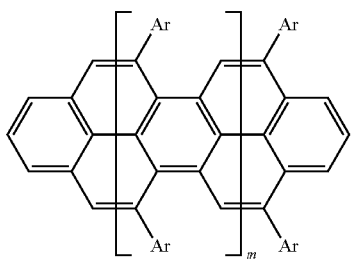

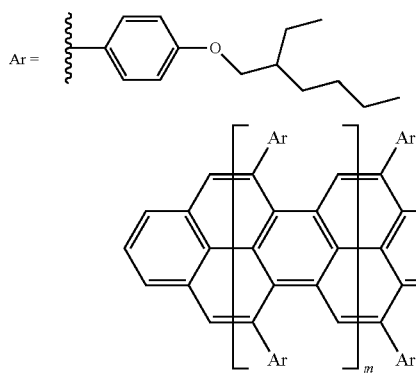

-continued

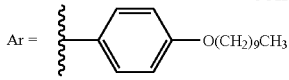
Ar = —⟨phenyl⟩—O(CH₂)₉CH₃

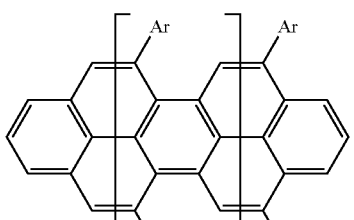

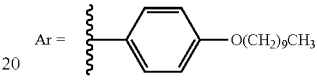
Ar = —⟨phenyl⟩—O(CH₂)₉CH₃

IV. Methods of Making Compounds

Disclosed herein are methods of making pyrene compounds, peropyrene-based compounds, and polymeric compounds satisfying the formulas described above.

Methods of making pyrene compounds are described below in Scheme 1. With reference to Scheme 1, 2,6-bis[(4-"R"-phenyl)ethynyl]biphenyl 104 was prepared and then subjected to cyclization conditions using a variety of Brønsted acids for the purpose of invoking a double cyclization reaction, presumably via monocyclized intermediate 106, to produce 4,10-diarylpyrene derivatives 108.

Results from embodiments using trifluoroacetic acid and different solvent systems and conditions are provided by Table 1. In some embodiments, it was determined that after treating 104 with 10 equivalents methanesulfonic acid or p-toluenesulfonic acid for 1 day in anhydrous $CH_2Cl_2$ at room temperature, 108 could be obtained in high yield, such as 60% or 73% yield, separately (see, for example, entries 4 and 5 in Table 1). All the results indicated that the strength of the acid had a direct effect on the yield of pyrene. Triflic acid resulted in the rapid (within 5 minutes) formation of pyrene 108 at −40° C. with no detection of mono-cyclized 106 in the crude product, and 108 was obtained in nearly quantitative yield (Entry 6, Table 1). Without being limited to a particular theory of operation, it is currently believed that the efficiency and yield of the reaction significantly improved with increasing acidity of Brønsted acid.

Scheme 1

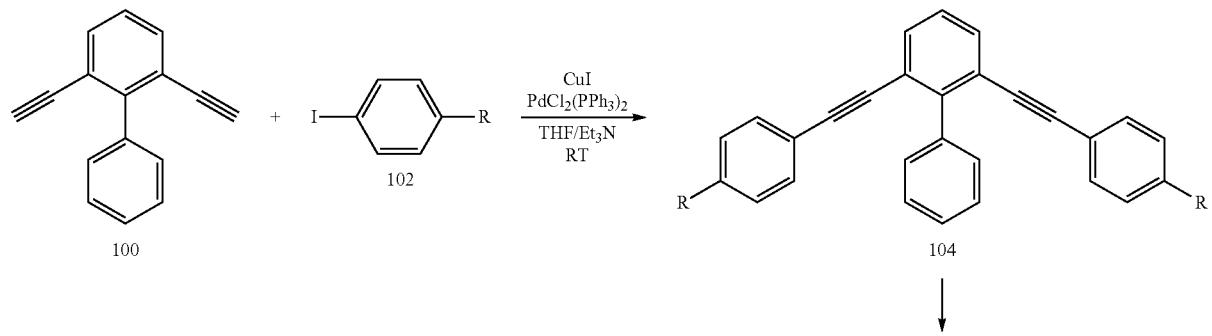

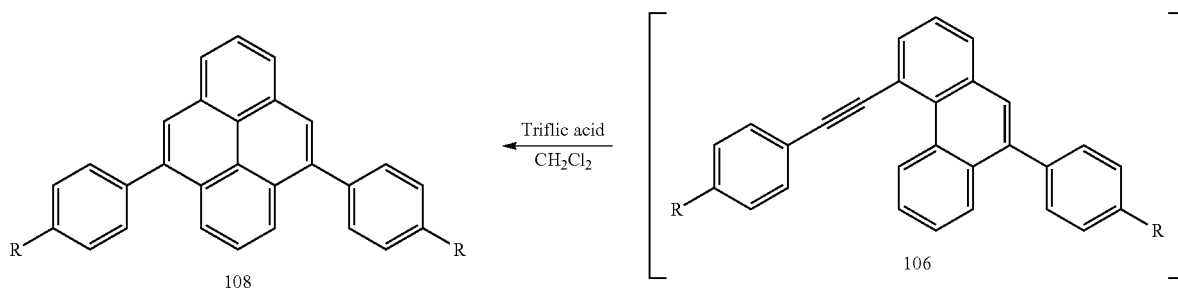

108

102a, 104a, 106a, 108a = R = OMe
102b, 104b, 106b, 108b = R = ethylhexyl
102c, 104c, 106c, 108c = R = N(CH$_3$)$_2$
102d, 104d, 106d, 108d = R = H
102e, 104e, 106e, 108e = R = Br
102f, 104f, 106f, 108f = R = NO$_2$
102g, 104g, 106g, 108ga = R = CF$_3$

106

TABLE 1

Brønsted acid screening for the cyclization of 104

| Entry | Acid | Solvent | T (° C.) | 108$^a$ (%) |
|---|---|---|---|---|
| 1 | TFA | DCM | 25 | 0 |
| 2 | TFA | DCM | 50 | 25b |
| 3 | TFA | DCE | 85 | 52b |
| 4 | methane-sulfonic acid | DCM | 25 | 60 |
| 5 | p-toluene-sulfonic acid | DCM | 25 | 73 |
| 6 | triflic acid | DCM | −40 | 99 |

$^a$Isolated yield;
bYield was determined by crude $^1$H NMR.

In some embodiments, additional pyrene and pero-pyrene based compounds are made using methods described below. As illustrated in Scheme 2, a starting diyne compound 206 can be made using the method steps illustrated below. In some embodiments, starting material 200 is halogenated to provide halogenated compound 202. Reaction of halogenated compound 202 with suitable reagents to effect an aromatic substitution reaction (e.g., reagents suitable for a radical-based aromatic substitution reaction) can provide compound 204, which can then be cross-coupled with two alkyne moieties to provide diyne 206.

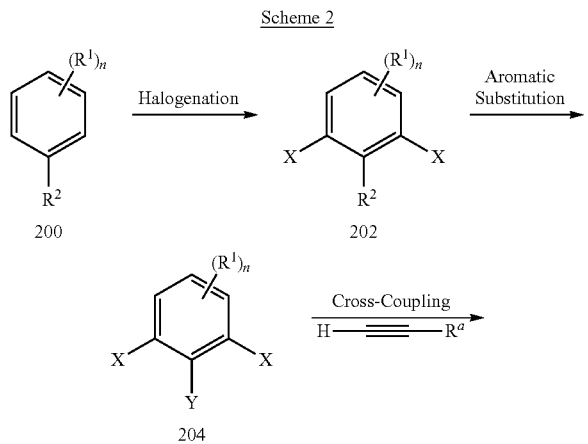

Scheme 2

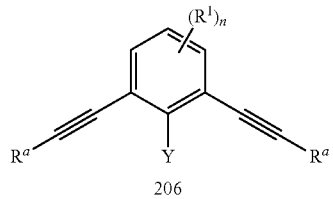

206

With reference to Scheme 2, R$^1$ can be as recited herein; R$^2$ can be an amine (e.g., NH$_2$); each of X and Y independently can be selected from a halogen, such as I, Br, F, and Cl; and each R$^a$ group independently can be as recited herein. In exemplary embodiments, R$^1$ is hydrogen or alkyl, R$^2$ is NH$_2$, X is I, and Y is Br. An exemplary embodiment of the above-described method is provided below in Scheme 3.

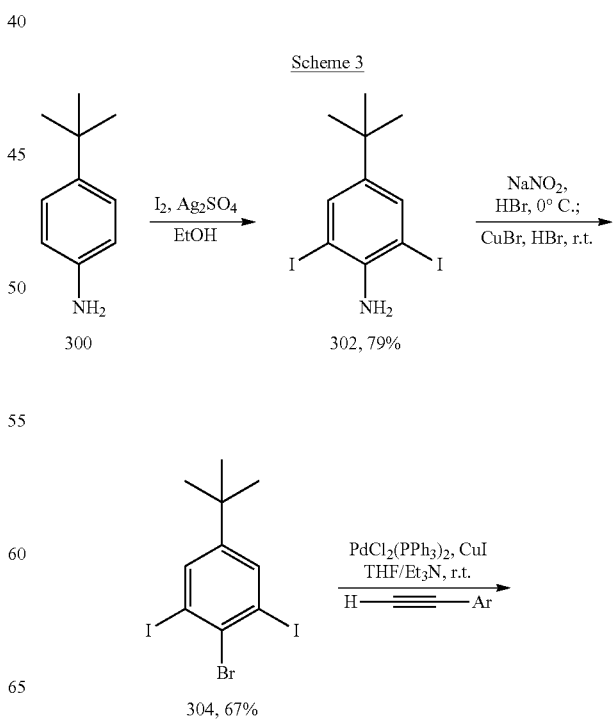

Scheme 3

-continued

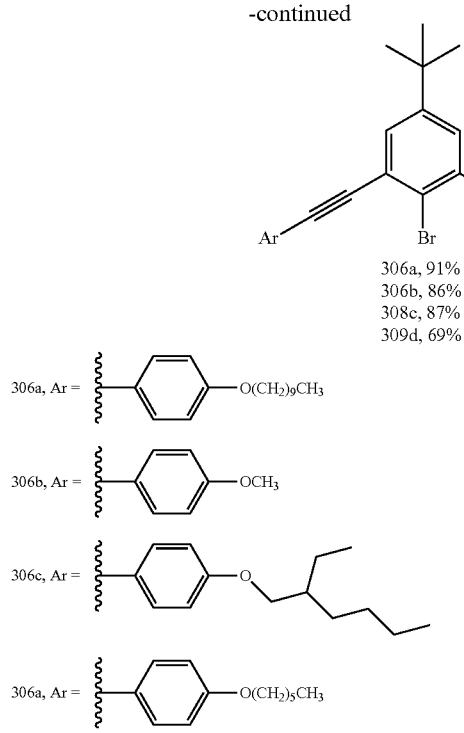

306a, 91%
306b, 86%
308c, 87%
309d, 69%

306a, Ar = —⟨C6H4⟩—O(CH2)9CH3

306b, Ar = —⟨C6H4⟩—OCH3

306c, Ar = —⟨C6H4⟩—O—CH2CH(C2H5)(CH2)3CH3

306a, Ar = —⟨C6H4⟩—O(CH2)5CH3

The synthesis illustrated in Scheme 3 started with iodination of 4-tert-butylaniline 300 to give 4-tert-butyl-2,6-diiodoaniline 302 followed by Sandmeyer reaction to give compound 304. Compound 304 was then subjected to a double cross-coupling reaction with an electron-rich alkyne to provide the 1-bromo-2,6-dialkynyl compound (306).

In some embodiments, diyne 206 can be converted to a suitable polymer precursor using a boronic acid-based coupling method as illustrated in Scheme 4. In some embodiments, the boronic acid-based coupling comprises exposing diyne 206 to a boronic pinacol ester, such as compound 402 (where $R^5$ is $B[-OC(R^6)_2C(R^6)_2O-]$, wherein each $R^6$ independently is selected from hydrogen, aliphatic, or aryl) to produce polymer precursor 406. In some embodiments, a halogen-metal exchange reaction using a metal-containing compound followed by boronic acid or boronic ester formation can be used to produce compound 400, which can then undergo a palladium-based reaction to provide 2,6-dialkynylbiphenyl derivative 406 using bromo compound 404. In yet other embodiments, the 2,6-dialkynylbiphenyl derivative 406 can be prepared directly by coupling diyne 206 with boronic pinacol ester 402. Diyne 406 can then be cyclized using an acid to form a pyrene product 412. Exemplary acids include, but are not limited to, $HCO_2CF_3$, $HOSO_2CH_3$, $HOSO_2CF_3$, and the like. In some embodiments, incomplete cyclization can provide compound 408, but this product can be avoided by allowing the reaction mixture to warm to room temperature from a lower temperature (e.g., 0° C. or lower).

Scheme 4
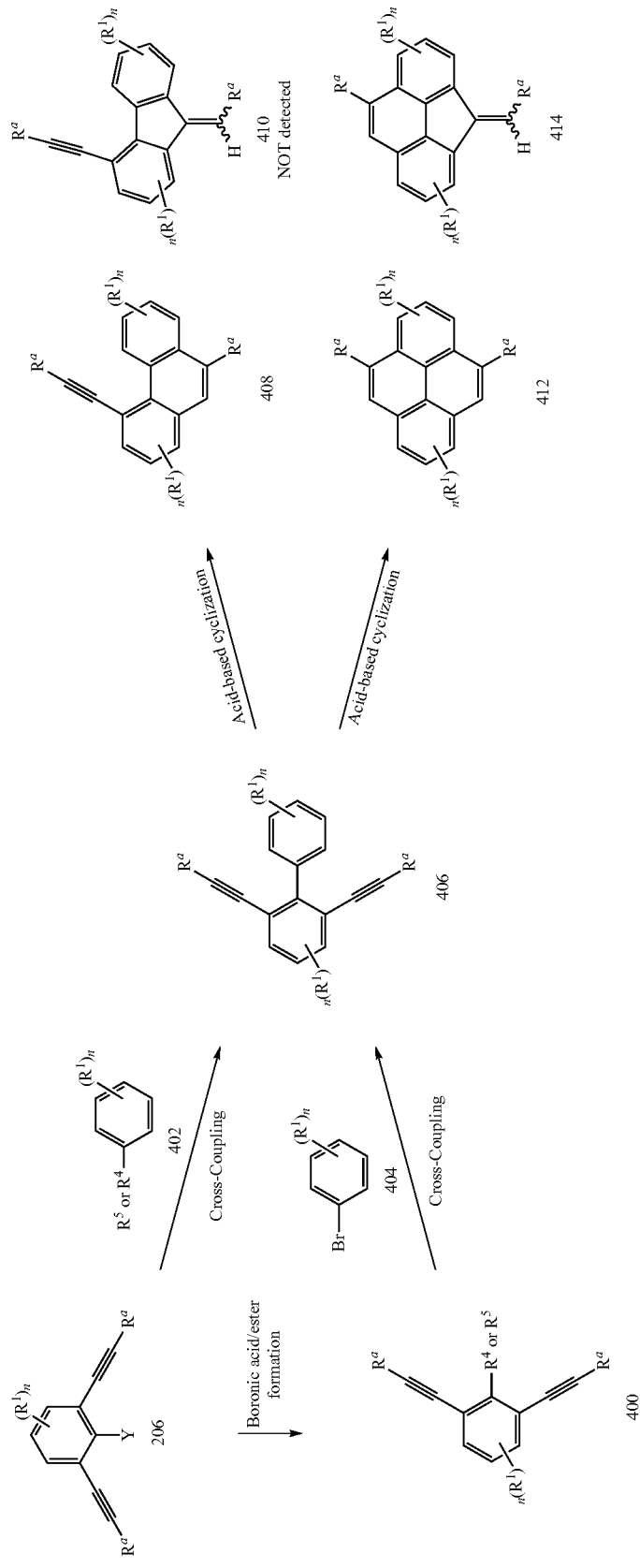

With reference to Scheme 4, each of $R^1$, Y, and Ar are as described above for Scheme 2; $R^4$ is a boronic acid; and $R^5$ is a boronic ester. In some embodiments, $R^4$ is $B(OH)_2$. In some embodiments, $R^5$ is $B[-OC(R^6)_2C(R^6)_2O-]$, wherein each $R^6$ independently is selected from hydrogen, aliphatic, or aryl. In exemplary embodiments, $R^5$ is $B[-OC(CH_3)_2C(CH_3)_2O-]$. In some embodiments, boronic ester or boronic acid formation can include exposing compound 206 to a metal-containing compound (e.g., n-BuLi, s-BuLi, t-BuLi, and the like) in solvent to facilitate halogen-metal exchange, followed by coupling of a boronic acid or a boronic ester (e.g., a boronic ester having a formula described above). In exemplary embodiments, a boronic ester, such as a pinacol boronic ester, is used. Cross-coupling reactions, such as those illustrated in Scheme 4, can comprise using a palladium-based reagent to facilitate coupling of a boronic ester compound or a boronic acid compound (e.g., compound 402) with compound 206. In yet some other embodiments, cross-coupling can comprise using a palladium-based reagent to facilitate coupling of compound 400 with a halogenated coupling partner, such as compound 404. Suitable palladium-based reagents include, but are not limited to, $Pd(PPh_3)_4$, $Pd(OAc)_2$, $PdCl_2$, Buchwald palladium reagents (e.g., XPhos Pd, SPhos Pd, RuPhos Pd, CPhos Pd, and the like), or Hartwig palladium reagents (e.g., Bis(tris(2-tolyl)phosphine)palladium $Pd[(o-tol)_3P]_2$, QPhos Pd, and the like). Exemplary embodiments of the methods illustrated in Scheme 4 are illustrated in Scheme 5.

In the exemplary embodiments illustrated in Scheme 5, Suzuki cross-coupling conditions were used. In some embodiments, cross-coupling reaction between 306a and 4-tert-butylphenylboronic acid pinacol ester 502 resulted in trace formation of desired 2,6-diynylbiphenyl product 506. In some embodiments, different coupling partners were evaluated by converted compound 306a into boronic acid pinacol ester 500, which was successful in cross-coupling with 4-tert-butylbromobenzene 504 to provide the 2,6-diynylbiphenyl 506 in moderate yield. The synthesis of substrate 506 allows determination of whether double cyclization was feasible and also to determine the regioselectivity of cyclization. In some embodiments, double cyclization of compound 506 involved using a catalytic amount of methanesulfonic acid at 0° C. The monocyclized phenanthrene product 508 can be formed, but in some embodiments can be a slow conversion. Increasing the amount of acid can improve the reaction speed significantly. The reaction can be completed within 10 minutes when using 2 to 3 equivalents of acid, which resulted in the exclusive formation of the monocyclized phenanthrene product 508 in near quantitative yield with no detection of the 5-membered product regioisomeric product 510. Warming the reaction to the room temperature did result in double cyclization to provide a pyrene product 512. 5-membered ring products 510 and 514 were not detected in most embodiments, but can potentially be isolated. In some embodiments, the coupling partners can be adjusted by converting compound 306a into a boronic acid pinacol ester using 502, which was successful in cross coupling with 1,4-diiodobenzene to provide the 2',2",6',6"-tetraynylterphenyl derivative 506 in moderate yield.

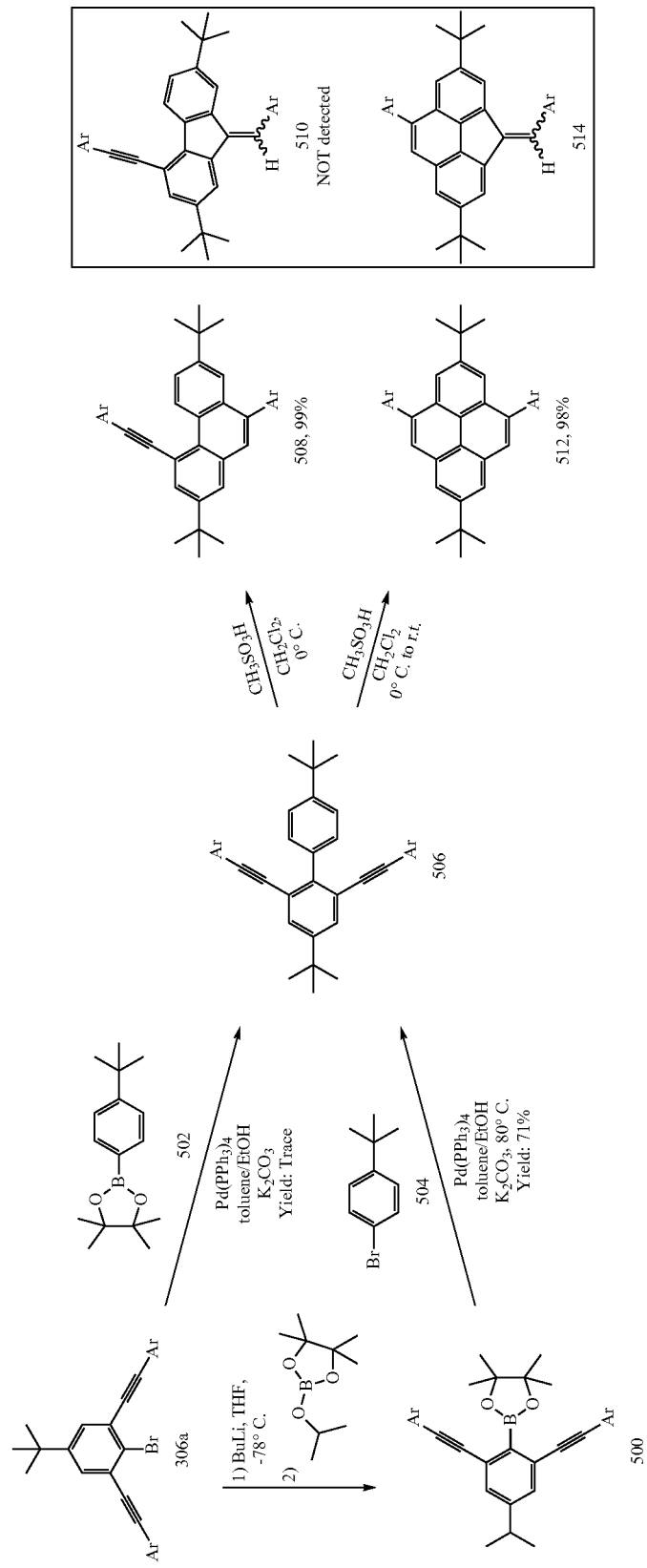
Scheme 5

In yet additional embodiments, peropyrene-based compounds can be formed using methods illustrated in Scheme 6. As with Schemes 4 and 5, a halogen-metal exchange reaction and a boronic ester (or boronic acid) coupling reaction sequence can be used to make compound 602. Compound 400 can be cross-coupled with a di-halogenated aryl compound, such as compound 600 illustrated in Scheme 6. This cross-coupling provides terphenyl derivative 602. Treatment of terphenyl derivative 602 with an acid at a first temperature provides intermediate 604. Treatment of intermediate 604 with another acid at a second temperature provides the fully cyclized peropyrene compound 606. In some embodiments, the use of a subsequent acid-catalyzed reaction is used to convert intermediate 604 to the desired peropyrene product.

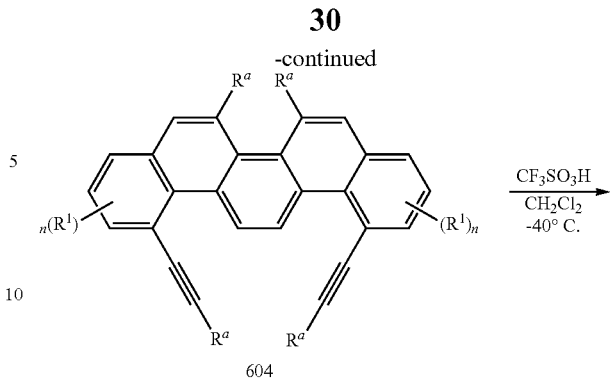

Exemplary embodiments of the methods illustrated in Scheme 6 are illustrated below in Scheme 7. In some embodiments, bis-cyclized intermediate 704b was obtained in 97% yield while TFA was added at room temperature, which was proved by NMR and X-ray crystal analysis. After screening various other Brønsted acids, it was determined that the tetra-cyclized product 706b (and other compounds like 706a, 706c, and 706d) could be formed cleanly and rapidly without any acidolysis compounds while using 2 equivalent of triflic acid (TfOH) at −40° C. In some embodiments, the bis-cyclization/tetra-cyclization sequence can be carried out as a "one-pot" process. In some embodiments, the one pot process can result in isolating 706a and 706c in 38% and 45% yield from 2',2'',6',6''-tetraynylterphenyl derivatives 702a and 702c, respectively (Scheme 7).

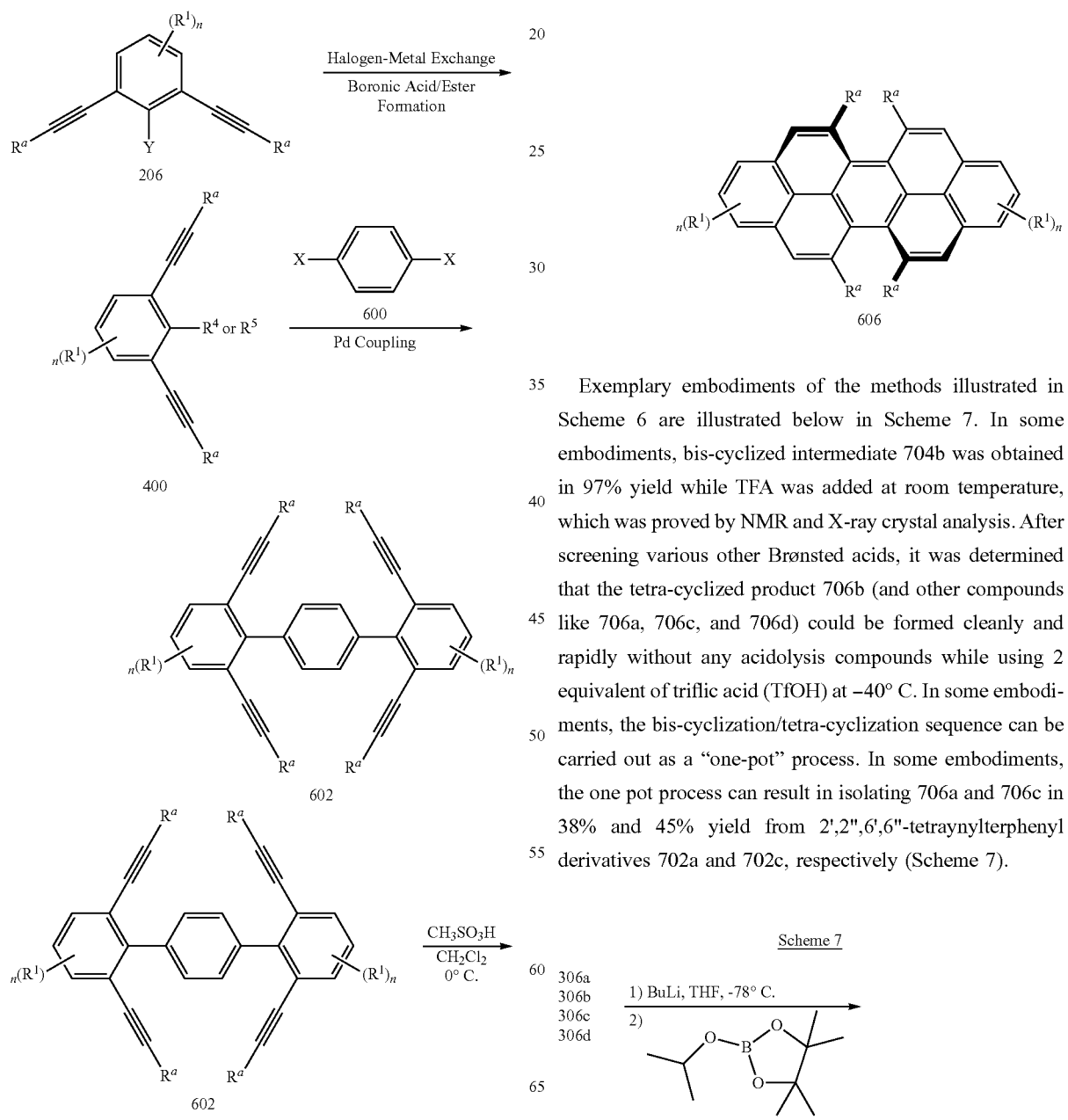

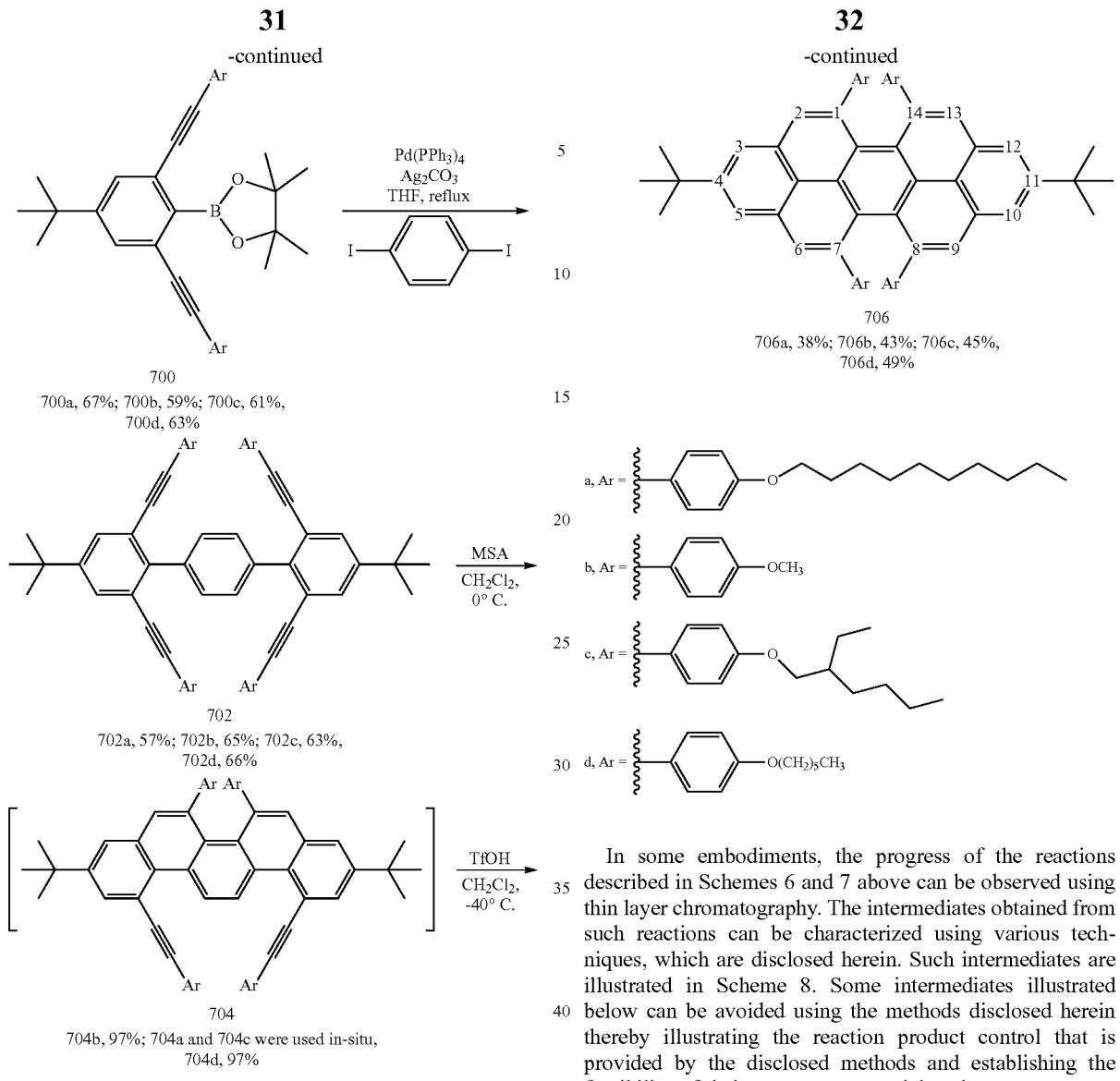

In some embodiments, the progress of the reactions described in Schemes 6 and 7 above can be observed using thin layer chromatography. The intermediates obtained from such reactions can be characterized using various techniques, which are disclosed herein. Such intermediates are illustrated in Scheme 8. Some intermediates illustrated below can be avoided using the methods disclosed herein thereby illustrating the reaction product control that is provided by the disclosed methods and establishing the feasibility of their use on commercial scale.

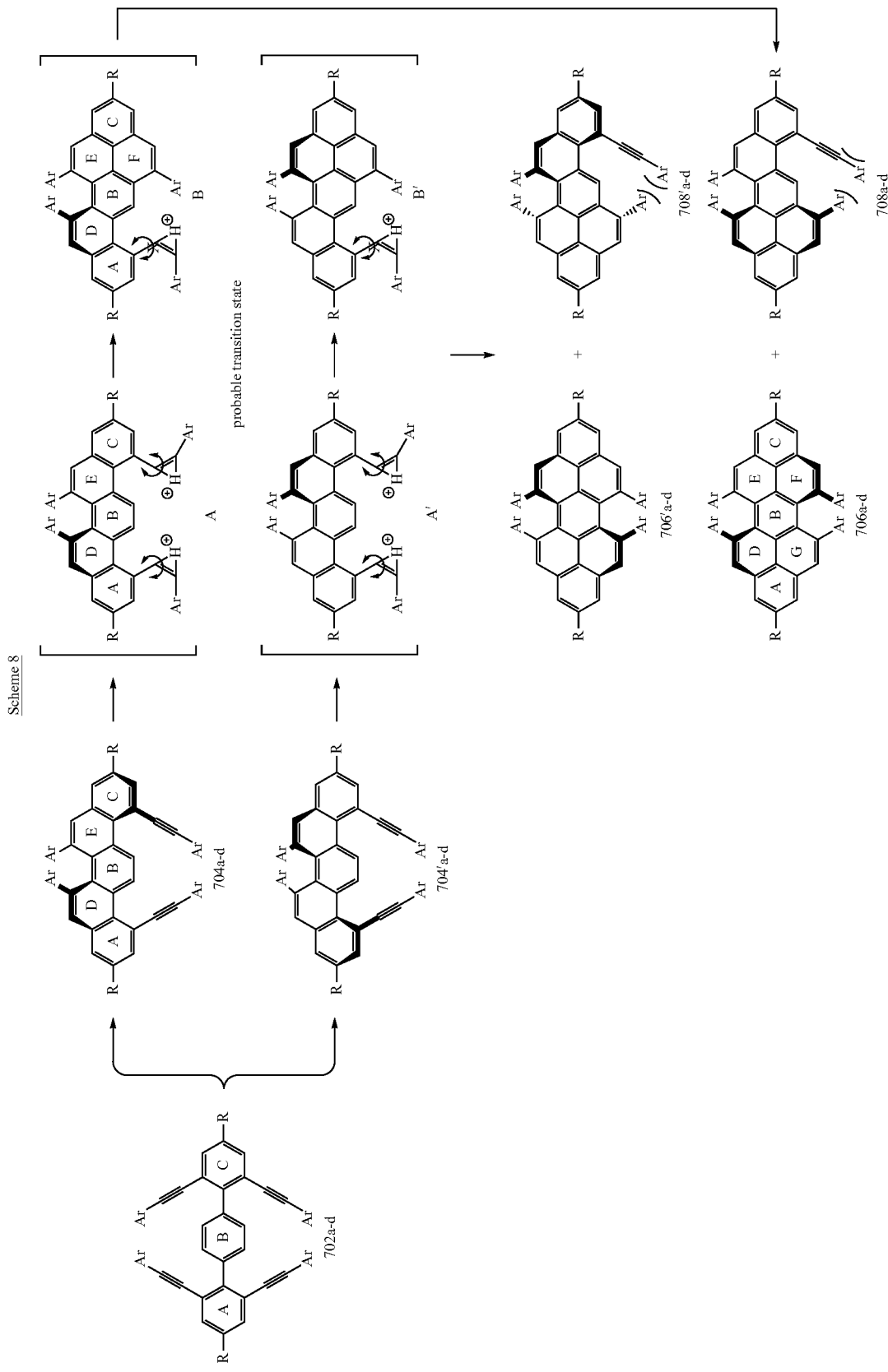

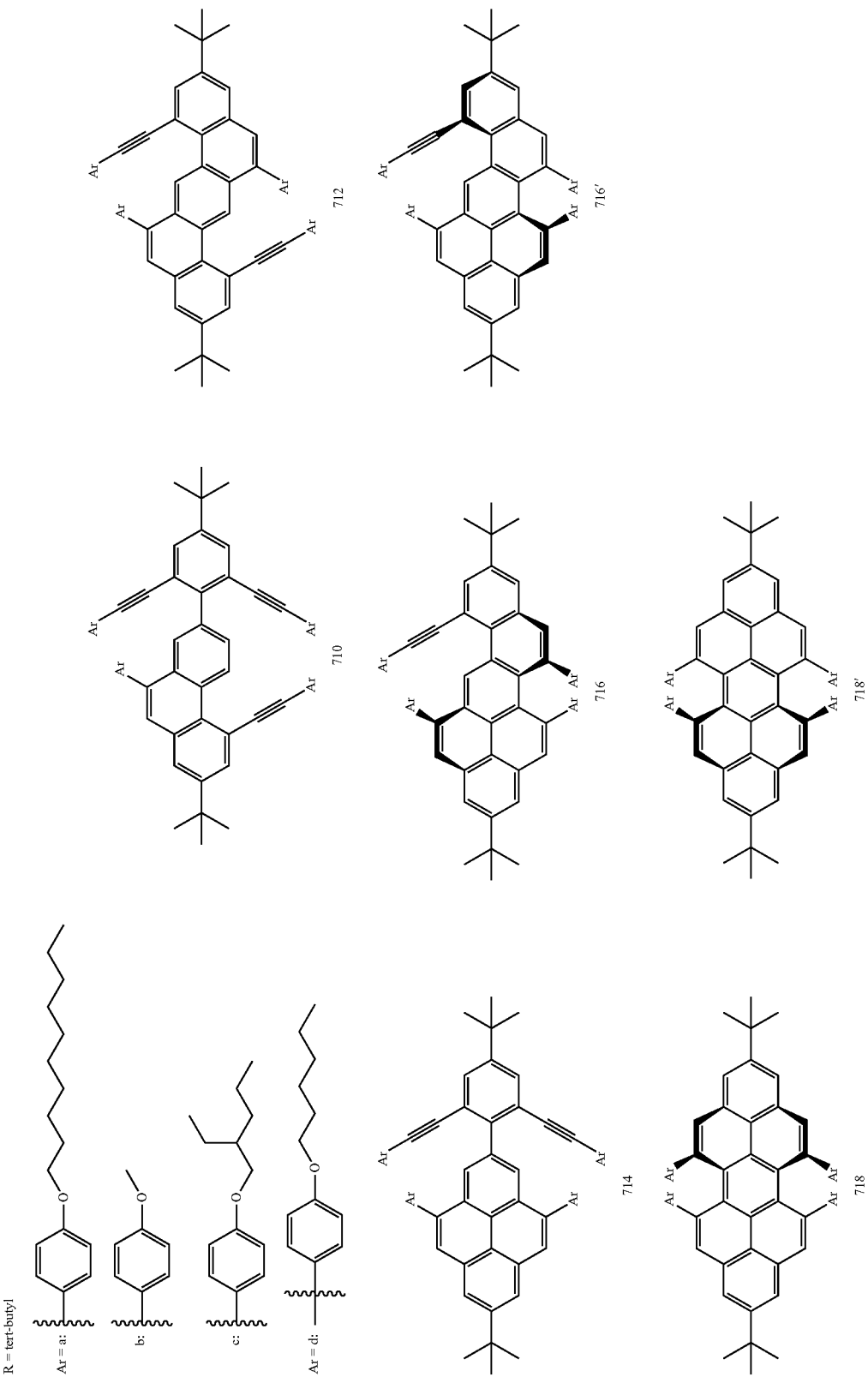

The bis-cyclized intermediates produced using the methods described above can be further converted to peropyrene products using acid-catalyzed cyclization reactions. In some embodiments, an acid, such as $CF_3SO_3H$, or any Brønsted acid having a pKa substantially similar to $CF_3SO_3H$, such as triflimidic acid ($HNTf_2$), methane sulfonic acid, benzene sulfonic acid, p-toluene sulfonic acid, and the like, can be used to cyclize bis-cyclized intermediates to peropyrene-based compounds. In some embodiments, low temperatures (e.g., below ambient temperatures, such as from above −100° C. to below 25° C., or above −50° C. to below 10° C., or −40° C. to below 0° C.) can be used during the acid-catalyzed conversion of bis-cyclized intermediate to peropyrene-based compounds.

In particular disclosed embodiments, the course of the reaction illustrated in Scheme 8 can be observed clearly by thin layer chromatography and the intermediates characterized by various techniques discussed herein. Scheme 8 illustrates various possible intermediates. The speed of the first two cyclizations between rings A and B and between B and C can be attributed to the flexibility of the substrate and free-rotation of the terphenyl benzene rings, which would allow for good orbital overlap of the newly forming carbon-carbon bond on rings D and E. Once ring D is formed to produce a planarized phenanthryl moiety, the second alkyne cyclization between rings A and B is rendered more difficult due to poor orbital overlap (Scheme 8). With free-rotation still possible between rings B and C, the second cyclization also can be rapid to produce ring E giving intermediate 704. The formation of intermediate 712 was not observed. Intermediate 704 can be isolated and X-ray crystallographic analysis can be used to confirm its structure. Compound 704 is axially chiral. From the structure of 704, there may be a preference for the third and fourth cyclizations to generate rings F and G to occur from the opposite direction to produce the axially chiral enantiomers 706 as opposed to the meso compound 718. Compound 716 can undergo a fourth cyclization to give the tetra-cyclized product 706 rapidly. Additional exemplary methods of making the compounds disclosed herein are provided by Schemes 9-14.

Scheme 9

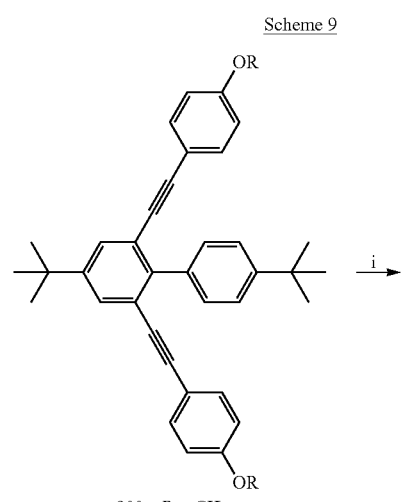

900a: R = CH₃
900b: R = C₆H₁₃
900c: R = C₁₀H₂₁

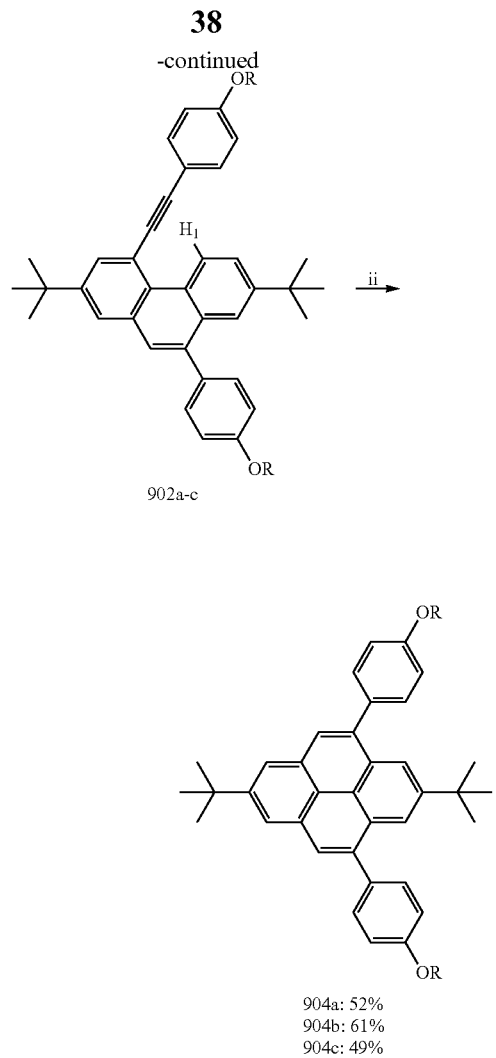

902a-c

904a: 52%
904b: 61%
904c: 49%

Scheme 10

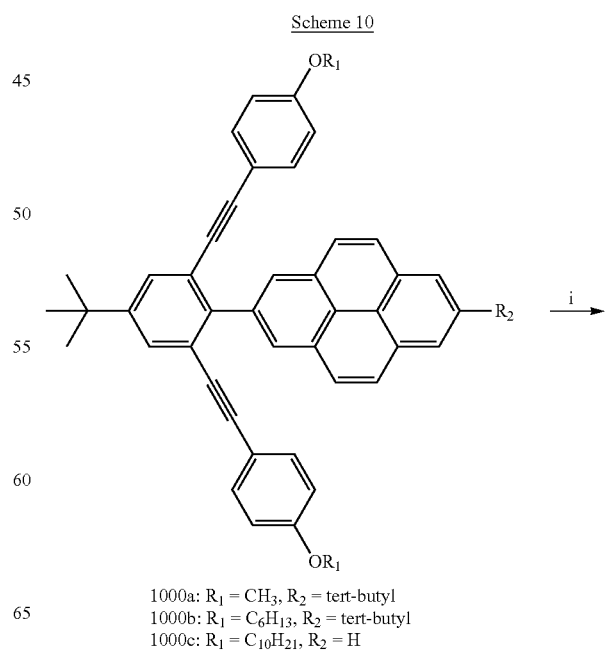

1000a: R₁ = CH₃, R₂ = tert-butyl
1000b: R₁ = C₆H₁₃, R₂ = tert-butyl
1000c: R₁ = C₁₀H₂₁, R₂ = H

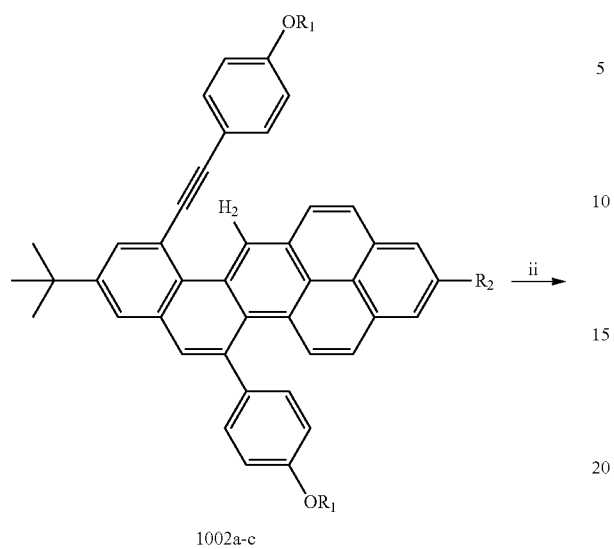
1002a-c
→ ii
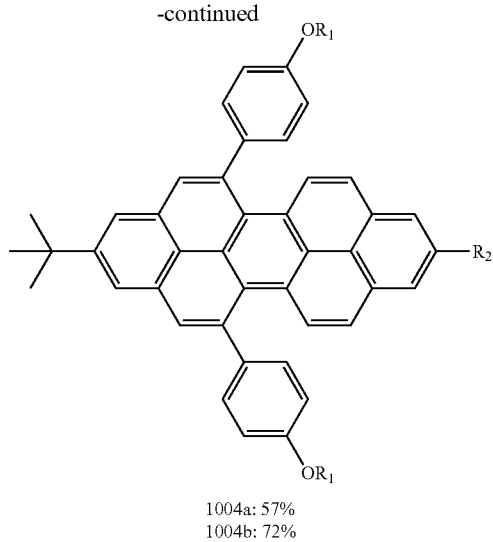
1004a: 57%
1004b: 72%
1004c: 65%

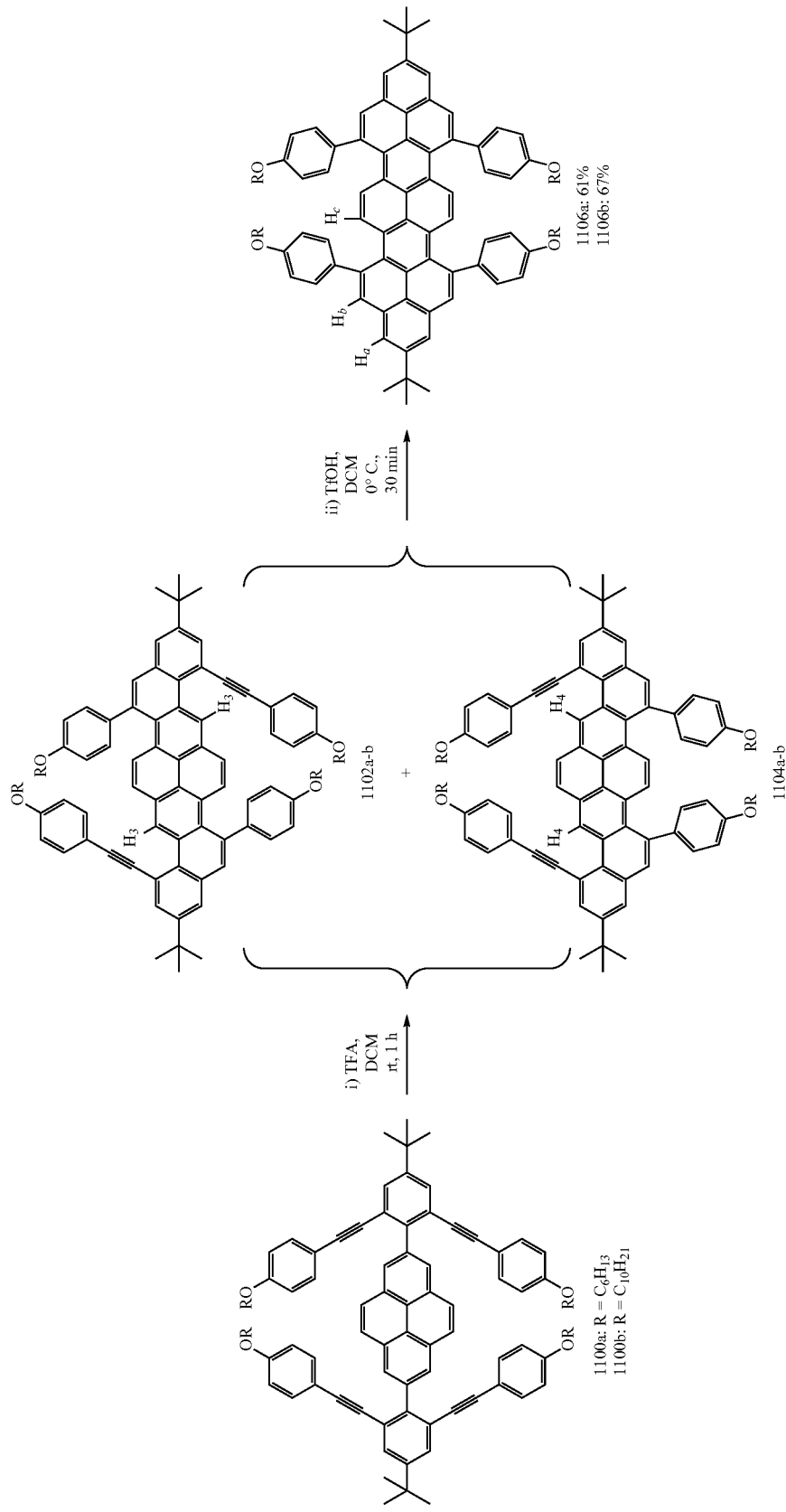

Scheme 12
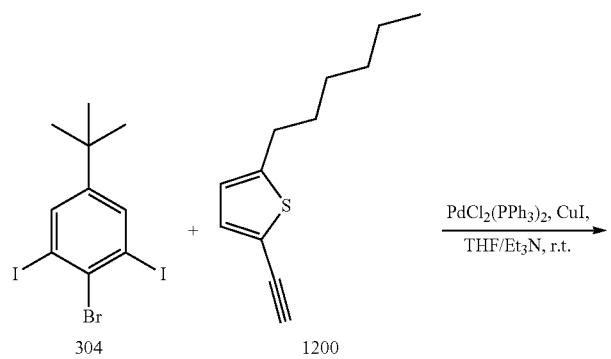
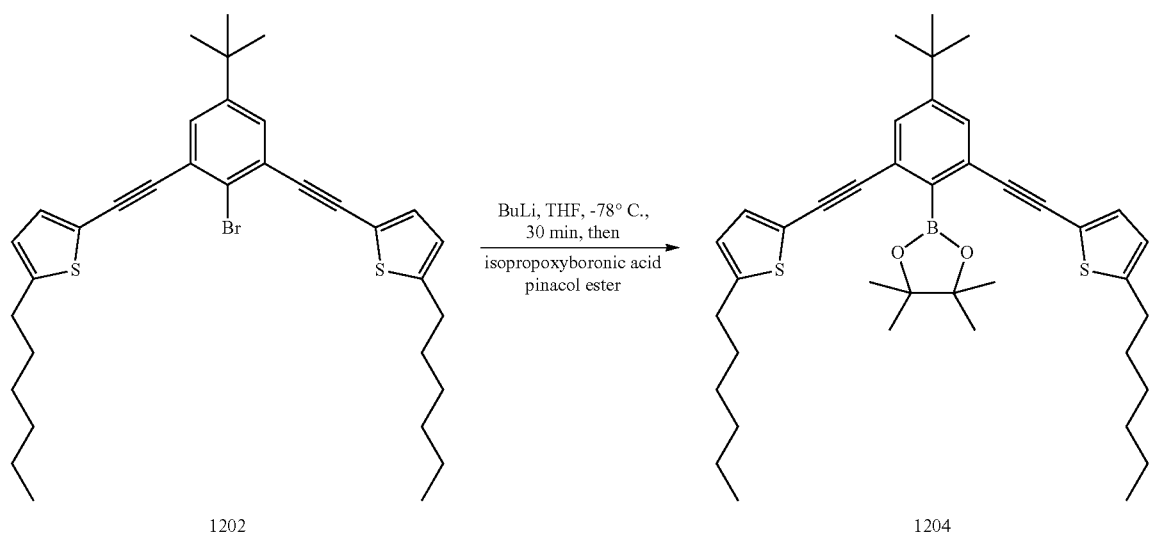
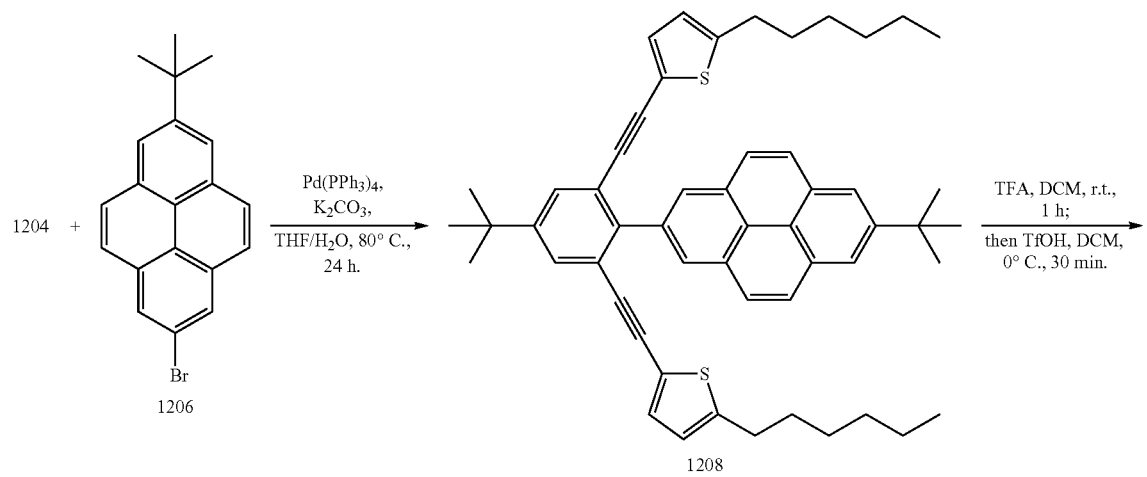

-continued
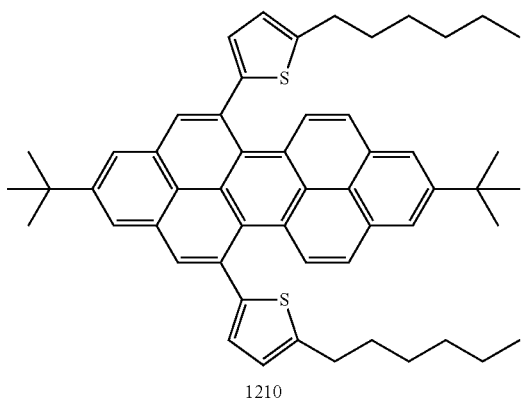
1210
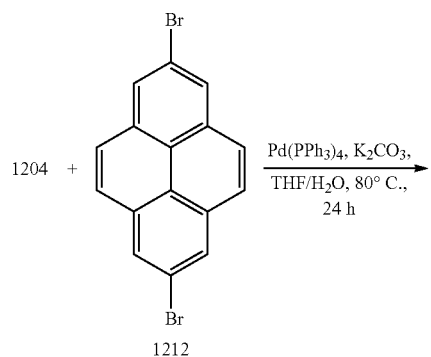
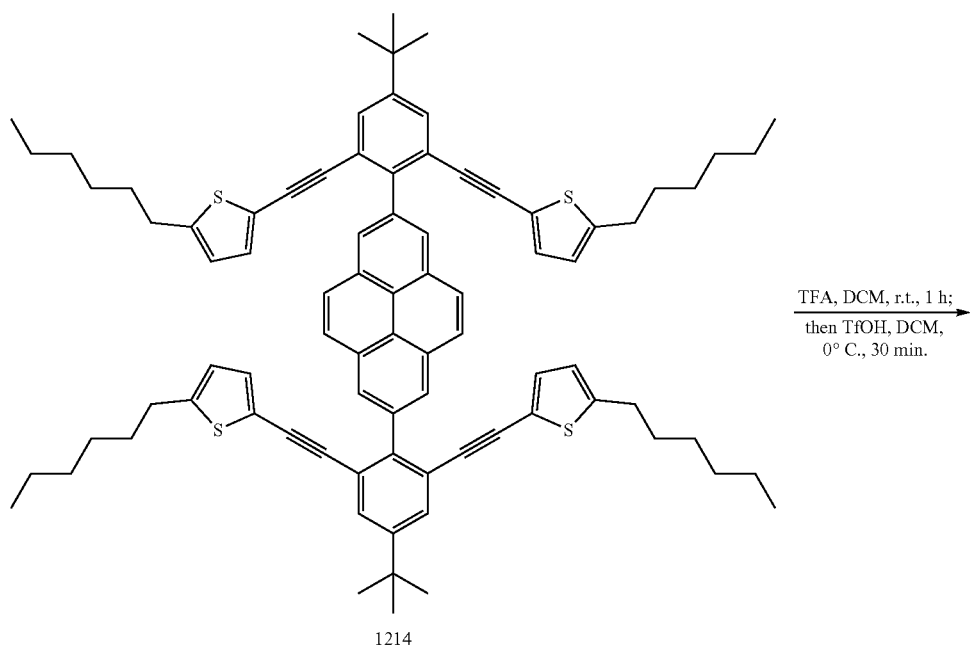
1214

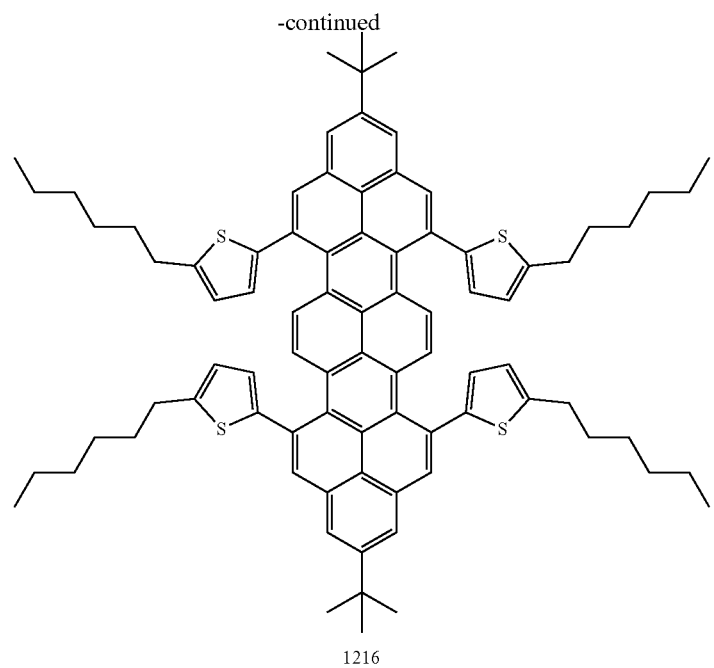
1216

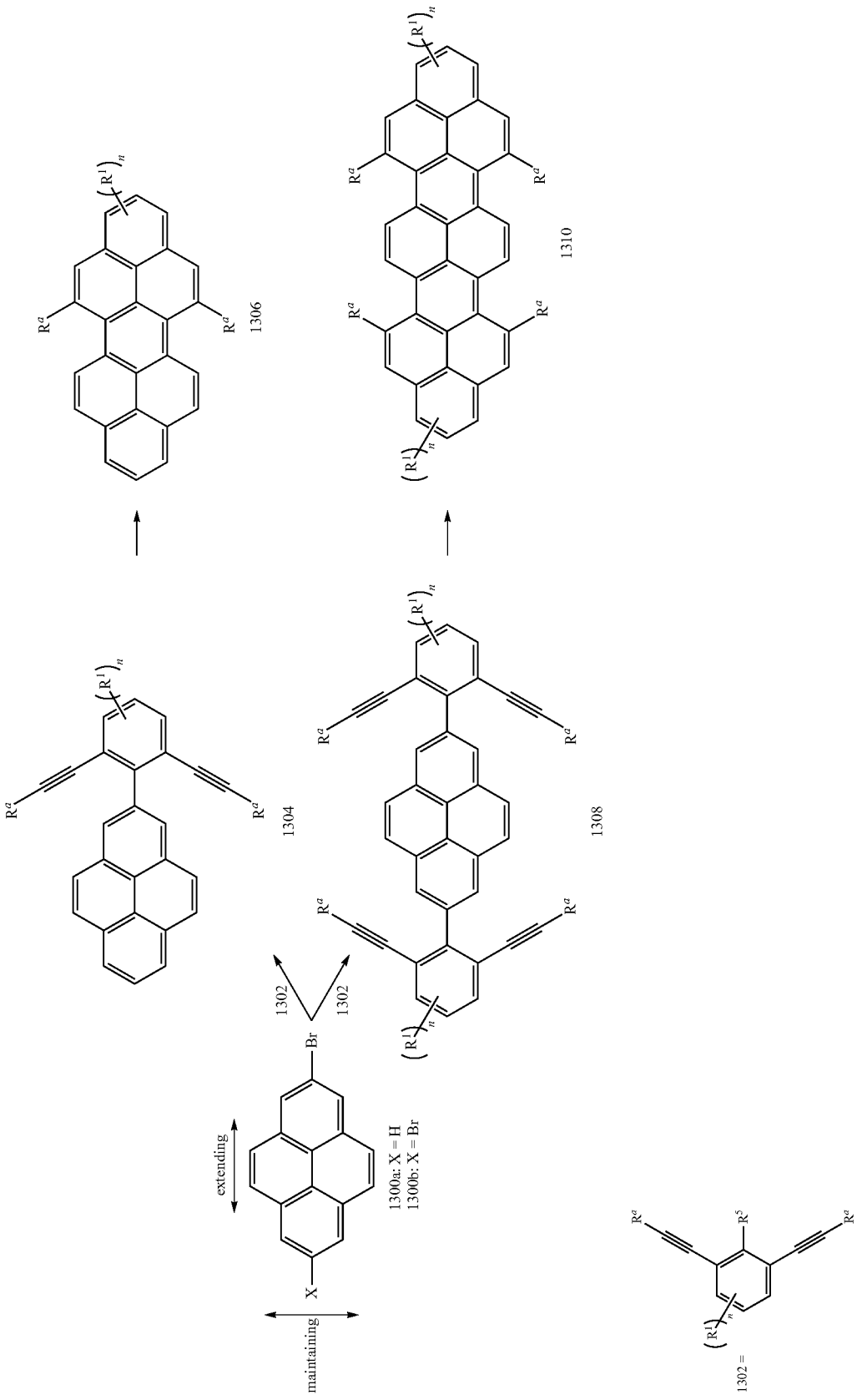

Scheme 13B
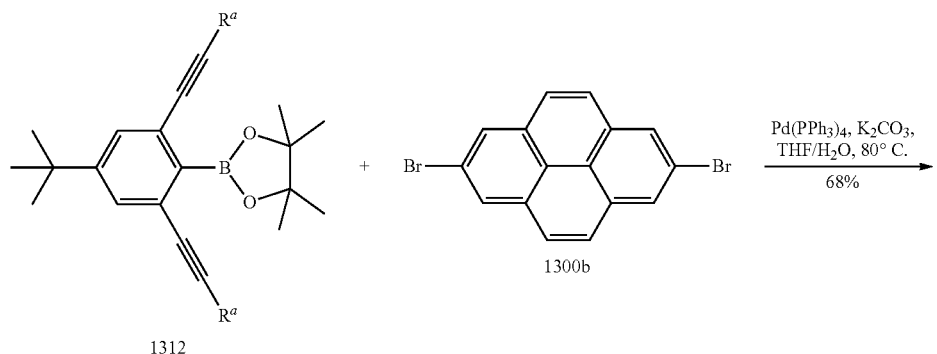
1312    1300b
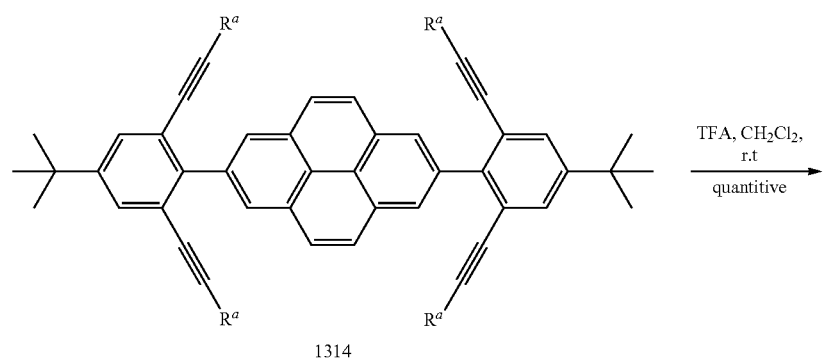
1314
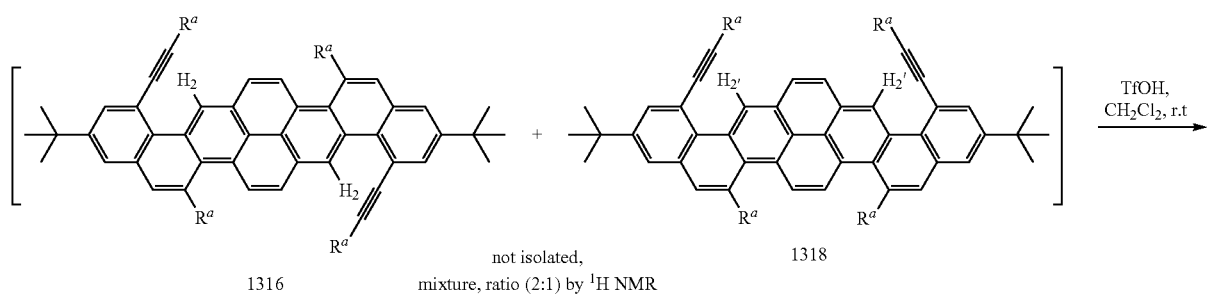
1316                    1318
not isolated,
mixture, ratio (2:1) by ¹H NMR
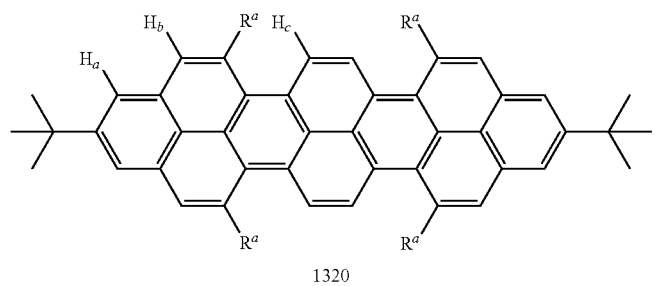
1320
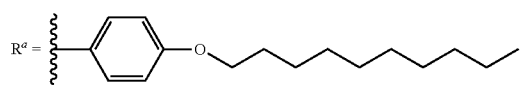

Scheme 14

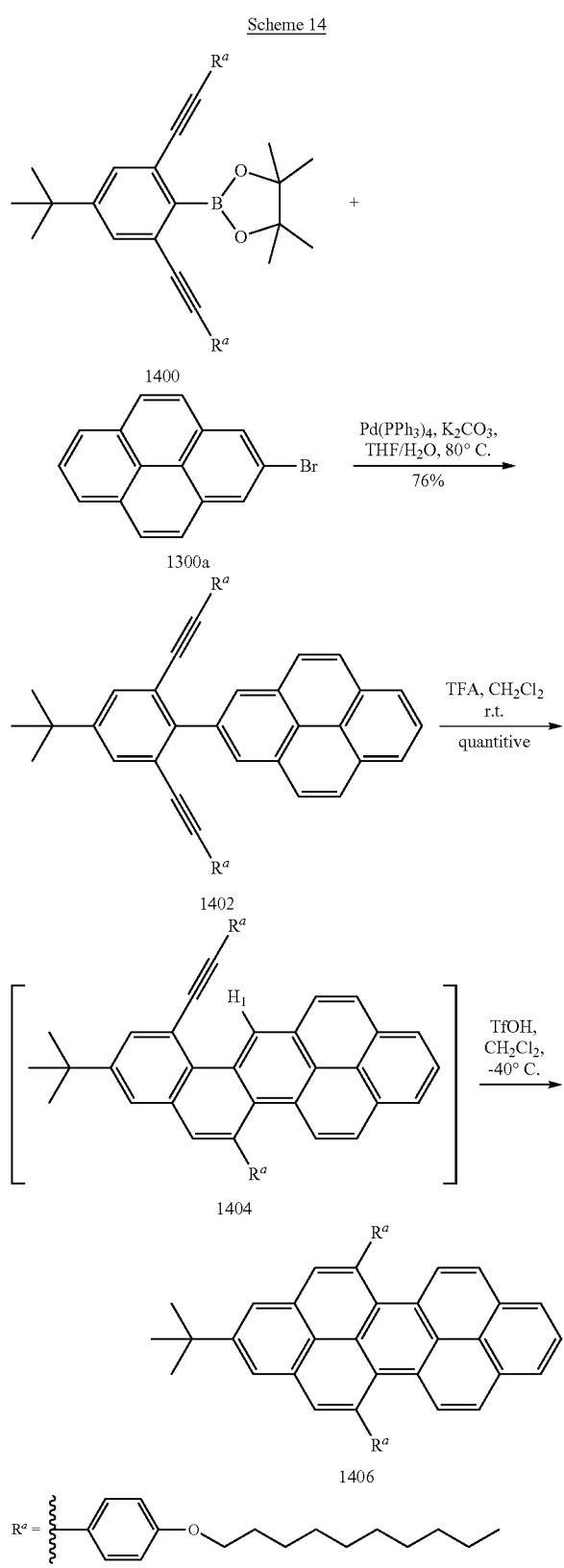

Using the methods described in Schemes 13 and 14, aromatic ring systems can be extended from the non-K-region without changing the width of the fused aromatic backbones, a feature that has not been accomplished by conventional methods. With reference to Scheme 14, a bis-cyclization reaction of compound 1402 can be performed to make peropyrene-based compound 1406. As shown in Scheme 14, compound 1402 was isolated in 76% yield by Suzuki coupling reaction of 2,6-dialkynebenzene pinacol boronate 1400 with 2-bromopyrene 1300a. Compound 1402 provided the mono benzannulated product 1404 almost quantitatively in the presence of excess trifluoroacetic acid (TFA) at room temperature. As determined from the $^1$H NMR of compound 1404, the proton in the cove position provides a sharp singlet signal around 11.12 ppm ($H_1$, Scheme 14). Without being limited to a particular theory, it is currently believed that this extreme deshielding is attributed to the planarized phenanthryl geometry formed in compound 1404 after the first cyclization placing Hi in the deshielding zone of the remaining alkyne. In some embodiments, compound 1406 was not observed in the presence of TFA at room temperature, even after long reaction times. No change in the reaction was observed after adding triflic acid (TfOH) (1 equiv.) to the solution at −78° C.; however, upon warming the reaction to −40° C., the second alkyne cyclization completed instantly, resulting in peropyrene 1406.

In particular disclosed embodiments, the peropyrene-based products disclosed herein can be made enantioselectively. As indicated herein, the formation of the bis-cyclized intermediates disclosed herein is rapid and these intermediates also are axially chiral. Therefore, the inventors of the present disclosure have discovered that it is possible to invoke a double cyclization to produce chiral peropyrene-based compounds using a mild, chiral Brønsted acid.

In additional embodiments, the methods described above in Schemes 1-8 can be used and/or modified to make long, polymeric peropyrene-containing products, such as nanostructures (e.g., graphene nanostructures or graphene-like nanostructures). In some embodiments, alternative methods to those described in Scheme 2 can be used to obtain compound 206. For example, starting material 1500 can be converted to triazene compound 1502, followed by selective double palladium-based cross-coupling to afford dialkynyltriazene 1504. Conversion of the dialkynyltriazene 1504 to intermediate 206 was achieved by treating dialkynyltriazene 1504 with an alkyl halide. Halogenated intermediate 206 was treated with BuLi to effect a lithium-halogen exchange and trimethoxyborane was added and worked up under acidic conditions to provide boronic acid 1506 in good yield. Conversion of boronic acid 1506 to the pinacol ester 1508 can be conducted using a suitable diol compound.

Scheme 15

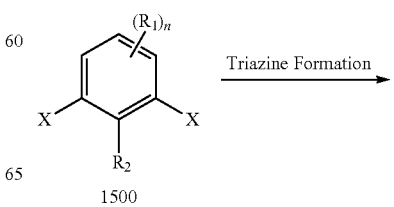

-continued

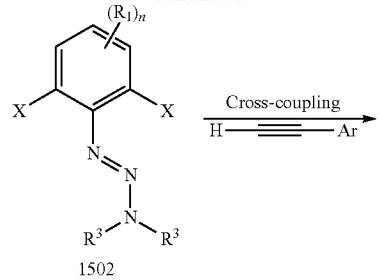
1502

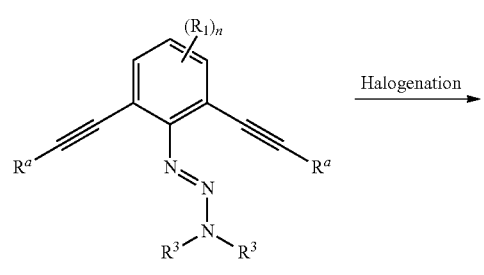
1504

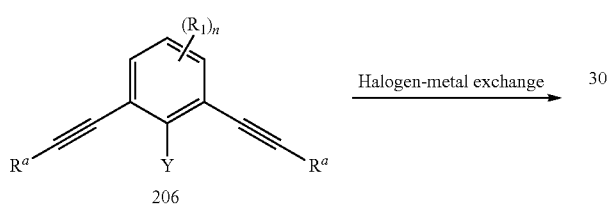
206

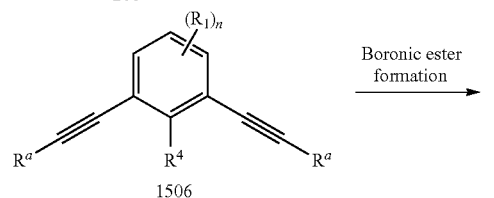
1506

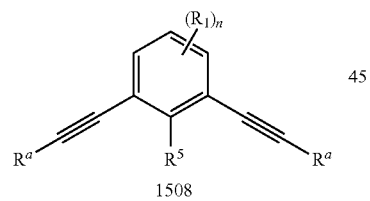
1508

With respect to Scheme 15, each of $R^1$, $R^2$, X, Y, and $R^a$ can be as recited herein. In some embodiments, $R^1$ can be a halogen selected from Br, I, F, or Cl, or OTf. In some embodiments, each $R^3$ independently can be selected from hydrogen, aliphatic or aryl; $R^4$ is a boronic acid; and $R^5$ is a boronic ester. In some embodiments, $R^1$ is Br. In some embodiments, $R^3$ is selected from alkyl, alkenyl, alkynyl, or aryl. In some embodiments, $R^4$ is $B(OH)_2$. In some embodiments, $R^5$ is $_{B[-OC(R^6)_2C(R^6)_2]}$, wherein each $R^6$ independently is selected from hydrogen, aliphatic, or aryl. In exemplary embodiments, $R^3$ can be selected from methyl, ethyl, propyl, butyl, pentyl, or the like. In exemplary embodiments, $R^5$ is $B[-OC(CH_3)_2C(CH_3)_2O-]$. An exemplary embodiment of the method illustrated in Scheme 15 is provided below in Scheme 16.

Scheme 16

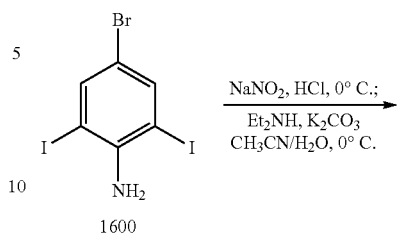
1600

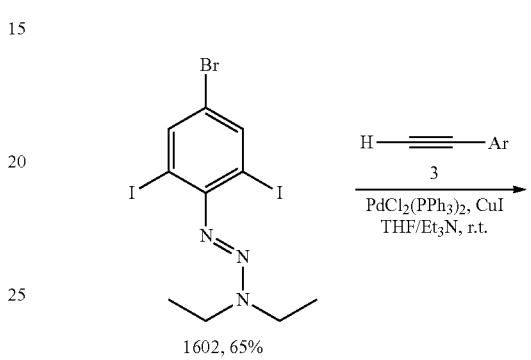
1602, 65%

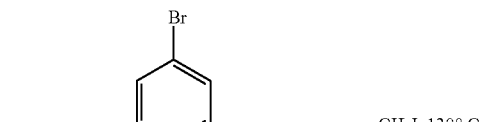
1604, 90%

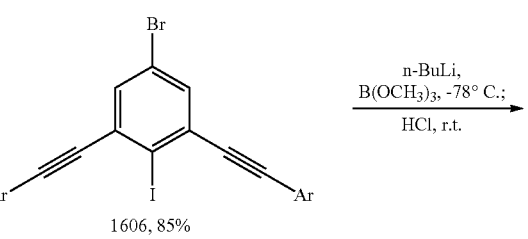
1606, 85%

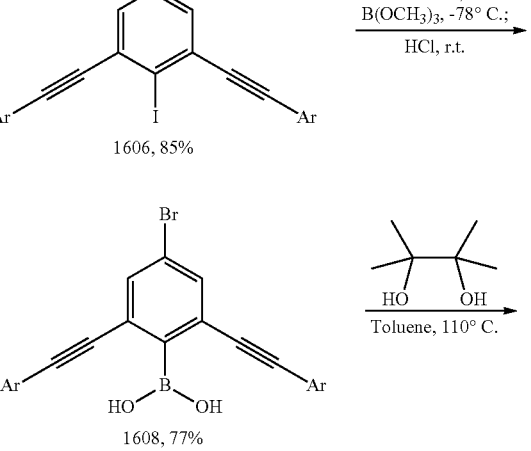
1608, 77%

-continued

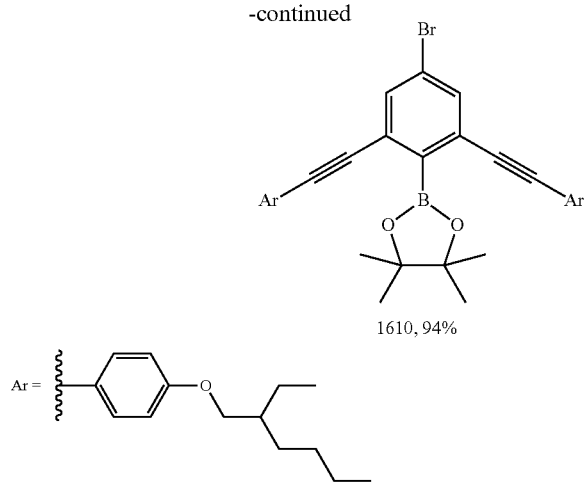

1610, 94%

With respect to the embodiment illustrated in Scheme 16, the synthesis of compound 1610 started with the conversion of aniline 1600 to triazene compound 1602 followed by selective double Sonogashira cross-coupling to afford dialkynyltriazene 1604. Conversion of dialkynyltriazene 1604 to bromoiododialkynylbenzene 1606 was achieved by treating dialkynyltriazene 1604 with methyl iodide. Bromoiododialkynylbenzene 1606 was treated with BuLi to effect a lithium-halogen exchange and trimethoxyborane was added and worked up under acidic conditions to provide boronic acid 1608 in good yield. Conversion of boronic acid 1608 to boronic ester 1610 was done in excellent yield.

Figure 17A:
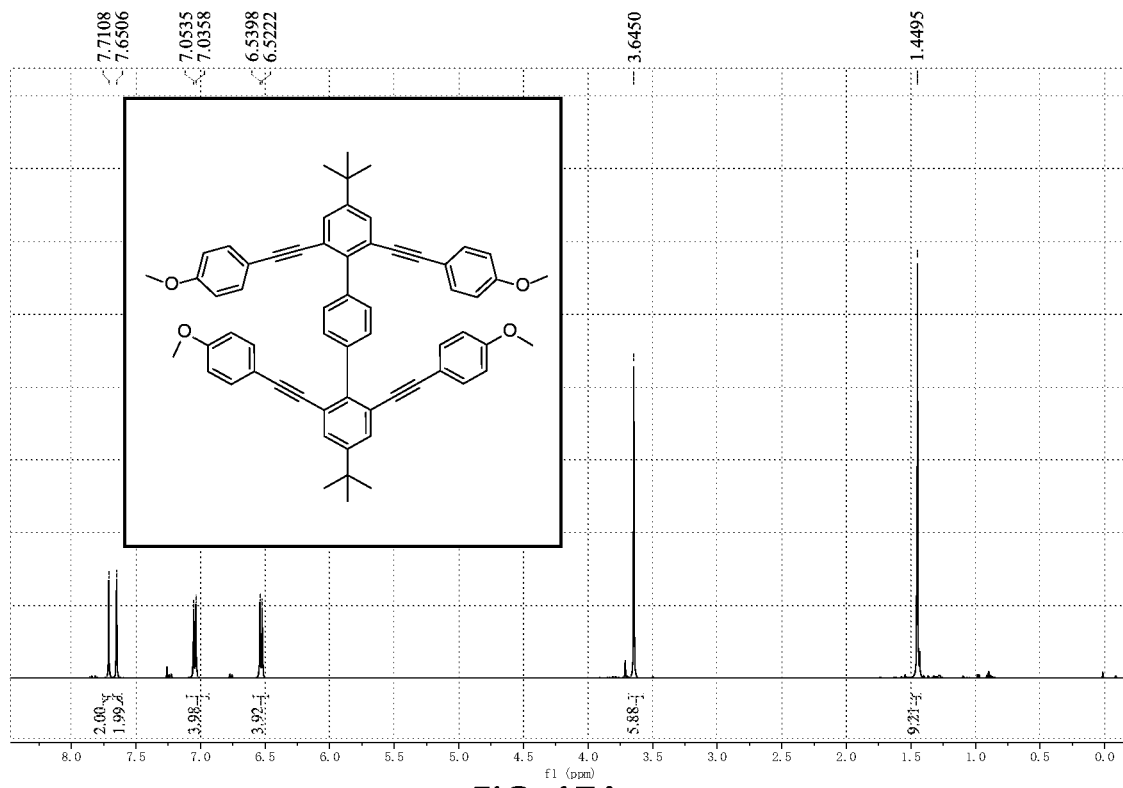
FIGS. 17A and 17B are $^{1}$H-NMR (FIG. 17A) and $^{13}$C-NMR (FIG. 17B) spectra of a representative peropyrene compound disclosed herein.
Figure 17B:
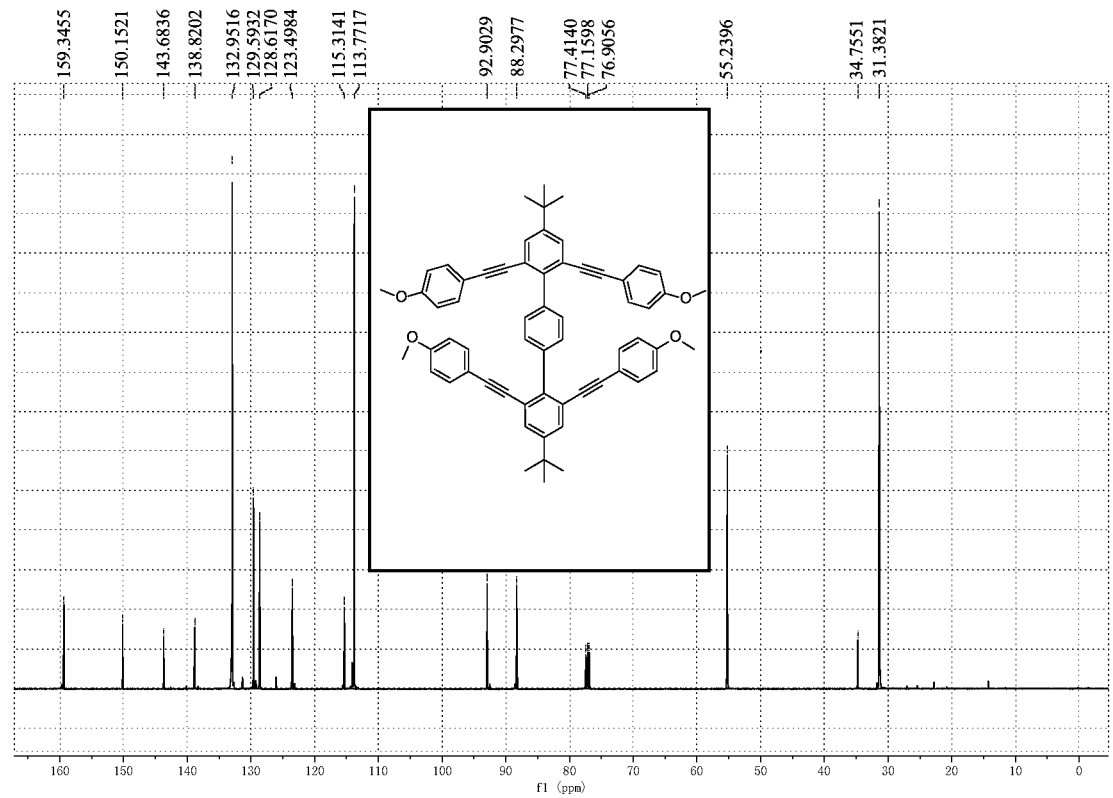

The pinacol boronic ester (or boronic acid) intermediates disclosed above in Schemes 15 and 16 can be polymerized to provide intermediate polymeric products that can then be converted to nanostructured compounds as illustrated in Schemes 17A and 17B below. For example, as illustrated in Schemes 17A and 17B, intermediate 400 can be converted to polymer intermediate 1700 using a palladium coupling reaction. Gel permeation chromatography can be used to analyze polymer 1700, to determine the polydispersity index (PDI). Upon exposure of polymer intermediate 1700 to an acid, nanostructured compound 1702 can be obtained. An exemplary method is illustrated in FIG. 17B.

Scheme 17A

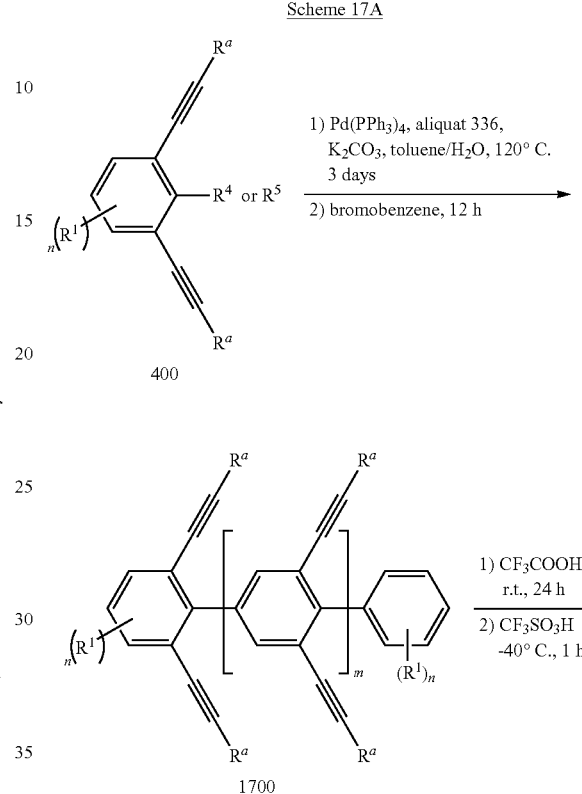

Scheme 17B

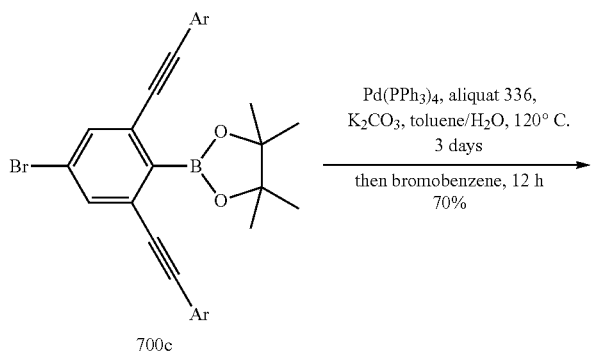

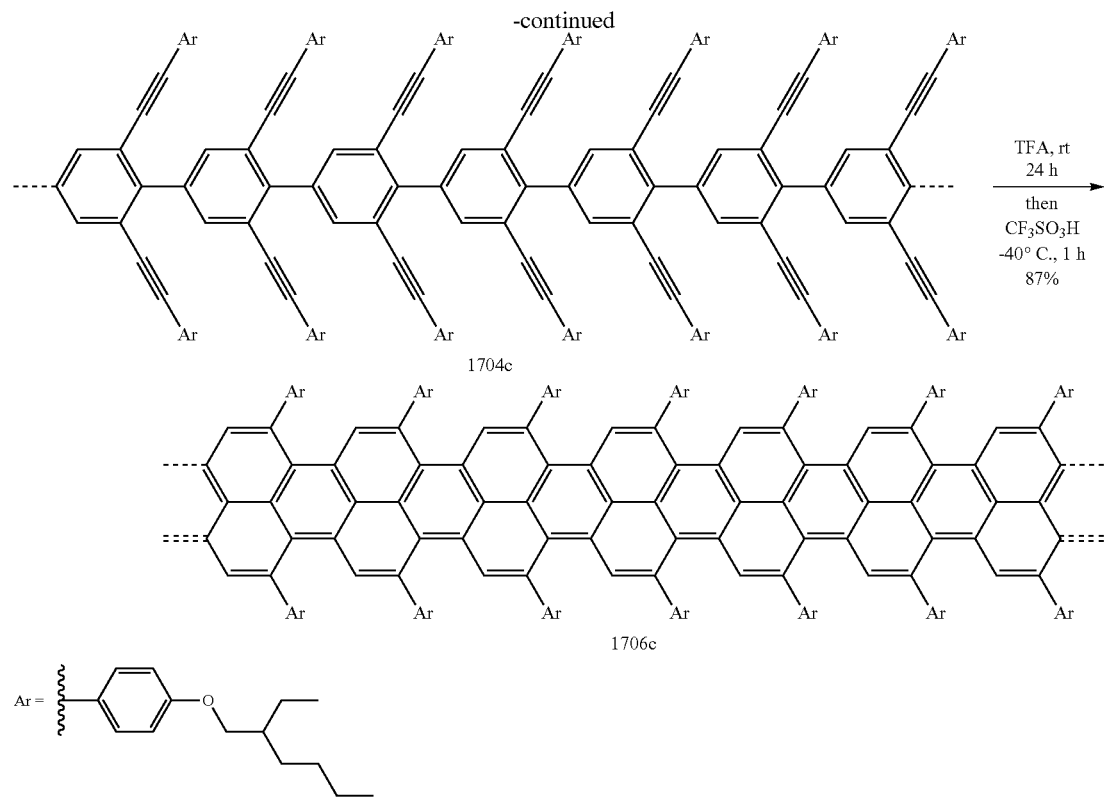

1704c

1706c

Ar =

Exemplary embodiments of the methods illustrated in Schemes 17A and 17B are illustrated below in Schemes 18A and 18B. As illustrated in Schemes 18A and 18B, pinacol boronic ester 700 is subjected it to Suzuki polymerization conditions to provide alkynyl-substituted poly(p-phenylene) polymer 1800 (where Ar is phenyl). Gel permeation chromatography was used to analyze polymer 1800, to determine the polydispersity index, with some embodiments having a PDI of 1.87 (in toluene) and 1.39 (in THF). The cyclization of the alkynes was successful using trifluoroacetic and triflic acid to provide polymer 1802 (where Ar is phenyl). The conversion of polymer 1800 to polymer 1802 was confirmed by $^1$H and $^{13}$C NMR, IR, and Raman spectroscopic analysis. An additional embodiment is shown in Scheme 18B, wherein different terminating groups are used to terminate the polymer.

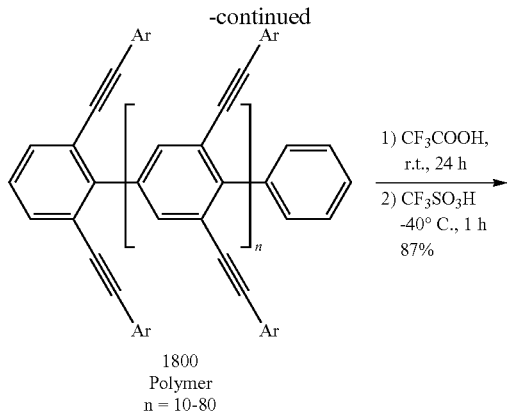

1800
Polymer
n = 10-80

Scheme 18A

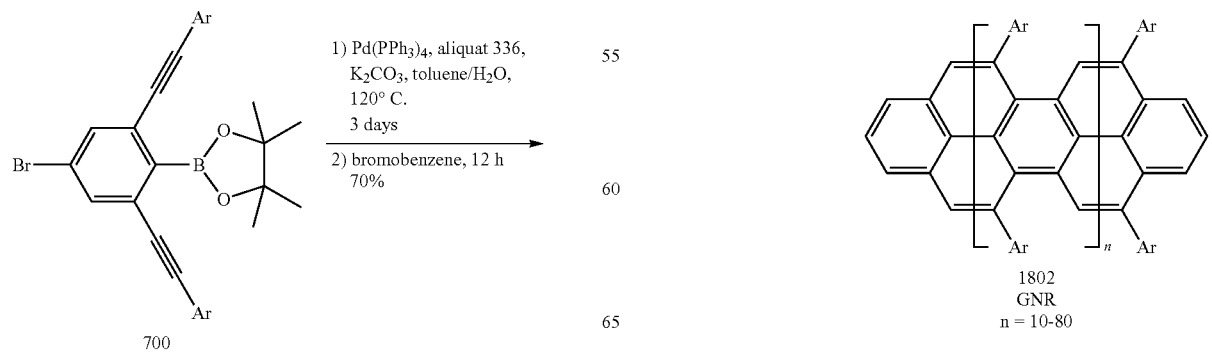

700

1802
GNR
n = 10-80

TABLE 2

| Entry | Solvent | T(h) | $M_w$(kgmol$^{-1}$) | $M_n$(kgmol$^{-1}$) | PDI |
|---|---|---|---|---|---|
| 1 | Toluene/H$_2$O | 84 | 6.6 | 4.6 | 1.6 |
| 2 | — | — | 6.4 | 4.7 | 1.4 |
| 3 | THF/H$_2$O | 48 | 21.1 | 10.8 | 2.0 |
| 4 | — | — | 22.5 | 11.6 | 1.9 |
| 5 | THF/H$_2$O | 132 | 41.9 | 28.9 | 1.5 |
| 6 | — | — | 38.2 | 24.6 | 1.6 |

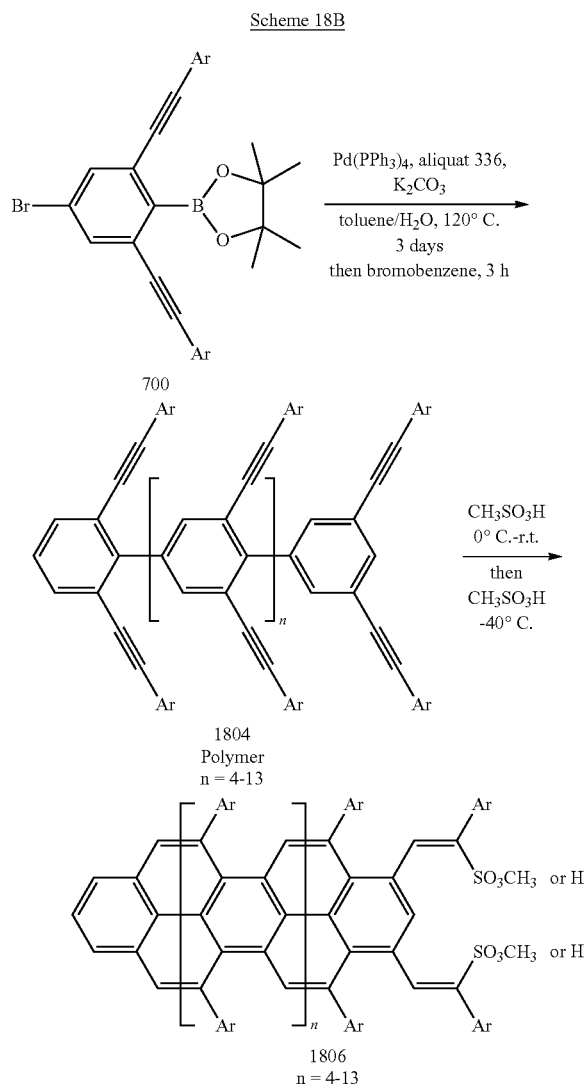

Scheme 18B

1804 Polymer n = 4-13

1806 n = 4-13

Figure 47:
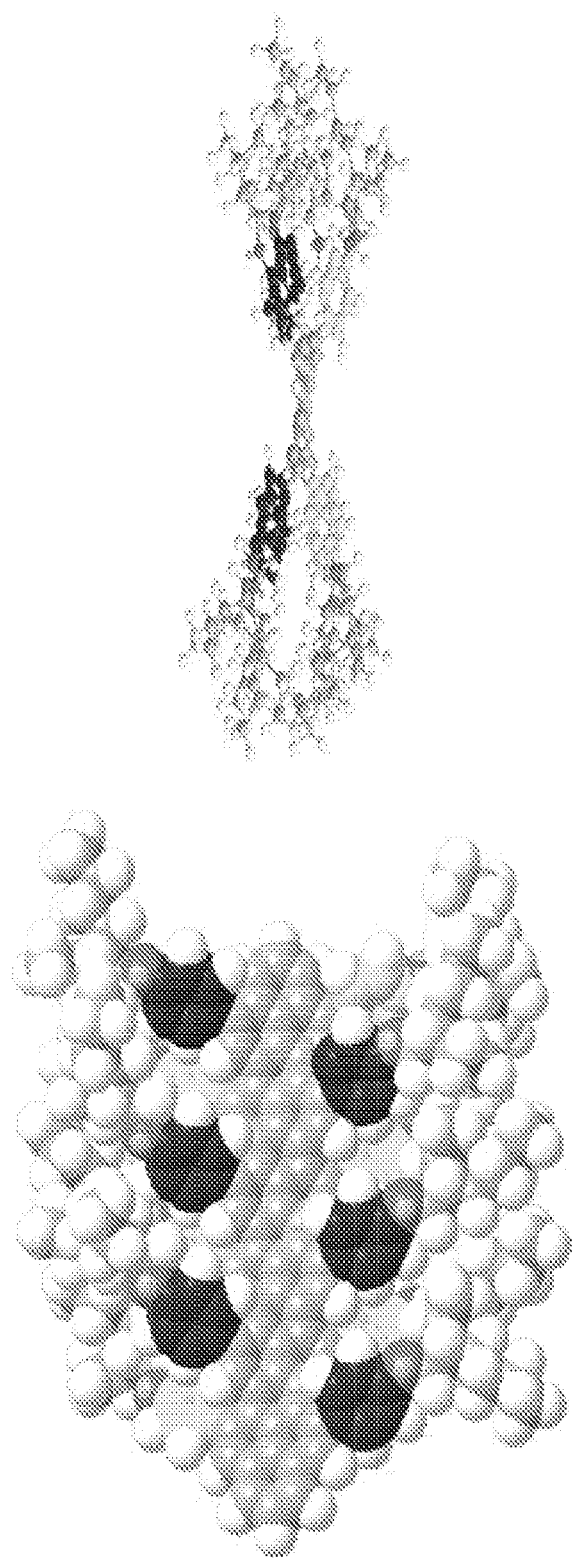
FIG. 47 is an image illustrating the twisting characteristics of nanostructured compounds disclosed herein.

In some embodiments, the choice of reaction solvent (e.g., toluene vs THF) can influence the difference on the molecular weights obtained after polymerization. In some embodiments, a polar solvent, such as THF can be used to achieve where higher molecular weights are achieved using THF (see Table 2 below). In some embodiments, complete benzannulation was observed after 24 hours using excess TFA at room temperature. Without being limited to a particular theory of operation, it is currently believed that this higher reactivity is due to the increased flexibility of the polymer and partially cyclized intermediates. In a flexible system, such as the partially cyclized intermediates from 1800 and even 1802 itself, the ability to "twist" allows for better orbital overlap, making benzannulation more facile (FIG. 47). Although significant cyclization of 1800 was observed according to the $^1$H-NMR, complete cyclization can be achieved, in some embodiments, by cooling the reaction mixture to −40° C. and adding a few drops (e.g., 1 to 10 drops) of triflic acid. The average length of the 1800 is estimated to be about 6 nm (toluene) and 20 nm (THF) based on the $M_w$ of the 1800 isolated. There was no change in the molecular weight distribution of the 1802, which indicates that no intermolecular reactions occurred during the benzannulation reaction.

With reference to Table 2, $M_w$ and $M_n$ were determined by SEC analyses of polymer precursor compounds like compound 1800 as obtained after the polymerization (eluent: THF). $M_w$ and $M_n$ are results based on PS standard calibration, respectively. PDI values were calculated by $M_w/M_n$. Entry 2 represents results obtained from analyzing the polymer promoted by TFA using the polymer from entry 1 as a precursor. Entry 4 is the polymer promoted by MSA using the entry 3 polymer as a precursor. Entry 5 is the polymer promoted by TFA-TfOH using the entry 4 polymer as a precursor.

In some embodiments, gel permeation chromatography (GPC) analysis of compound 1800 with a polystyrene (PS) standard indicated a number-average molecular weight of $M_n$=4.36 kg mol$^1$ (toluene) and 11.2 kg mol$^{-1}$ (THF) and a weight average molecular weight $M_w$=6.1 kg mol$^{-1}$ (toluene) and 20.8 kg mol$^{-1}$ (THF), with a polydispersity index (PDI) of 1.87 (toluene) and 1.39 (THF).

Figure 35:
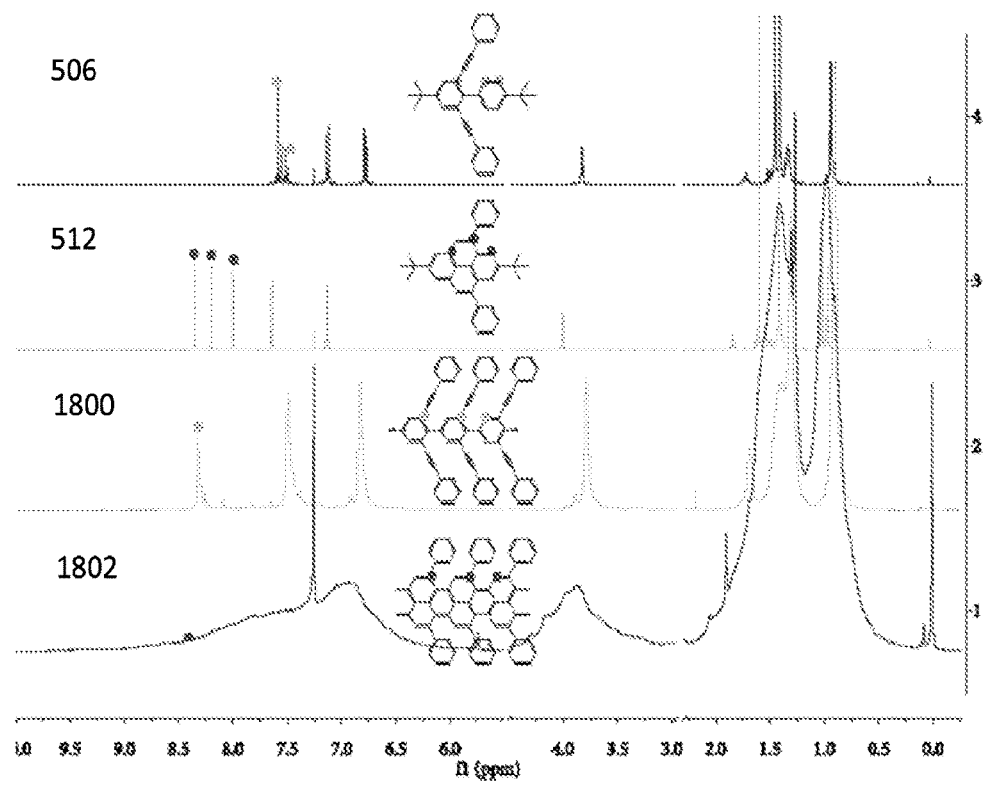
FIG. 35 is a combined ¹H-NMR spectrum illustrating results from ¹H-NMR analysis of an intermediate embodiment, a pyrene embodiment, a polymer embodiment, and a polymer embodiment.
Figure 36:
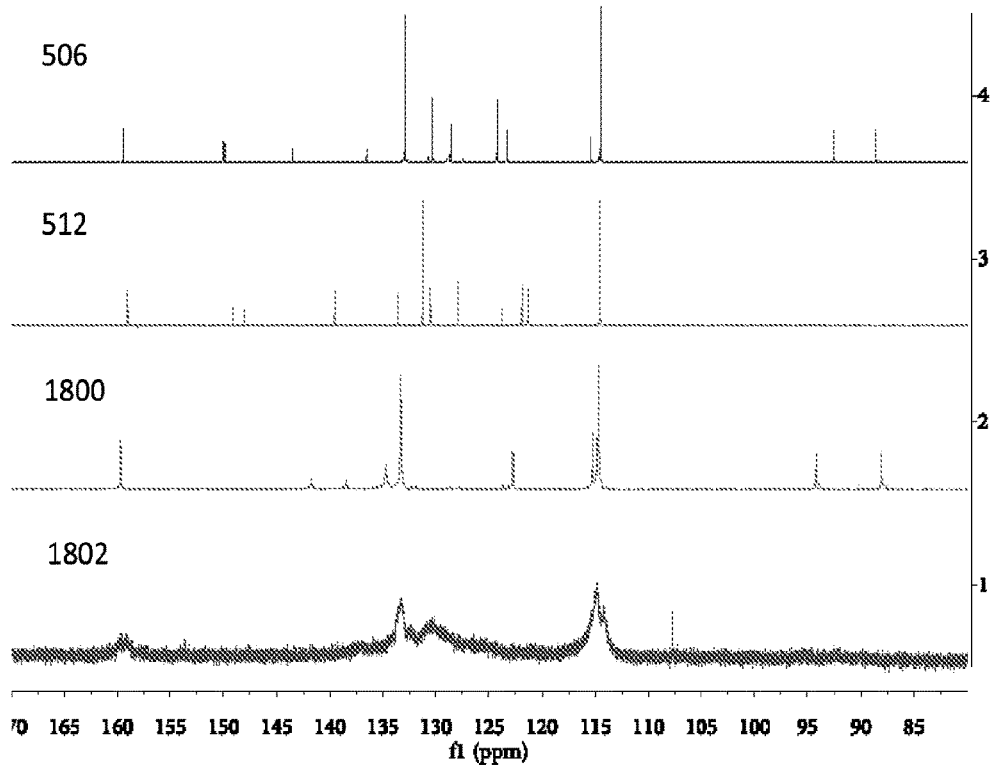
FIG. 36 is a combined ¹³C-NMR spectrum illustrating results from ¹³C-NMR analysis of the intermediate embodiment, pyrene embodiment, polymer embodiment, and polymer embodiment of FIG. 35.

In some embodiments, the conversion of 1800 to polymer 1802 was confirmed by $^1$H and $^{13}$C NMR spectroscopic analysis (e.g., FIGS. 35 and 36). The disappearance of the peak at 8.32 ppm in the $^1$H-NMR for polymer 1800 (attributed to Hx, see FIG. 35) and the alkyne signals (88.1 and 94.1 ppm, see FIG. 36) in the $^{13}$C NMR. In some embodiments, the disappearance of the alkyne signal in the IR spectra of polymer 1800 and GNR 1802 and integration can be interpreted as corroborating that cyclization has occurred, with some embodiment confirming greater than 95% cyclization had occurred (e.g., see FIGS. 37 and 38).

Figure 26:
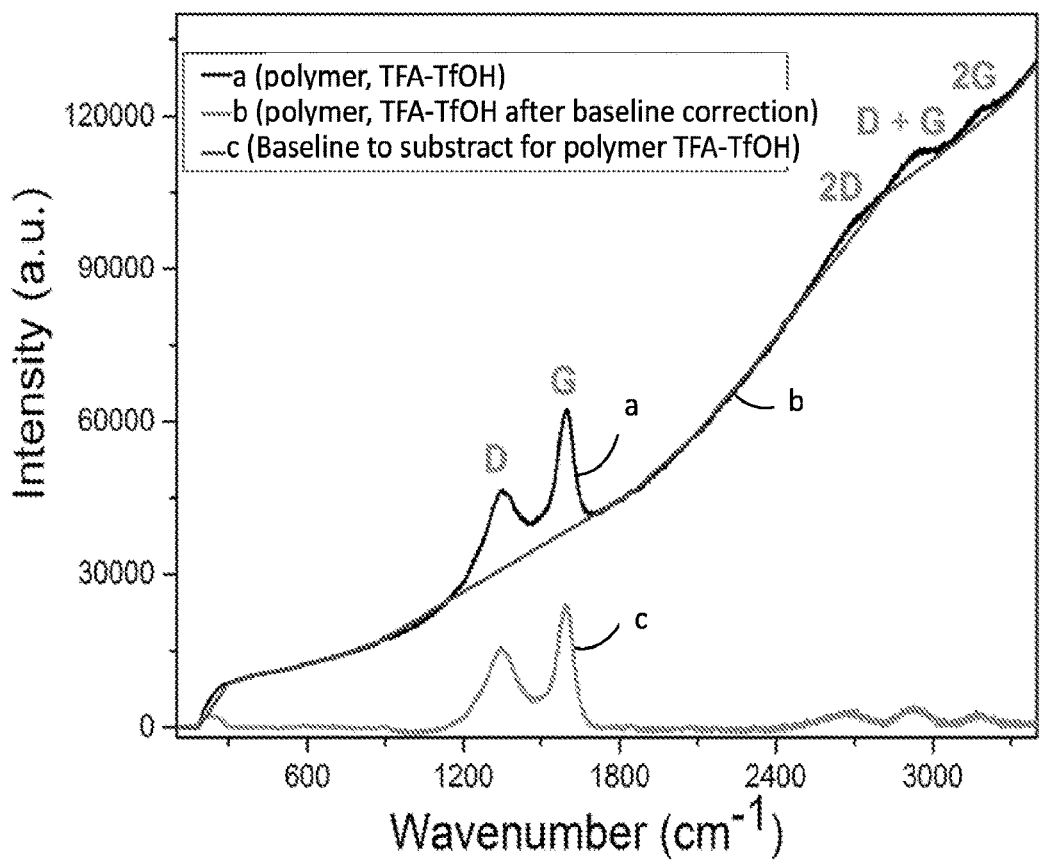
FIG. 26 is a combined Raman spectrum illustrating spectra of an exemplary compound embodiment, the compound after baseline correction, and a baseline spectrum.
Figure 27:
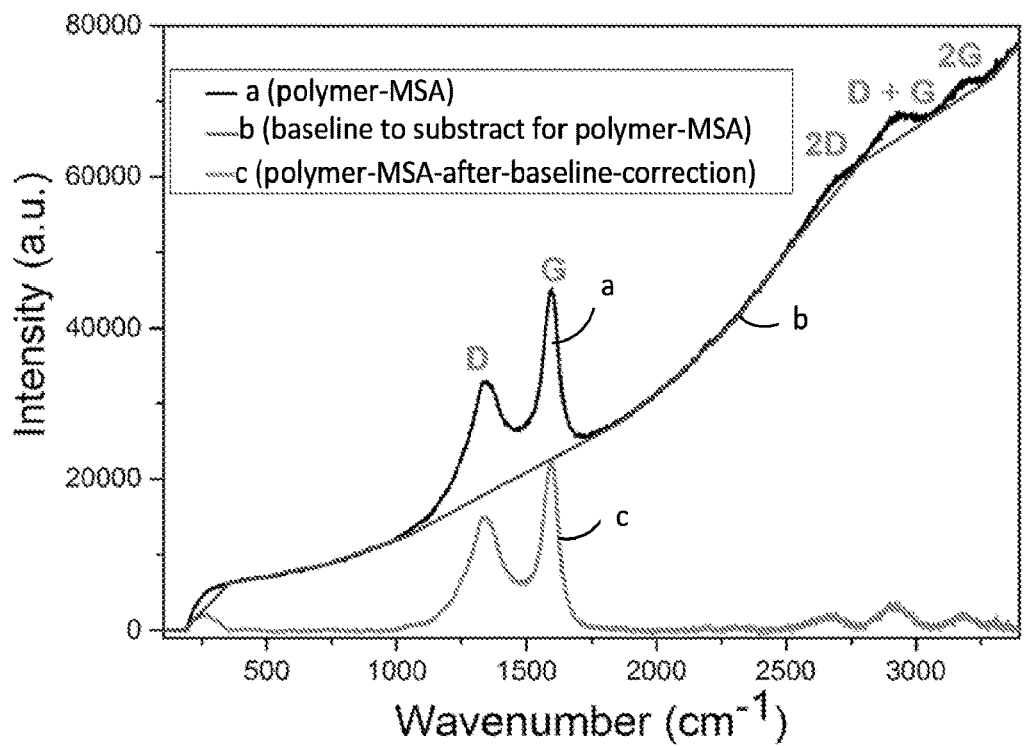
FIG. 27 is a combined Raman spectrum illustrating spectra of an exemplary compound embodiment, the compound after baseline correction, and a baseline spectrum.

In some embodiments, the Raman spectrum of nano structured compound 1802 exhibits the signature features that would be expected for a graphene nanoribbon, such as a D-band (at 1300-1500 cm$^{-1}$), a G-band (at 1500-1600 cm$^{-1}$), a 2D-band (at 2600-2800 cm$^{-1}$) and a D+G-band (at 2900-3000 cm$^{-1}$). In a representative embodiment, the Raman spectrum of 1802 contains the signature features for GNRs (11, 14, 26), which showed the typical D-band (1345 cm$^{-1}$) and G-band (at 1595 cm$^{-1}$) (FIGS. 26 and 27). Well-resolved double resonant signals were also observed at 2690, 2940, and 3190 cm$^{-1}$, which can be assigned to 2D, D+G, and 2G bands, respectively. Furthermore, there is a distinct peak ~235 cm$^{-1}$ that can be attributed to the radial breathing-like mode (RBLM) indicating high uniformity of the width of polymer 1802.

Figure 28:
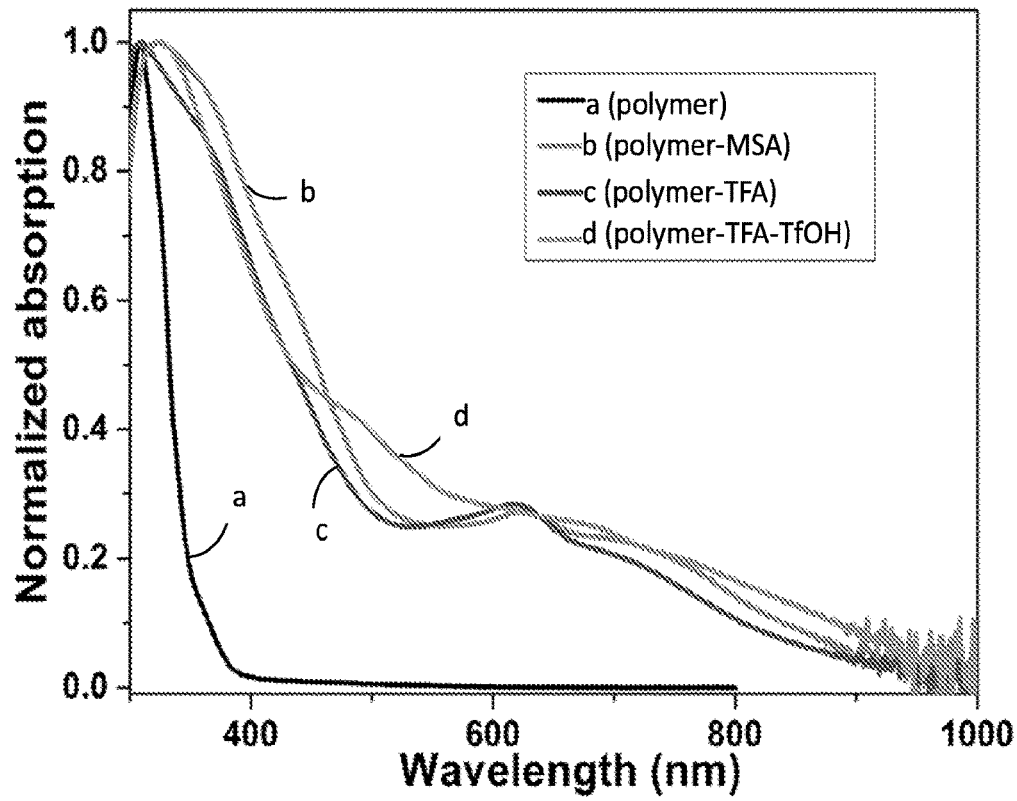
FIG. 28 is a combined UV-Vis spectrum illustrating spectra of an exemplary peropyrene polymer and a polymer synthesized using various different acids disclosed herein.

In yet additional embodiments, MALDI-TOF mass spectrometry can be used to confirm that some embodiments of the polymeric structures take on a nanoribbon structure, as isotopic patterns corresponding to predicted distributions can be observed. In yet additional embodiments, the structure of polymer 1802 can also characterized by UV-vis spectroscopic analysis. For example, in some embodiments, the UV-vis spectrum of 1800 in CH$_2$Cl$_2$ solution exhibited a relatively high energy and sharp absorbance ($\lambda_{max}$=309 nm). After benzannulation, it was observed that 1802 absorbs from the UV region beyond the visible region and into the near IR (FIG. 28). There is a low-energy broad absorption with a $\lambda_{max}$ ~700 nm (1.77 eV) and trails off to and absorption edge ~1200 cm$^{-1}$ (1.03 eV).

Figure 39A:
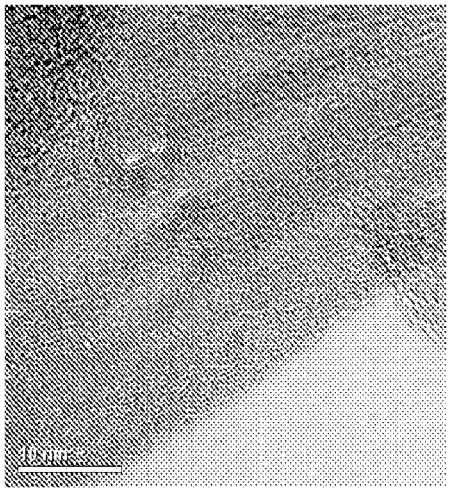
FIGS. 39A-39G are images of polymer embodiments.
Figure 39B:
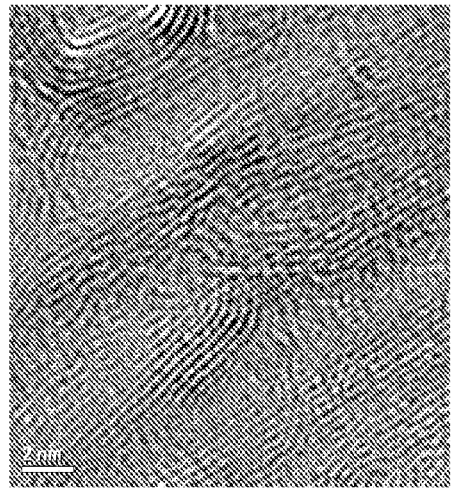
Figure 39C:
Figure 39D:
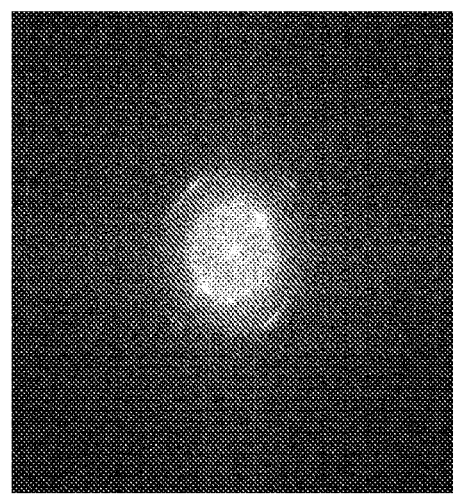
Figure 39E:
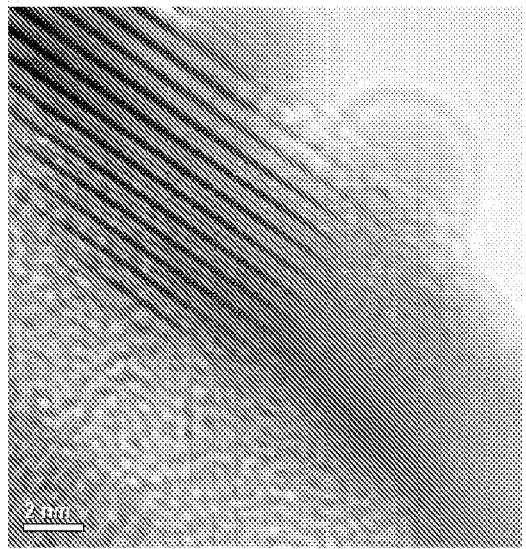
Figure 39F:
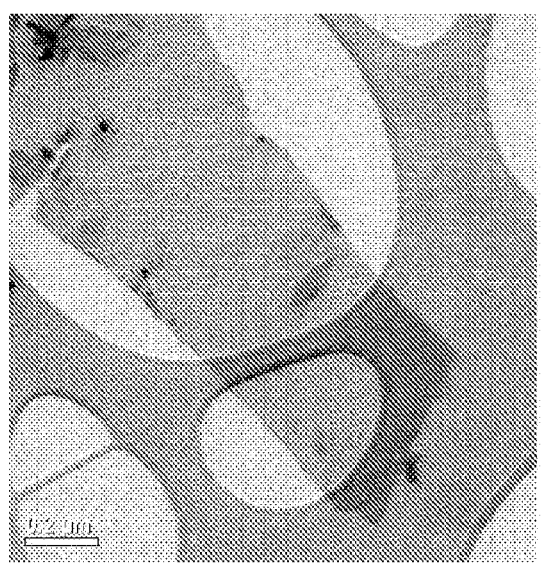
Figure 39G:
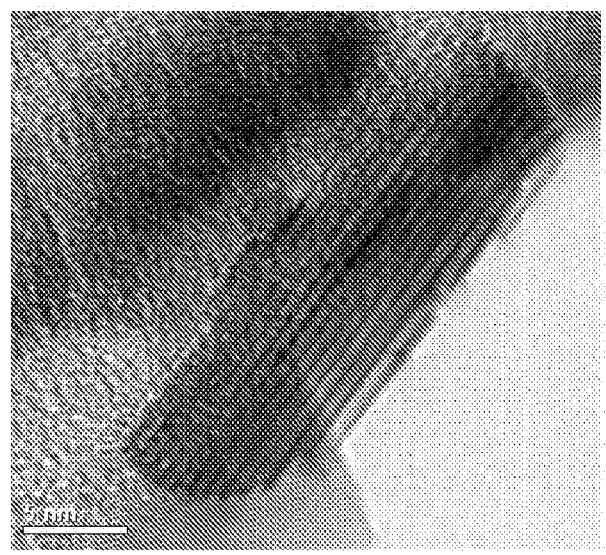

In yet additional embodiments, transmission electron microscopy (TEM) can be conducted on the compound disclosed herein (such as illustrated by FIGS. 39A-39G). In some embodiments, a polymer sample is deposited on lacey carbon grids. At low magnification, the polymeric compounds can be in the form of a large thin film that likely arise from polymer agglomeration during solvent evaporation (See FIG. 39F for an example). In some representative embodiments, the HRTEM images showed areas with multiple layers of the polymeric compounds (FIG. 39B, 39C, 39E, and 39G). The area with curving layers indicated that the polymeric compounds are flexible (FIG. 39B). In exemplary embodiments, monolayer films formed by 1802 were detected, which clearly showed a polymer having a single strip (or ribbon) of 1802 (FIGS. 39E and 39G). The width of 1802 is about 0.5 nm and is in agreement with the theoretical value. The distance between two ribbons of 1802 is narrower (ca. 0.2 nm) than the width of 1802 when the side-chains are included, indicating that there can be partial stacking of the nanostructures. The bundle of polymeric compounds shown in FIG. 39G range from about 8-25 nm, which is consistent with the calculated result from GPC. The selected area electron diffraction (SAED) pattern obtained from polymer 1802 demonstrated crystallinity of the sample and revealed hexagonal patterns typical of graphene (FIG. 39D).

Figure 40:
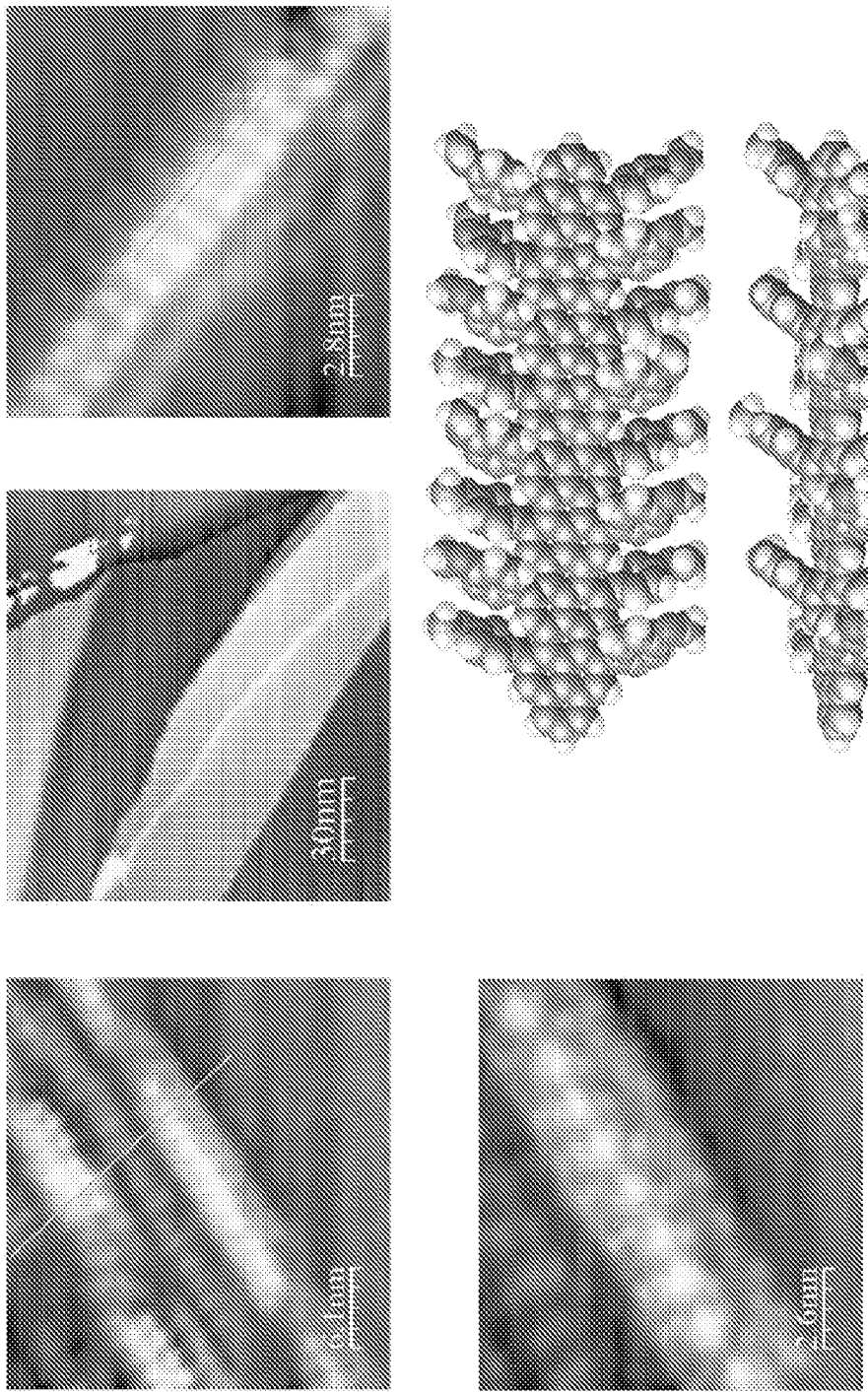
FIG. 40 provides exemplary STM and space-filled images of exemplary nanostructured compounds.

In yet additional embodiments, scanning tunneling microscopy (STM) images of polymeric compounds disclosed herein at the solid—liquid interface of highly oriented pyrolytic graphite (HOPG)/1,2,4-trichlorobenzene (TCB) can be obtained. After deposition of nanostructures (e.g., 1802) from a TCB dispersion on the HOPG substrate, the nanostructures showed side by side aggregation, also seen by TEM (FIG. 40, 39E and 39G). The nanostructures also showed extension along one-dimensional direction, which were observed to be over 100 nm in length (FIG. 40). The length (7~20 nm, FIG. 40) of the ribbons is in agreement with the results from the GPC and TEM characterization methods. The pattern seen in the STM images showed regions of alternating height, implying that the aryl substituents on the ribbon are alternating up and down, which may be explained by two kinds of intramolecular H . . . H repulsion: one from the two phenyl groups off the backbone, and one from the phenyl group and the bay region hydrogen, which result in a significant tilt of the latter with respect to the surface (e.g., FIG. 40). Semi empirical methods (PM3) were used for a short model of 1802 to better understand this alternating pattern. The result supports that the aryl groups are alternating up and down (e.g., FIG. 40). The observed periodicity (~1.16 nm) of the aryl substituents corresponded closely to the longitudinal length of one repeating unit (~0.9 nm), and the width (~1 nm, including two phenyls off the backbone, FIG. 40) of nanostructures of 1802 was also close to the calculated value (ca. 1.1 nm).

IV. EXAMPLES

General Experimental Section—Chemicals and solvents were purchased from Oakwood Products Inc., and Sigma-Aldrich and used directly without further purification unless otherwise stated. Anhydrous tetrahydrofuran (THF) and dichloroethane (DCM) was obtained by passing the solvent (HPLC grade) through an activated alumina column on a JC Meyer solvent drying system. All reactions dealing with air- or moisture-sensitive compounds were carried out in a dry reaction vessel under nitrogen.

$^1$H and $^{13}$C NMR spectra were recorded on Varian 400 MHz or Varian 500 MHz NMR Systems Spectrometers. Spectra were recorded in deuterated chloroform (CDCl$_3$). Tetramethylsilane (TMS, set to 0 ppm) was used as an internal standard for chemical shifts. Solvent peaks (7.26 ppm for $^1$H and 77.16 ppm for $^{13}$C, respectively) as reference. Chemical shifts are reported in part per million (ppm) from low to high frequency and referenced to the residual solvent resonance. Coupling constants (J) are reported in Hz. The multiplicity of 1H signals are indicated as: s=singlet, d=doublet, t=triplet, dd=double doublet, m=multiplet, br=broad.

Mass spectra were recorded using an Agilent 6230 TOF MS. The instrument was operated with an atmospheric pressure photoionization (APPI) source on a time of flight (TOF) instrument in the positive mode. Toluene was added to samples to promote ionization.

UV-visible and fluorescence spectra were acquired at ambient temperature; $\lambda$ in nm ($\varepsilon$ in L·mol$^1$·cm$^{-1}$).

High resolution ESI mass spectrometry was recorded using an Agilent 6230 TOF MS. TFA was added to samples to promote ionization.

Solution UV-vis absorption spectra were recorded at room temperature on a Perkin-Elmer Lambda 900 spectrophotometer.

Figure 2:
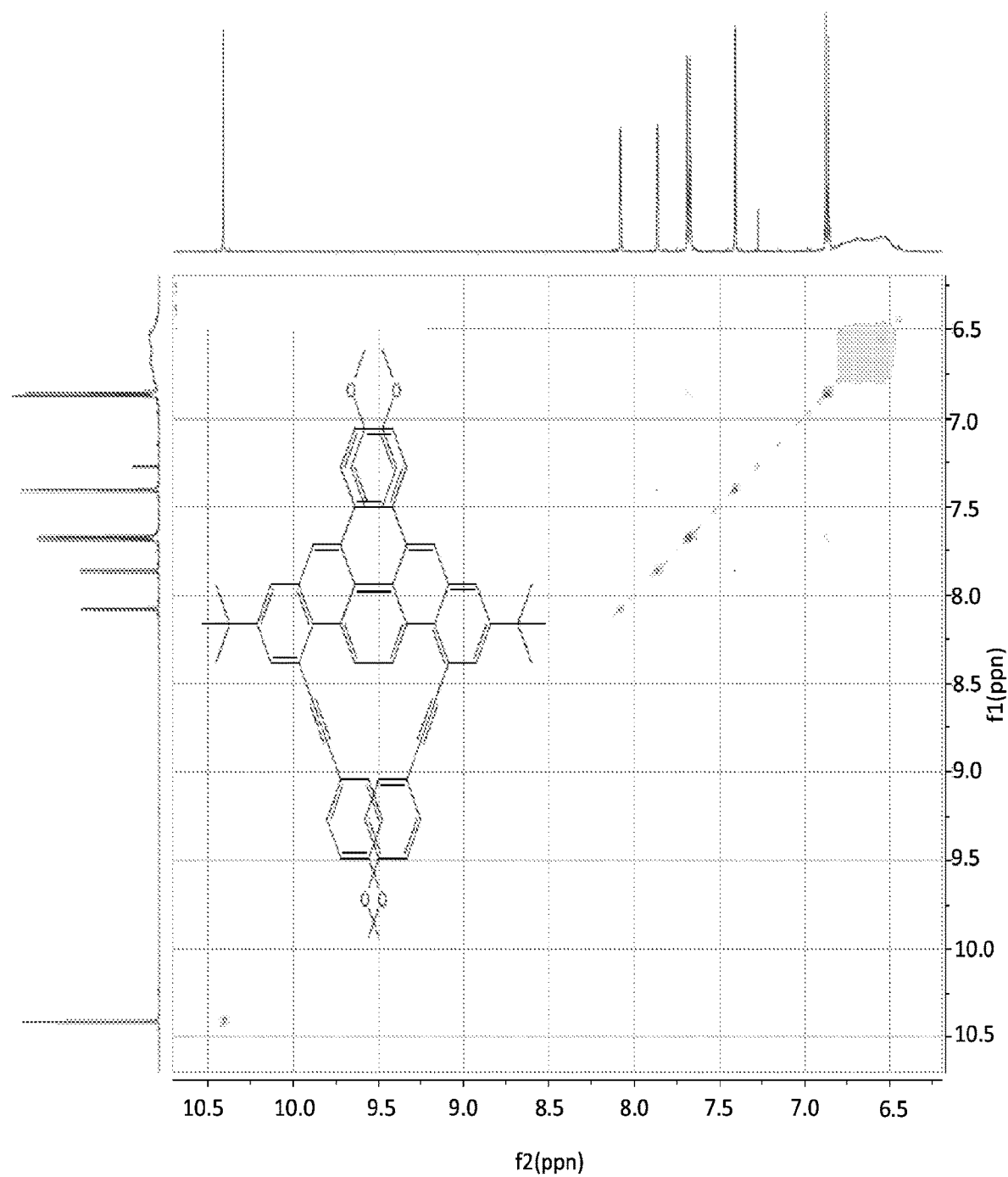
FIG. 2 is a rotating frame Overhauser effect spectrum (ROESY spectrum) of a representative intermediate compound disclosed herein.
Figure 3:
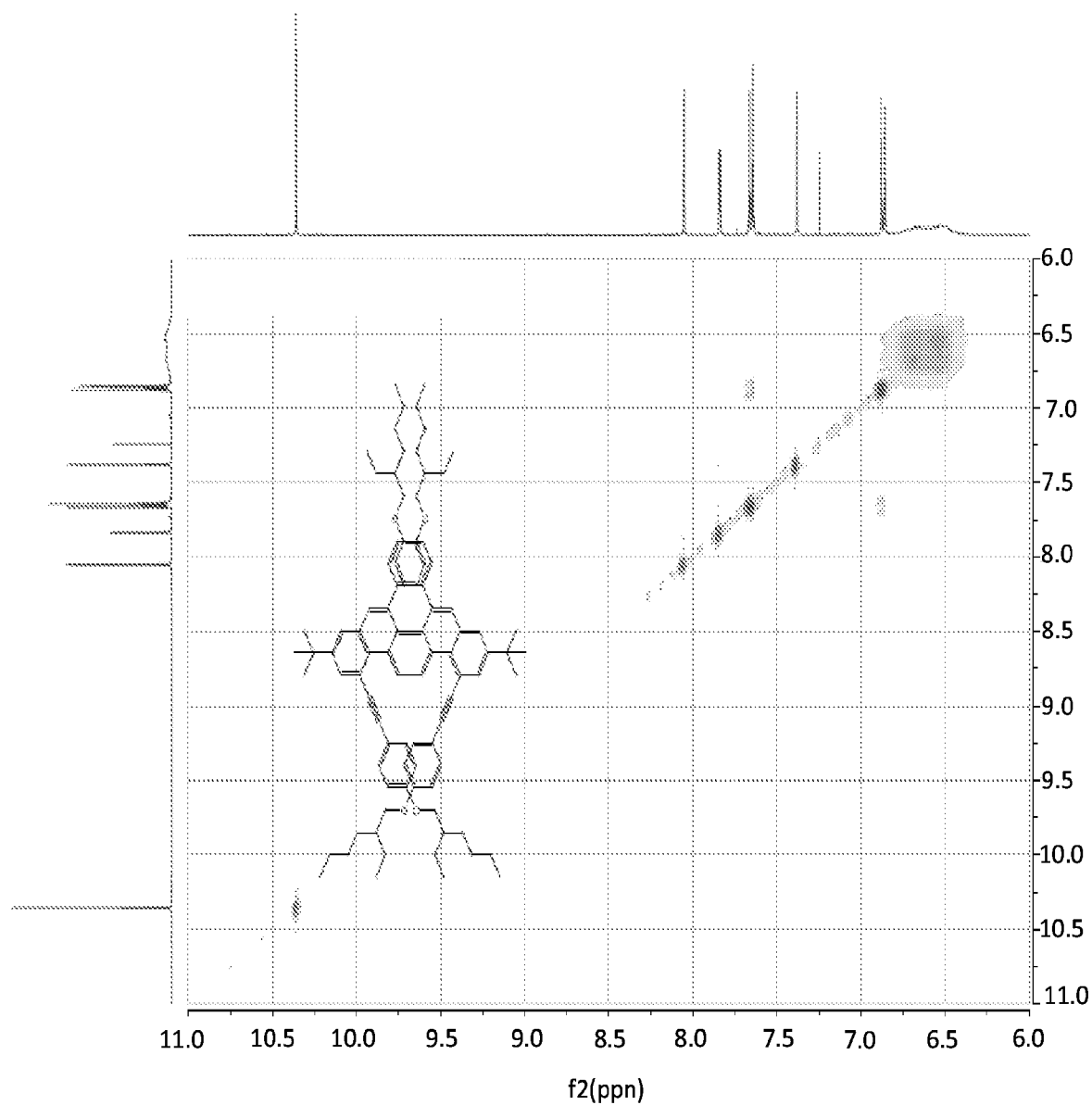
FIG. 3 is a NOESY spectrum of a representative intermediate compound disclosed herein.
Figure 48A:
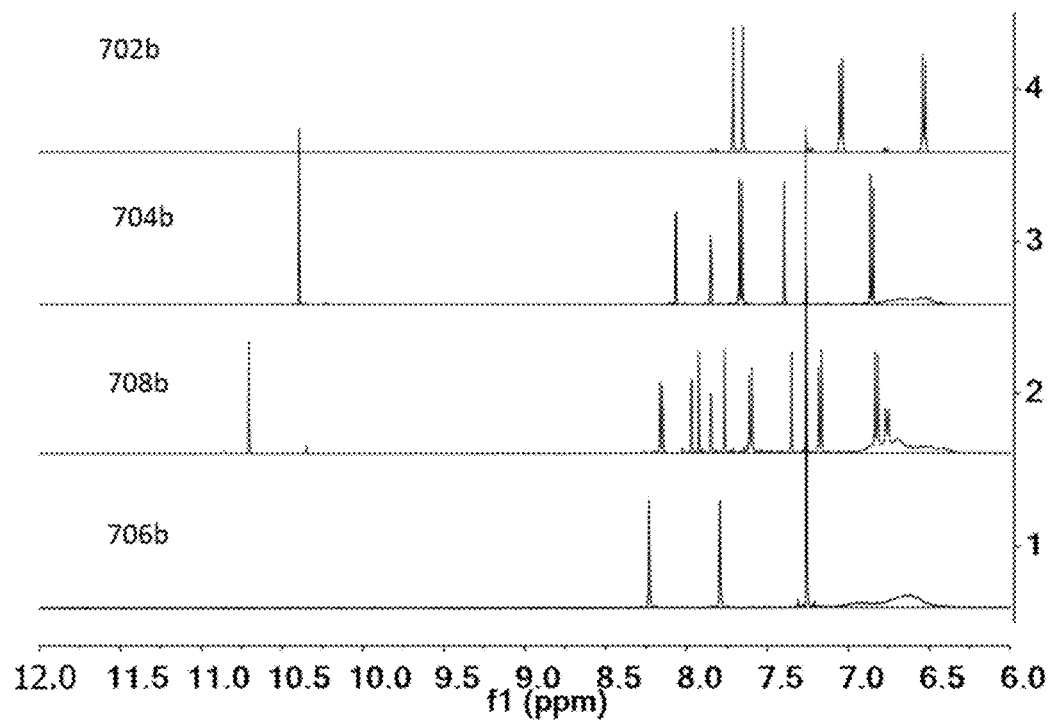
FIGS. 48A and 48B are combined ¹H-NMR spectra of compounds disclosed herein.
Figure 48B:
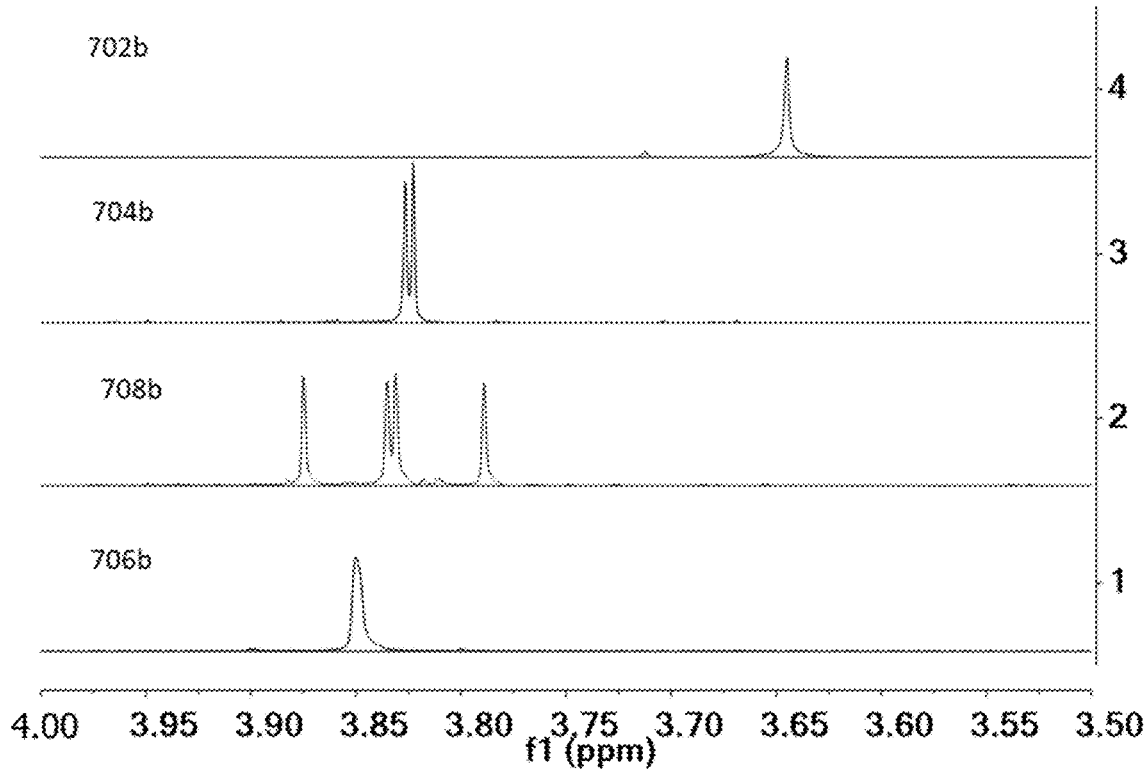
Figure 49A:
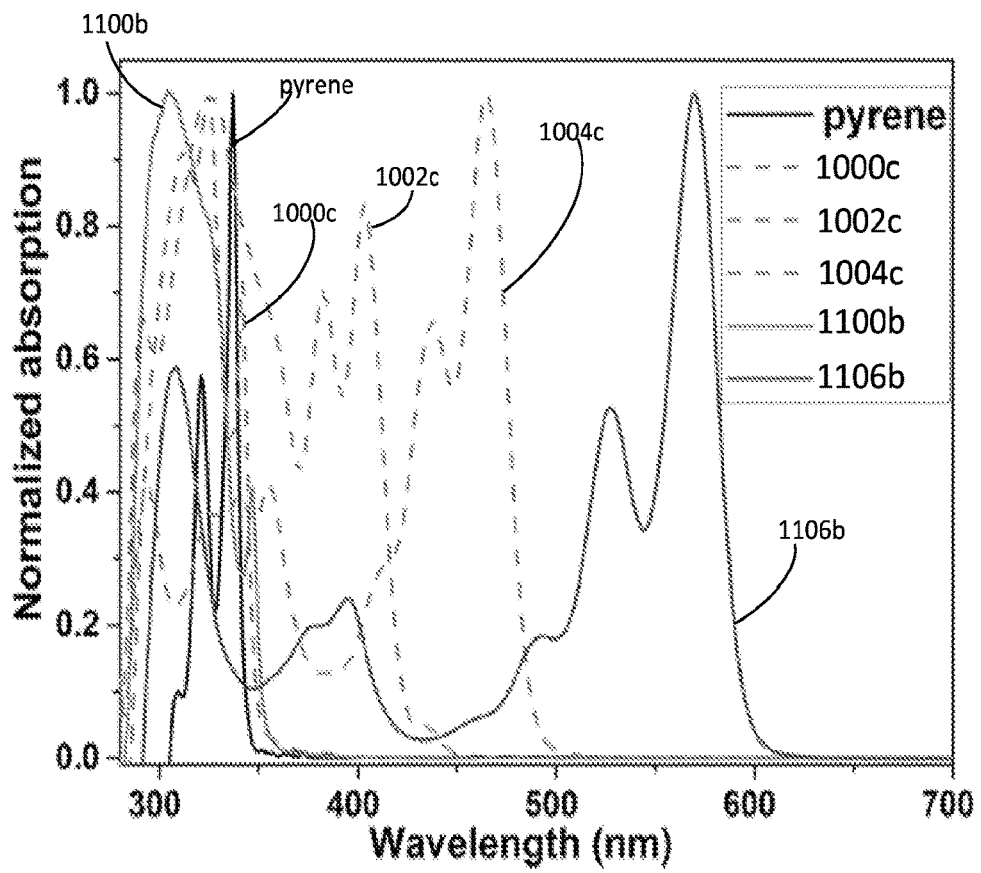
FIGS. 49A and 49B are spectra obtained from representative compounds disclosed herein.
Figure 49B:
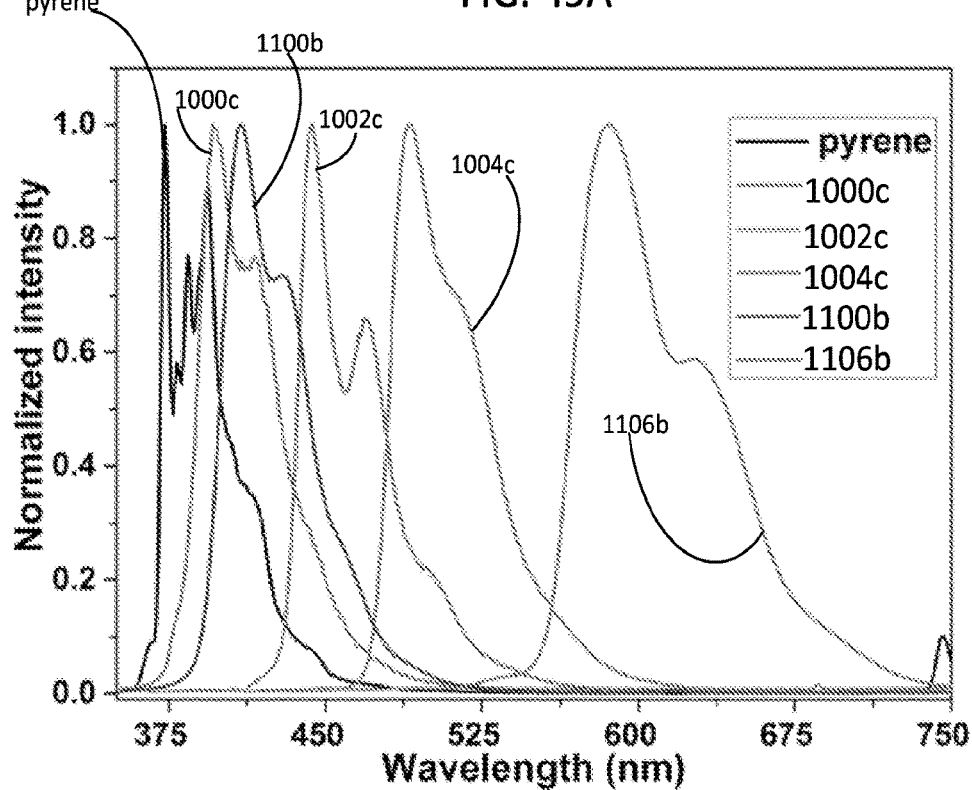

With reference to Scheme 8, various techniques can be used to determine the products and intermediates involved in making the peropyrene compounds disclosed herein. In some embodiments, $^1$H NMR, UV-vis and fluorescence spectra showed big difference. From the $^1$H NMR spectra comparison, it was determined that planarized picene moiety was formed in the bis-cyclized product, due to the deshielding effect of the alkyne, the signals for the proton in the cove position exhibited substantial downfield-shift to 10.39 ppm (12b, FIG. 48A). Besides, a broad peak appeared in the aromatic region should be attributed to the two phenyl rings on the picene moiety. This is because the Ar groups are too close to each other which limit their free rotation. The broad peak showed no correlation with the other two phenyl groups connection on the alkynes in the ROESY and NOESY spectra, which also confirmed that no intermediate 712 or 714 formed (FIGS. 2 and 3, respectively). The deshielding effect of the alkyne got stronger while the whole system became more planarized in the tri-cyclized product, which leaded more downfield-shift of the signal for the proton in the cove position to 10.71 ppm (12c, FIG. 48A). The $^1$H NMR of methoxyl groups exhibited much more directly, which showed one singlet in compounds 702a-d and 704a-d because they were center symmetrical, while showed two singlets in axisymmetric compound 702a-d and four different singlets in unsymmetric compound 708a-d (FIG. 48B).

Figure 4:
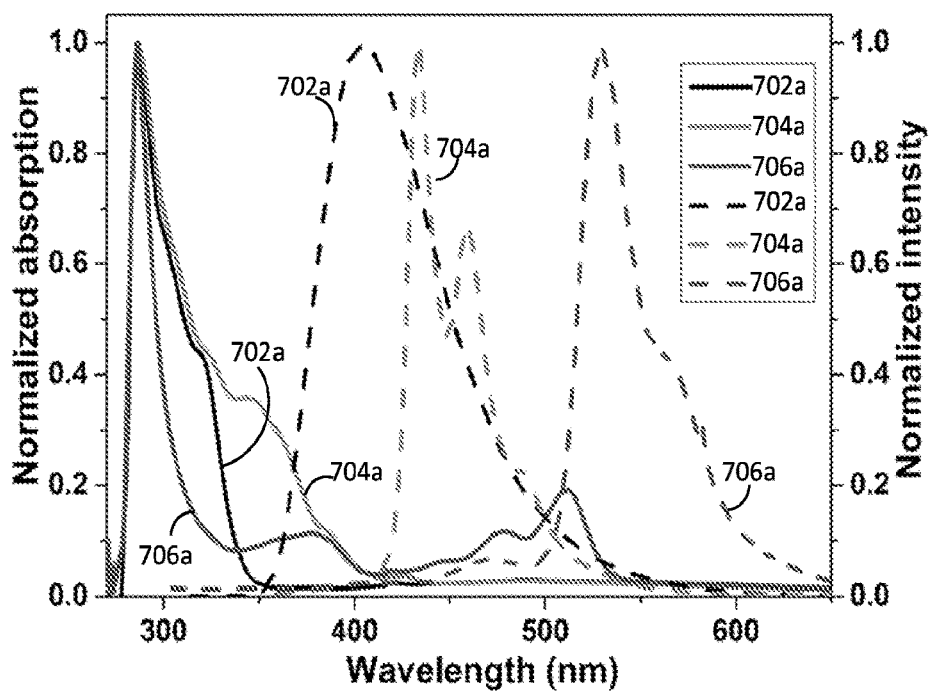
FIG. 4 is a combined UV-Vis spectrum and fluorescence spectrum of representative intermediates and compounds disclosed herein.
Figure 5:
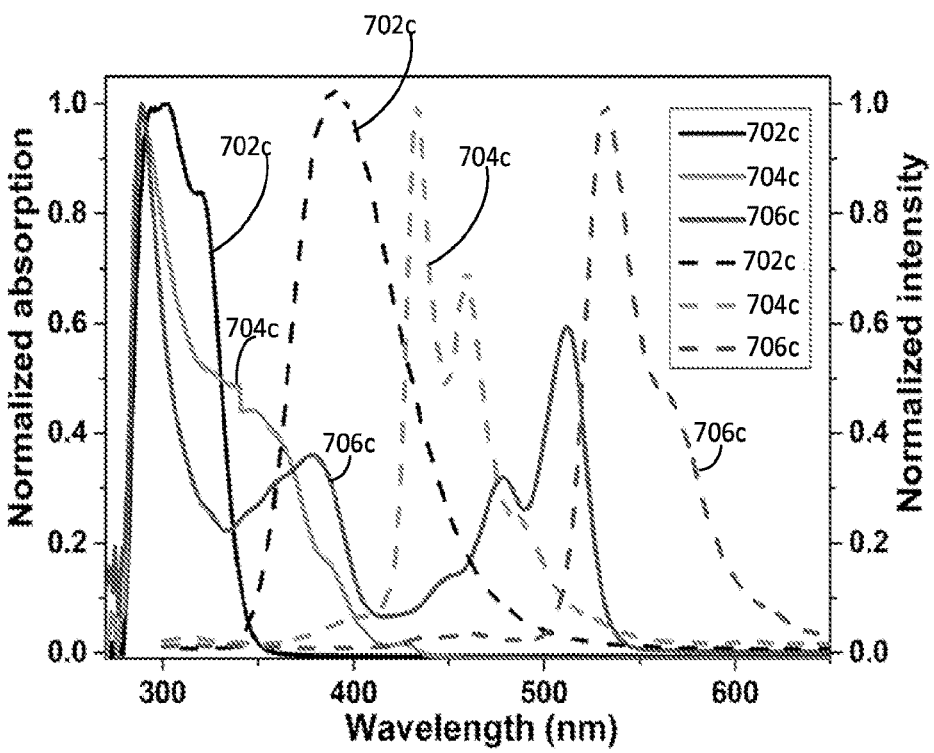
FIG. 5 is a combined UV-Vis spectrum and fluorescence spectrum of representative intermediates and compounds disclosed herein.
Figure 6:
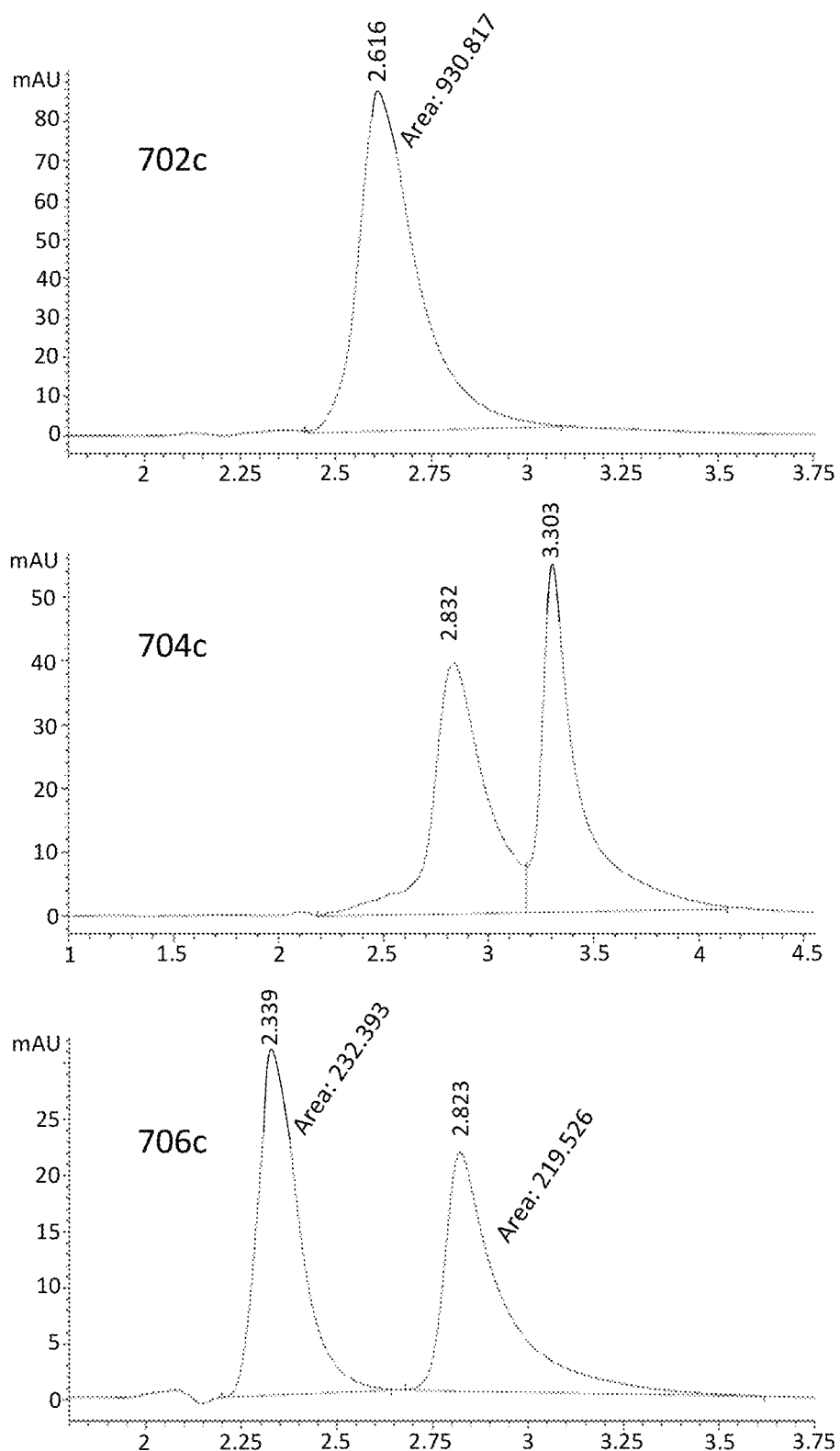
FIG. 6 is a combined HPLC trace of representative intermediates disclosed herein.
Figure 8:
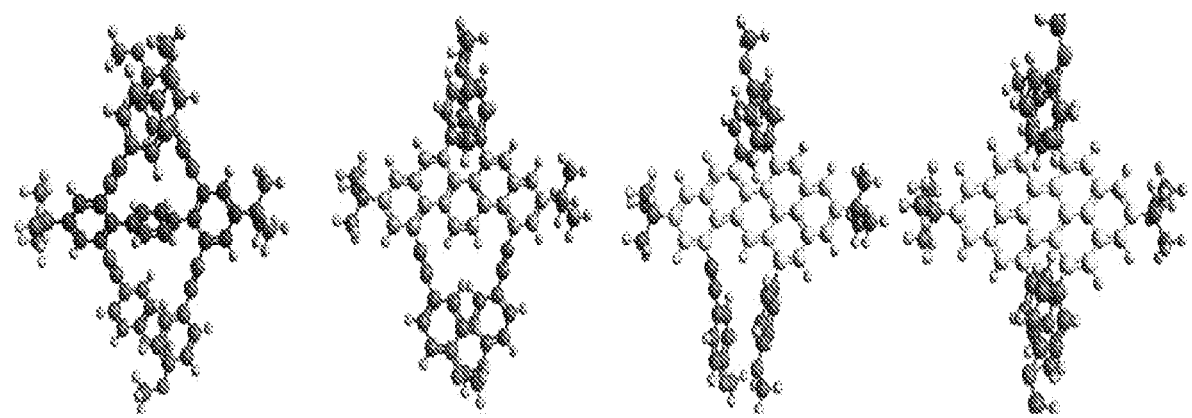
FIG. 8 illustrates representative intermediate compounds disclosed herein.
Figure 9:
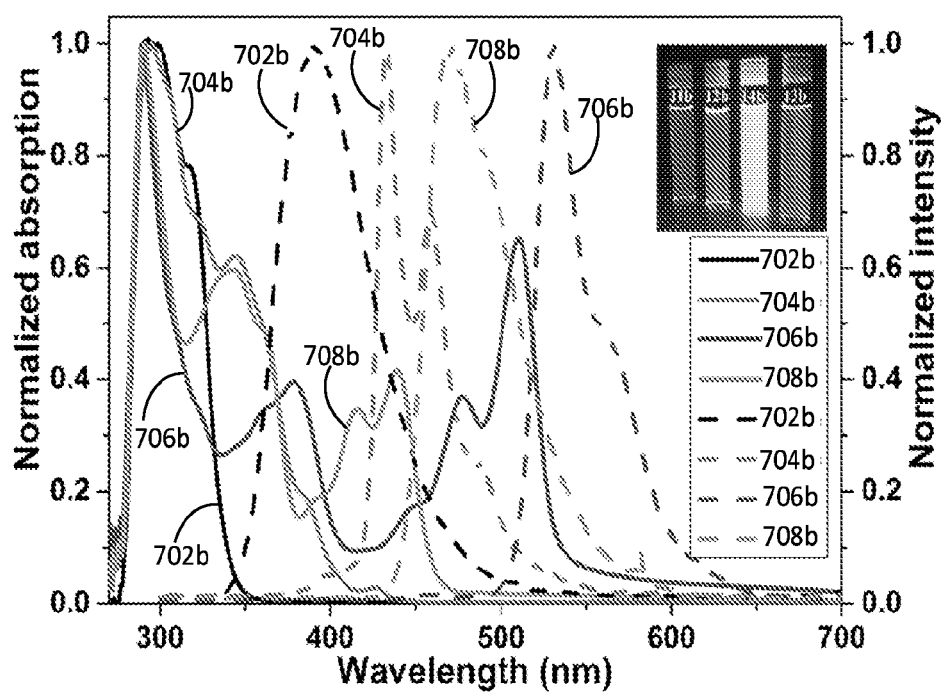
FIG. 9 is a combined UV-Vis and fluorescence spectrum of representative compounds disclosed herein.

As the cyclization reaction gradually completed, the whole compound skeleton became more and more conjugated, which was clearly reflected by UV-vis absorption and fluorescence emission spectrum (FIGS. 4 and 5). Additional images of representative compounds, including absorption and fluorescence spectra are provided by FIGS. 8 and 9. From the UV-vis absorption spectra, the maximum absorption peaks were observed as moving to the longer wavelengths with the cyclization completion (293, 345, 510 nm). The maximum emission peaks moved to the longer wavelengths too (389, 432, 530 nm).

Synthesis and Characterization

Synthesis of Pyrene Compounds

| Compound | R | Acid | Amount | Temp | Time | 4:5 | Yield |
|---|---|---|---|---|---|---|---|
| 108a | 4-OMe—$C_6H_4$ | TFA | Excess | Reflux | 2 Days | 4:5 | <50% |
|  | 4-OMe—$C_6H_4$ | $CF_3SO_3H$ | Excess | 0° C. | 5 min | 0:1 | <50% |
|  | 4-OMe—$C_6H_4$ | $CF_3SO_3H$ | 10 mol % | RT | 1 Hour | 1:0 | 70% |
|  | 4-OMe—$C_6H_4$ | $(CF_3SO_2)_2NH$ | 10 mol % | RT | 30 min | 0:1 | 48% |
| 108b | 4-O-ethylhexyl-$C_6H_4$ | $CF_3SO_3H$ | 10 mol % | RT | 24 hours | 0:1 | 80% |
|  | 4-O-ethylhexyl-$C_6H_4$ | $CF_3SO_3H$ | 10 mol % | RT | 3 hours | 0:1 | 82% |
|  | 4-O-ethylhexyl-$C_6H_4$ | $(CF_3SO_2)_2NH$ | 10 mol % | RT | 24 hours | 0:1 | 54% |
|  | 4-O-ethylhexyl-$C_6H_4$ | $(CF_3SO_2)_2NH$ | 10 mol % | RT | 3 hours | 0:1 | 63% |
| 108c | 4-N$(CH_3)_2C_6H_4$ |  |  |  |  |  |  |
| 108d | $C_6H_5$ | $(CF_3SO_2)_2NH$ | 10 mol % | Reflux | 16 hours | 1:0 | 25% |
|  | $C_6H_5$ | $CF_3SO_3H$ | 10 mol % | RT |  |  |  |
| 108e | 4-Br$C_6H_4$ | $(CF_3SO_2)_2NH$ | 10 mol % | 60° C. | 1 Hour | 1:0 |  |
| 108f | 4-$NO_2C_6H_4$ | $CF_3SO_3H$ | Excess | 60° C. | 24 hours | 0:0 | 0% |
| 108g | 4-$CF_3C_6H_4$ | $CH_3SO_3H$ | Excess | RT | 30 min | 0:0 | 0% |
|  | 4-$CF_3C_6H_4$ | $(CF_3SO_2)_2NH$ | 10 mol % | 60° C. | 18 hours | 0:0 | Decomposed |
|  | 4-$CF_3C_6H_4$ | $CF_3SO_3H$ | Excess | RT | 1 hour | 0:0 | Decomposed |
| 8 | TMS | $(CF_3SO_2)_2NH$ | 10 mol % | RT | 5 min | — | H Pdt |
| 9 | H | $(CF_3SO_2)_2NH$ | 10 mol % | RT | 24 hours | — | Addition Pdt |
| 10 | $C_6H_{13}$ |  |  |  |  |  |  |

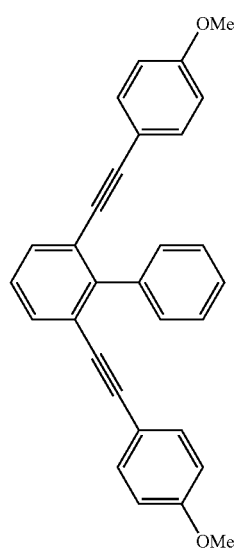 [SMILES: COc1ccc(C#Cc2cccc(C#Cc3ccc(OC)cc3)c2-c2ccccc2)cc1]

Compound 104a: To a solution of 100 bis triflate (1.0 g, 2.22 mmol) in anhydrous DMF (75 mL) was added 102a (0.681 g, 5.15 mmol), Bis(triphenylphosphine)palladium II dichloride (0.324 g, 0.462 mmol), Tetraethylammonium iodide (1.15 g, 4.47 mmol), triethylamine (4.02 mL, 54.7 mmol), and copper (I) iodide (0.180 g, 0.945 mmol) in that order. The flask was heated to 85° C. and stirred until it was confirmed complete by TLC; ca. 18 hours. The reaction was quenched with saturated aqueous ammonium chloride at room temperature, taken up in 100 mL diethyl ether, and the layers separated. The organic phase was washed with saturated aqueous ammonium chloride (3×50 mL), brine (3×50 mL), dried over $MgSO_4$, and the mixture filtered. The solvent was removed in vacuo and the crude product purified by column chromatography (silica gel, 1:1 $CH_2Cl_2$/benzene) to yield 104a (446 mg, 48%) as an white crystalline solid: $^1$H-NMR (400 MHz, $CDCl_3$): δ 7.55-7.51 (m, 2H), 7.46 (d, 2H), 7.41-7.30 (m, 3H), 7.18 (t, 1H), 7.07-7.02 (m, 4H), 6.69-6.65 (m, 4H), 3.65 (s, 6H); $^{13}$C NMR (500 MHz, $CDCl_3$): δ 143.1, 139.6, 139.1, 136.6, 130.6, 129.6, 127.9, 127.7, 127.0, 112.6, 0.2.

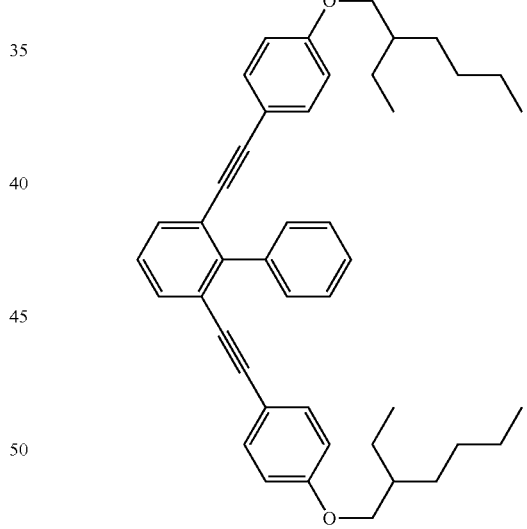

Compound 104b: To a solution of 100 (0.539 g, 2.67 mmol) in THF (50 mL) was added 102b (1.79 g, 5.63 mmol), Bis(triphenylphosphine)palladium II dichloride (0.096 g, 0.137 mmol), triethylamine (1.86 mL, 13.3 mmol), and copper (I) iodide (0.105 g, 0.551 mmol) in that order. The flask was left at room temperature and stirred until it was confirmed complete by TLC; ca. 18 hours. The reaction was quenched with saturated aqueous ammonium chloride at room temperature, taken up in 100 mL diethyl ether, and the layers separated. The organic phase was washed with saturated aqueous ammonium chloride (3×50 mL), brine (3×50 mL), dried over $MgSO_4$, and the mixture filtered. The solvent was removed in vacuo and the crude product purified by column chromatography (silica gel, 1:5 CH$_2$Cl$_2$/Hexane) to yield 104b (552 mg, 34%) as yellow oil. $^1$H NMR (500 MHz, CDCl$_3$): δ 7.64-7.60 (m, 2H), 7.56 (d, 2H), 7.51-7.40 (m, 3H), 7.29 (t, 1H), 7.15-7.10 (m, 4H), 6.81-6.76 (m, 4H), 3.85-3.78 (m, 4H), 1.76-1.67 (m, 2H), 1.55-1.25 (m, 18H), 0.96-0.87 (m, 13H); $^{13}$C NMR (500 MHz, CDCl$_3$): δ 159.4, 145.8, 139.3, 132.7, 131.4, 130.4, 127.4, 127.3, 127.0, 123.5, 115.0, 114.4, 93.1, 87.6, 70.5, 53.4, 39.3, 30.5, 29.0, 23.8, 23.0, 14.1, 11.1.

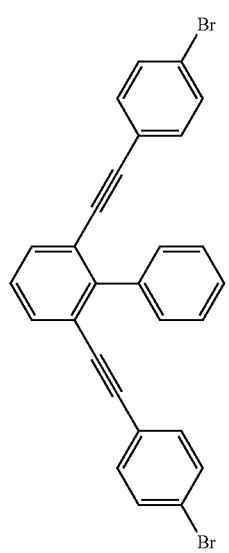 [SMILES: Brc1ccc(C#Cc2cccc(C#Cc3ccc(Br)cc3)c2-c2ccccc2)cc1]

Compound 104e: To a solution of 100 (0.503 g, 2.49 mmol) in THF (50 mL) was added 102e (1.76 g, 6.22 mmol), Bis(triphenylphosphine)palladium II dichloride (0.088 g, 0.125 mmol), triethylamine (1.73 mL, 12.4 mmol), and copper (I) iodide (0.101 g, 0.530 mmol) in that order. The flask was left at room temperature and stirred until it was confirmed complete by TLC; ca. 18 hours. The reaction was quenched with saturated aqueous ammonium chloride at room temperature, taken up in 100 mL diethyl ether, and the layers separated. The organic phase was washed with saturated aqueous ammonium chloride (3×50 mL), brine (3×50 mL), dried over MgSO$_4$, and the mixture filtered. The solvent was removed in vacuo and the crude product purified by recrystallization (super saturate in hot toluene; triturate with cold hexane) to yield 104e (292 mg, 23%) as a beige powder solid. $^1$H NMR (500 MHz, CDCl$_3$): δ 7.62-7.55 (m, 4H), 7.51-7.41 (m, 3H), 7.40-7.36 (m, 4H), 7.33 (t, 1H), 7.05-7.01 (m, 4H); $^{13}$C NMR (500 MHz, CDCl$_3$): δ 146.5, 138.9, 132.7, 132.2, 131.5, 130.2, 127.7, 127.4, 127.2, 123.0, 122.5, 122.0, 92.0, 89.8.

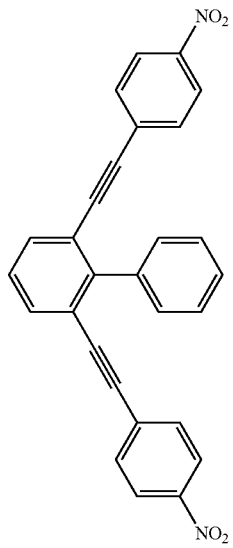 [SMILES: O=[N+]([O-])c1ccc(C#Cc2cccc(C#Cc3ccc([N+](=O)[O-])cc3)c2-c2ccccc2)cc1]

Compound 104f: To a solution of 100 (0.205 g, 1.01 mmol) in THF (50 mL) was added 102f (0.518 g, 2.08 mmol), Bis(triphenylphosphine)palladium II dichloride (0.040 g, 0.057 mmol), triethylamine (0.690 mL, 4.95 mmol), and copper (I) iodide (0.046 g, 0.242 mmol) in that order. The flask was left at room temperature and stirred until it was confirmed complete by TLC; ca. 18 hours. The reaction was quenched with saturated aqueous ammonium chloride at room temperature, taken up in 100 mL diethyl ether, and the layers separated. The organic phase was washed with saturated aqueous ammonium chloride (3×50 mL), brine (3×50 mL), dried over MgSO$_4$, and the mixture filtered. The solvent was removed in vacuo and the crude product purified by recrystallization (super saturate in hot toluene; triturate with cold hexane) to yield 104f (270 mg, 60%) as an orange powder solid. $^1$H-NMR (500 MHz, CDCl$_3$): δ 8.15-8.10 (m, 4H), 7.69 (d, 2H), 7.60-7.56 (m, 2H), 7.55-7.48 (m, 3H), 7.41 (t, 1H) 7.31-7.27 (m, 4H); $^{13}$C NMR (500 MHz, CDCl$_3$): δ 147.5, 147.0, 138.6, 133.1, 132.0, 130.1, 129.8, 128.1, 127.6, 127.5, 123.5, 122.4, 93.6, 91.3.

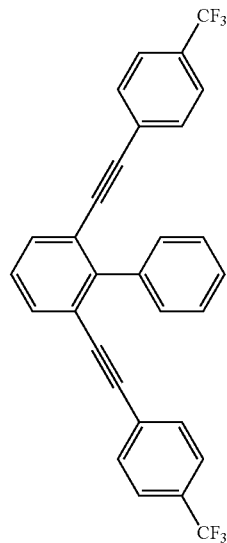 [SMILES: FC(F)(F)c1ccc(C#Cc2cccc(C#Cc3ccc(C(F)(F)F)cc3)c2-c2ccccc2)cc1]

Compound 104g: To a solution of 100 (0.500 g, 2.47 mmol) in THF (150 mL) was added 102g (0.910 mL, 6.19 mmol), Bis(triphenylphosphine)palladium II dichloride (0.089 g, 0.127 mmol), triethylamine (1.72 mL, 12.3 mmol), and copper (I) iodide (0.100 g, 0.525 mmol) in that order. The flask was left at room temperature and stirred until it was confirmed complete by TLC; ca. 18 hours. The reaction was quenched with saturated aqueous ammonium chloride at room temperature, taken up in 100 mL diethyl ether, and the layers separated. The organic phase was washed with saturated aqueous ammonium chloride (3×50 mL), brine (3×50 mL), dried over $MgSO_4$, and the mixture filtered. The solvent was removed in vacuo and the crude product purified by column chromatography (silica gel, 1:6 $CH_2Cl_2$/hexane) to yield 104g (480 mg, 40%) as a beige powder solid. $^1$H-NMR (500 MHz, $CDCl_3$): δ 7.65 (d, 2H), 7.61-7.57 (m, 2H), 7.54-7.44 (m, 7H), 7.37 (t, 1H), 7.29-7.26 (m, 4H); $^{13}$C NMR (500 MHz, $CDCl_3$): δ 147.1, 138.8, 138.0, 132.6, 131.5, 130.2, 130.0, 129.7, 127.9, 127.5, 127.3, 126.8, 125.2, 125.1, 125.0, 122.7, 91.7, 90.9.

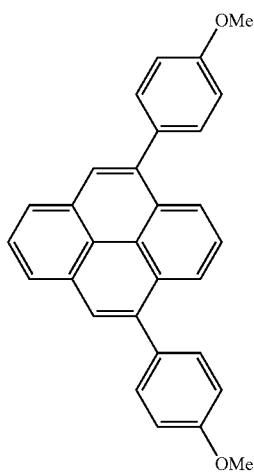 [SMILES: COc1ccc(-c2cc3cccc4cc(-c5ccc(OC)cc5)c5cccc2c5c34)cc1]

Compound 108a: To a flask containing CH2Cl2 (10 mL) was added 50 µL of a stock solution (1 mL of triflic acid dissolved in 49 mL $CH_2Cl_2$ in a sealed schlenk tube). To a separate flask containing 104a (0.065 g, 0.106 mmol) was added $CH_2Cl_2$ (10 mL). The resultant solution was taken up in a syringe and was slowly added to the first flask, dropwise, over 1 hour at room temperature. The flask was left at room temperature and stirred until it was confirmed complete by TLC; ca. 24 hours. The reaction was quenched with saturated aqueous sodium hydroxide at room temperature and the layers separated. The organic phase was washed with saturated aqueous sodium hydroxide (2×20 mL), $H_2O$ (2×20 mL), dried over $MgSO_4$, and the mixture filtered. The solvent was removed in vacuo and the crude product purified by column chromatography (silica gel, 1:5 $CH_2Cl_2$/hexane) to yield 108a (52 mg, 80%) as a yellow oil. $^1$H-NMR (500 MHz, $CDCl_3$): δ 8.28 (d, 2H), 8.19 (d, 2H), 8.06-8.02 (m, 3H), 7.91 (t, 1H), 7.63-7.59 (m, 4H) 7.10-7.15, 4.03-3.96 (m, 4H), 1.84 (sp, 2H), 1.67-1.36 (m, 19H), 1.05-0.95 (m, 13H); $^{13}$C NMR (500 MHz, $CDCl_3$): δ 159.0, 139.4, 133.0, 131.1, 131.0, 130.8, 127.6, 126.3, 125.4, 125.4, 124.7, 124.1, 123.6, 114.4, 39.5, 30.6, 29.1, 24.0, 23.1, 14.1, 11.2.

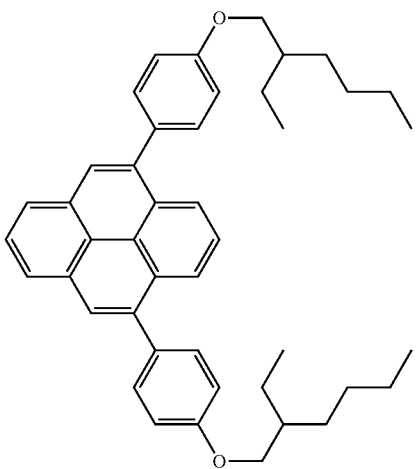 [SMILES: CCCCC(CC)COc1ccc(-c2cc3cccc4cc(-c5ccc(OCC(CC)CCCC)cc5)c5cccc2c5c34)cc1]

Compound 108b: To a flask containing $CH_2Cl_2$ (10 mL) was added 50 µL of a stock solution (1 mL of triflic acid dissolved in 49 mL $CH_2Cl_2$ in a sealed schlenk tube). To a separate flask containing 104b (0.065 g, 0.106 mmol) was added $CH_2Cl_2$ (10 mL). The resultant solution was taken up in a syringe and was slowly added to the first flask, dropwise, over 1 hour at room temperature. The flask was left at room temperature and stirred until it was confirmed complete by TLC; ca. 24 hours. The reaction was quenched with saturated aqueous sodium hydroxide at room temperature and the layers separated. The organic phase was washed with saturated aqueous sodium hydroxide (2×20 mL), $H_2O$ (2×20 mL), dried over $MgSO_4$, and the mixture filtered. The solvent was removed in vacuo and the crude product purified by column chromatography (silica gel, 1:5 $CH_2Cl_2$/hexane) to yield 108b (52 mg, 80%) as a yellow oil. $^1$H-NMR (500 MHz, $CDCl_3$): δ 8.28 (d, 2H), 8.19 (d, 2H), 8.06-8.02 (m, 3H), 7.91 (t, 1H), 7.63-7.59 (m, 4H) 7.10-7.15, 4.03-3.96 (m, 4H), 1.84 (sp, 2H), 1.67-1.36 (m, 19H), 1.05-0.95 (m, 13H); $^{13}$C NMR (500 MHz, $CDCl_3$): δ 159.0, 139.4, 133.0, 131.1, 131.0, 130.8, 127.6, 126.3, 125.4, 125.4, 124.7, 124.1, 123.6, 114.4, 39.5, 30.6, 29.1, 24.0, 23.1, 14.1, 11.2.

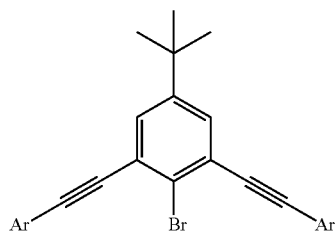

306

Synthesis of Compound 306:

To the solution of 2-bromo-5-(tert-butyl)-1,3-diiodobenzene 304 (4.65 g, 10 mmol, 1.0 equiv.) and the terminal alkyne (2.5 equiv.) in $Et_3N$ (40 mL) and THF (80 mL), were added $Pd(PPh_3)_2Cl_2$ (70 mg, 0.1 mmol) and CuI (38 mg, 0.2 mmol). The resulting mixture was stirred under a N2 atmosphere at room temperature for 14 h. The ammonium salt was then removed by filtration. The solvent was removed under reduced pressure and the residue was purified by column chromatography ($SiO_2$, hexane/DCM) to afford the corresponding product 306.

Figure 10A:
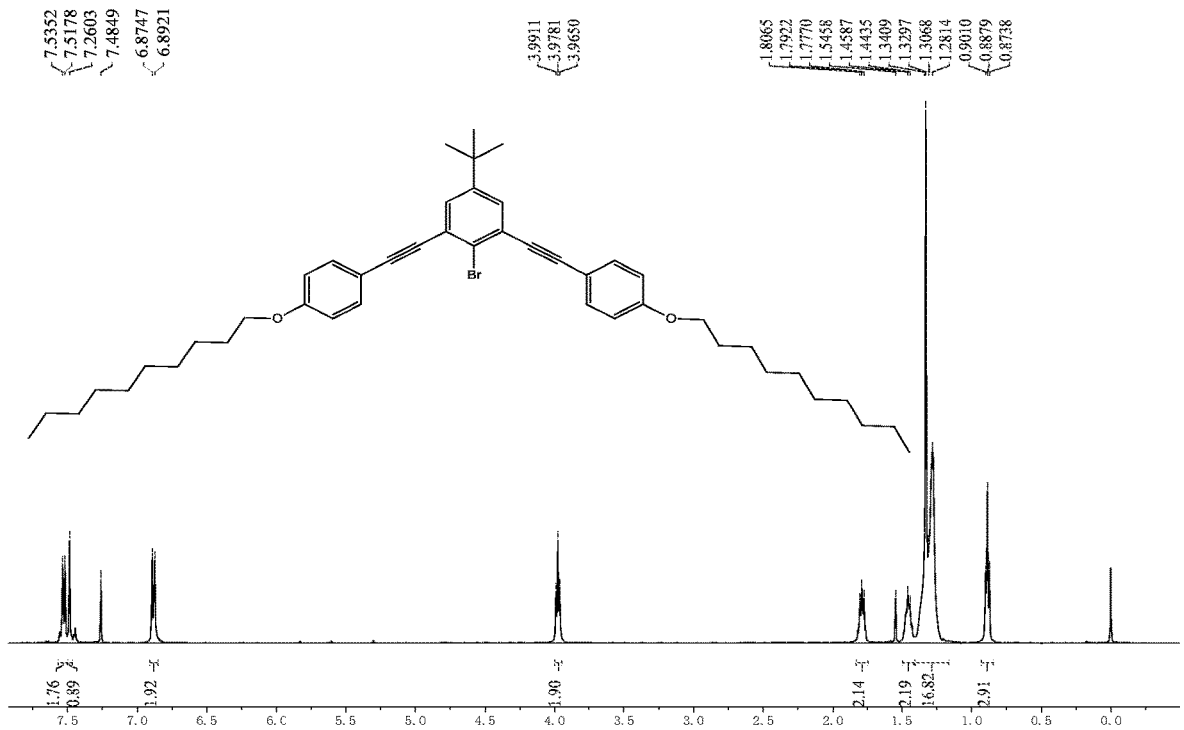
FIGS. 10A and 10B are $^{1}$H-NMR (FIG. 10A) and $^{13}$C-NMR (FIG. 10B) spectra of a representative intermediate compound disclosed herein.
Figure 10B:
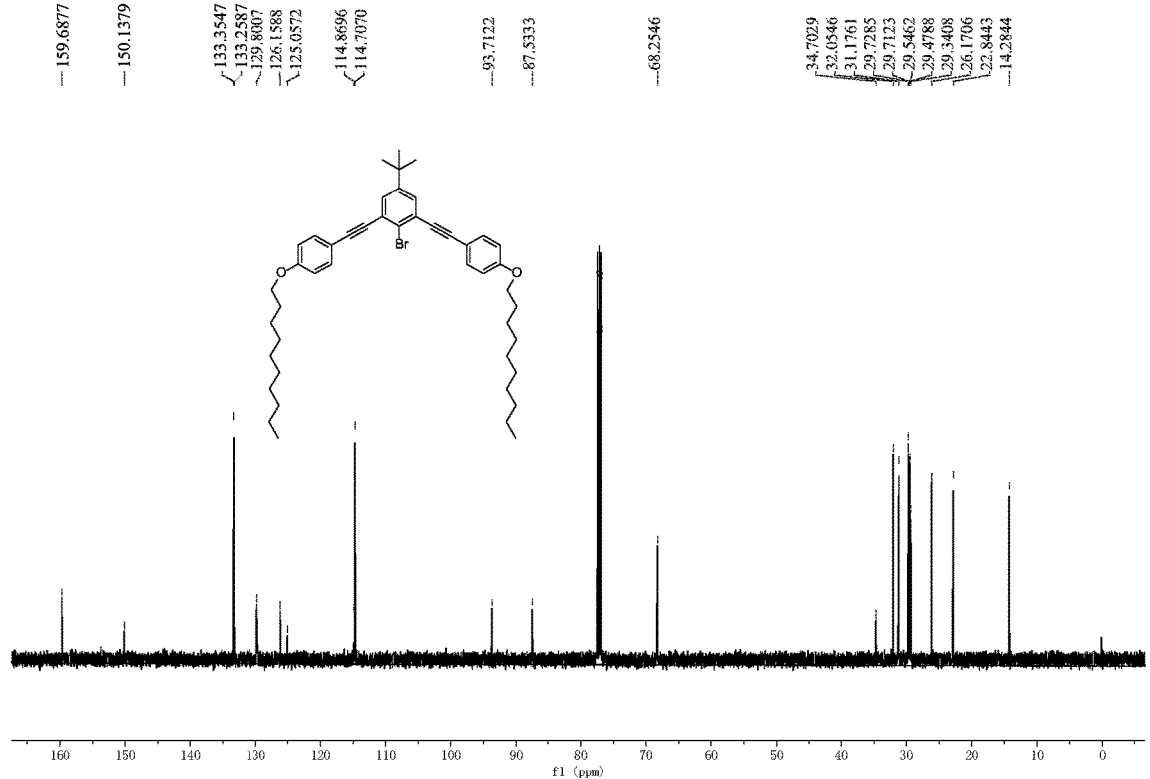

306a (4.3 g, 91%). $^1$H NMR (500 MHz, CDCl$_3$) δ 7.53 (d, J=8.7 Hz, 2H), 7.48 (s, 1H), 6.88 (d, J=8.7 Hz, 2H), 3.98 (t, J=6.5 Hz, 2H), 1.83-1.75 (m, 2H), 1.45 (m, 2H), 1.31 (m, 17H), 0.89 (t, J=6.8 Hz, 3H). $^{13}$C NMR (126 MHz, CDCl$_3$) δ 159.69, 150.14, 133.35, 133.26, 129.80, 126.16, 125.06, 114.87, 114.71, 93.71, 87.53, 68.25, 34.70, 32.05, 31.18, 29.73, 29.71, 29.55, 29.48, 29.34, 26.17, 22.84, 14.28. HRMS (ESI, positive) m/z calcd for C$_{28}$H$_{25}$BrO$_2$ [M]$^+$ 472.1038, found 472.1043 (see FIGS. 10A and 10B for NMR spectra).

Figure 11A:
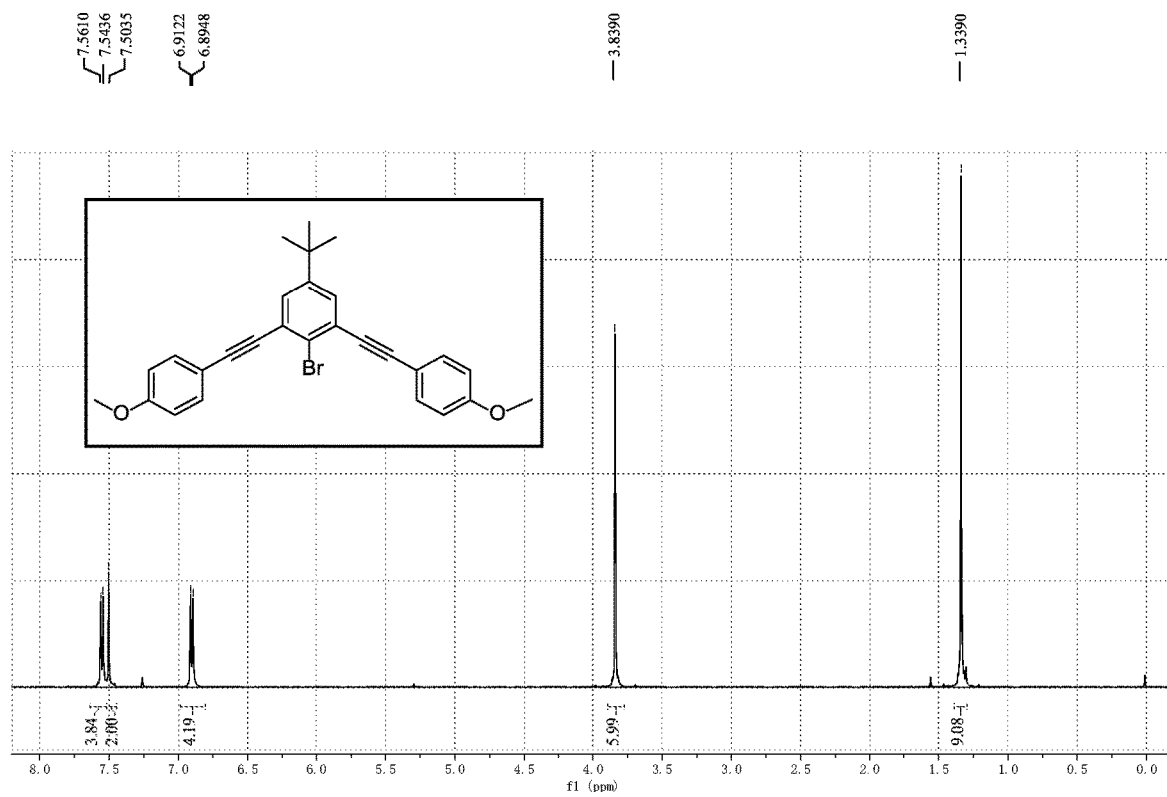
FIGS. 11A and 11B are $^{1}$H-NMR (FIG. 11A) and $^{13}$C-NMR (FIG. 11B) spectra of a representative intermediate compound disclosed herein.
Figure 11B:
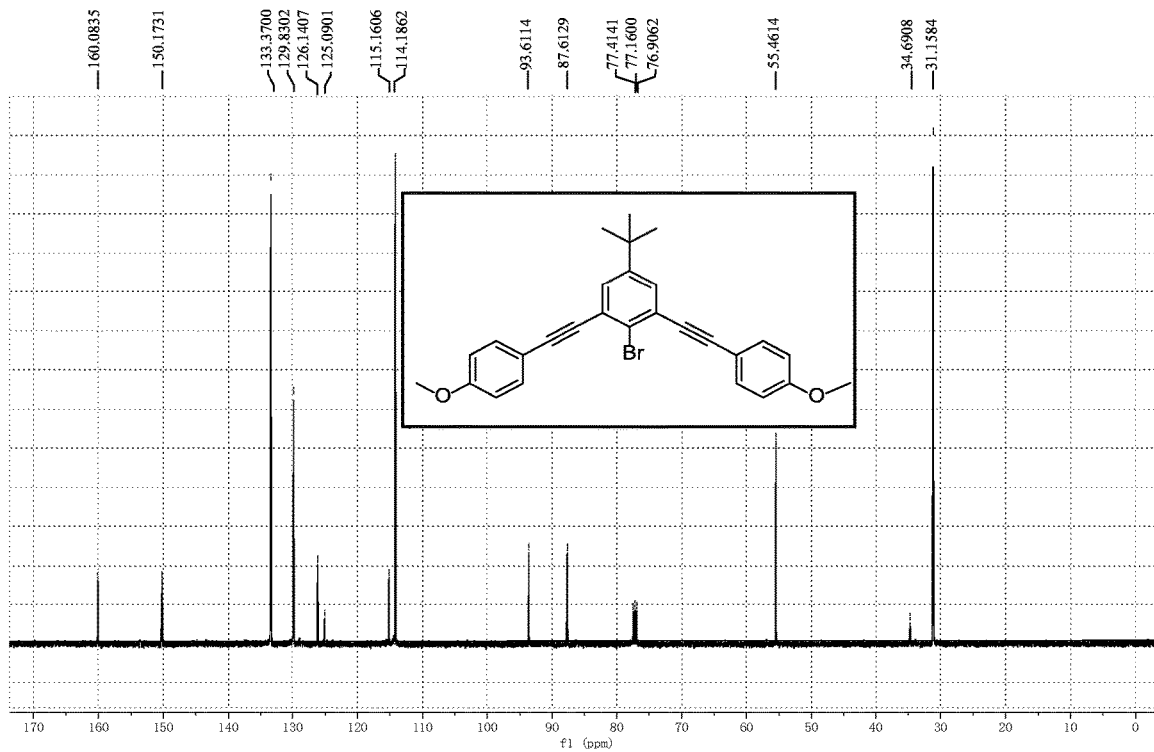

306b (4.3 g, 86%). $^1$H NMR (400 MHz, CDCl$_3$) δ 7.55 (d, J=8.9 Hz, 4H), 7.49 (s, 2H), 6.90 (d, J=8.9 Hz, 4H), 3.84 (s, 6H), 1.33 (s, 9H). $^{13}$C NMR (126 MHz, CDCl$_3$) δ 160.09, 150.18, 133.48, 133.39, 133.31, 133.24, 129.95, 129.85, 129.75, 126.14, 125.10, 115.18, 114.48, 114.39, 114.20, 114.02, 113.91, 113.73, 93.60, 87.62, 55.58, 55.39, 34.71, 31.25, 31.18, 31.10. HRMS (ESI, positive) m/z calcd for C$_{28}$H$_{25}$BrO$_2$ [M]$^+$ 472.1038, found 472.1043 (see FIGS. 11A and 11B for NMR spectra).

Figure 12A:
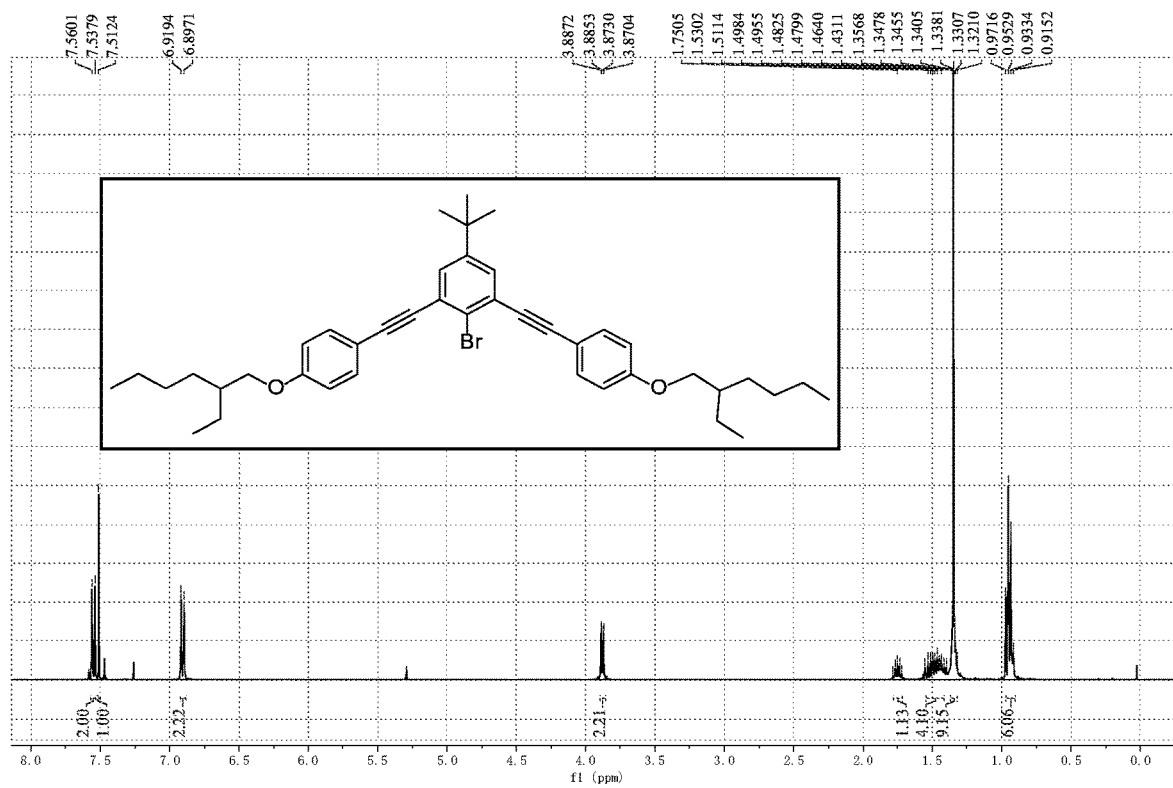
FIGS. 12A and 12B are $^{1}$H-NMR (FIG. 12A) and $^{13}$C-NMR (FIG. 12B) spectra of a representative intermediate compound disclosed herein.
Figure 12B:
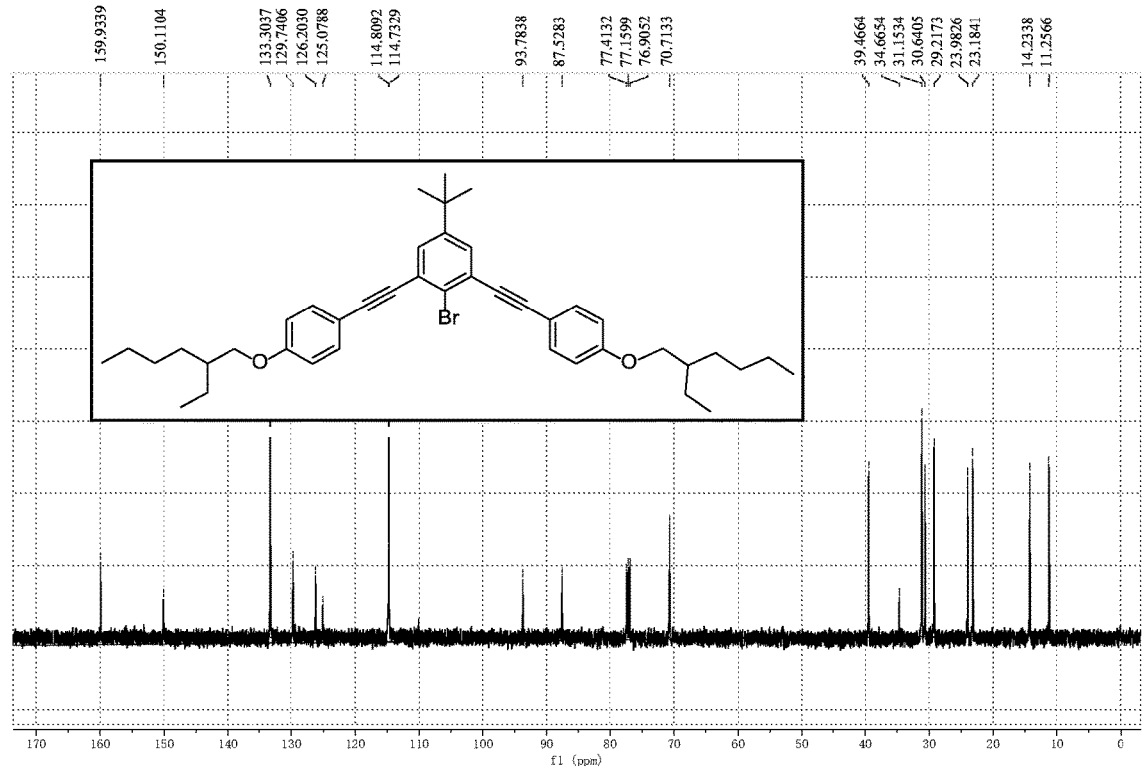

306c (5.76 g, 87%). $^1$H NMR (400 MHz, CDCl$_3$) δ 7.55 (d, J=8.9 Hz, 2H), 7.51 (s, 1H), 6.91 (d, J=8.9 Hz, 2H), 3.88 (dd, J=5.8, 0.9 Hz, 2H), 1.78-1.71 (m, 1H), 1.54-1.41 (m, 4H), 1.37-1.32 (m, 9H), 0.97-0.90 (m, 6H). $^{13}$C NMR (126 MHz, CDCl$_3$) δ 159.93, 150.11, 133.30, 129.74, 126.20, 125.08, 114.81, 114.73, 93.78, 87.53, 77.41, 77.16, 76.91, 70.71, 39.47, 34.67, 31.15, 30.64, 29.22, 23.98, 23.18, 14.23, 11.26. HRMS (ESI, positive) m/z calcd for C$_{42}$H$_{53}$BrO$_2$ [M]$^+$ 668.3229, found 668.3219 (see FIGS. 12A and 12B for NMR spectra).

306d (4.24 g, 69%). R$_f$=0.25 (hexane/DCM 10:1). FTIR (neat) 2953, 2940, 2208, 1603, 1562, 1508, 1472, 1936, 1284, 1245, 1172, 1024, 829 cm$^{-1}$. $^1$H NMR (400 MHz, cdcl$_3$) δ 7.53 (d, J=8.7 Hz, 4H), 7.49 (s, 2H), 6.89 (d, J=8.8 Hz, 4H), 3.98 (t, J=6.6 Hz, 4H), 1.82-1.76 (m, 4H), 1.50-1.33 (m, 21H), 0.92 (t, J=6.9 Hz, 6H). $^{13}$C NMR (100 MHz, cdcl$_3$) δ 159.70, 150.14, 133.35, 129.79, 126.18, 125.07, 114.89, 114.72, 93.73, 87.54, 68.26, 34.70, 31.73, 31.17, 29.31, 25.85, 22.75, 14.19.

Figure 13A:
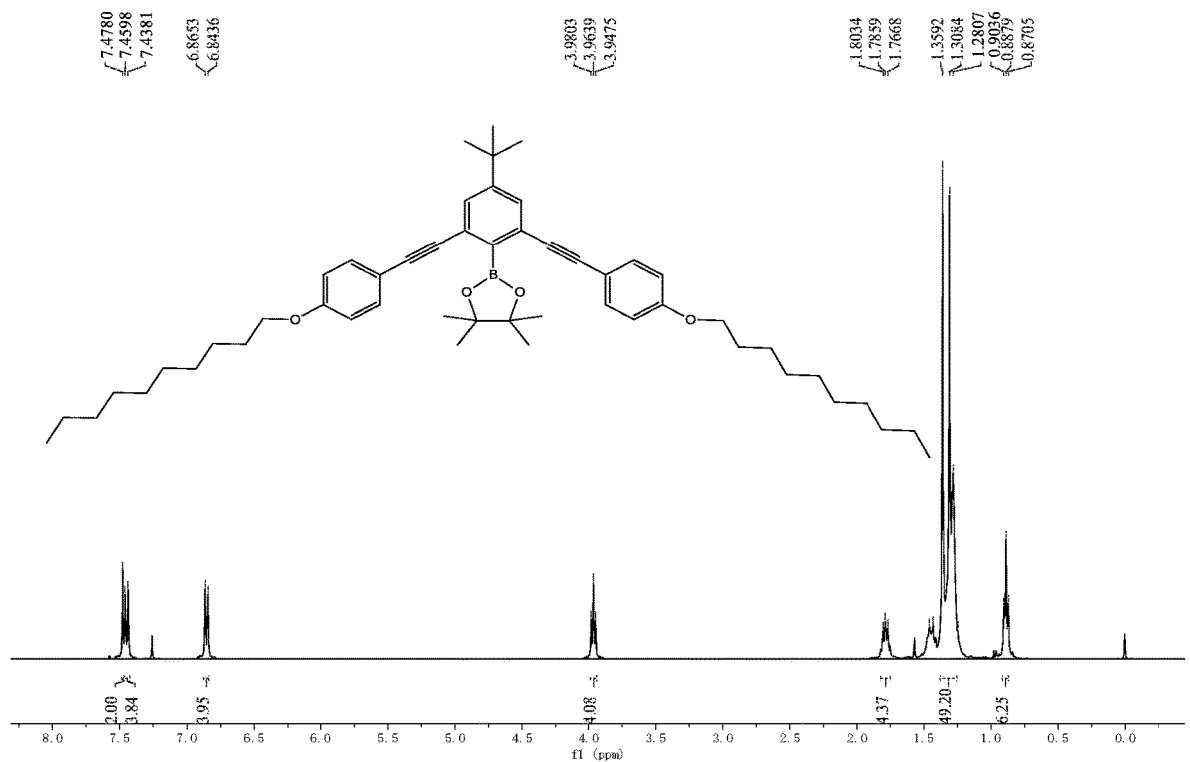
FIGS. 13A and 13B are $^{1}$H-NMR (FIG. 13A) and $^{13}$C-NMR (FIG. 13B) spectra of a representative boronic ester compound disclosed herein.
Figure 13B:
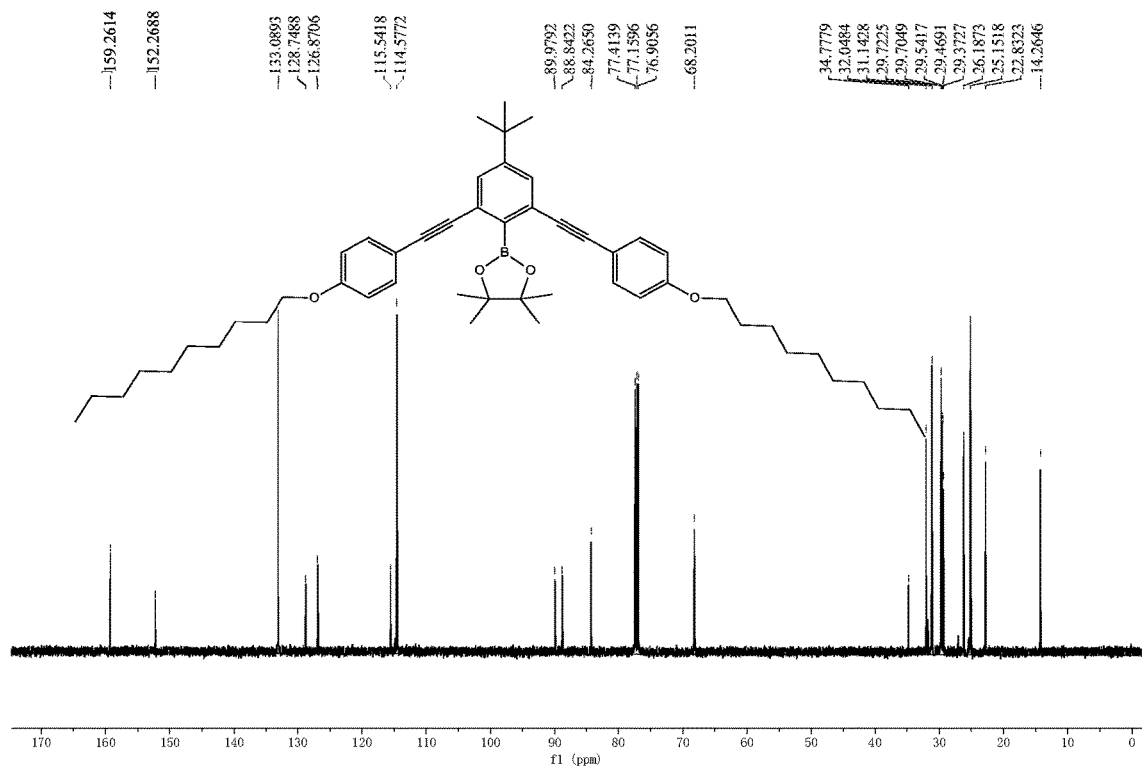

700a (3.49 g, 67%). $^1$H NMR (400 MHz, CDCl$_3$) δ 7.48 (s, 2H), 7.45 (d, J=8.7 Hz, 4H), 6.85 (d, J=8.7 Hz, 4H), 3.96 (t, J=6.6 Hz, 4H), 1.82-1.75 (m, 4H), 1.38-1.25 (m, 49H), 0.89 (t, J=6.6 Hz, 6H). $^{13}$C NMR (126 MHz, CDCl$_3$) δ 159.26, 152.27, 133.09, 128.75, 126.87, 115.54, 114.58, 89.98, 88.84, 84.26, 77.41, 77.16, 76.91, 68.20, 34.78, 32.05, 31.14, 29.72, 29.70, 29.54, 29.47, 29.37, 26.19, 25.15, 22.83, 14.26. HRMS (ESI, positive) m/z calcd for C$_{34}$H$_{37}$BO$_4$Na[M+Na]$^+$ 543.2683, found 543.2690 (see FIGS. 13A and 13B for NMR spectra).

Figure 14A:
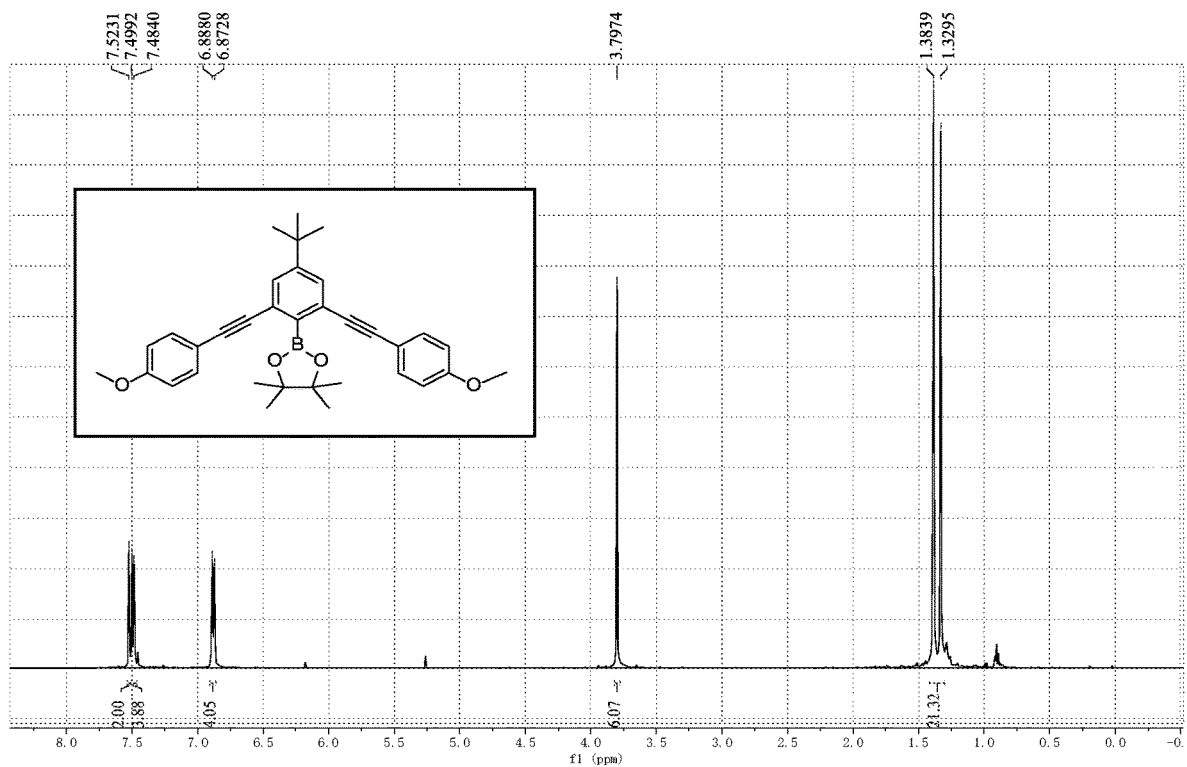
FIGS. 14A and 14B are $^{1}$H-NMR (FIG. 14A) and $^{13}$C-NMR (FIG. 14B) spectra of a representative boronic ester compound disclosed herein.
Figure 14B:
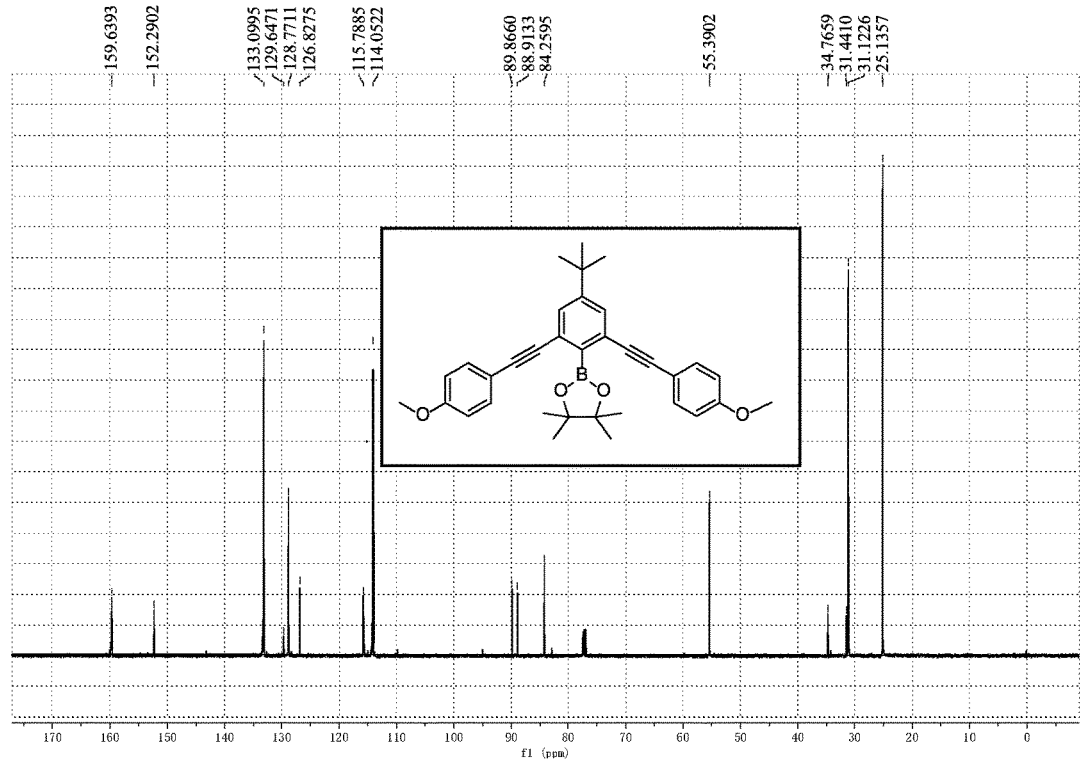

700b (3.49 g, 59%). $^1$H NMR (500 MHz, CDCl$_3$) δ 7.52 (s, 2H), 7.49 (d, J=7.6 Hz, 4H), 6.88 (d, J=7.6 Hz, 4H), 3.80 (s, 6H), 1.36 (d, J=27.2 Hz, 21H). $^{13}$C NMR (126 MHz, CDCl$_3$) δ 159.64, 152.29, 133.10, 129.65, 128.77, 126.83, 115.79, 114.05, 89.87, 88.91, 84.26, 55.39, 34.77, 31.44, 31.12, 25.14. HRMS (ESI, positive) m/z calcd for C$_{34}$H$_{37}$BO$_4$Na [M+Na]$^+$ 543.2683, found 543.2690 (see FIGS. 14A and 14B for NMR spectra).

Figure 15A:
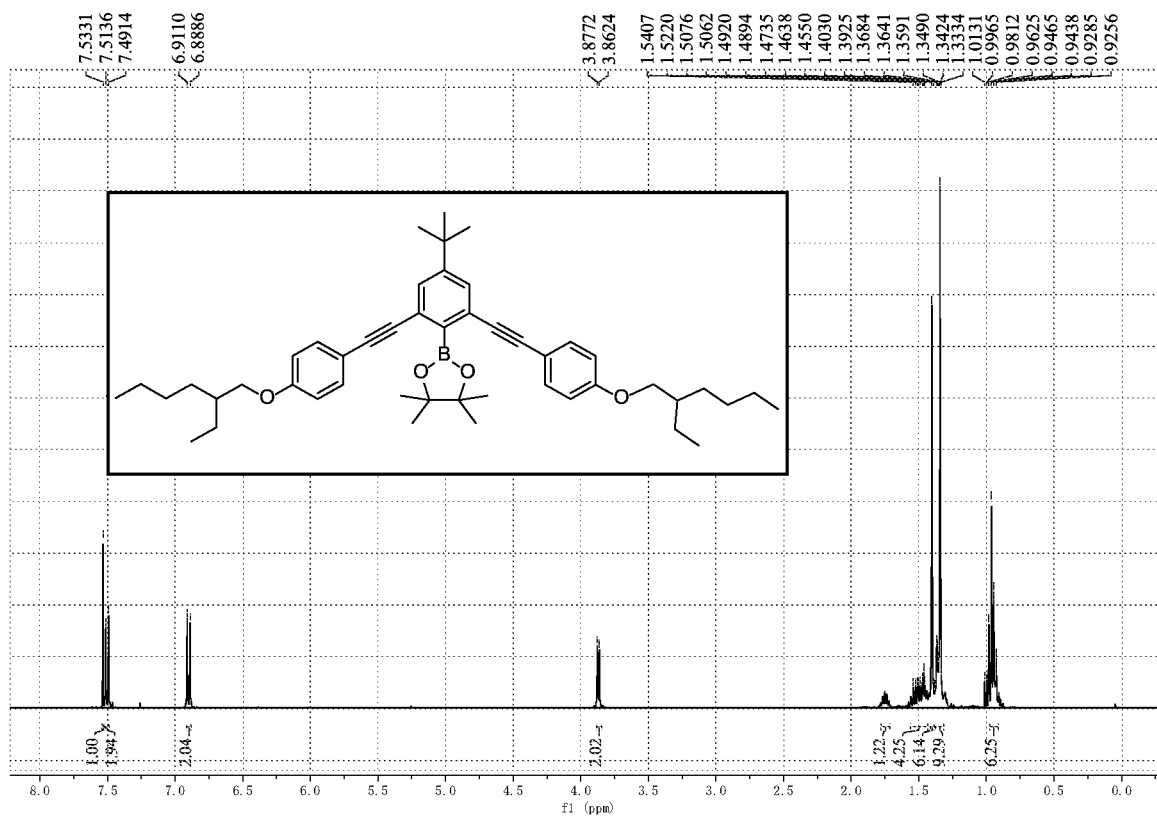
FIGS. 15A and 15B are $^{1}$H-NMR (FIG. 15A) and $^{13}$C-NMR (FIG. 15B) spectra of a representative boronic ester compound disclosed herein.
Figure 15B:
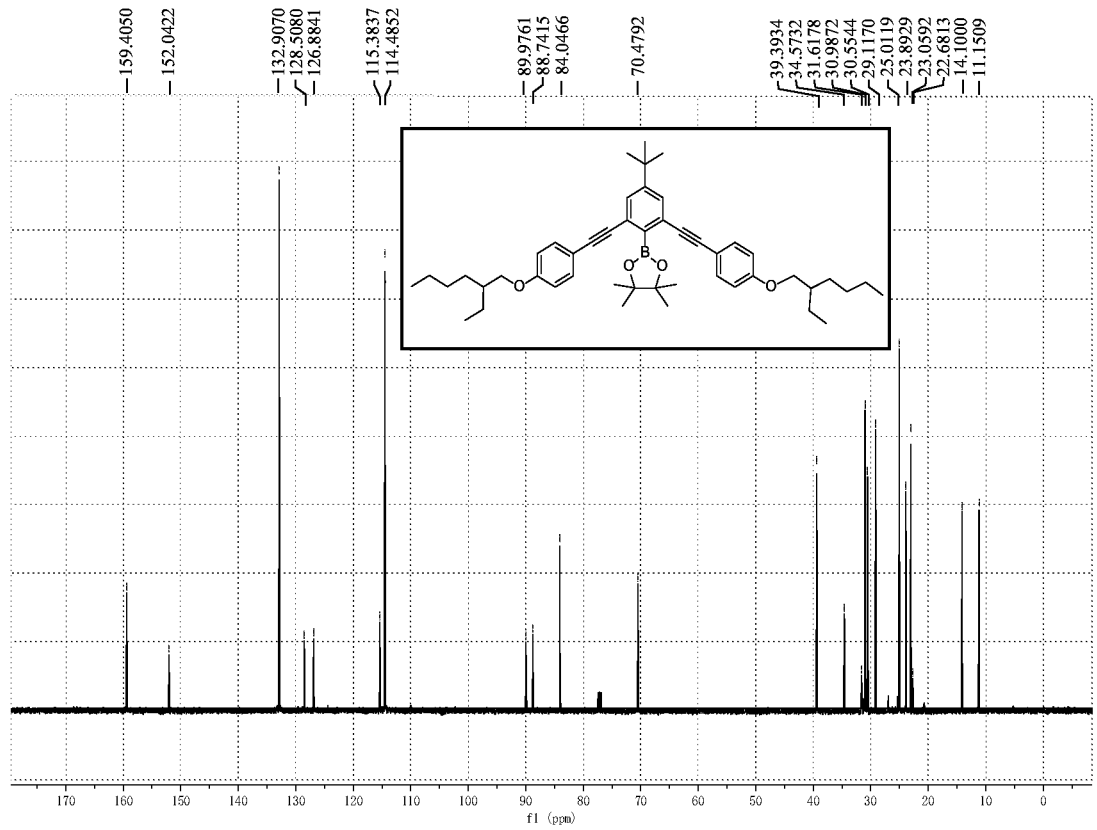

700c (4.23 g, 61%). $^1$H NMR (400 MHz, CDCl$_3$) δ 7.53 (s, 1H), 7.50 (d, J=8.9 Hz, 2H), 6.90 (d, J=8.9 Hz, 2H), 3.87 (d, J=5.9 Hz, 2H), 1.78-1.71 (m, 1H), 1.56-1.44 (m, 4H), 1.40 (s, 6H), 1.38-1.31 (m, 9H), 0.97-0.91 (m, 6H). $^{13}$C NMR (126 MHz, CDCl$_3$) δ 159.40, 152.04, 132.91, 128.51, 126.88, 115.38, 114.49, 89.98, 88.74, 84.05, 70.48, 39.39, 34.57, 31.62, 30.99, 30.55, 29.12, 25.01, 23.89, 23.06, 22.68, 14.10, 11.15. HRMS (ESI, positive) m/z calcd for C$_{48}$H$_{66}$BO$_4$ [M+H]$^+$ 717.5054, found 717.5053 (see FIGS. 15A and 15B for NMR spectra).

700d (4.19 g, 63%). R$_f$=0.20 (hexane/DCM 4:1). FTIR (neat) 2954, 2931, 2869, 2205, 1605, 1587, 1508, 1467, 1331, 1315, 1245, 1133, 854, 829 cm$^{-1}$. $^1$H NMR (400 MHz, cdcl$_3$) δ 7.48 (s, 2H), 7.45 (d, J=8.8 Hz, 4H), 6.86 (d, J=8.8 Hz, 4H), 3.97 (t, J=6.6 Hz, 4H), 1.81-1.75 (m, 4H), 1.46-1.30 (m, 37H), 0.91 (t, J=6.9 Hz, 6H). $^{13}$C NMR (100 MHz, cdcl$_3$) δ 159.25, 152.25, 133.08, 128.73, 126.86, 115.52, 114.56, 89.97, 88.83, 84.25, 68.18, 34.76, 31.72, 31.13, 29.32, 25.85, 25.14, 22.74, 14.17.

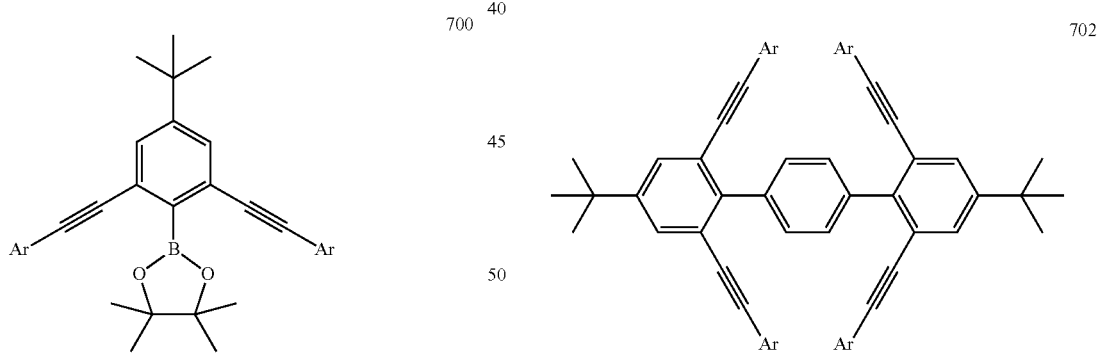

Synthesis of Compound 700:

To a solution of aryl bromide 306 (10 mmol, 1.0 equiv.) in THF (50 mL) at −78° C. was added a solution of n-butyllithium in hexanes (5 mL, 2.5 M, 1.25 equiv.). After stirring for 1 h at −78° C., isopropoxyboronic acid pinacol ester (2.79 g, 15 mmol, 1.5 equiv.) was added, the reaction removed from the cooling bath and allowed to warm. Upon reaching room temperature the reaction was quenched by the addition of H$_2$O, and then extracted with DCM. The extract was washed with water, dried with Na$_2$SO$_4$, filtered and concentrated in vacuo. The residue was purified by flash column chromatography (SiO$_2$, hexane/DCM) to afford the corresponding product 700.

Synthesis of Trimer 702:

1,4-diiodobenzene (0.33 g, 1 mmol, 0.5 equiv.), 2,6-diynylphenyl borate 700 (2 mmol, 1.0 equiv.) and Ag$_2$CO$_3$ (1.1 g, 4 mmol, 2.0 equiv.) were dissolved in anhydrous THF (60 mL). Pd(PPh$_3$)$_4$ (231 mg, 0.2 mmol, 0.1 equiv.) was added to the solution before degassing the mixture via bubbling nitrogen for 30 min. The resulting mixture was stirred under a N$_2$ atmosphere at 80° C. for 24 h. After the reaction was complete, the mixture was diluted with DCM, washed with H$_2$O and dried over Na$_2$SO$_4$. The solvent was removed under reduced pressure and the residue was purified by column chromatography (SiO2, hexane/DCM) to give the desired head-to-head Sandwich-like trimer 702.

Figure 16A:
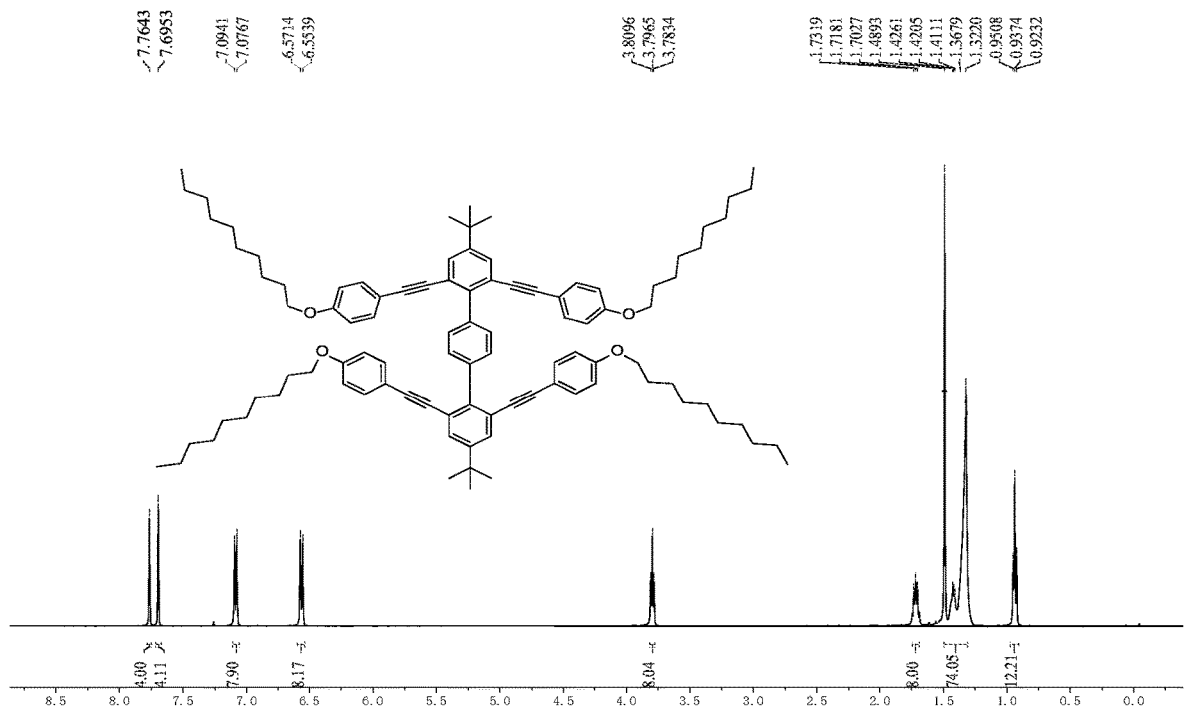
FIGS. 16A and 16B are $^{1}$H-NMR (FIG. 16A) and $^{13}$C-NMR (FIG. 16B) spectra of a representative peropyrene precursor compound disclosed herein.
Figure 16B:
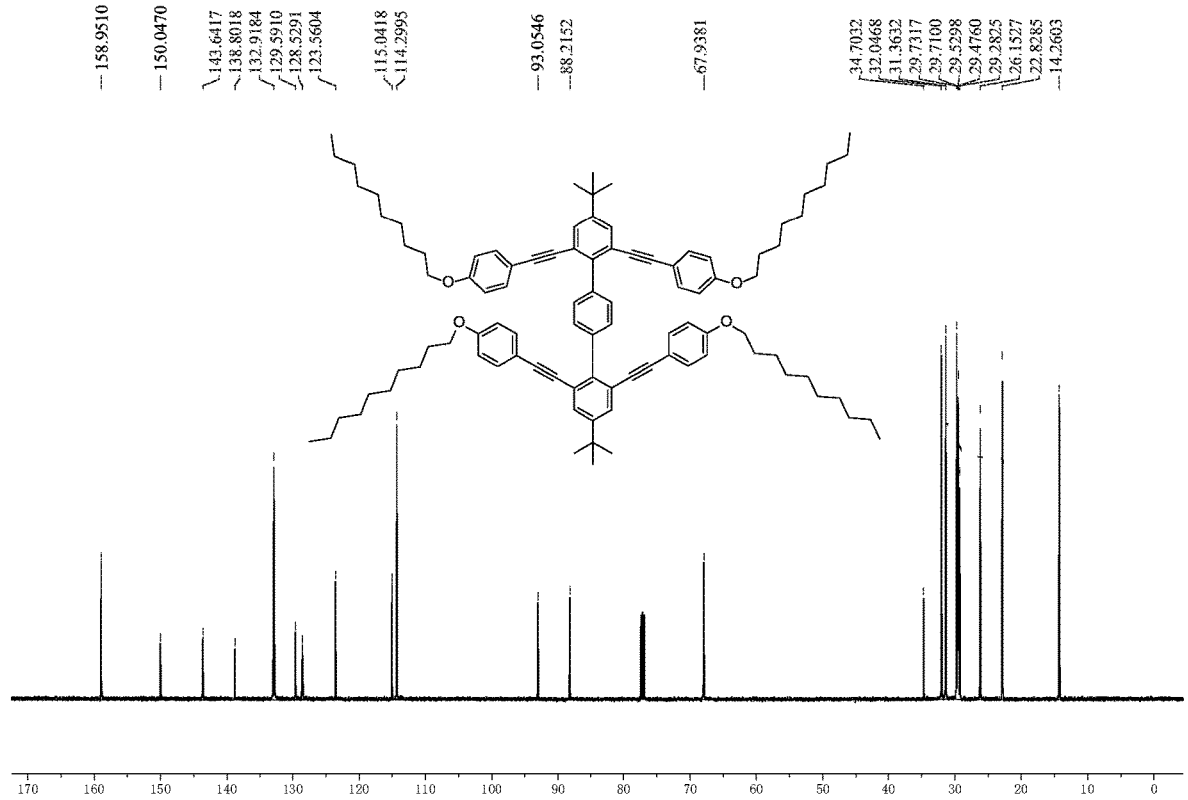

702a (0.45 g, 57%). $^1$H NMR (500 MHz, CDCl$_3$) δ 7.76 (s, 4H), 7.70 (s, 4H), 7.09 (d, J=8.7 Hz, 8H), 6.56 (d, J=8.8 Hz, 8H), 3.80 (t, J=6.6 Hz, 8H), 1.74-1.69 (m, 8H), 1.50-1.31 (m, 74H), 0.94 (t, J=6.9 Hz, 12H). $^{13}$C NMR (126 MHz, CDCl$_3$) δ 158.95, 150.05, 143.64, 138.80, 132.92, 129.59, 128.53, 123.56, 115.04, 114.30, 93.05, 88.22, 67.94, 34.70, 32.05, 31.36, 29.73, 29.71, 29.53, 29.48, 29.28, 26.15, 22.83, 14.26. HRMS (ESI, positive) m/z calcd for C$_{62}$H$_{54}$O$_4$ [M]$^+$ 862.4022, found 862.4012 (see FIGS. 16A and 16B for NMR spectra).

702b (0.45 g, 65%). $^1$H NMR (500 MHz, CDCl$_3$) δ 7.71 (s, 2H), 7.65 (s, 2H), 7.04 (d, J=8.8 Hz, 4H), 6.53 (d, J=8.8 Hz, 4H), 3.64 (s, 6H), 1.45 (s, 9H). $^{13}$C NMR (126 MHz, CDCl$_3$) δ 159.35, 150.15, 143.68, 138.82, 132.95, 129.59, 128.62, 123.50, 115.31, 113.77, 92.90, 88.30, 77.41, 77.16, 76.91, 55.24, 34.76, 31.38. HRMS (ESI, positive) m/z calcd for C$_{62}$H$_{54}$O$_4$ [M]$^+$ 862.4022, found 862.4012 (see FIGS. 17A and 17B for NMR spectra).

Figure 18A:
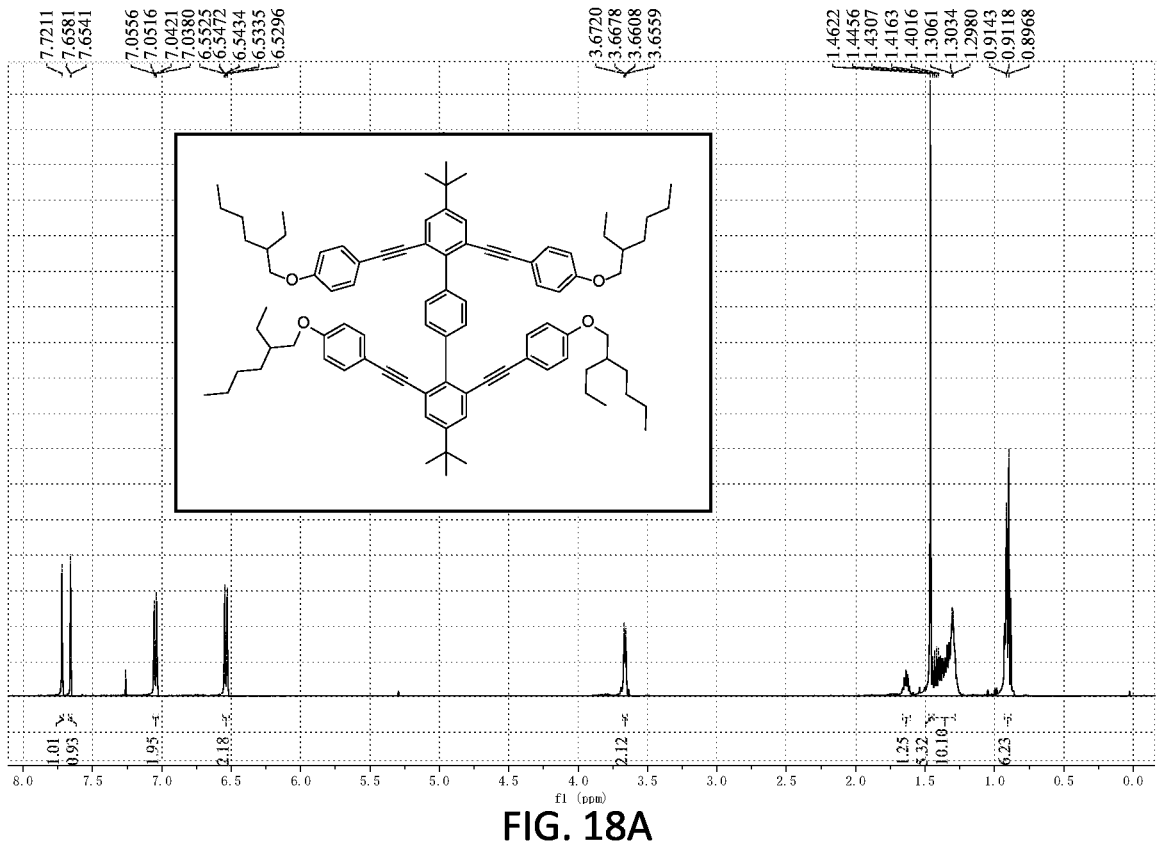
FIGS. 18A and 18B are $^{1}$H-NMR (FIG. 18A) and $^{13}$C-NMR (FIG. 18B) spectra of a representative peropyrene precursor compound disclosed herein.
Figure 18B:
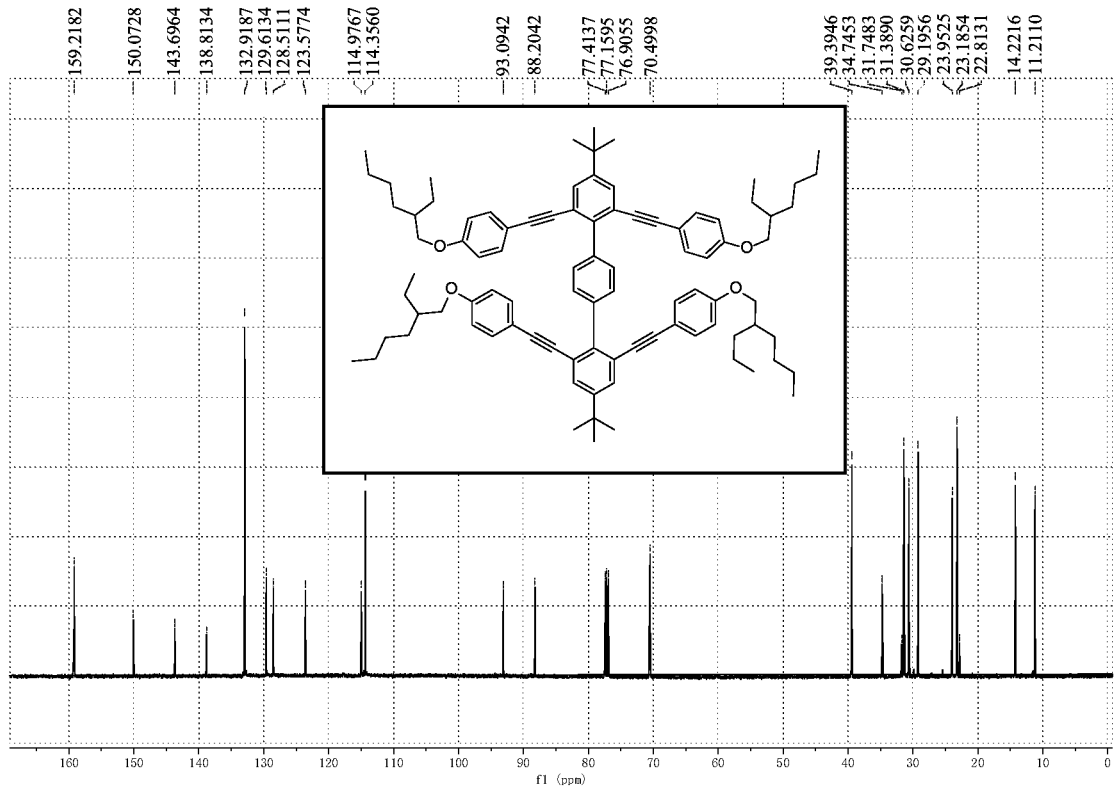

702c (0.76 g, 63%). $^1$H NMR (500 MHz, CDCl$_3$) δ 7.72 (s, 1H), 7.66 (s, 1H), 7.05 (d, J=8.8 Hz, 2H), 6.54 (d, J=8.8 Hz, 2H), 3.69-3.64 (m, 2H), 1.66-1.61 (m, 1H), 1.46 (s, 5H), 1.43-1.28 (m, 10H), 0.93-0.88 (m, 6H). $^{13}$C NMR (126 MHz, CDCl$_3$) δ 159.22, 150.07, 143.70, 138.81, 132.92, 129.61, 128.51, 123.58, 114.98, 114.36, 93.09, 88.20, 77.41, 77.16, 76.91, 70.50, 39.39, 34.75, 31.75, 31.39, 30.63, 29.20, 23.95, 23.19, 22.81, 14.22, 11.21. HRMS (ESI, positive) m/z calcd for C$_{90}$H$_{110}$O$_4$ [M]$^+$ 1254.8404, found 1254.8371 (see FIGS. 18A and 18B for NMR spectra).

702d (0.76 g, 66%) $^1$H NMR (400 MHz, cdcl$_3$) δ 7.78 (s, 4H), 7.71 (s, 4H), 7.10 (d, J=8.7 Hz, 8H), 6.58 (d, J=8.8 Hz, 8H), 3.80 (t, J=6.5 Hz, 8H), 1.76-1.68 (m, 8H), 1.51-1.34 (m, 42H), 0.95 (t, J=6.8 Hz, 12H). $^{13}$C NMR (100 MHz, cdcl$_3$) δ 157.99, 149.51, 139.93, 136.56, 131.59, 128.12, 126.09, 124.10, 122.79, 120.43, 68.34, 35.34, 32.06, 31.86, 29.53, 25.95, 22.83, 14.26.

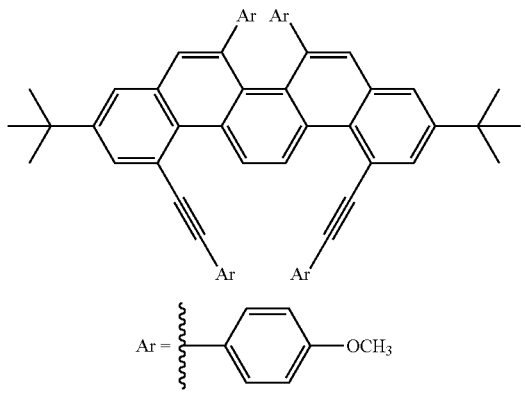

704b

Figure 7:
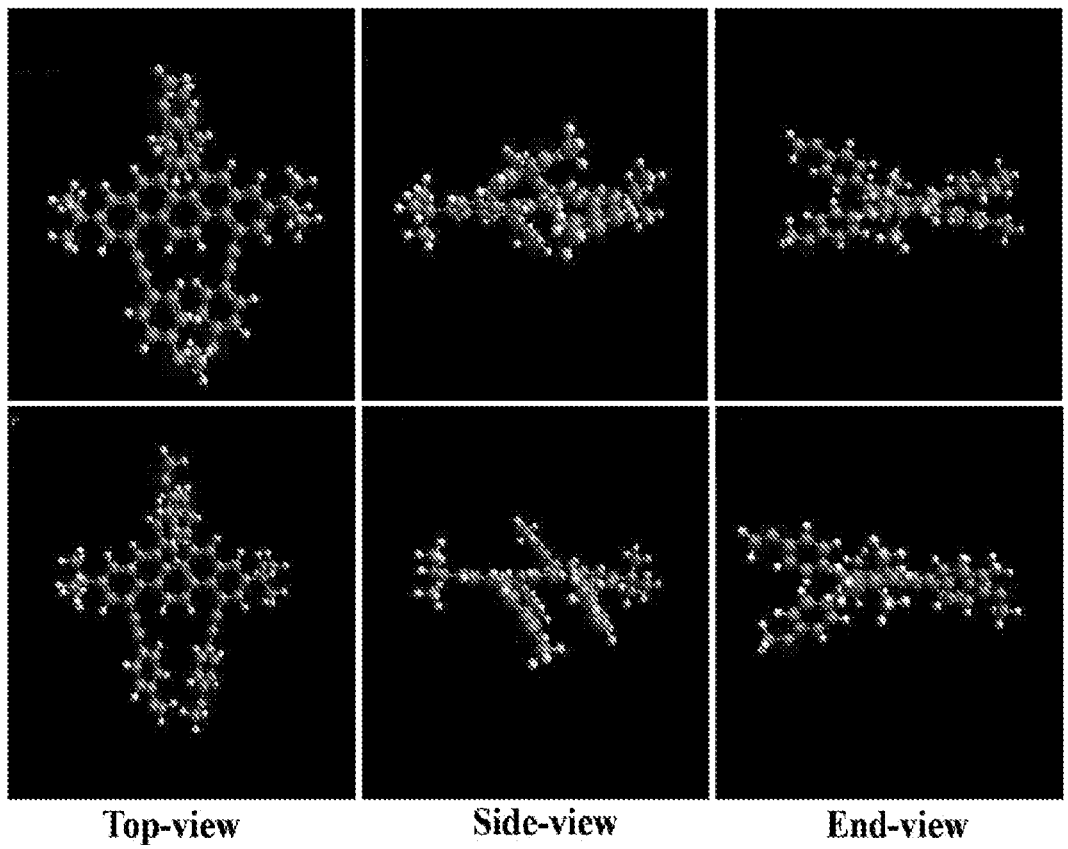
FIG. 7 is a Merck Molecular Force Field 94 calculation image of representative compounds disclosed herein.
Figure 20A:
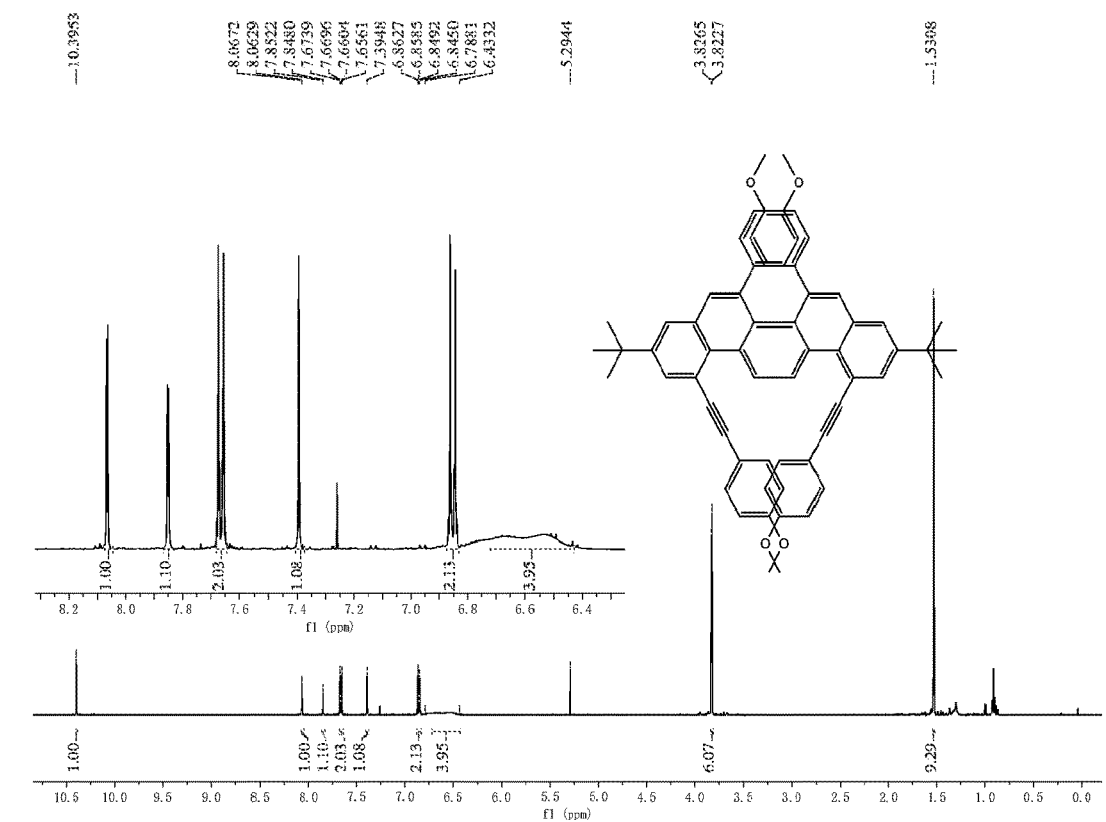
FIGS. 20A and 20B are $^{1}$H-NMR (FIG. 20A) and $^{13}$C-NMR (FIG. 20B) spectra of a representative intermediate compound disclosed herein.
Figure 20B:
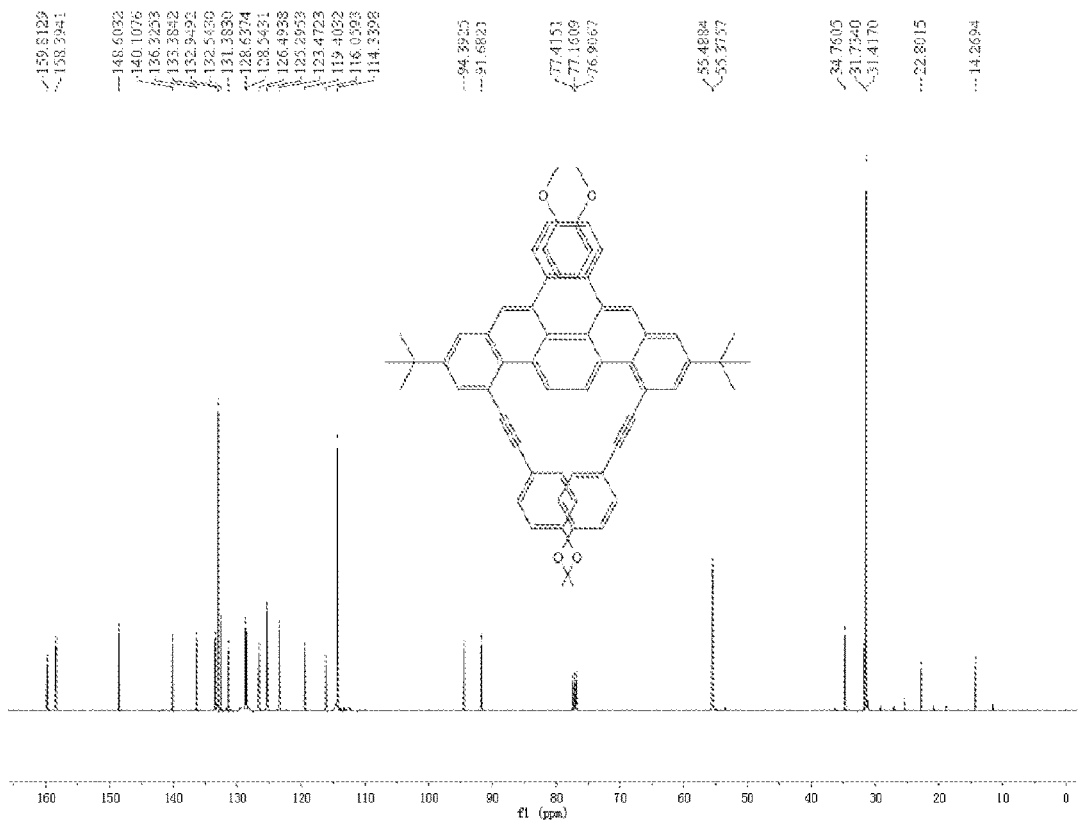

Synthesis of Bis-cyclization Trimer 704b:

In a flame dried flask under a nitrogen atmosphere, 702b (100 mg, 0.11 mmol) was dissolved in anhydrous DCM (50 mL), and cooled to 0° C. Methanesulfonic acid (3 drops) was added by syring to the solution. The reaction mixture was stirred for 1 h, and then quenched with saturated NaHCO$_3$ aqueous solution (1.0 mL). The mixture was washed with H$_2$O (2×20 mL) and dried over Na$_2$SO$_4$. The solvent was then removed under reduced pressure and the residue was purified by column chromatography (SiO$_2$, hexane/DCM, 80/20, v/v) to give the bis-cyclization trimer 704b (97 mg, 97%) as yellow solids. $^1$H NMR (500 MHz, CDCl$_3$) δ 10.40 (s, 1H), 8.07 (d, J=2.2 Hz, 1H), 7.85 (d, J=2.1 Hz, 1H), 7.68-7.64 (m, 2H), 7.39 (s, 1H), 6.87-6.83 (m, 2H), 6.43-6.78 (br, 4H), 3.82 (d, J=1.9 Hz, 6H), 1.53 (s, 9H). $^{13}$C NMR (126 MHz, CDCl$_3$) δ 159.81, 158.39, 148.60, 140.11, 136.33, 133.38, 132.95, 132.54, 131.38, 128.64, 128.54, 126.49, 125.30, 123.47, 119.40, 116.06, 114.34, 94.39, 91.68, 77.42, 77.16, 76.91, 55.49, 55.38, 34.76, 31.73, 31.42, 22.80, 14.27. HRMS (ESI, positive) m/z calcd for C$_{62}$H$_{54}$O$_4$ [M]$^+$ 862.4022, found 862.4016 (see FIGS. 20A and 20B for NMR spectra). In some embodiments, the structures of 702b, 704b, and 706b were optimized by Merck Molecular Force Field 94 (MMFF94) calculations (grey, carbon; white, hydrogen; red, oxygen) as illustrated in FIGS. 7.

704a and 704c were also can be prepared following the same procedure.

Figure 19A:
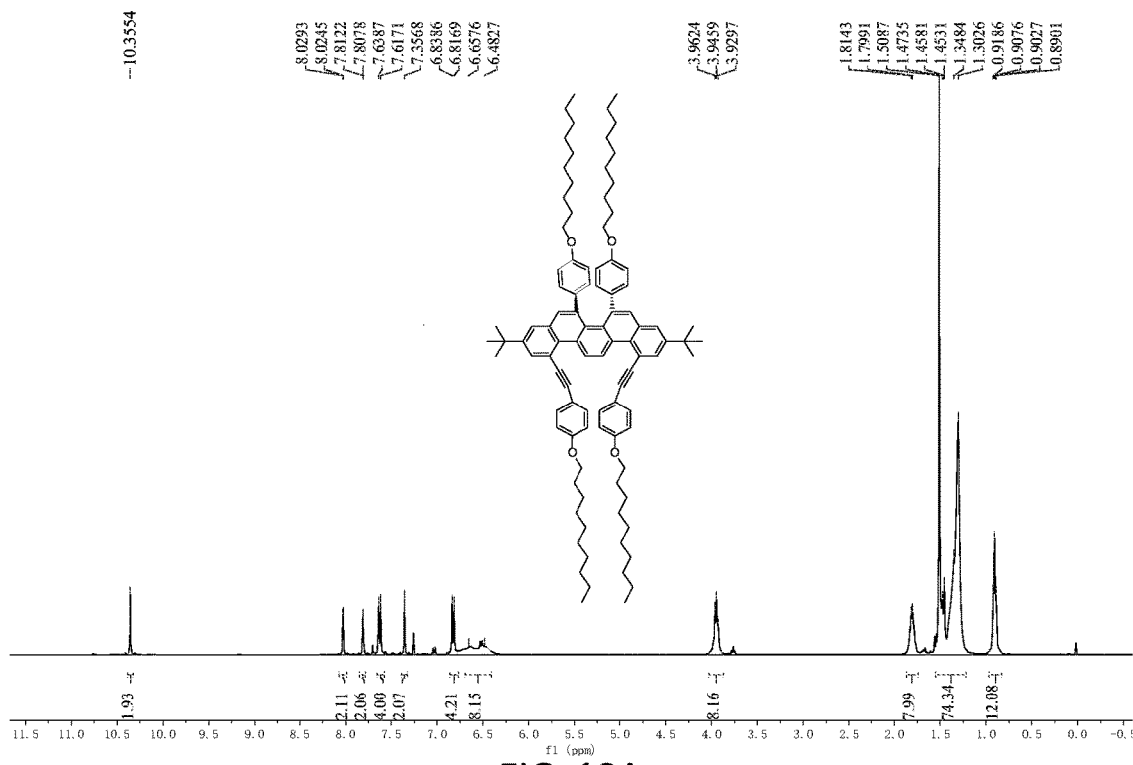
FIGS. 19A and 19B are $^{1}$H-NMR (FIG. 19A) and $^{13}$C-NMR (FIG. 19B) spectra of a representative intermediate compound disclosed herein.
Figure 19B:
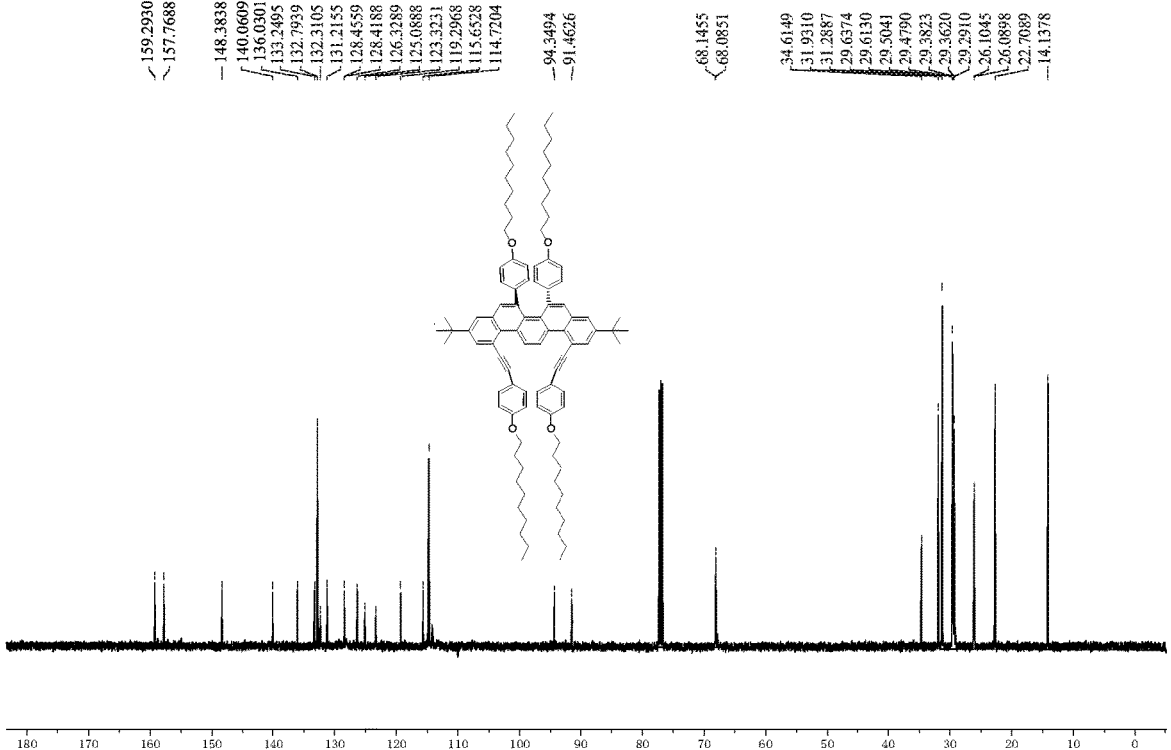

704a: $^1$H NMR (400 MHz, CDCl$_3$) δ 10.36 (s, 2H), 8.03 (d, J=1.9 Hz, 2H), 7.81 (d, J=1.8 Hz, 2H), 7.63 (d, J=8.6 Hz, 4H), 7.36 (s, 2H), 6.83 (d, J=8.7 Hz, 4H), 6.48-6.57 (br, 8H), 4.03-3.87 (m, 8H), 1.81 (d, J=6.0 Hz, 8H), 1.55-1.21 (m, 74H), 0.90 (m, 12H). $^{13}$C NMR (126 MHz, cdcl$_3$) δ 159.29, 157.77, 148.38, 140.06, 136.03, 133.25, 132.79, 132.31, 131.22, 128.46, 128.42, 126.33, 125.09, 123.32, 119.30, 115.65, 114.72, 94.35, 91.46, 68.15, 68.09, 34.61, 31.93, 31.29, 29.64, 29.61, 29.50, 29.48, 29.38, 29.36, 29.29, 26.10, 26.09, 22.71, 14.14. HRMS (ESI, positive) m/z calcd for C$_{62}$H$_{54}$O$_4$ [M]$^+$ 862.4022, found 862.4016 (see FIGS. 19A and 19B for NMR spectra).

Figures 21A, 21B:
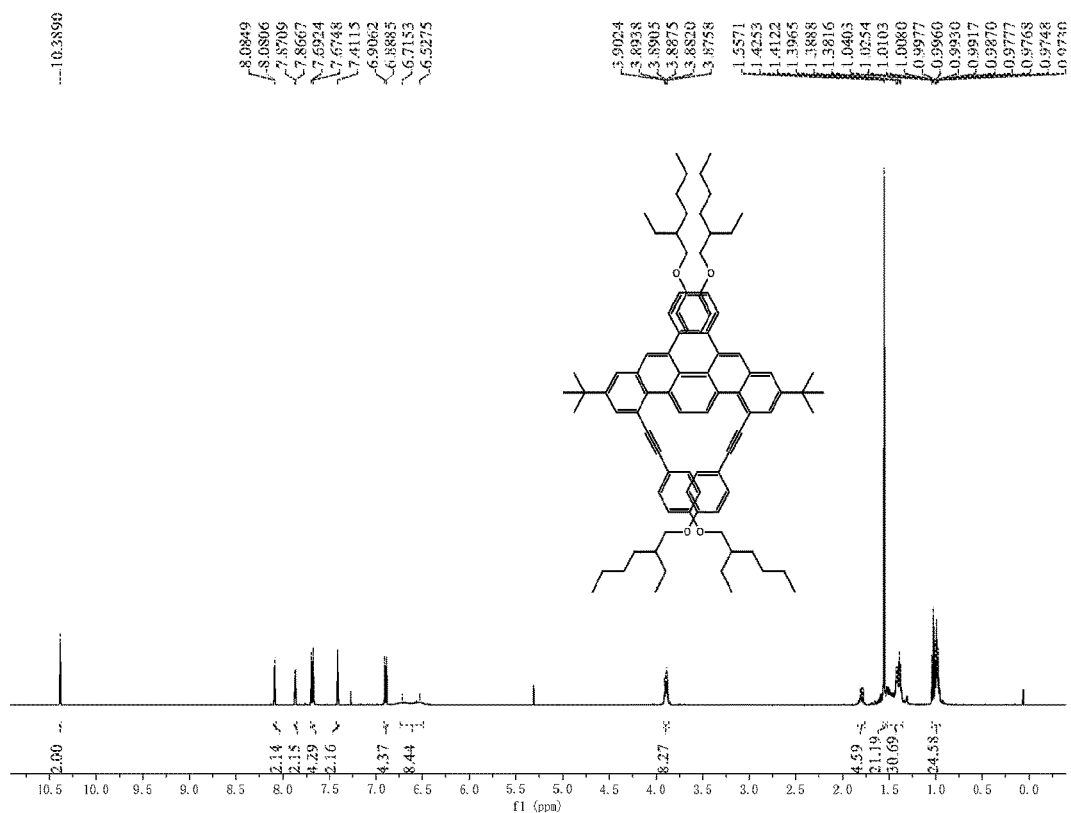
FIGS. 21A and 21B are ¹H-NMR (FIG. 21A) and ¹³C-NMR (FIG. 21B) spectra of a representative intermediate compound disclosed herein.

704c: $^1$H NMR (500 MHz, cdcl$_3$) δ 10.39 (s, 2H), 8.08 (d, J=2.1 Hz, 2H), 7.87 (d, J=2.1 Hz, 2H), 7.68 (d, J=8.8 Hz, 4H), 7.41 (s, 2H), 6.90 (d, J=8.8 Hz, 4H), 6.25-6.71 (br, 8H), 3.92-3.86 (m, 8H), 1.80 (m, 5H), 1.56 (s, 21H), 1.52-1.36 (m, 31H), 1.04-0.96 (m, 24H). $^{13}$C NMR (126 MHz, cdcl$_3$) δ 159.71, 158.21, 158.20, 148.52, 140.27, 136.13, 133.39, 132.92, 132.39, 131.37, 128.65, 128.60, 126.53, 125.19, 123.51, 119.47, 115.73, 114.90, 94.50, 91.58, 77.41, 77.16, 76.91, 70.93, 70.91, 70.79, 70.77, 39.56, 39.51, 34.76, 31.50, 31.44, 30.73, 30.67, 30.65, 29.30, 29.26, 29.24, 24.05, 24.00, 23.99, 23.28, 23.25, 23.24, 23.22, 14.30, 14.25, 11.30, 11.29, 11.27, 11.26. HRMS (ESI, positive) m/z calcd for C$_{62}$H$_{54}$O$_4$ [M]$^+$ 862.4022, found 862.4016 (see FIGS. 21A and 21B for NMR spectra).

704d (97 mg, 97%) $^1$H NMR (400 MHz, cdcl$_3$) δ 10.35 (s, 2H), 8.02 (s, 2H), 7.80 (s, 2H), 7.61 (d, J=7.4 Hz, 4H), 7.35 (s, 2H), 6.81 (d, J=8.3 Hz, 4H), 6.52 (br, 8H), 3.97-3.86 (m, 8H), 1.83-1.74 (m, 8H), 1.50-1.33 (m, 42H), 0.92 (d, J=2.4 Hz, 12H). $^{13}$C NMR (100 MHz, cdcl$_3$) δ 159.43, 157.90, 148.53, 140.20, 136.15, 133.39, 132.92, 132.45, 131.35, 128.59, 128.55, 126.46, 125.22, 123.46, 119.44, 115.77, 114.85, 94.50, 91.60, 68.26, 68.19, 53.53, 34.74, 31.82, 31.76, 31.41, 29.46, 29.36, 25.90, 25.88, 22.79, 22.76, 14.22, 14.19.

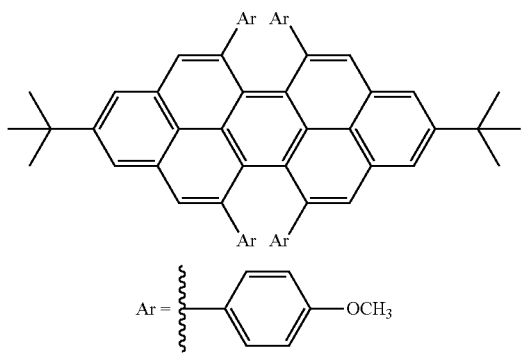

Figure 23A:
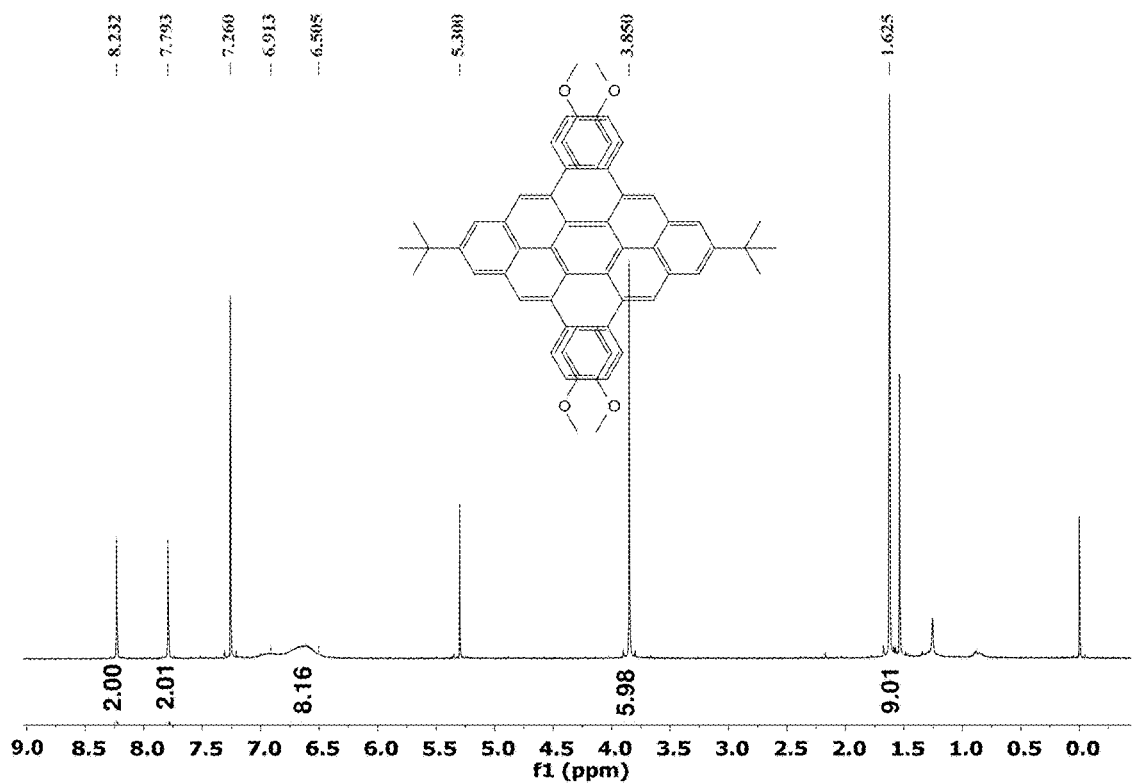
FIGS. 23A and 23B are ¹H-NMR (FIG. 23A) and ¹³C-NMR (FIG. 23B) spectra of a representative chiral peropyrene compound disclosed herein.
Figure 23B:
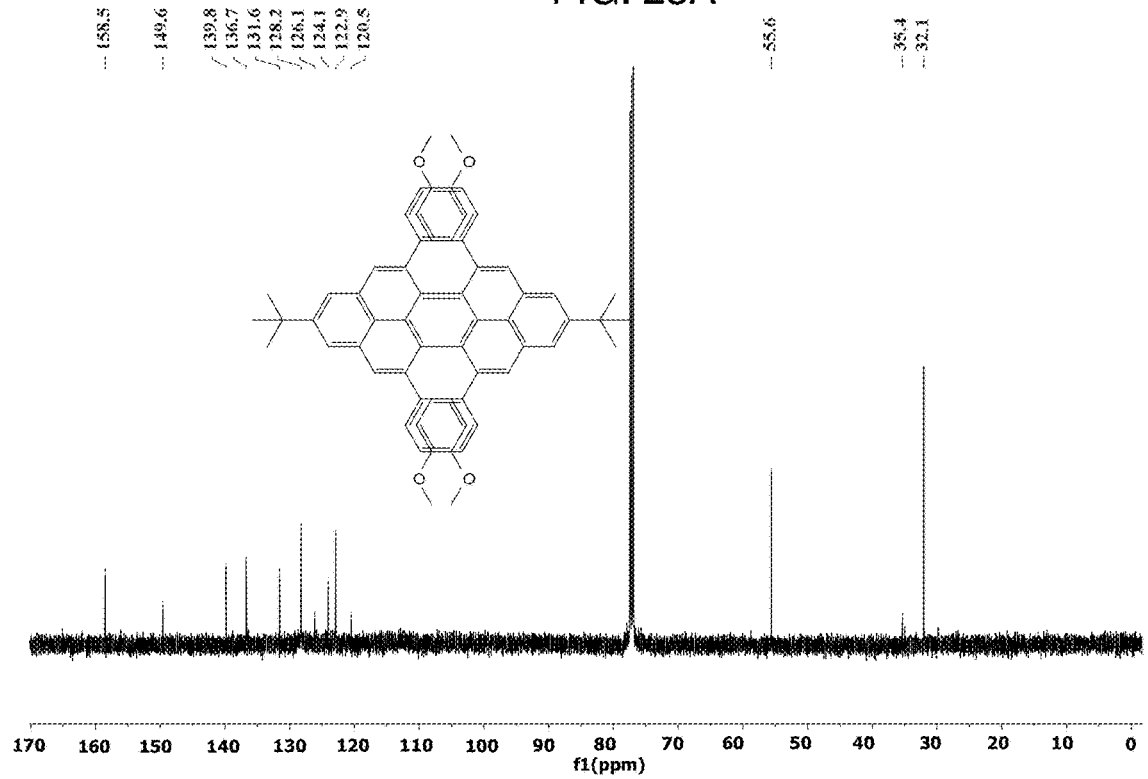

Synthesis of Tetra-cyclization Trimer 706b:

To a solution of 704b (50 mg, 0.058 mmol) in 20 mL of anhydrous CH$_2$Cl$_2$ was added 0.1 mL of triflic acid at −40° C. After 1 hour, TLC indicated the reaction was complete. The solution was quenched with saturated NaHCO$_3$ solution (2.0 mL), and then washed with H$_2$O (2×10 mL). The solvent was dried (Na$_2$SO$_4$) and removed under reduced pressure. The residue was purified by column chromatography (First: SiO$_2$, hexane/DCM, 75/25, v/v; Second: neutral Al$_2$O$_3$, toluene) to give the tetra-cyclization trimer 706b (21 mg, 43%) as orange solids. $^1$H NMR (400 MHz, CDCl$_3$) δ 8.23 (s, 2H), 7.79 (s, 2H), 6.51-6.91 (br, 8H), 3.85 (s, 6H), 1.62 (s, 9H). $^{13}$C NMR (126 MHz, CDCl$_3$) δ 158.48, 149.59, 139.83, 136.74, 131.57, 128.23, 126.11, 124.06, 122.89, 120.46, 55.60, 35.36, 32.06. HRMS (ESI, positive) m/z calcd for C$_{62}$H$_{54}$O$_4$ [M]$^+$ 862.4022, found 862.3993 (see FIGS. 23A and 23B for NMR spectra).

One-step Synthesis of Tetra-cyclization Trimer 706:

In a flame dried flask under a nitrogen atmosphere, 702 (0.08 mmol) was dissolved in anhydrous DCM (50 mL), and cooled to 0° C. Methanesulfonic acid (5 drops) was added by syring to the solution. After 1 hour, the reaction was cooled down to −40° C., then 0.1 mL of triflic acid was added and the reaction was allowed to continue for additional 1 hour. The solution was quenched with saturated NaHCO$_3$ solution (2.0 mL), and then washed with H$_2$O (2×20 mL). The solvent was dried (Na$_2$SO$_4$) and removed under reduced pressure. The residue was purified by column chromatography (First: SiO$_2$, hexane/DCM; Second: neutral Al$_2$O$_3$, hexane/toluene,) to give the tetra-cyclization trimer 706.

Figure 22A:
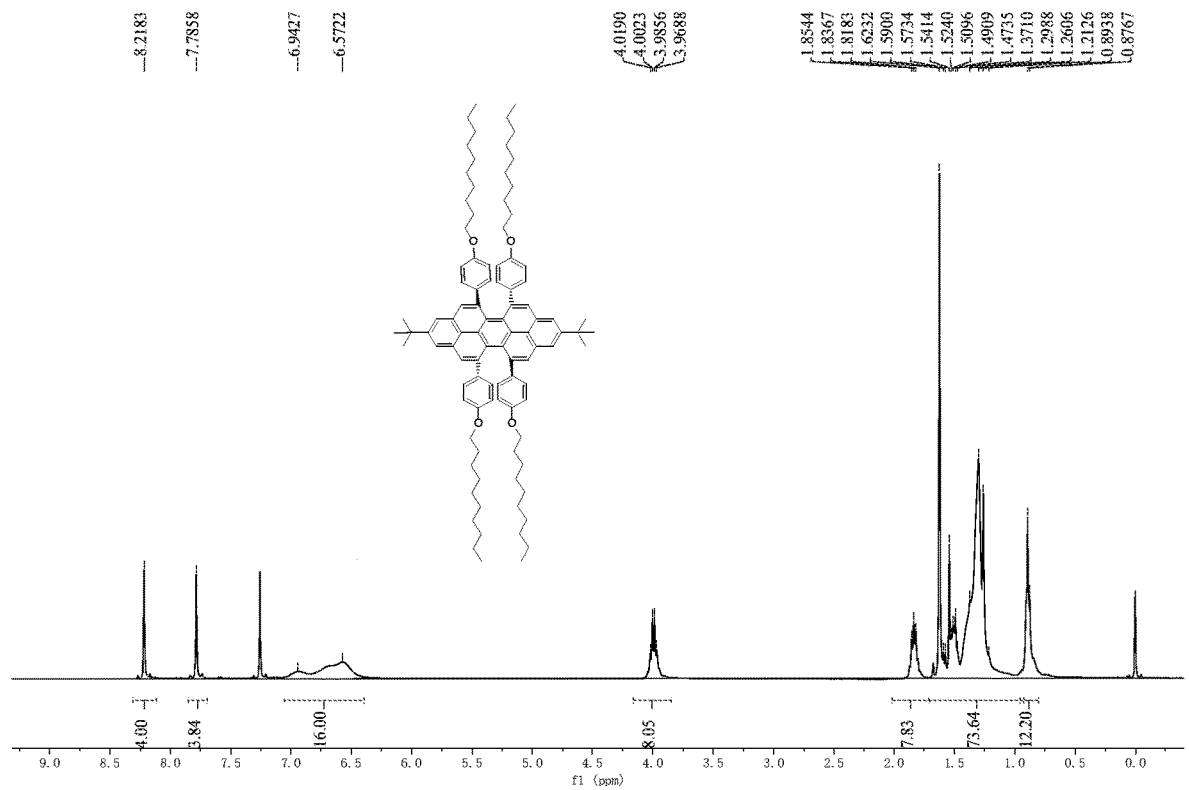
FIGS. 22A and 22B are ¹H-NMR (FIG. 22A) and ¹³C-NMR (FIG. 22B) spectra of a representative chiral peropyrene compound disclosed herein.
Figure 22B:
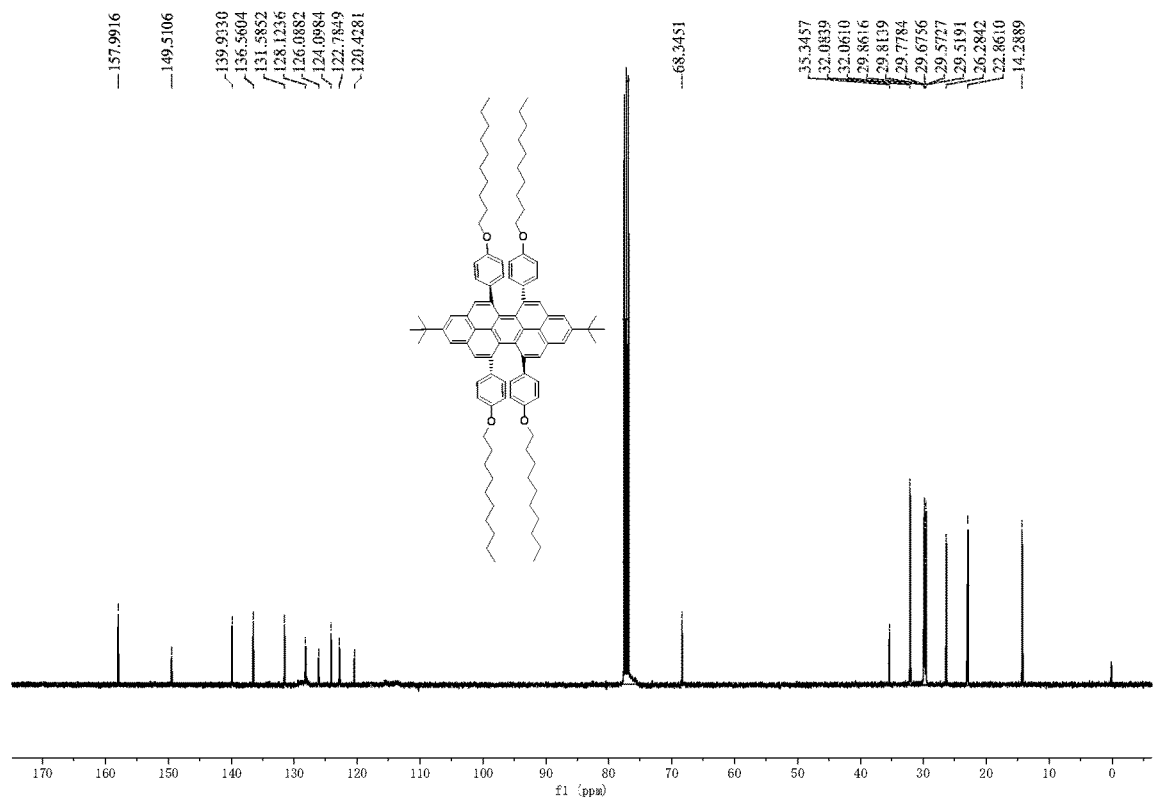

706a (41 mg, 38%). $^1$H NMR (400 MHz, CDCl$_3$) δ 8.22 (s, 4H), 7.79 (s, 4H), 6.76 (d, J=148.2 Hz, 16H), 3.99 (m, 8H), 2.01-1.71 (m, 8H), 1.70-0.92 (m, 74H), 0.89 (d, J=6.8 Hz, 12H). $^{13}$C NMR (101 MHz, cdcl$_3$) δ 157.99, 149.51, 139.93, 136.56, 131.59, 128.12, 126.09, 124.10, 122.78, 120.43, 68.35, 35.35, 32.08, 32.06, 29.86, 29.81, 29.78, 29.68, 29.57, 29.52, 26.28, 22.86, 14.29. HRMS (ESI, positive) m/z calcd for C$_{90}$H$_{110}$O$_4$ [M]$^+$ 1254.8404, found 1254.8389 (see FIGS. 22A and 22B for NMR spectra).

Figure 24A:
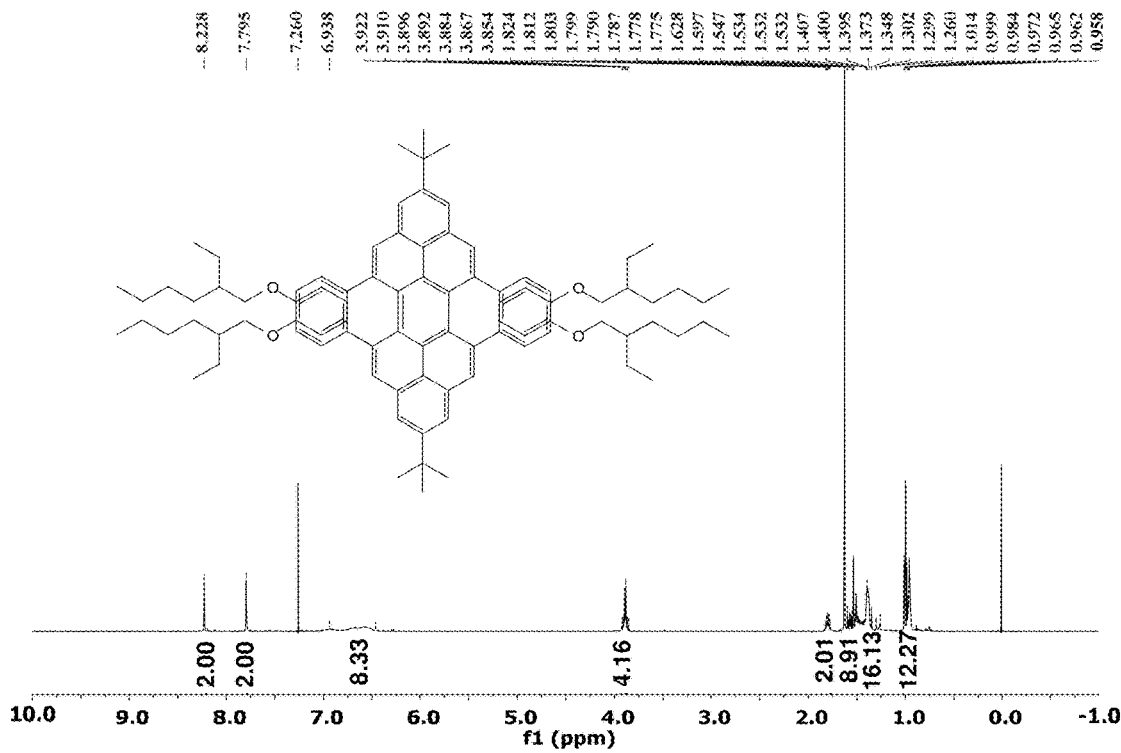
FIGS. 24A and 24B are ¹H-NMR (FIG. 24A) and ¹³C-NMR (FIG. 24B) spectra of a representative chiral peropyrene compound disclosed herein.
Figure 24B:
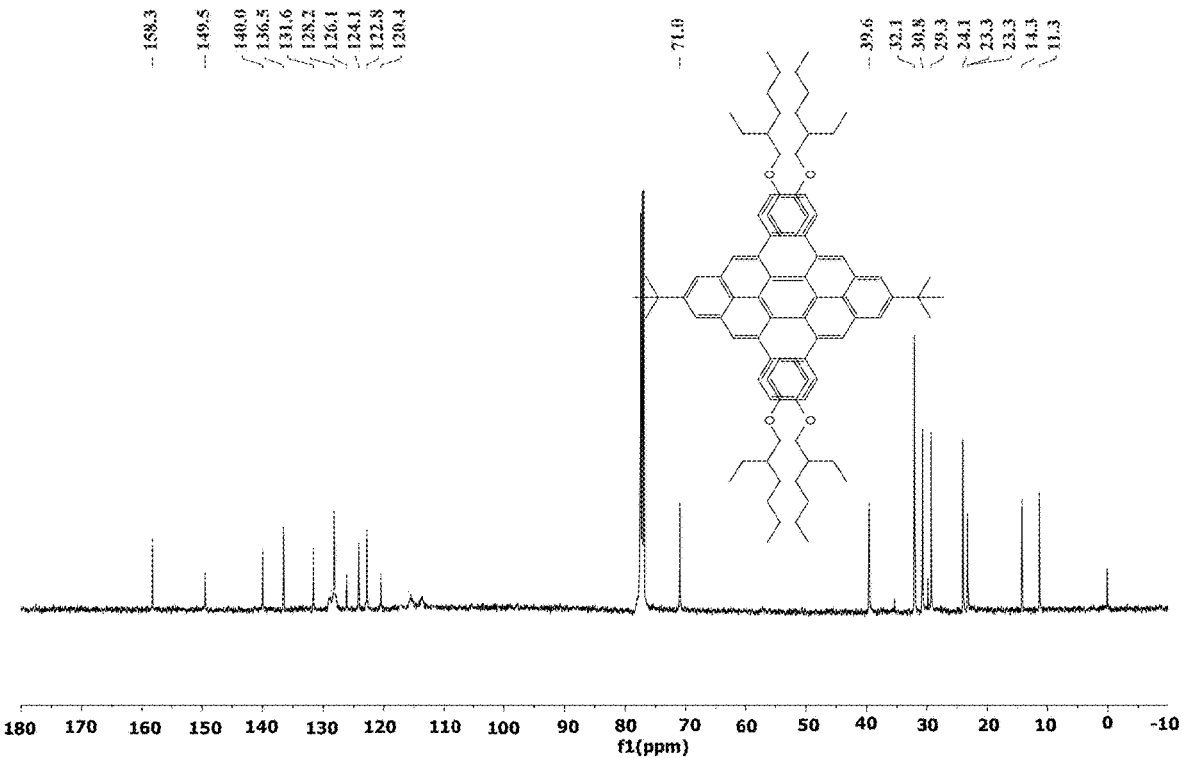

706c (45 mg, 45%). $^1$H NMR (500 MHz, CDCl$_3$) δ 8.23 (s, 2H), 7.79 (s, 2H), 6.46-6.94 (br, 8H), 3.92-3.85 (m, 4H), 1.83-1.78 (m, 2H), 1.63 (s, 9H), 1.52-1.35 (m, 16H), 1.02-0.94 (m, 12H). $^{13}$C NMR (126 MHz, CDCl$_3$) δ 158.28, 149.49, 139.96, 136.52, 131.59, 128.17, 126.12, 124.11, 122.77, 120.44, 70.96, 70.94, 39.59, 39.55, 35.35, 32.07, 30.75, 29.86, 29.33, 24.08, 23.31, 23.28, 14.33, 14.32, 11.32, 11.31. HRMS (ESI, positive) m/z calcd for C$_{90}$H$_{110}$O$_4$ [M]$^+$ 1254.8404, found 1254.8389 (see FIGS. 24A and 24B for NMR spectra).

Figure 51:
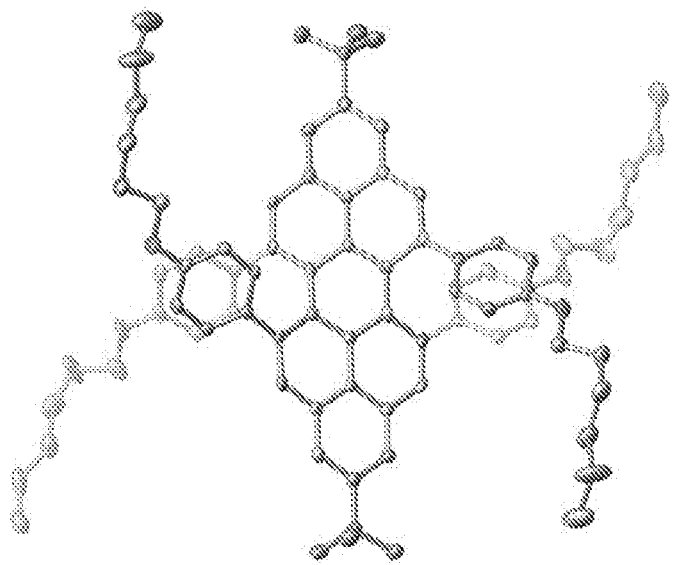
FIG. 51 is an X-ray image of a representative compound.

706d (49 mg, 49%) $^1$H NMR (400 MHz, cdcl$_3$) δ 8.23 (s, 4H), 7.80 (s, 4H), 6.85 (br, 16H), 4.12-3.87 (m, 8H), 1.97-1.74 (m, 8H), 1.74-1.19 (m, 42H), 1.05-0.85 (m, 12H). $^{13}$C NMR (100 MHz, cdcl$_3$) δ 157.99, 149.51, 139.93, 136.56, 131.59, 128.12, 126.09, 124.10, 122.79, 120.43, 68.34, 35.34, 32.06, 31.86, 29.53, 25.95, 22.83, 14.26 (see FIG. 51 for NMR spectrum).

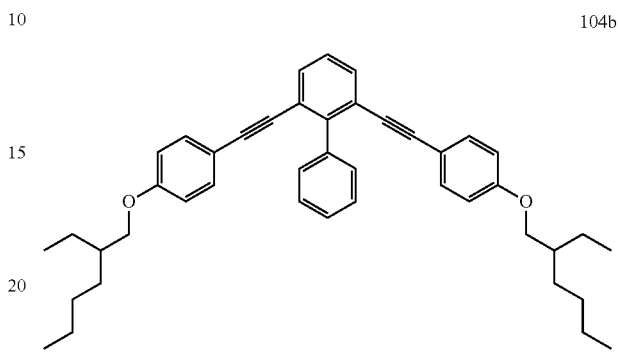

Synthesis of Compound 104b:

To the solution of biphenyl-2,2'-ditrifluoromethanesulfonate (2.25 g, 5 mmol, 1.0 equiv.) and the terminal alkyne (2.54 g, 11 mmol, 2.2 equiv.) in Et$_3$N (30 mL) and DMF (50 mL), were added Pd(PPh$_3$)$_2$Cl$_2$ (35 mg, 0.05 mmol) and CuI (19 mg, 0.1 mmol). The resulting mixture refluxed under N$_2$ atmosphere overnight. The solvent was removed under reduced pressure and the residue was purified by column chromatography (SiO$_2$, hexane/DCM) to afford the corresponding compound 104b (2.38 g, 78%) as yellow oil. $^1$H NMR (500 MHz, CDCl$_3$) δ 7.68 (d, J=7.2 Hz, 2H), 7.59 (d, J=7.7 Hz, 2H), 7.52 (t, J=7.4 Hz, 2H), 7.47 (d, J=7.3 Hz, 1H), 7.31 (t, J=7.7 Hz, 1H), 7.17 (d, J=8.7 Hz, 4), 6.82 (d, J=8.7 Hz, 4H), 3.84 (d, J=5.4 Hz, 4H), 1.77-1.71 (m, 2H), 1.59-1.28 (m, 17H), 0.96 (m, 12H). $^{13}$C NMR (126 MHz, CDCl$_3$) δ 159.53, 145.88, 139.47, 132.89, 131.50, 130.57, 127.52, 127.41, 127.11, 123.65, 115.16, 114.55, 93.26, 87.73, 70.63, 39.42, 30.61, 29.18, 23.95, 23.16, 14.21, 11.21. HRMS (ESI, positive) m/z calcd for C$_{44}$H$_{50}$O$_2$ [M]$^+$ 610.3811, found 610.3814.

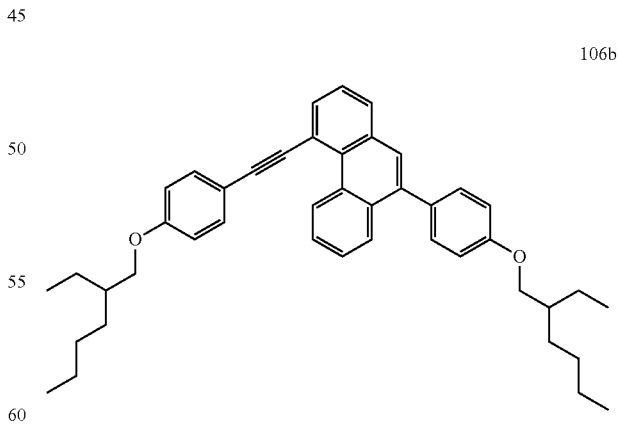

Synthesis of Compound 106b:

In a 250 mL flame-dried flask, compound 104b (61 mg, 0.1 mmol) was dissolved in 150 mL of anhydrous CH$_2$Cl$_2$. Trifluoroacetic acid (0.1 mL, 1.3 mmol) was added and the reaction stirred under nitrogen. After stirring for 1 h at room temperature, the reaction was quenched with saturated NaHCO₃ solution (5.0 mL), washed with H₂O (2×30 mL) and dried (Na₂SO₄). After removal of the solvent under reduced pressure, the residue was purified by column chromatography (SiO₂, hexane/DCM) to afford the corresponding compound 106b (60 mg, 98%) as yellow oil. ¹H NMR (500 MHz, CDCl₃) δ 10.54 (d, J=8.5 Hz, 1H), 8.03 (d, J=8.0 Hz, 1H), 8.00-7.96 (m, 1H), 7.87 (d, J=7.3 Hz, 1H), 7.73 (t, J=7.3 Hz, 1H), 7.69-7.64 (m, 3H), 7.60 (m, 2H), 7.50 (d, J=8.5 Hz, 2H), 7.09 (d, J=8.5 Hz, 2H), 7.00 (d, J=8.7 Hz, 2H), 4.01-3.90 (m, 4H), 1.87-1.77 (m, 2H), 1.64-1.36 (m, 16H), 1.11-0.88 (m, 12H). ¹³C NMR (126 MHz, CDCl₃) δ 159.69, 158.96, 139.10, 134.40, 132.79, 132.75, 132.63, 132.36, 131.24, 131.02, 129.30, 129.25, 127.92, 126.70, 126.52, 125.78, 125.58, 119.53, 115.59, 114.81, 114.39, 95.23, 91.11, 70.66, 70.61, 39.50, 39.39, 30.64, 30.56, 29.18, 29.13, 23.97, 23.90, 23.14, 23.10, 14.17, 14.14, 11.22, 11.17. HRMS (ESI, positive) m/z calcd for $C_{44}H_{50}O_2$ [M]⁺ 610.3811, found 610.3807.

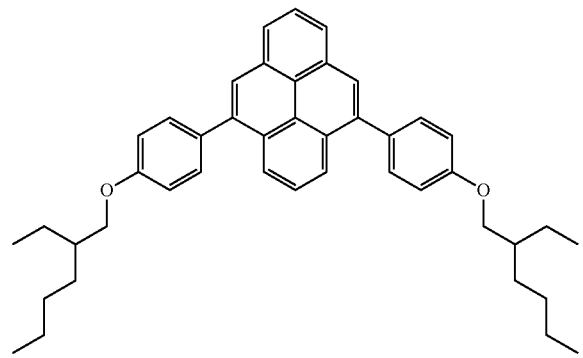

108b

Synthesis of Compound 108b:

Using MSA: In a 250 mL flame-dried flask, compound 104b (61 mg, 0.1 mmol) was dissolved in 150 mL of anhydrous CH₂Cl₂. Methanesulfonic acid (0.065 mL, 1.0 mmol) was added drop wise at 0° C. under nitrogen and then the reaction warmed to room temperature. After stirring for 3 h at room temperature, the reaction was quenched with saturated NaHCO₃ solution (5.0 mL), washed with H₂O (2×30 mL) and dried (Na₂SO₄). After removal of the solvent under reduced pressure, the residue was purified by column chromatography (SiO₂, hexane/DCM) to afford the corresponding compound 108b (52 mg, 85%) as yellow oil.

Procedure c:

Using TFA-TfOH: In a 250 mL flame-dried flask, compound 104b (61 mg, 0.1 mmol) was dissolved in 150 mL of anhydrous CH₂Cl₂. Trifluoroacetic acid (0.1 mL, 1.3 mmol) was added and the reaction stirred under nitrogen. After stirring for 1 h at room temperature (TLC showed no 104b residual), the reaction was cool down to −40° C., 5 drops of triflic acid was added into the reaction mixture. The color changed to dark blue immediately. The reaction was quenched with saturated NaHCO₃ solution (5.0 mL) while TLC showed no intermediate compound residual and the solution was allowed to warm to room temperature slowly, then washed with H₂O (2×30 mL) and dried (Na₂SO₄). After removal of the solvent under reduced pressure, the residue was purified by column chromatography (SiO₂, hexane/DCM) to afford the corresponding compound 108b (55 mg, 90%) as yellow oil. ¹H NMR (500 MHz, CDCl₃) δ 8.29 (d, J=7.9 Hz, 2H), 8.20 (d, J=7.6 Hz, 2H), 8.07-8.03 (m, 3H), 7.92 (t, J=7.9 Hz, 1H), 7.62 (d, J=8.6 Hz, 4H), 7.14 (d, J=8.6 Hz, 4H), 4.03-3.97 (m, 4H), 1.85 (m, 2H), 1.62-1.40 (m, 16H), 1.01 (m, 12H). ¹³C NMR (126 MHz, CDCl₃) δ 159.14, 139.58, 133.20, 131.28, 131.13, 130.95, 127.72, 126.41, 125.57, 124.86, 124.24, 123.73, 114.59, 70.77, 39.65, 30.78, 29.32, 24.11, 23.27, 14.30, 11.35. HRMS (ESI, positive) m/z calcd for $C_{44}H_{50}O_2$ [M]⁺ 610.3811, found 610.3803.

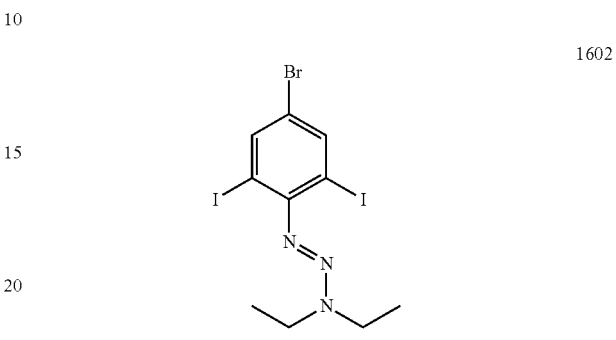

1602

Figure 29A:
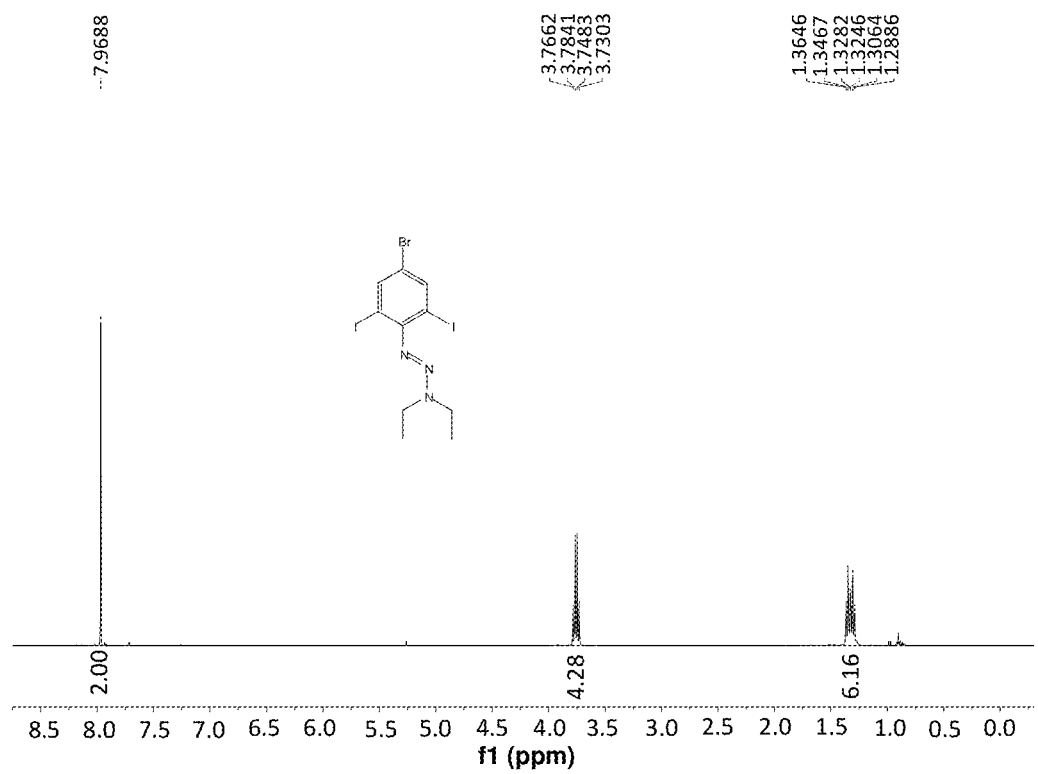
FIGS. 29A and 29B are ¹H-NMR (FIG. 29A) and ¹³C-NMR (FIG. 29B) spectra of a representative intermediate compound used in methods disclosed herein.
Figure 29B:
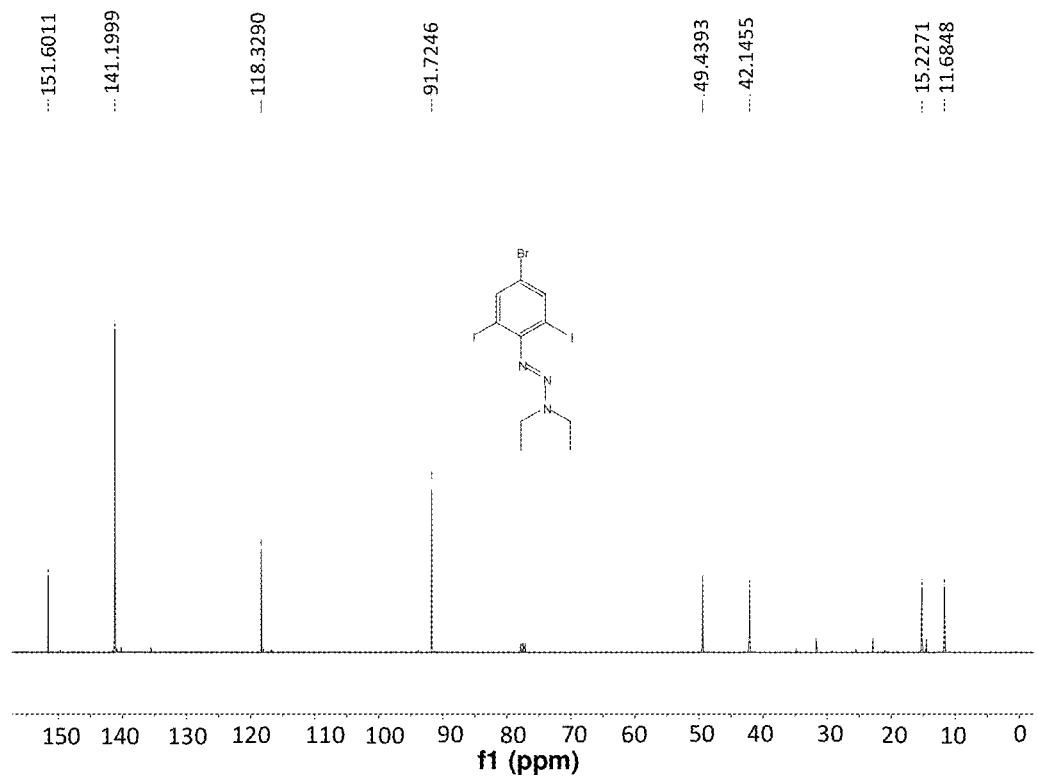

Synthesis of Compound 1602:

A solution of 4-bromo-2,6-diiodoaniline (1600, 4.24 g, 10.0 mmol) in 20.0 mL of 6 M HCl was cooled in an ice bath while a solution of NaNO₂ (0.83 g, 12.0 mmol) in 5 mL of cold water was added dropwise. After the resulting solution of the diazonium salt was stirred at 0° C. for 30 min, this solution was added dropwise to a solution of diethylamine (1.83 g, 25.0 mmol) and K₂CO₃ (6.9 g, 50.0 mmol) in 1:2 CH₃CN/water (30 mL). The reaction mixture was then stirred at 0° C. for 30 min and was extracted with CH₂Cl₂ (2×50 mL). The organic layer was then washed with brine, dried over Na₂SO₄, filtered, and concentrated by evaporation. The crude product was purified by column chromatography (SiO₂, hexane/DCM) to give the pure product 1602 (3.3 g, 65% yield) as brown oil. ¹H NMR (400 MHz, CDCl₃) δ 7.97 (s, 2H), 3.76 (q, J=7.2 Hz, 4H), 1.36-1.29 (m, 6H). ¹³C NMR (101 MHz, CDCl₃) δ 151.60, 141.20, 118.33, 91.72, 49.44, 42.15, 15.23, 11.68. HRMS (TOFMS) calcd for $C_{10}H_{12}BrI_2N_3$ [M]⁺ 506.8304, found 506.8297 (see FIGS. 29A and 29B for NMR spectra).

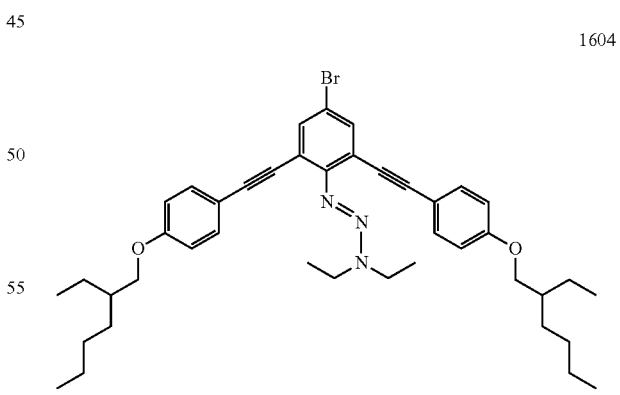

1604

Figure 30A:
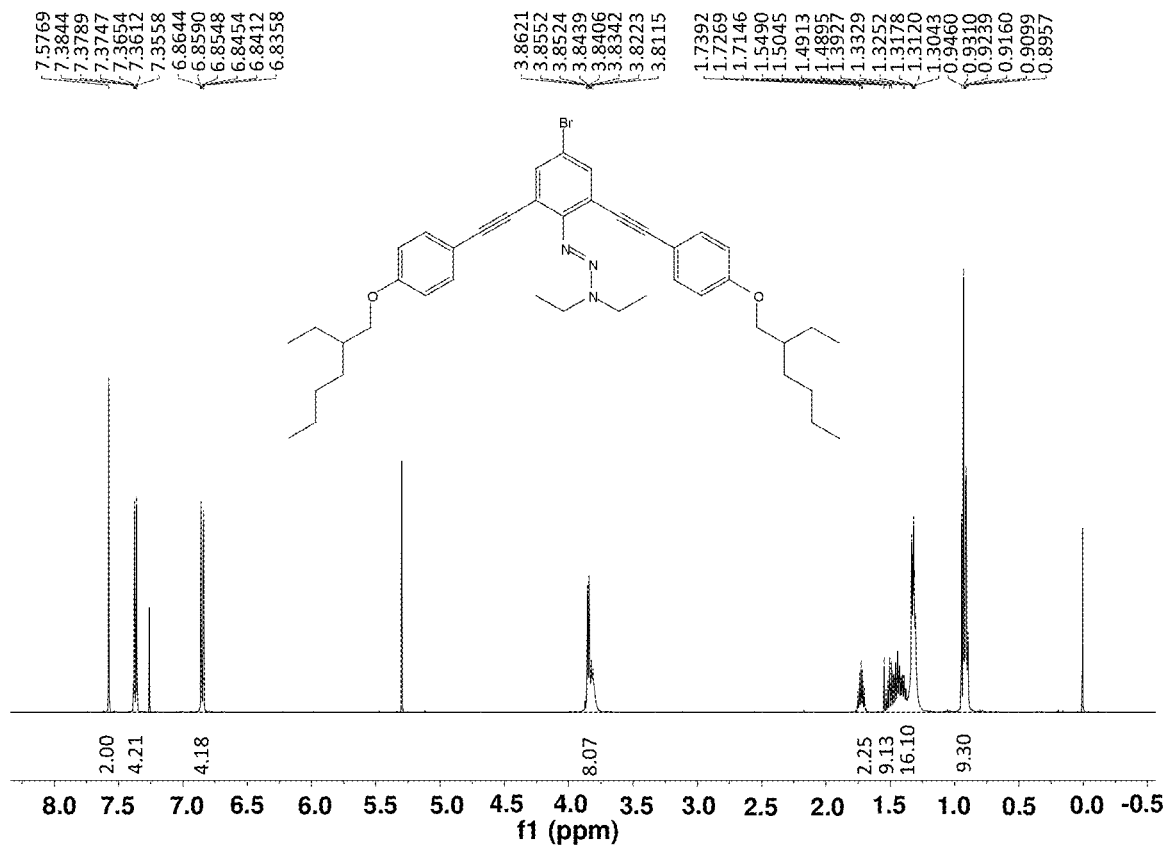
FIGS. 30A and 30B are ¹H-NMR (FIG. 30A) and ¹³C-NMR (FIG. 30B) spectra of a representative intermediate compound used in methods disclosed herein.
Figure 30B:
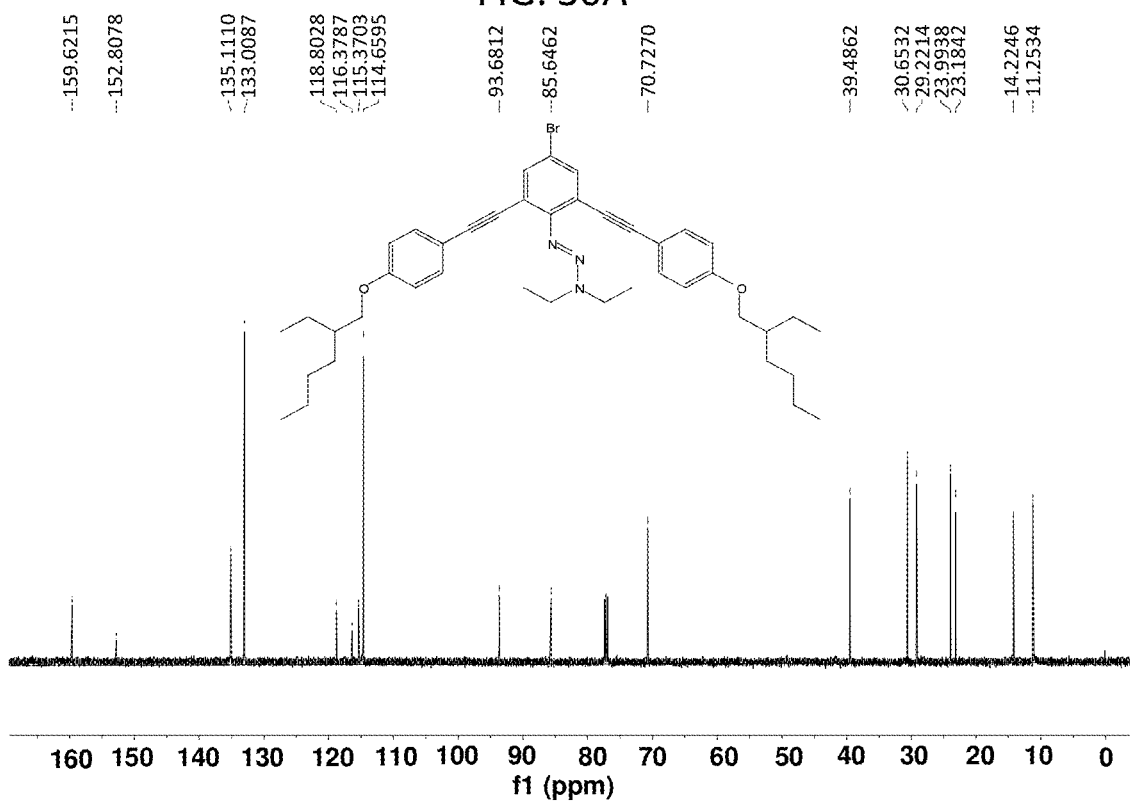

Synthesis of Compound 1604: To the solution of compound 1602 (2.54 g, 5 mmol, 1.0 equiv.) and the terminal alkyne H—CC—Ph-4-OiBu (2.54 g, 11 mmol, 2.2 equiv.) in Et₃N (30 mL) and THF (60 mL), were added Pd(PPh₃)₂Cl₂ (35 mg, 0.05 mmol) and CuI (19 mg, 0.1 mmol). The resulting mixture was stirred under a N₂ atmosphere at room temperature overnight. The ammonium salt was then removed by filtration. The solvent was removed under reduced pressure and the residue was purified by column chromatography (SiO$_2$, hexane/DCM) to afford the corresponding product 1604 (3.2 g, 90%) as brown oil. $^1$H NMR (500 MHz, CDCl$_3$) δ 7.58 (s, 2H), 7.38-7.35 (m, 4H), 6.86-6.84 (m, 4H), 3.86-3.80 (m, 8H), 1.72 (m, 2H), 1.47 (m, 9H), 1.36-1.28 (m, 16H), 0.94-0.91 (m, 9H). $^{13}$C NMR (126 MHz, CDCl$_3$) δ 159.62, 152.81, 135.11, 133.01, 118.80, 116.38, 115.37, 114.66, 93.68, 85.65, 70.73, 39.49, 30.65, 29.22, 23.99, 23.18, 14.22, 11.25. HRMS (TOFMS) calcd for C$_{42}$H$_{54}$BrN$_3$O$_2$ [M]$^+$ 711.3399, found 711.3393 (see FIGS. 30A and 30B for NMR spectra).

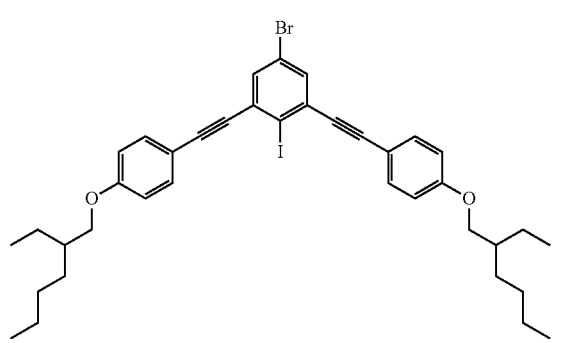

1606

Figure 31A:
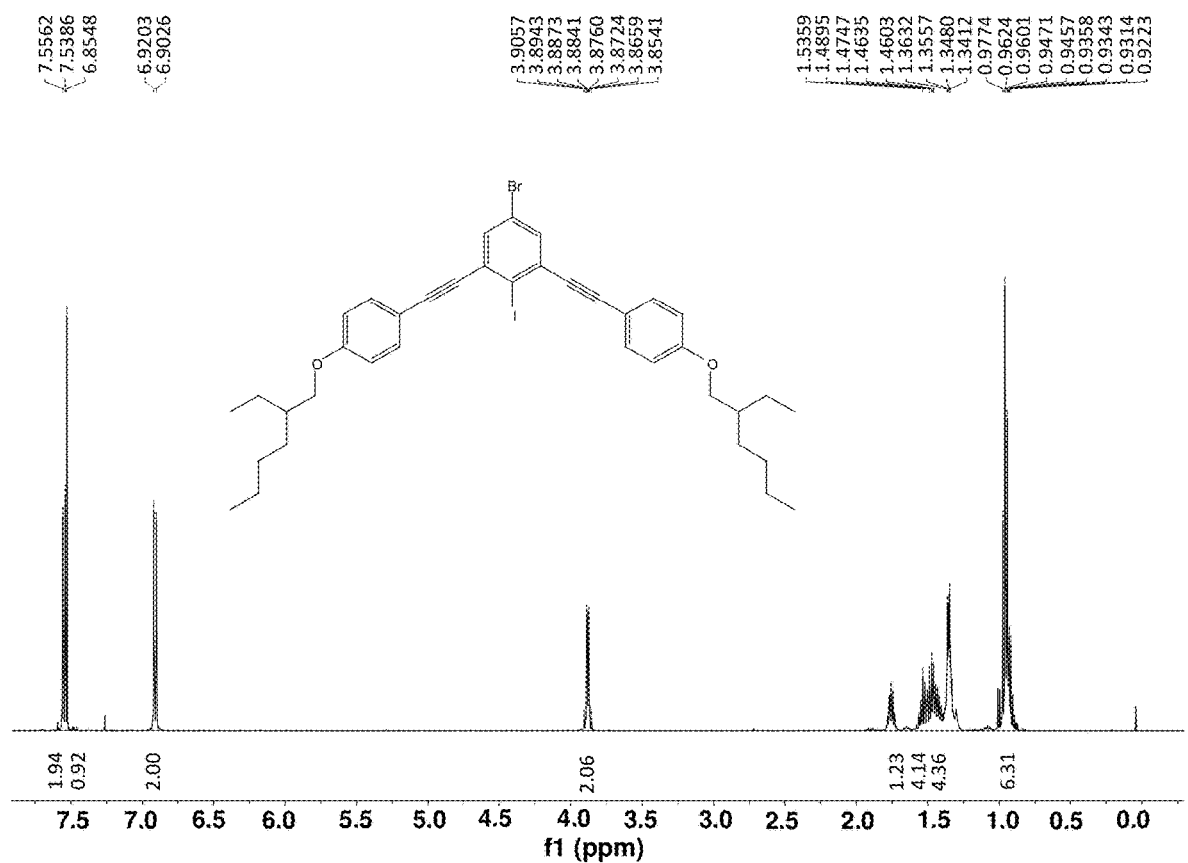
FIGS. 31A and 31B are ¹H-NMR (FIG. 31A) and ¹³C-NMR (FIG. 31B) spectra of a representative intermediate compound used in methods disclosed herein.
Figure 31B:
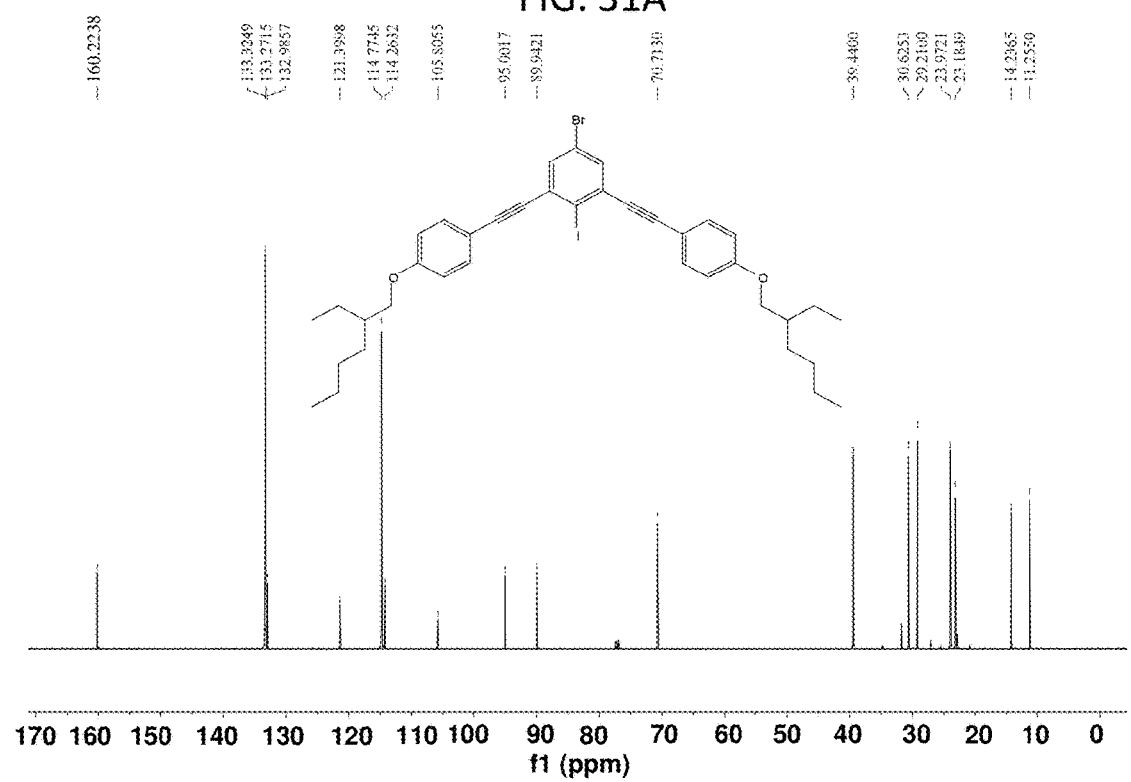

Synthesis of Compound 1606: Triazene 1604 (1.43 g, 2.0 mmol) was dissolved in iodomethane (20.0 mL) and the solution was heated in a sealed heavy-walled tube at 130° C. for 24 h. The reaction mixture was cooled, and the solvent was evaporated to dryness. The residue was then dissolved in CH$_2$Cl$_2$ and the solution was filtered through a short plug of silica gel. After evaporation, the crude product was purified by column chromatography (SiO$_2$, hexane/DCM) to afford the iodide 1606 (1.26 g, 85%) as yellow oil. $^1$H NMR (500 MHz, CDCl$_3$) δ 7.55 (d, J=8.8 Hz, 2H), 7.53 (s, 1H), 6.91 (d, J=8.9 Hz, 2H), 3.91-3.85 (m, 2H), 1.75 (m, 1H), 1.58-1.42 (m, 4H), 1.35 (m, 4H), 0.98-0.91 (m, 6H). $^{13}$C NMR (126 MHz, CDCl$_3$) δ 160.22, 133.32, 133.27, 132.99, 121.40, 114.77, 114.26, 105.81, 95.00, 89.94, 70.71, 39.44, 30.63, 29.21, 23.97, 23.18, 14.24, 11.26. HRMS (TOFMS) calcd for C$_{38}$H$_{44}$BrIO$_2$ [M]$^+$ 738.1569, found 738.1561 (See FIGS. 31A and 31B for NMR spectra).

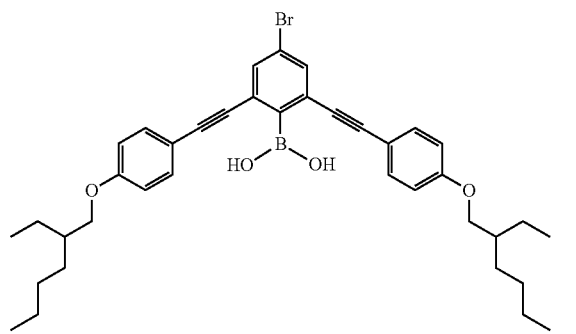

1608

Figure 32A:
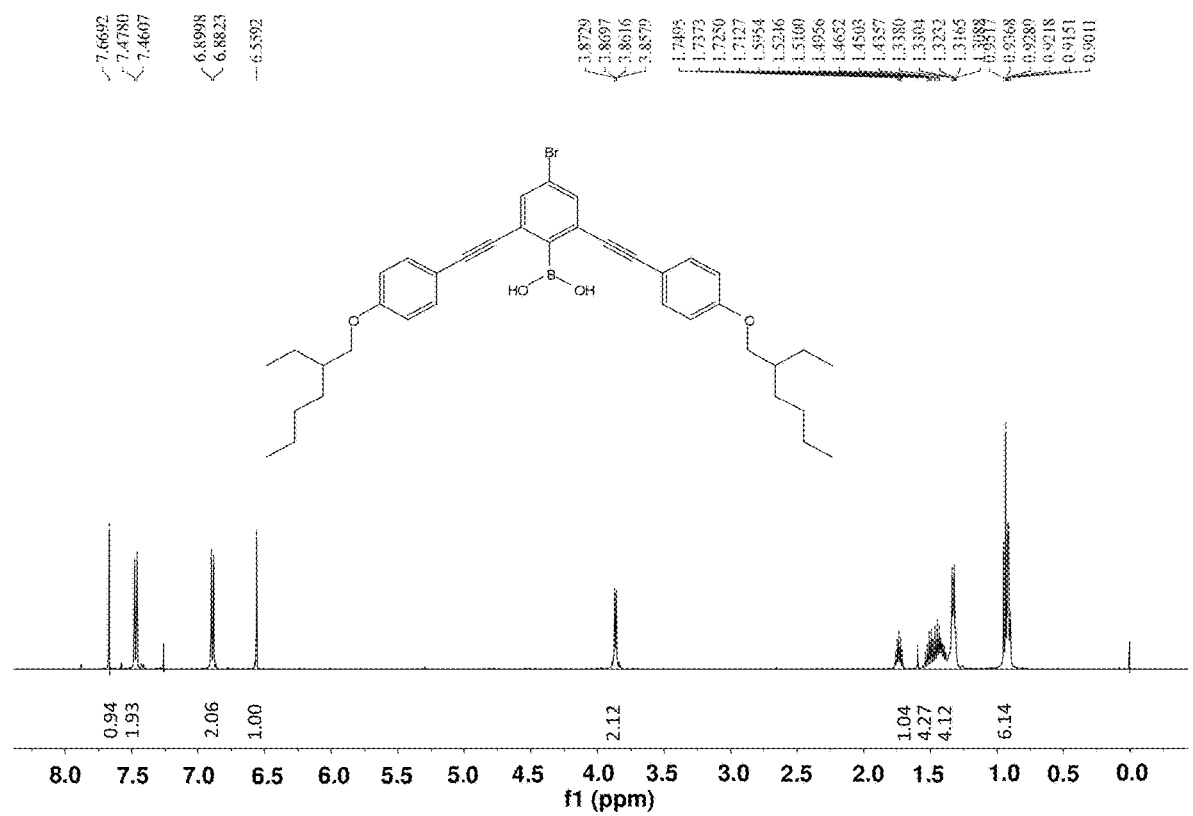
FIGS. 32A and 32B are ¹H-NMR (FIG. 32A) and ¹³C-NMR (FIG. 32B) spectra of a representative intermediate compound used in methods disclosed herein.
Figure 32B:
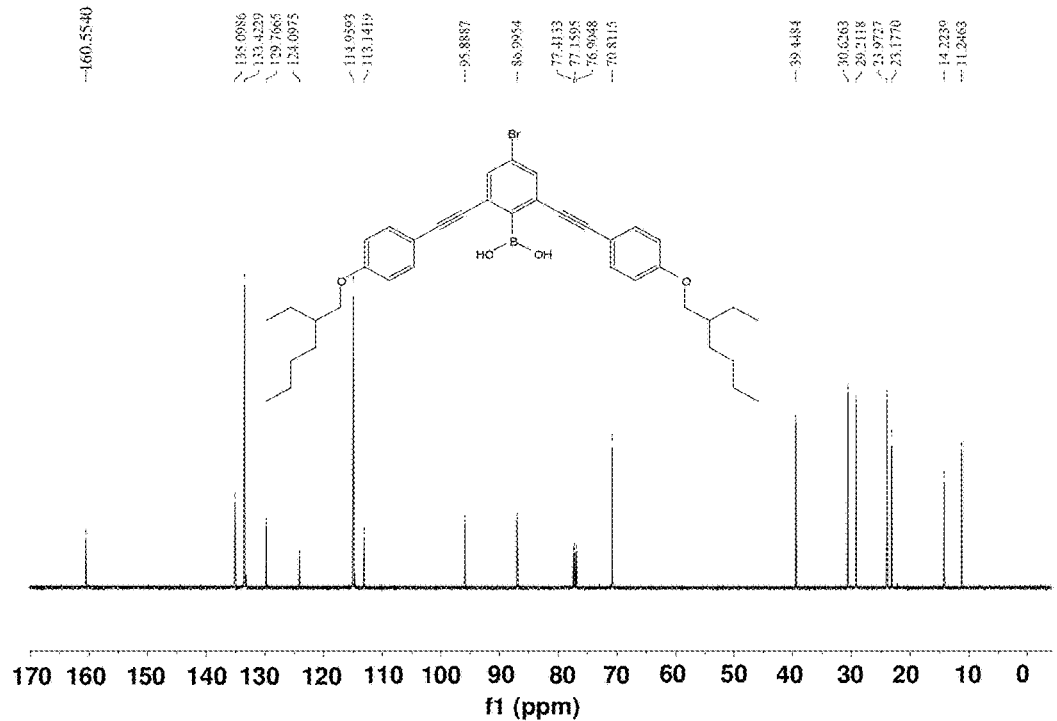

Synthesis of Compound 1608: To a solution of aryl iodide 1606 (1.11 g, 1.5 mmol, 1.0 equiv.) in THF (20 mL) at −78° C. was added a solution of n-butyllithium in hexanes (0.6 mL, 1.5 mmol, 2.5 M, 1.0 equiv.). After stirring for 30 min at −78° C., trimethyl borate (0.16 g, 1.5 mmol, 1.0 equiv.) was added; the reaction removed from the cooling bath and allowed to warm. Upon reaching room temperature the reaction was quenched by the addition of 2 N HCl, then extracted with DCM. The extract was washed with water, dried with Na$_2$SO$_4$, filtered and concentrated in vacuo. The crude residue was purified by column chromatography (SiO$_2$, hexane/DCM) to afford the aryl boronic acid 1608 (0.76 g, 77%) as yellow oil. $^1$H NMR (500 MHz, CDCl$_3$) δ 7.67 (s, 1H), 7.47 (d, J=8.7 Hz, 2H), 6.89 (d, J=8.7 Hz, 2H), 6.56 (s, 1H), 3.87 (dd, J=5.7, 1.7 Hz, 2H), 1.74 (dd, J=12.2, 6.1 Hz, 1H), 1.53-1.41 (m, 4H), 1.33 (m, 4H), 0.96-0.91 (m, 6H). $^{13}$C NMR (126 MHz, CDCl$_3$) δ 160.55, 135.10, 133.42, 129.77, 124.10, 114.96, 113.14, 95.89, 87.00, 77.41, 77.16, 76.90, 70.81, 39.45, 30.63, 29.21, 23.97, 23.18, 14.22, 11.25. MALDI-TOF calcd for C$_{38}$H$_{46}$BBrO$_4$ [M+K+H]$^+$ 696.2, found 696.7 (see FIGS. 32A and 32B for NMR spectra).

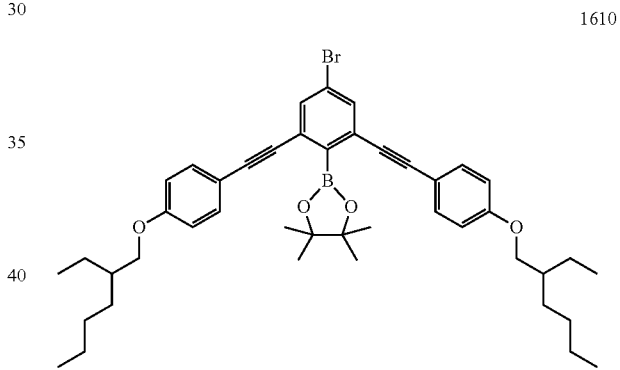

1610

Figure 33A:
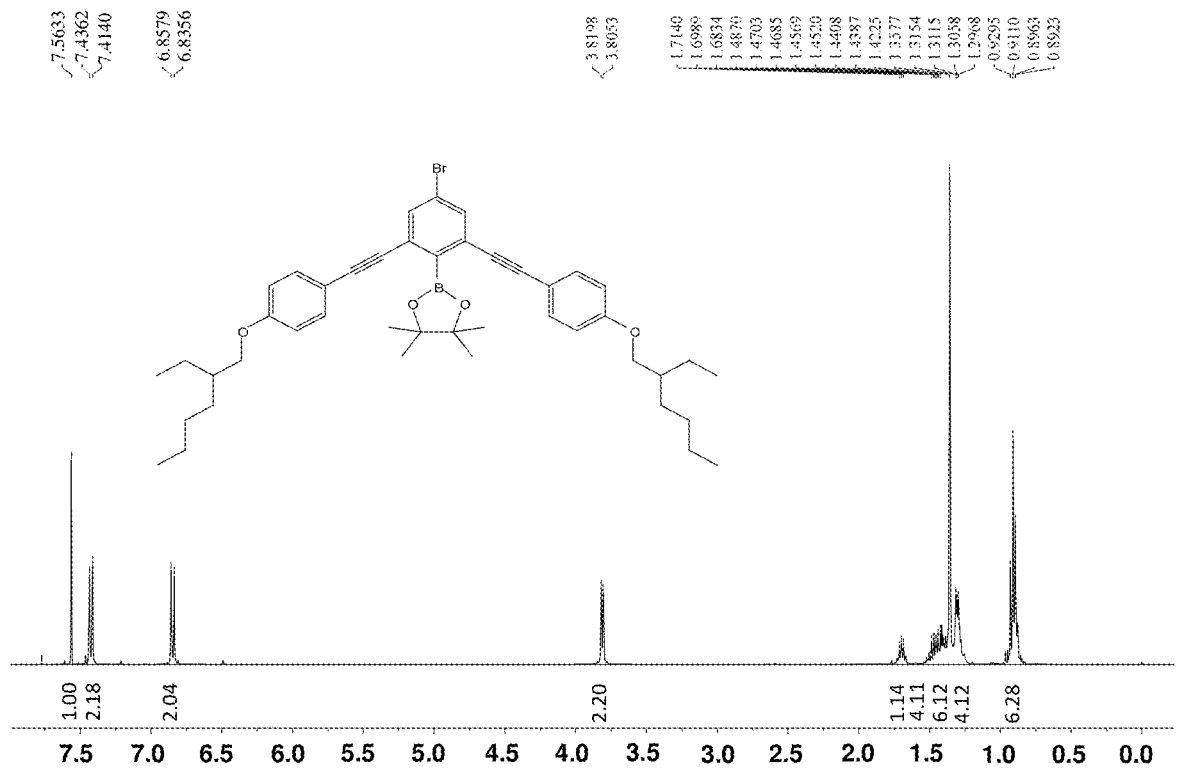
FIGS. 33A and 33B are ¹H-NMR (FIG. 33A) and ¹³C-NMR (FIG. 33B) spectra of a representative boronic ester compound used in methods disclosed herein.
Figure 33B:
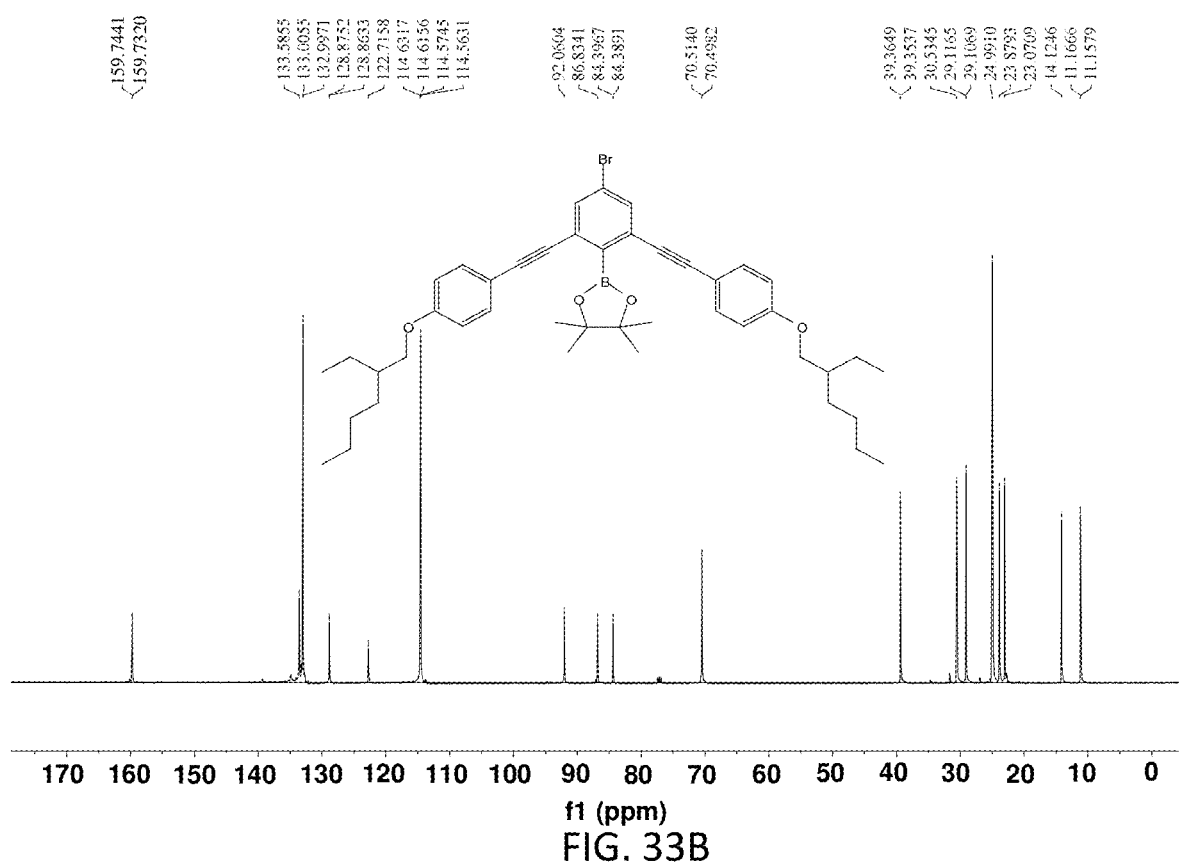

Synthesis of Compound 1610: The aryl boronic acid 1608 (0.66 g, 1.0 mmol) and pinacol (0.14 g, 1.2 mmol) were dissolved in toluene (20.0 mL) and the solution was heated at 120° C. for 2 h. The solvent was evaporated to dryness and the residue was purified by flash column chromatography (SiO$_2$, hexane/DCM) to afford the monomer 1610 (0.69 g, 94%) as yellow oil that solidified upon standing. $^1$H NMR (400 MHz, CDCl$_3$) δ 7.56 (s, 1H), 7.43 (d, J=8.9 Hz, 2H), 6.85 (d, J=8.9 Hz, 2H), 3.81 (d, J=5.8 Hz, 2H), 1.73-1.67 (m, 1H), 1.45 (m, 4H), 1.36 (s, 6H), 1.31 (m, 4H), 0.91 (m, 6H). $^{13}$C NMR (126 MHz, CDCl$_3$) δ 159.74, 159.73, 133.59, 133.01, 133.00, 128.88, 128.86, 122.72, 114.63, 114.62, 114.57, 114.56, 92.06, 86.83, 84.40, 84.39, 70.51, 70.50, 39.36, 39.35, 30.53, 29.12, 29.11, 24.99, 23.88, 23.07, 14.12, 11.17, 11.16. MALDI-TOF calcd for C$_{44}$H$_{56}$BBrO$_4$ [M]$^+$ 738.3, found 738.7 (see FIGS. 33A and 33B for NMR spectra).

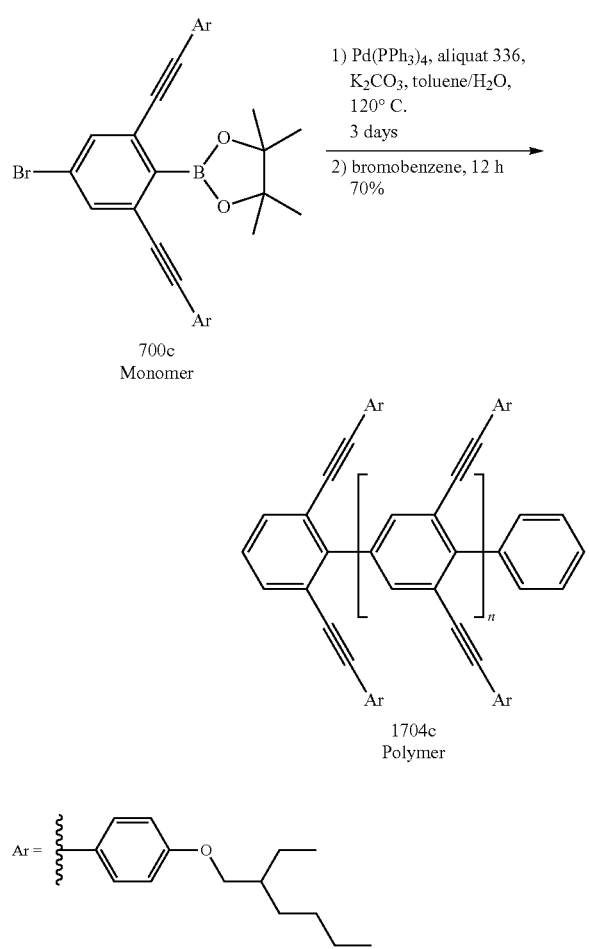

700c
Monomer

1704c
Polymer

Ar = [4-(2-ethylhexyloxy)phenyl group structure]

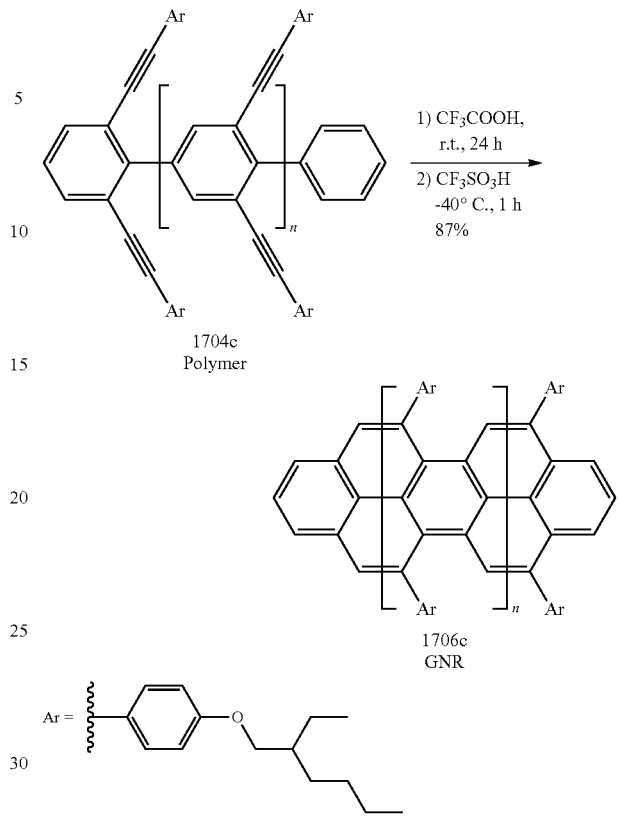

1704c
Polymer

1706c
GNR

Ar = [4-(2-ethylhexyloxy)phenyl group structure]

Figure 34A:
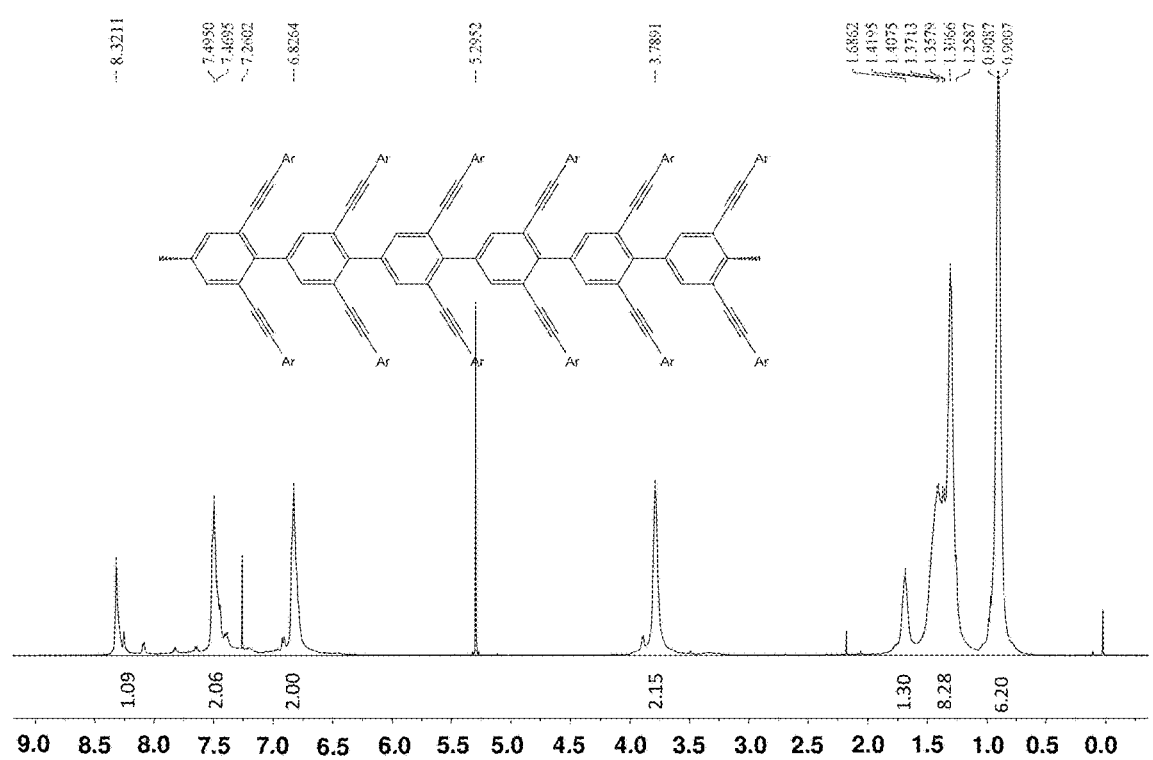
FIGS. 34A and 34B are ¹H-NMR (FIG. 34A) and ¹³C-NMR (FIG. 34B) spectra of a representative polymer precursor used in methods disclosed herein.
Figure 34B:
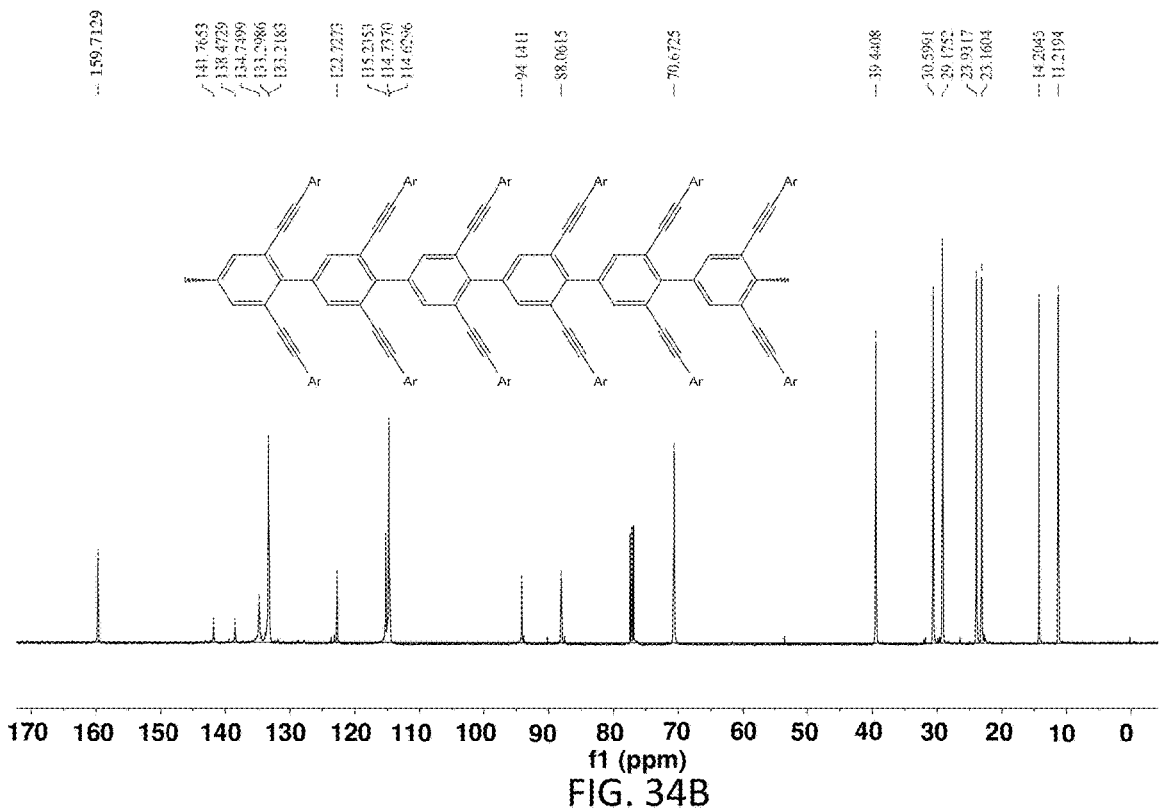

Synthesis of polymer 1704c: To a degassed solution of monomer 700c (100 mg, 0.135 mmol), $K_2CO_3$ (2 M/H2O, 1.5 mL, 3 mmol) and Aliquat® 336 (1 drop) in toluene (8 mL) in a Schlenk tube, $Pd(PPh_3)_4$ (4.5 mg, 0.004 mmol) was added quickly. The mixture was stirred at 120° C. for 3 days. Then, a degassed solution of bromobenzene (16 mg, 0.1 mmol) in toluene (0.5 mL) was added into the reaction mixture via a syringe and the reaction was refluxed for another 12 hours. The solution was cooled to room temperature and precipitated into cold methanol (200 mL). The resulting solid was collected by filtration and purified by column chromatography ($SiO_2$, hexane/DCM) to afford the desired polymer 1704c (70 mg, 70%) as orange solid. $^1$H NMR (500 MHz, $CDCl_3$) δ 8.32 (br, 1H), 7.48 (br, 2H), 6.83 (br, 2H), 3.79 (br, 2H), 1.69 (br, 1H), 1.35 (br, 8H), 0.90 (br, 6H). $^{13}$C NMR (126 MHz, $CDCl_3$) δ 159.71, 141.77, 138.47, 134.75, 133.30, 133.22, 122.73, 115.24, 114.74, 114.63, 94.14, 88.06, 70.67, 39.44, 30.60, 29.18, 23.93, 23.16, 14.20, 11.22 (see FIGS. 34A and 34B for NMR spectra).

Synthesis of nanostructures 1706c: In a 250 mL flame-dried flask, polymer 1704c (50.0 mg) was dissolved in 200 mL of anhydrous $CH_2Cl_2$. To the degassed solution was added trifluoroacetic acid (0.5 mL). After stirring at room temperature for 24 h, the reaction was cool down to −40° C., and then 5 drops of triflic acid was added. The reaction was quenched with saturated $NaHCO_3$ solution (5.0 mL) after 1 h and the solution was warmed to room temperature, washed with $H_2O$ (2×10 mL) and dried ($Na_2SO_4$). After removal of the solvent under reduced pressure, the residue was re-dissolved in $CH_2Cl_2$ (1.0 mL) and precipitated into cold methanol (200 mL). The resulting solid was collected by filtration washed with methanol and dried in vacuum to give nanostructures 1706c as a black solid (47 mg, 94%). $^1$H NMR (500 MHz, $CDCl_3$) δ 8.42-5.75 (br, 5H), 4.39-3.13 (br, 2H), 2.56-0.24 (br, 11H). $^{13}$C NMR (126 MHz, $CDCl_3$) δ 159.69, 159.13, 133.27, 130.32, 114.89, 107.77, 77.41, 77.16, 76.91, 70.81, 39.63, 34.18, 31.60, 30.76, 29.86, 29.37, 28.88, 28.14, 28.00, 26.04, 24.99, 24.07, 23.27, 14.30, 11.36.

Figure 41:
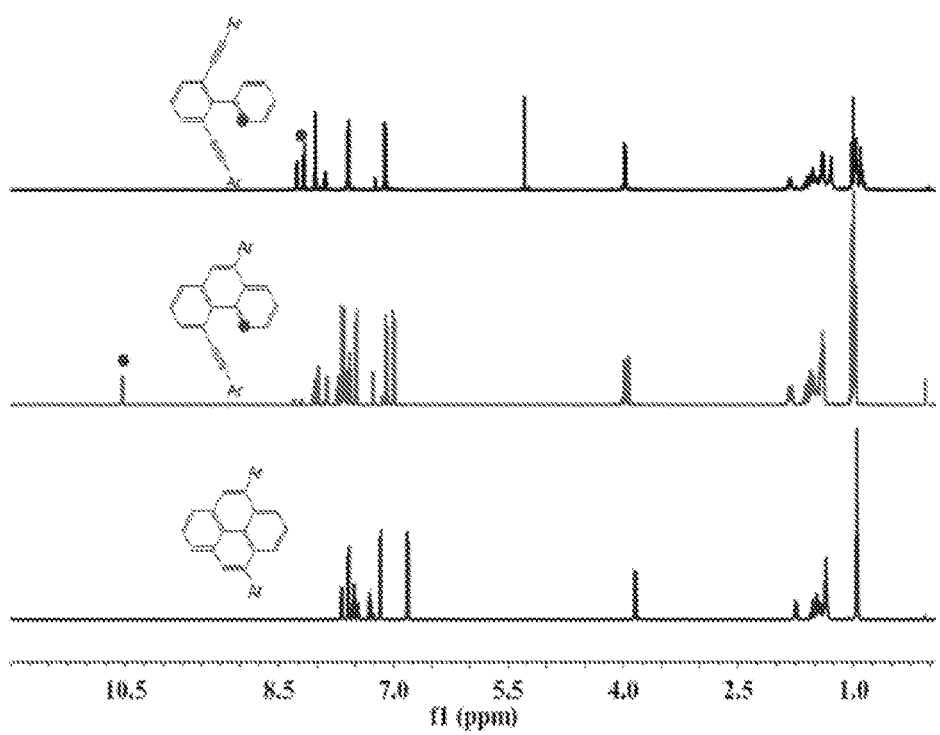
FIG. 41 is a combined ¹H-NMR spectrum of pyrene intermediates and compounds disclosed herein.
Figure 42:
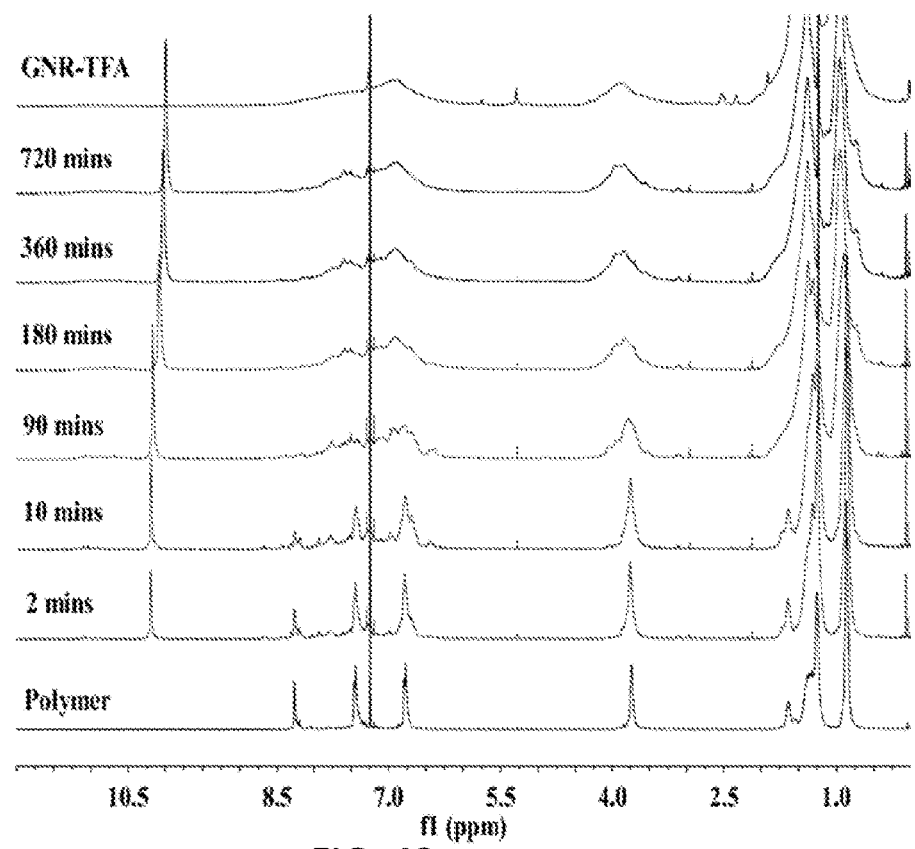
FIG. 42 is a combined ¹H-NMR spectrum of polymer and polymer products disclosed herein.
Figure 43:
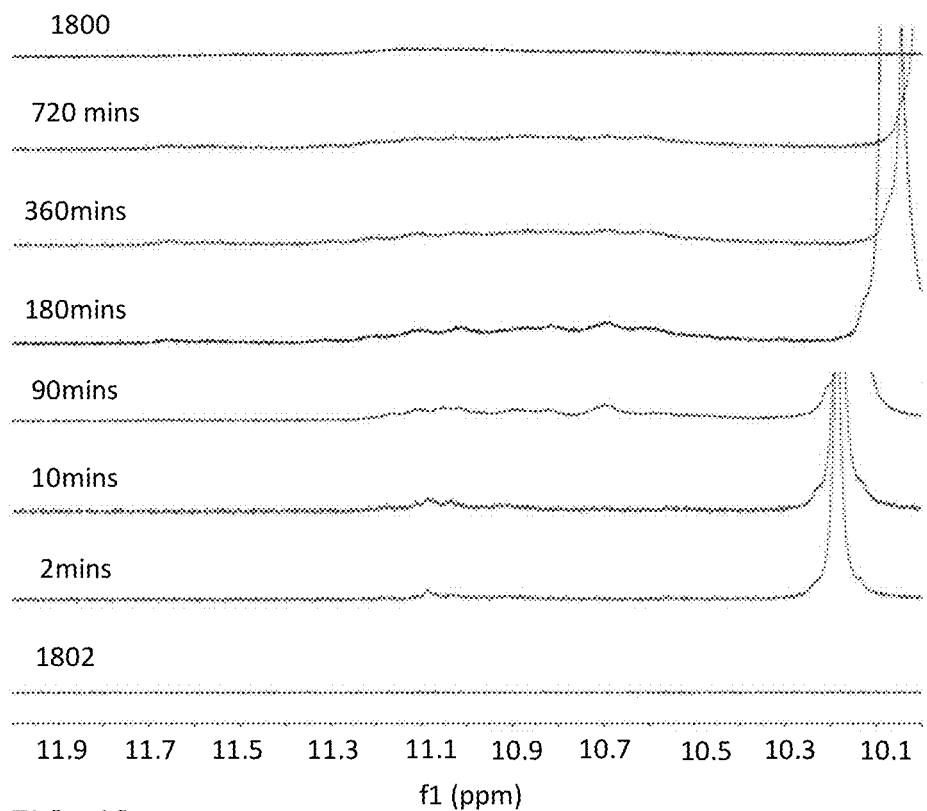
FIG. 43 is a combined ¹H-NMR spectrum of polymer and polymer products disclosed herein.
Figure 44:
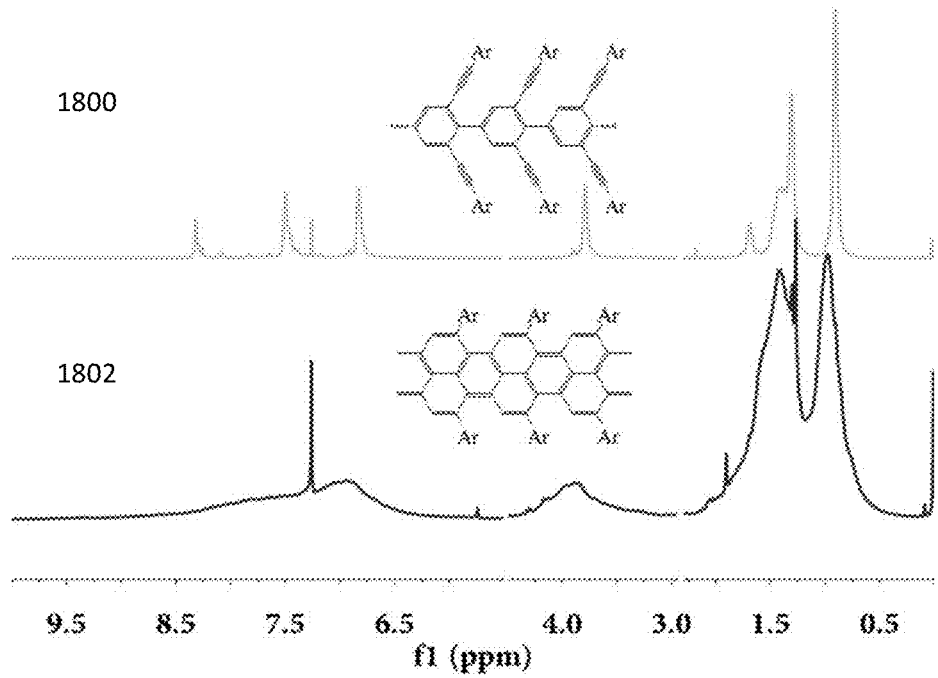
FIG. 44 is a combined ¹H-NMR spectrum of a representative polymer and a representative polymer product disclosed herein.

By comparing the $^1$H-NMR spectra (FIG. 41) for 104b, 106b and 108b (see above for structures), the signal located around 10.5 ppm should be attributed to the proton pointing to the alkyne in the mono-cyclized product, and the signal disappeared in the bis-cyclized product (pyrene derivative). So, the appearance and disappearance of this signal can be a strong evidence of the efficiency of the alkyne benzannulation. Based on this, a small scale reaction was performed in the NMR tube, using deuterated trifluoroacetic acid (TFA-d) as Lewis acid to promote the reaction. First, a NMR tube was charged with polymer 8 (2 mg, 0.004 mmol (based on repeat unit molecular weight)) and CDCl3 (0.6 mL). After complete dissolution, the first NMR test of just polymer was taken. The second NMR test was run immediately after TFA-d (15 μl, 0.2 mmol) was added, and the next NMR tests were run one by one after certain time to record the reaction (FIG. 42). The results showed that some new signals appeared and strengthened increasingly in the region of 10.5~11.3 ppm after addition of TFA-d, which indicated the formation of mono-cyclized products; as time goes on, these signals weakened gradually but still a little residual even after 12 hours. The other parallel reaction with more TFA (100 equiv.) was run at the same time and quenched after 12 hours. The NMR of GNR-TFA showed trace signals around 10.5-11.0 ppm, which mean the vast majority of alkynes participated in the cyclization reaction (FIG. 43). Comparing the $^1$H NMR of polymer and GNR, all the peaks were relatively sharp before cyclization, which is due to the flexibility of the polymer (FIG. 44). After cyclization, because of the rigidity of GNRs, the peaks became broad and weak, which also indicated the happening of cyclization.

Figure 45:
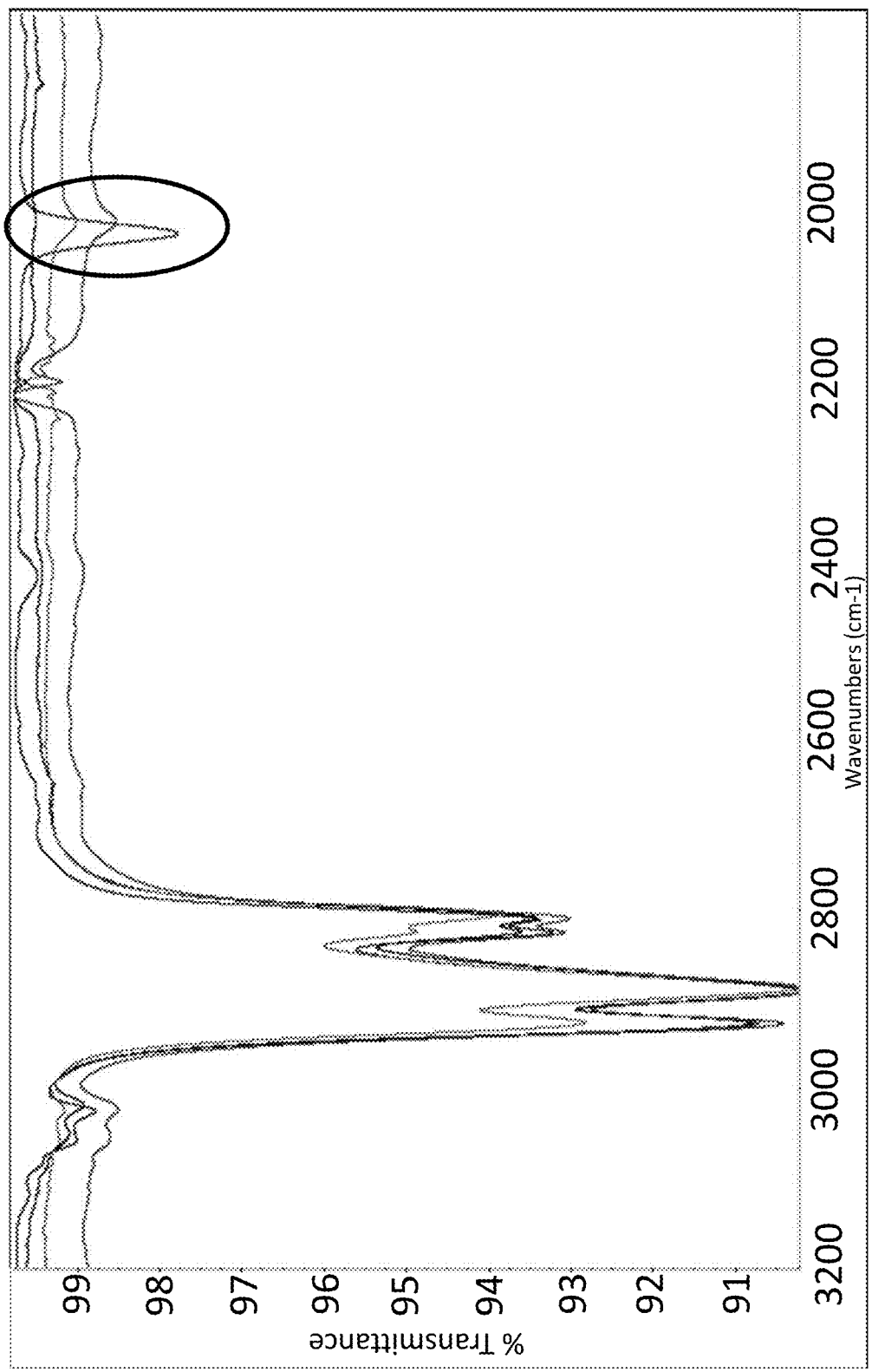
FIG. 45 is a combined IR spectrum of polymer and polymer products disclosed herein.

FIG. 45 provides partial IR spectra of polymer (blue) and polymer promoted by TFA (red), MSA (light blue) and TFA-TfOH (green), separately. The yellow oval shape marked the infrared absorption peak of alkyne. The polymer exhibited strong absorption of alkyne in this area (blue), while the polymer promoted by TFA and MSA showed weak absorption (red and light blue). The polymer promoted by TFA-TfOH did not show any absorption of alkyne in this area, which indicated that no alkyne residue in this nanoribbon, confirming that TFA-TfOH promoted full cyclization of alkynes.

Figure 46:
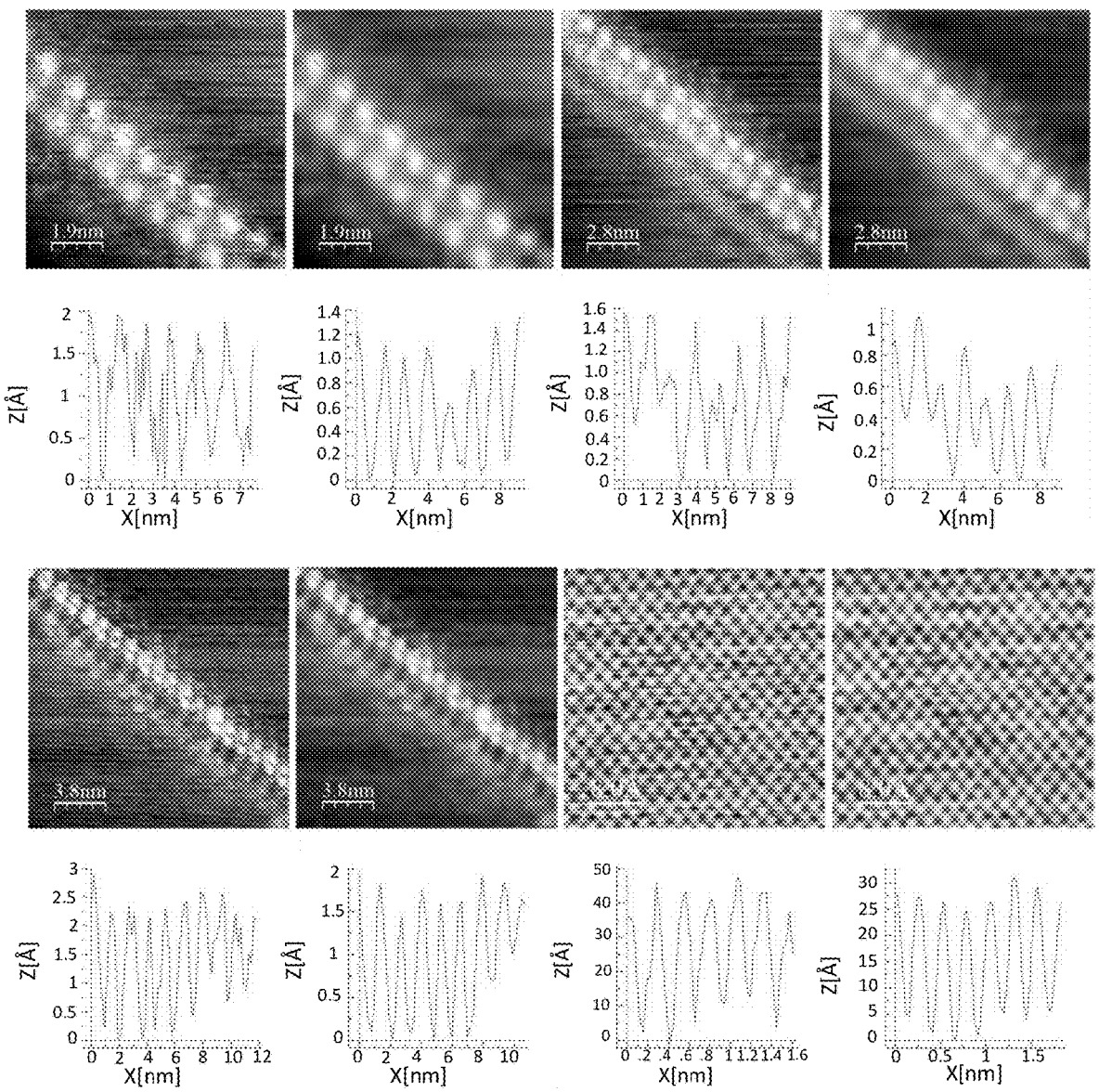
FIG. 46 shows STM images of compounds disclosed herein.

As shown in FIG. 46, due to the intramolecular H . . . H repulsion between the phenyl groups at the backbone of the molecules results in a significant tilt of the latter with respect to the surface. The line profiles referring to the GNR (lower part of corresponding STM images) show that the distance between two phenyl groups on the same side is around 1.25 nm before calibration. Using atomic resolution STM image of HOPG as standard, it was found that the distance between two carbon atoms was 0.27 nm on HOPG, which is greater than the theoretical value (0.25 nm). According to this, the distance between two phenyl groups on the same side is around 1.16 nm after calibration, which is corresponded closely to the longitudinal length of three repeating units (around 0.9 nm). The internal alkyl chains on the edge of the GNR could be also observed (FIG. 47).

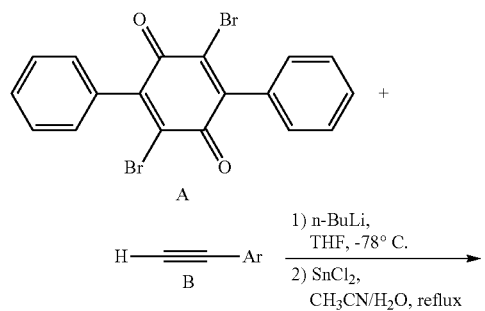

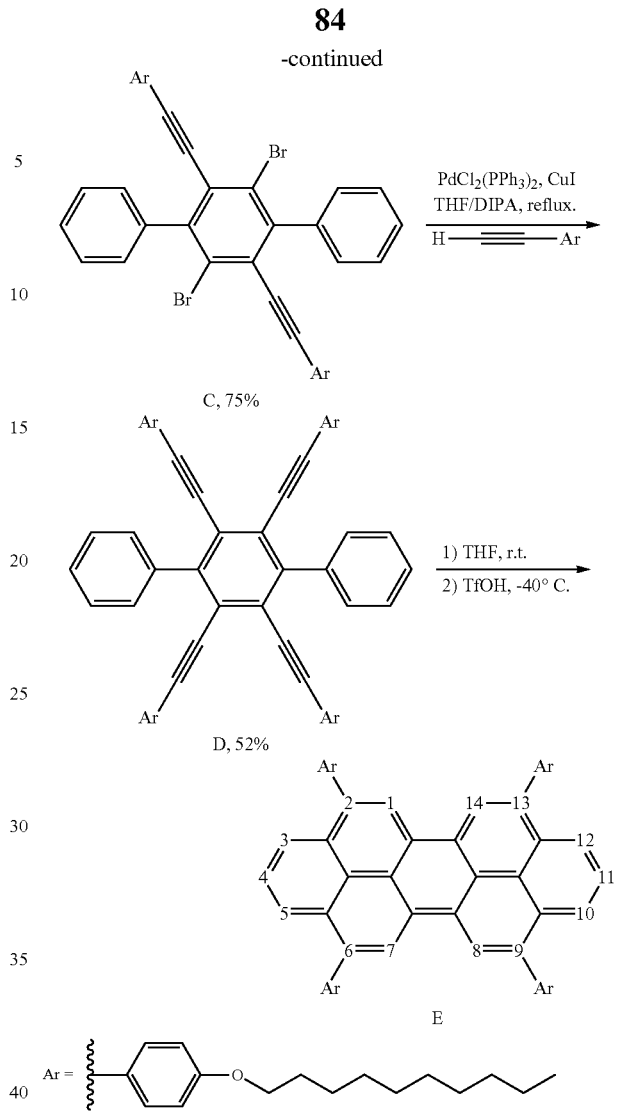

Synthesis of Compound C: To a solution of terminal alkyne compound B (1.85 g, 7.2 mmol) in THF (50 mL) at −78° C. under nitrogen atmosphere was added a hexane solution of n-BuLi (2.5 M, 2.8 mL, 7 mmol). After being stirred at −78° C. for 30 min and then at 0° C. for 15 min, to the resulting solution at 0° C. was added compound A (1.0 g, 2.4 mmol). After being stirred at room temperature for 16 h, the reaction mixture was quenched with saturated NH$_4$Cl and then extracted with CH$_2$Cl$_2$. The organic layer was washed with H$_2$O and brine and dried over Na$_2$SO$_4$. After evaporation of solvents, the residue was dissolved in CH$_3$CN (100 mL). SnCl$_2$ (1.3 g, 7 mmol) and 2 mL of water was added and the reaction refluxed for 12 hrs. After evaporation of solvents, the residue was purified by column chromatography (SiO$_2$, hexane/DCM) to afford the compound C (1.62 g, 75%). $^1$H NMR (500 MHz, CDCl$_3$) δ 7.55-7.47 (m, 6H), 7.43-7.39 (m, 4H), 7.01 (d, J=8.4 Hz, 4H), 6.75 (d, J=8.4 Hz, 4H), 3.92 (t, J=6.6 Hz, 4H), 1.79-1.73 (m, 4H), 1.45-1.28 (m, 28H), 0.90 (t, J=6.9 Hz, 6H). $^{13}$C NMR (126 MHz, CDCl$_3$) δ 159.80, 145.53, 141.10, 133.22, 129.67, 128.20, 128.05, 126.71, 125.13, 114.56, 100.63, 87.62, 68.21, 32.04, 29.70, 29.69, 29.51, 29.46, 29.28, 26.13, 22.83, 14.27.

Synthesis of compound D: To a mixture of B (155 mg, 0.6 mmol), C (180 mg, 0.2 mmol), PdCl$_2$(PPh3)$_2$ (14.3 mg, 0.02 mmol), CuI (7.6 mg, 0.04 mmol), and PPh₃ (10.4 mg, 0.04 mmol) under nitrogen atmosphere was added Et₃N (30 mL). The resulting mixture was stirred at refluxing temperature for 24 h. After evaporation of Et3N, the residue was purified by column chromatography (SiO₂, hexane/DCM) to afford the compound D (130 mg, 52%). $^1$H NMR (500 MHz, CDCl₃) δ 7.65 (d, J=7.1 Hz, 4H), 7.54-7.44 (m, 6H), 7.13 (d, J=8.7 Hz, 8H), 6.76 (d, J=8.7 Hz, 8H), 3.93 (t, J=6.6 Hz, 8H), 1.79-1.73 (m, 8H), 1.45-1.26 (m, 56H), 0.88 (t, J=6.8 Hz, 12H). $^{13}$C NMR (101 MHz, CDCl₃) δ 159.49, 145.31, 139.51, 133.06, 130.50, 127.75, 127.60, 124.90, 115.43, 114.60, 98.70, 87.47, 68.22, 32.05, 29.72, 29.70, 29.53, 29.47, 29.32, 26.16, 22.84, 14.27.

1-Bromo-4-tert-butylbenzene (213 mg, 1 mmol), 2,6-diynylphenyl borate (1 mmol) and K₂CO₃ (276 mg, 2 mmol) were dissolved in THF (60 mL) and water (10 mL) solution. Pd(PPh₃)₄ (58 mg, 0.05 mmol) was added to the solution before degassing the mixture via bubbling nitrogen for 30 min. The resulting mixture was stirred under a N₂ atmosphere at 80° C. for 24 h. After the reaction was complete, the mixture was diluted with DCM, washed with H₂O and dried over Na₂SO₄. The solvent was removed under reduced pressure and the residue was purified by column chromatography to give compound 902.

902a: 86% yield. $^1$H NMR (500 MHz, cdcl₃) δ 7.59 (s, 2H), 7.55 (d, J=8.3 Hz, 2H), 7.50 (d, J=8.3 Hz, 2H), 7.13 (d, J=8.7 Hz, 4H), 6.78 (d, J=8.7 Hz, 4H), 3.79 (s, 6H), 1.44 (s, 9H), 1.40 (s, 9H). $^{13}$C NMR (125 MHz, cdcl₃) δ 159.59, 150.07, 149.92, 143.60, 136.56, 133.24, 132.95, 130.31, 128.71, 124.28, 123.18, 115.75, 114.17, 113.93, 92.40, 88.72, 55.40, 34.81, 34.68, 31.65, 31.33.

902b: $^1$H NMR (400 MHz, cdcl₃) δ 7.60 (s, 2H), 7.57 (d, J=8.4 Hz, 2H), 7.52 (d, J=8.4 Hz, 2H), 7.13 (d, J=8.7 Hz, 4H), 6.78 (d, J=8.8 Hz, 4H), 3.94 (t, J=6.5 Hz, 4H), 1.81-1.75 (m, 4H), 1.45 (s, 9H), 1.42 (s, 9H), 1.36 (m, 12H), 0.93 (t, J=6.1 Hz, 6H). $^{13}$C NMR (100 MHz, cdcl₃) δ 159.19, 150.02, 149.87, 143.58, 136.59, 132.92, 130.32, 128.63, 124.26, 123.22, 115.47, 114.45, 92.53, 88.64, 68.15, 34.80, 34.67, 31.71, 31.65, 31.32, 29.30, 25.83, 22.74, 14.17.

902c: $^1$H NMR (400 MHz, cdcl₃) δ 7.61 (s, 2H), 7.58 (d, J=8.6 Hz, 2H), 7.53 (d, J=8.6 Hz, 2H), 7.14 (d, J=8.9 Hz, 4H), 6.79 (d, J=8.9 Hz, 4H), 3.94 (t, J=6.6 Hz, 4H), 1.82-1.75 (m, 4H), 1.39 (dd, J=47.3, 14.7 Hz, 46H), 0.93 (t, J=6.9 Hz, 6H). $^{13}$C NMR (100 MHz, cdcl₃) δ 159.16, 149.98, 149.84, 143.57, 136.58, 132.90, 130.33, 128.60, 124.25, 123.22, 115.45, 114.42, 92.53, 88.63, 68.11, 34.78, 34.65, 32.05, 31.65, 31.31, 29.72, 29.70, 29.53, 29.47, 29.33, 26.15, 22.84, 14.28.

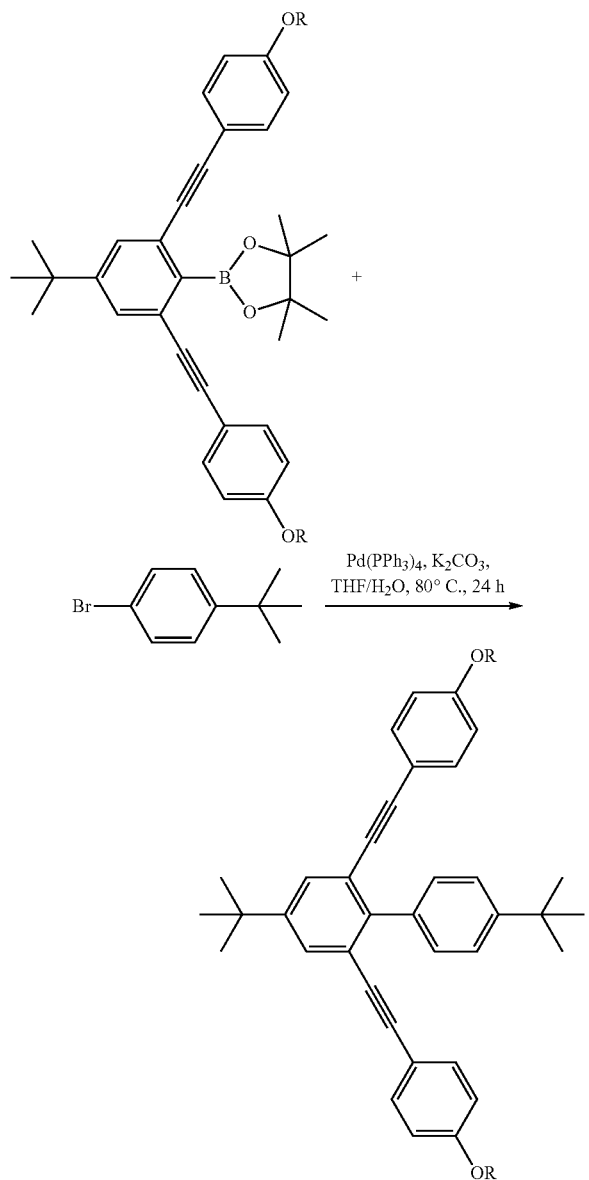

902a: R = CH₃
902b: R = C₆H₁₃
902c: R = C₁₀H₂₁

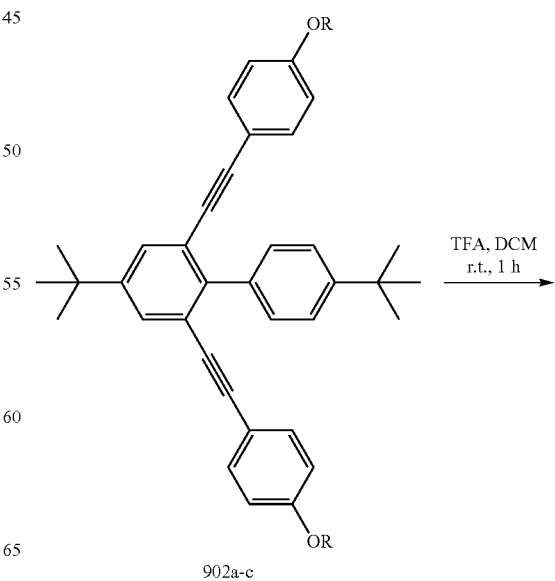

902a-c

-continued

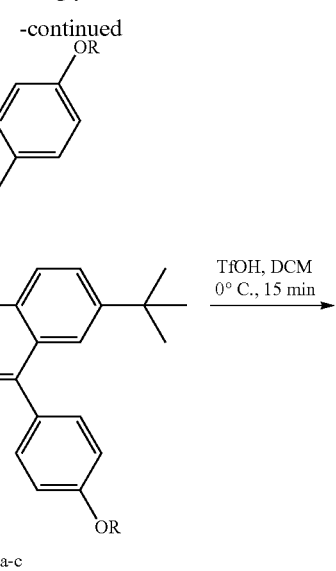

902'a-c

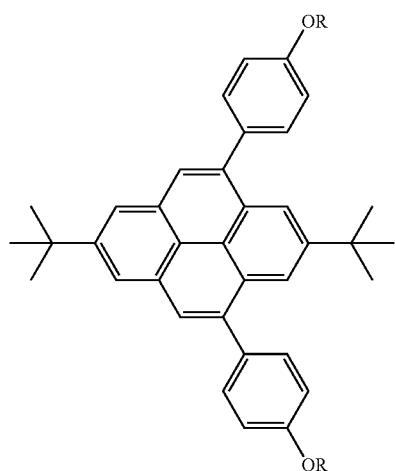

904a: R = CH₃
904b: R = C₆H₁₃
904c: R = C₁₀H₂₁

902': In a 100 mL flame-dried flask, compound 900 (53 mg, 0.1 mmol) was dissolved in 50 mL of anhydrous CH$_2$Cl$_2$. Trifluoroacetic acid (570 mg, 5 mmol) was added and the reaction stirred under nitrogen. After stirring for 1 h at room temperature (TLC showed no residual 900), the reaction was quenched with saturated NaHCO$_3$ solution (5 mL). The solution was then washed with H$_2$O (2×30 mL) and dried (Na$_2$SO$_4$). After removal of the solvent under reduced pressure, the residue was purified by column chromatography (SiO$_2$, DCM) to afford the compound 902' (52 mg, 99%) as yellow solid. $^1$H NMR (400 MHz, cdcl$_3$) δ 10.37 (d, J=9.0 Hz, 1H), 8.00 (d, J=2.2 Hz, 1H), 7.98 (d, J=2.2 Hz, 1H), 7.83 (d, J=2.2 Hz, 1H), 7.75 (dd, J=9.0, 2.2 Hz, 1H), 7.70-7.67 (m, 2H), 7.64 (s, 1H), 7.53-7.49 (m, 2H), 7.10-7.05 (m, 2H), 7.02-6.98 (m, 2H), 3.93 (s, 3H), 3.89 (s, 3H), 1.48 (s, 9H), 1.38 (s, 9H). $^{13}$C NMR (126 MHz, cdcl$_3$) δ 159.86, 159.07, 149.10, 148.20, 139.17, 133.44, 133.23, 132.99, 132.73, 132.62, 132.01, 131.27, 131.17, 129.09, 128.41, 127.20, 126.12, 125.80, 123.81, 122.63, 118.91, 116.25, 114.36, 114.16, 113.95, 113.83, 94.24, 91.84, 55.51, 55.48, 35.03, 34.67, 31.47, 31.43.

904a: In a 200 mL flame-dried flask, the 902' (52 mg, 0.1 mmol) was dissolved in 100 mL of anhydrous CH$_2$Cl$_2$. 1 drop of triflic acid was added into the reaction mixture at 0° C., and the color of the solution changed to dark blue immediately. After stirring for 15 min at 0° C., the reaction was quenched with saturated NaHCO$_3$ solution (5 mL). The solution was then washed with H$_2$O (2×30 mL) and dried (Na$_2$SO$_4$). After removal of the solvent under reduced pressure, the residue was purified by column chromatography (SiO$_2$, hexane/DCM 3:1) to afford the compound 904a (27 mg, 52%) as yellow solid. Single crystal was obtained by recrystallizing from a chloroform and methanol solution of 904a via slow evaporation at room temperature. $^1$H NMR (500 MHz, cdcl$_3$) δ 8.30 (s, 2H), 8.19 (s, 2H), 7.98 (s, 2H), 7.64 (d, J=8.7 Hz, 4H), 7.13 (d, J=8.7 Hz, 4H), 3.96 (s, 6H), 1.59 (s, 9H), 1.39 (s, 9H). $^{13}$C NMR (100 MHz, cdcl$_3$) δ 159.15, 149.16, 148.06, 139.44, 133.84, 131.28, 130.58, 130.54, 127.91, 123.71, 121.95, 121.24, 113.95, 55.53, 35.60, 35.36, 32.09, 31.95.

One-step synthesis of Compound 904: In a 100 mL flame-dried flask, compound 900 (0.1 mmol) was dissolved in 50 mL of anhydrous CH$_2$Cl$_2$. Trifluoroacetic acid (570 mg, 5 mmol) was added and the reaction stirred under nitrogen. After stirring for 1 h at room temperature (TLC showed no residual 1), the reaction was cool down to 0° C., then 1 drop of triflic acid was added. After stirring for 15 min at 0° C., the reaction was quenched with saturated NaHCO$_3$ solution (5 mL). The solution was then washed with H$_2$O (2×30 mL) and dried (Na$_2$SO$_4$). After removal of the solvent under reduced pressure, the residue was purified by column chromatography (SiO$_2$, hexane/DCM 3:1) to afford the compound 904.

904b: $^1$H NMR (400 MHz, cdcl$_3$) δ 8.34 (s, 2H), 8.21 (s, 2H), 8.01 (s, 2H), 7.65 (d, J=8.6 Hz, 4H), 7.13 (d, J=8.7 Hz, 4H), 4.12 (t, J=6.6 Hz, 4H), 1.94-1.86 (m, 4H), 1.61 (s, 9H), 1.58-1.40 (m, 21H), 1.00-0.94 (m, 6H). $^{13}$C NMR (100 MHz, cdcl$_3$) δ 158.73, 149.11, 148.02, 139.53, 133.63, 131.24, 130.61, 130.55, 127.87, 123.73, 121.96, 121.90, 121.27, 114.51, 68.29, 35.60, 35.35, 32.09, 31.96, 31.84, 29.55, 26.00, 22.82, 14.24.

904c: $^1$H NMR (400 MHz, cdcl$_3$) δ 8.32 (s, 2H), 8.19 (s, 2H), 7.99 (s, 2H), 7.63 (d, J=8.7 Hz, 4H), 7.12 (d, J=8.8 Hz, 4H), 4.11 (t, J=6.6 Hz, 4H), 1.96-1.81 (m, 4H), 1.59 (s, 9H), 1.53-1.09 (m, 37H), 0.92 (t, J=6.8 Hz, 6H). $^{13}$C NMR (101 MHz, cdcl$_3$) δ 158.73, 149.11, 148.02, 139.52, 133.63, 131.24, 130.61, 130.55, 129.53, 127.87, 123.72, 121.90, 121.27, 114.51, 68.31, 35.60, 35.35, 32.09, 31.96, 29.80, 29.77, 29.65, 29.60, 29.52, 26.33, 22.87, 14.30.

Compound 1000 was prepared as described for compound 900, using compound 1000' and 2-bromopyrene as starting material.

1000a: $^1$H NMR (400 MHz, cdcl$_3$) δ 8.54 (s, 2H), 8.27 (s, 2H), 8.12 (m, 4H), 7.73 (s, 2H), 7.00 (d, J=8.9 Hz, 4H), 6.62 (d, J=9.0 Hz, 4H), 3.69 (s, 6H), 1.64 (s, 9H), 1.48 (s, 9H). $^{13}$C NMR (100 MHz, cdcl$_3$) δ 159.53, 150.36, 149.13, 142.82, 136.39, 132.88, 131.40, 130.29, 129.42, 127.78, 127.58, 127.53, 124.11, 123.59, 123.21, 122.17, 115.35, 113.92, 92.40, 88.64, 55.28, 35.43, 34.78, 32.14, 31.36.

1000b: $^1$H NMR (400 MHz, cdcl$_3$) δ 8.59 (s, 2H), 8.30 (s, 2H), 8.14 (m, 4H), 7.77 (s, 2H), 7.02 (d, J=8.9 Hz, 4H), 6.63 (d, J=8.9 Hz, 4H), 3.83 (t, J=6.6 Hz, 4H), 1.83-1.59 (m, 13H), 1.54-1.44 (m, 9H), 1.35 (m, 12H), 0.91 (t, J=6.9 Hz, 6H). $^{13}$C NMR (100 MHz, cdcl$_3$) δ 159.13, 150.32, 149.09, 142.77, 136.41, 132.84, 131.39, 130.28, 129.35, 127.79, 127.61, 127.51, 124.10, 123.64, 123.21, 122.15, 115.06, 114.43, 92.55, 88.57, 68.02, 35.40, 34.76, 32.13, 31.65, 31.36, 29.20, 25.75, 22.69, 14.14.

1000c: $^1$H NMR (400 MHz, cdcl$_3$) δ 8.61 (s, 2H), 8.14 (m, 7H), 7.75 (s, 2H), 7.00 (d, J=8.7 Hz, 4H), 6.62 (d, J=8.7 Hz, 4H), 3.82 (t, J=6.5 Hz, 4H), 1.74-1.63 (m, 4H), 1.53-1.25 (m, 37H), 0.91 (t, J=6.9 Hz, 6H). $^{13}$C NMR (100 MHz, cdcl$_3$) δ 159.17, 150.41, 142.61, 136.80, 132.85, 131.56, 130.48, 129.40, 127.90, 127.80, 127.33, 125.93, 124.98, 124.90, 124.16, 123.65, 115.04, 114.44, 92.59, 88.52, 68.05, 34.77, 32.03, 31.75, 31.36, 29.67, 29.48, 29.45, 29.25, 26.08, 22.82, 14.26.

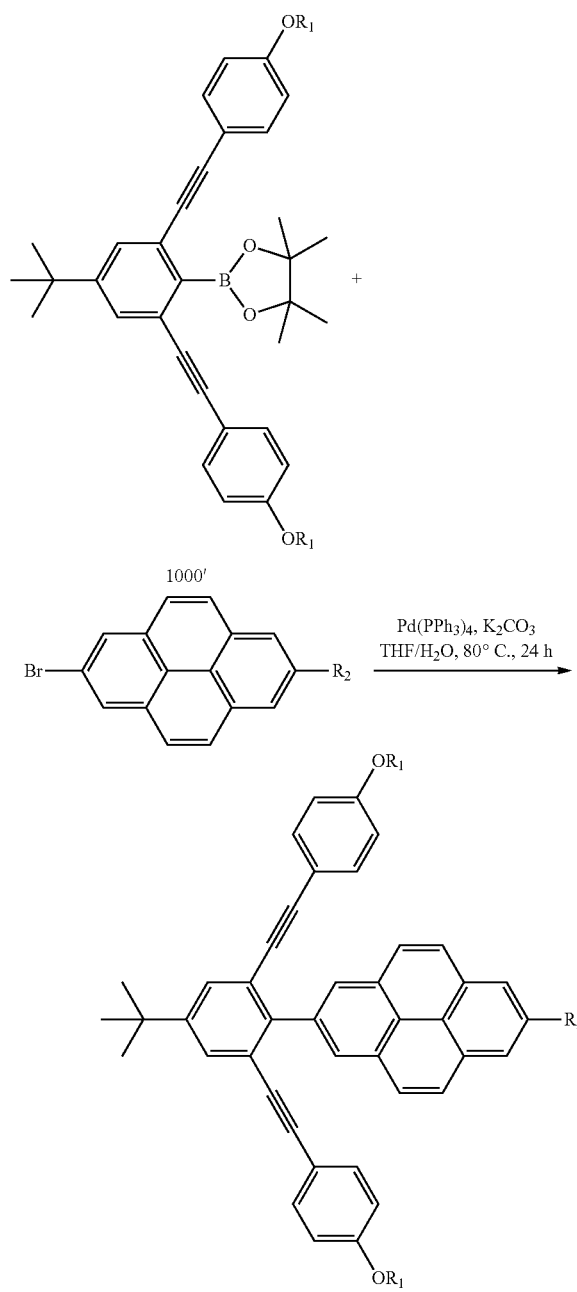

1000a: R$_1$ = CH$_3$, R$_2$ = tert-butyl
1000b: R$_1$ = C$_6$H$_{13}$, R$_2$ = tert-butyl
1000c: R$_1$ = C$_{10}$H$_{21}$, R$_2$ = H

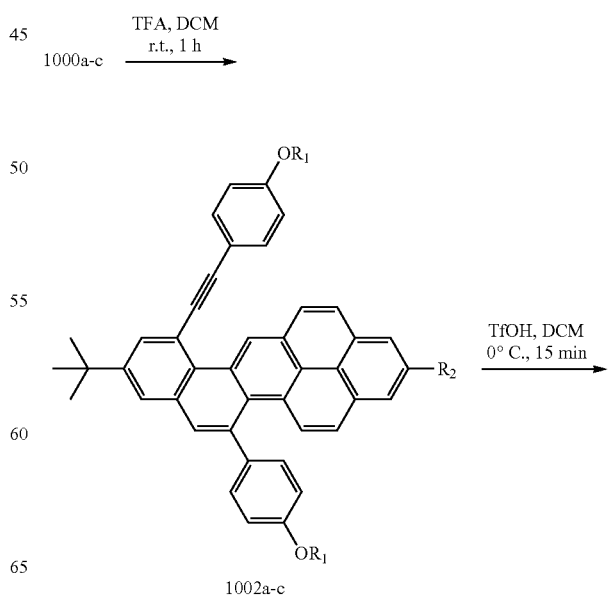

1002a-c

-continued

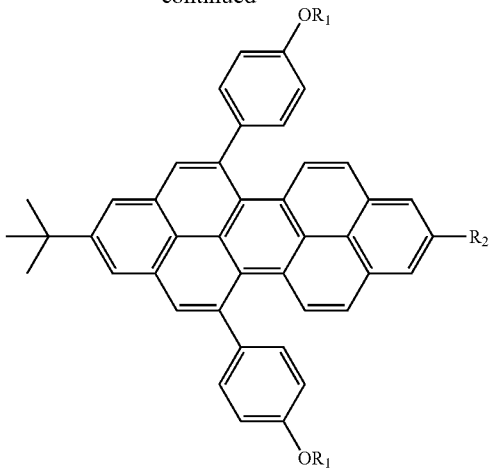

1004a: R₁ = CH₃, R₂ = tert-butyl
1004b: R₁ = C₆H₁₃, R₂ = tert-butyl
1004c: R₁ = C₁₀H₂₁, R₂ = H 1002a: $^1$H NMR (400 MHz, cdcl$_3$) δ 11.17 (s, 1H), 8.25 (d, J=1.7 Hz, 1H), 8.23-8.16 (m, 4H), 8.08 (d, J=9.0 Hz, 1H), 8.03 (d, J=2.2 Hz, 1H), 7.90 (s, 1H), 7.80 (m, 3H), 7.46 (d, J=8.7 Hz, 2H), 7.08-7.03 (m, 4H), 3.95 (s, 3H), 3.91 (s, 3H), 1.64 (s, 9H), 1.60 (s, 9H). $^{13}$C NMR (100 MHz, cdcl$_3$) δ 159.92, 158.93, 149.36, 148.96, 138.55, 138.15, 133.02, 132.84, 132.45, 131.63, 131.06, 130.61, 130.20, 129.77, 128.89, 128.50, 128.12, 128.07, 127.64, 127.21, 126.39, 125.41, 124.72, 124.46, 123.55, 122.99, 122.43, 121.90, 119.74, 116.12, 114.43, 114.42, 94.46, 92.07, 55.45, 55.44, 35.29, 34.78, 32.01, 31.46.

1002c: FTIR (neat) cm$^{-1}$. $^1$H NMR (400 MHz, cdcl$_3$) δ 11.13 (s, 1H), 8.17 (dd, J=9.2, 4.5 Hz, 2H), 8.11 (q, J=6.7 Hz, 3H), 8.03 (d, J=9.0 Hz, 1H), 7.99-7.95 (m, 2H), 7.84 (s, 1H), 7.74 (dd, J=11.5, 9.1 Hz, 3H), 7.39 (d, J=8.7 Hz, 2H), 7.01 (dd, J=8.7, 1.7 Hz, 4H), 4.06 (m, 4H), 1.89-1.82 (m, 4H), 1.53 (s, 12H), 1.40-1.26 (m, 25H), 0.90 (t, J=6.8 Hz, 6H). $^{13}$C NMR (100 MHz, cdcl$_3$) δ 159.61, 158.57, 149.14, 138.66, 137.97, 133.04, 132.90, 132.51, 131.82, 131.25, 130.80, 130.18, 129.98, 128.98, 128.69, 128.18, 127.82, 127.57, 127.53, 126.50, 126.22, 125.40, 125.09, 124.82, 124.73, 124.55, 124.54, 123.76, 119.83, 115.84, 115.09, 115.01, 94.64, 91.88, 68.34, 34.82, 32.09, 32.07, 31.48, 29.86, 29.79, 29.76, 29.74, 29.65, 29.59, 29.56, 29.52, 29.50, 29.42, 26.30, 26.23, 22.86, 14.29.

1004a: $^1$H NMR (400 MHz, cdcl$_3$) δ 8.34 (s, 2H), 8.25 (d, J=9.4 Hz, 2H), 8.21 (s, 4H), 7.77 (d, J=9.5 Hz, 2H), 7.48 (d, J=8.6 Hz, 4H), 7.05 (d, J=8.7 Hz, 4H), 3.95 (s, 6H), 1.64 (s, 9H), 1.59 (s, 9H). $^{13}$C NMR (100 MHz, cdcl$_3$) δ 158.92, 149.75, 149.27, 139.29, 138.71, 133.07, 131.14, 131.01, 130.83, 130.29, 128.28, 125.97, 125.56, 124.83, 124.63, 124.43, 122.60, 122.47, 121.70, 114.51, 55.56, 35.35, 35.30, 32.05, 31.48.

1004b: $^1$H NMR (400 MHz, cdcl$_3$) δ 8.35 (s, 2H), 8.28 (d, J=9.4 Hz, 2H), 8.22 (d, J=1.1 Hz, 4H), 7.78 (d, J=9.5 Hz, 2H), 7.46 (d, J=8.7 Hz, 4H), 7.04 (d, J=8.7 Hz, 4H), 4.10 (t, J=6.6 Hz, 4H), 1.89 (m, 4H), 1.65 (s, 9H), 1.60 (s, 9H), 1.57-1.32 (m, 12H), 0.98 (t, J=7.1 Hz, 6H). $^{13}$C NMR (100 MHz, cdcl$_3$) δ 158.49, 149.71, 149.23, 139.38, 138.50, 131.10, 131.03, 130.84, 130.25, 128.33, 125.99, 125.57, 124.86, 124.59, 124.42, 122.69, 122.55, 122.43, 121.68, 115.11, 68.32, 35.34, 35.29, 32.05, 31.86, 29.55, 25.99, 22.82, 14.26.

1004c: $^1$H NMR (400 MHz, cdcl$_3$) δ 8.34 (s, 2H), 8.30 (d, J=9.4 Hz, 2H), 8.21 (s, 2H), 8.16 (d, J=7.6 Hz, 2H), 8.01 (dd, J=8.0, 7.1 Hz, 1H), 7.77 (d, J=9.5 Hz, 2H), 7.45 (d, J=8.7 Hz, 4H), 7.03 (d, J=8.7 Hz, 4H), 4.09 (t, J=6.6 Hz, 4H), 1.94-1.84 (m, 4H), 1.63 (s, 9H), 1.55-1.26 (m, 28H), 0.91 (t, J=6.9 Hz, 6H). $^{13}$C NMR (101 MHz, cdcl$_3$) δ 158.51, 149.85, 139.38, 138.46, 131.23, 131.04, 130.98, 130.24, 128.36, 126.13, 126.08, 125.67, 125.15, 124.93, 124.53, 124.46, 124.34, 122.64, 121.58, 115.14, 68.35, 35.37, 32.09, 32.05, 29.80, 29.77, 29.67, 29.58, 29.52, 26.31, 22.87, 14.30.

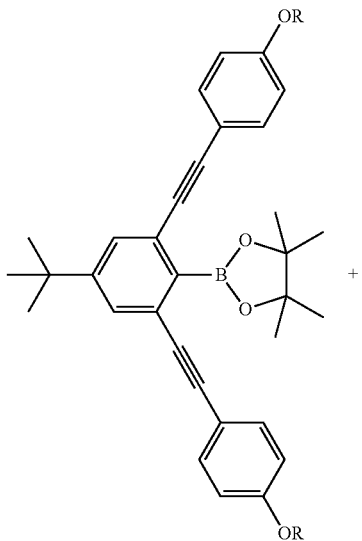

+

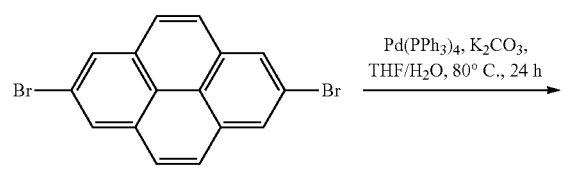

Pd(PPh₃)₄, K₂CO₃,
THF/H₂O, 80° C., 24 h

-continued

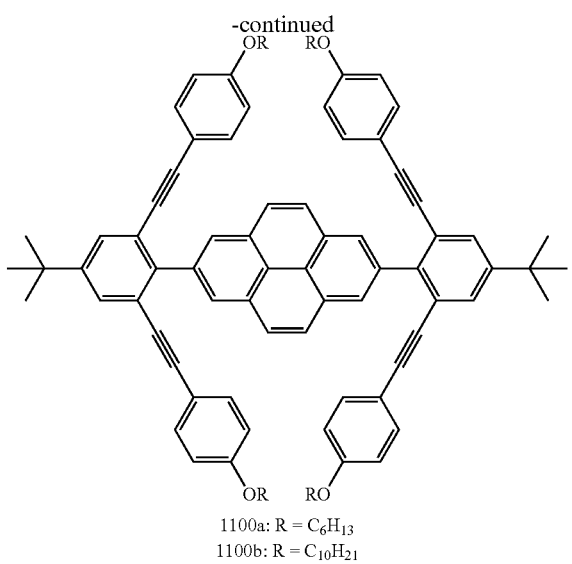

1100a: R = C₆H₁₃
1100b: R = C₁₀H₂₁

Compound 1100: 2,7-dibromopyrene (360 mg, 1 mmol), 2,6-diynylphenyl borate (2.5 mmol) and K₂CO₃ (552 mg, 4 mmol) were dissolved in toluene (80 mL) and water (20 mL) solution. Pd(PPh₃)₄ (116 mg, 0.1 mmol) was added to the solution before degassing the mixture via bubbling nitrogen for 30 min. The resulting mixture was stirred under a N₂ atmosphere at 80° C. for 48 h. After the reaction was complete, the mixture was diluted with DCM, washed with H₂O and dried over Na₂SO₄. The solvent was removed under reduced pressure and the residue was purified by column chromatography to give compound 1100.

1100a: $^1$H NMR (400 MHz, cdcl₃) δ 8.63 (s, 4H), 8.20 (s, 4H), 7.76 (s, 4H), 7.03 (d, J=8.9 Hz, 8H), 6.61 (d, J=8.9 Hz, 8H), 3.76 (t, J=6.6 Hz, 8H), 1.67 (m, 8H), 1.50 (s, 18H), 1.39-1.23 (m, 24H), 0.87 (t, J=6.9 Hz, 12H). $^{13}$C NMR (100 MHz, cdcl₃) δ 159.21, 150.39, 142.62, 136.69, 132.86, 130.74, 129.42, 127.72, 127.64, 124.33, 123.65, 114.98, 114.51, 92.69, 88.63, 68.02, 34.79, 31.65, 31.37, 29.19, 25.72, 22.68, 14.13.

1100b: $^1$H NMR (400 MHz, cdcl₃) δ 8.60 (s, 4H), 8.17 (s, 4H), 7.73 (s, 4H), 7.00 (d, J=8.9 Hz, 8H), 6.58 (d, J=9.0 Hz, 8H), 3.74 (t, J=6.6 Hz, 8H), 1.69-1.58 (m, 8H), 1.51 (s, 18H), 1.41-1.09 (m, 56H), 0.87 (t, J=6.9 Hz, 12H). $^{13}$C NMR (101 MHz, cdcl₃) δ 159.22, 150.39, 142.62, 136.69, 132.87, 130.74, 129.42, 127.72, 127.64, 124.33, 123.65, 114.99, 114.52, 92.69, 88.63, 68.05, 34.80, 32.03, 31.38, 29.68, 29.67, 29.49, 29.45, 29.25, 26.07, 22.82, 14.26.

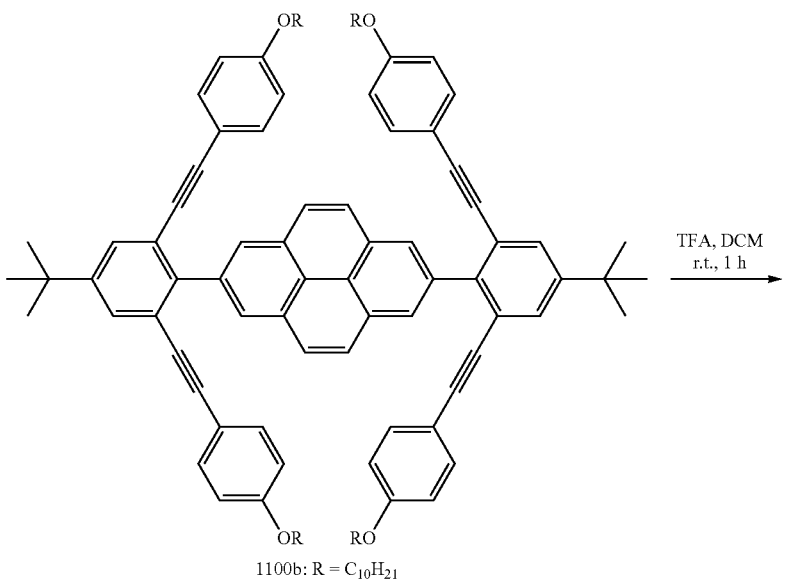

1100b: R = C₁₀H₂₁

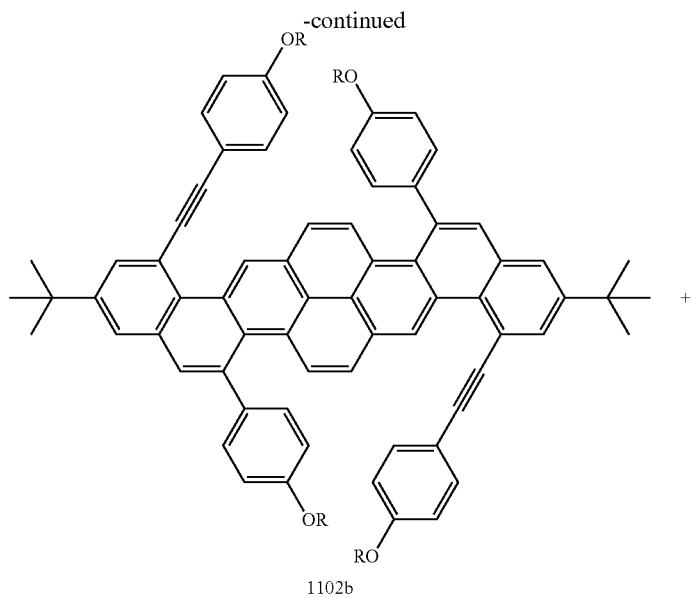

1102b

+

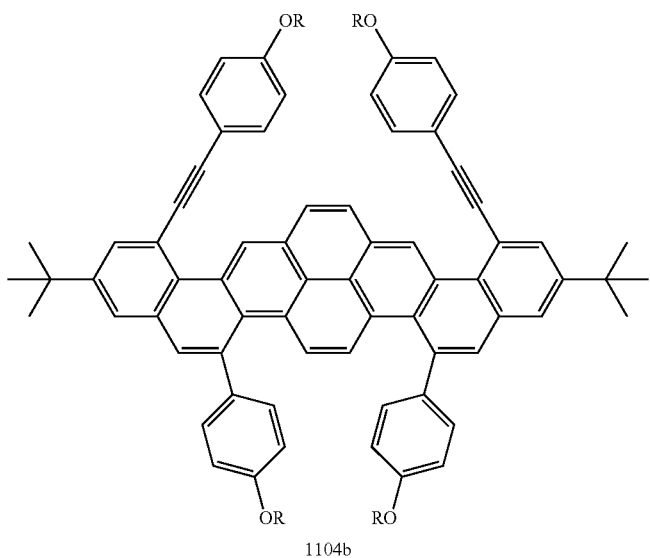

1104b

Figure 53:
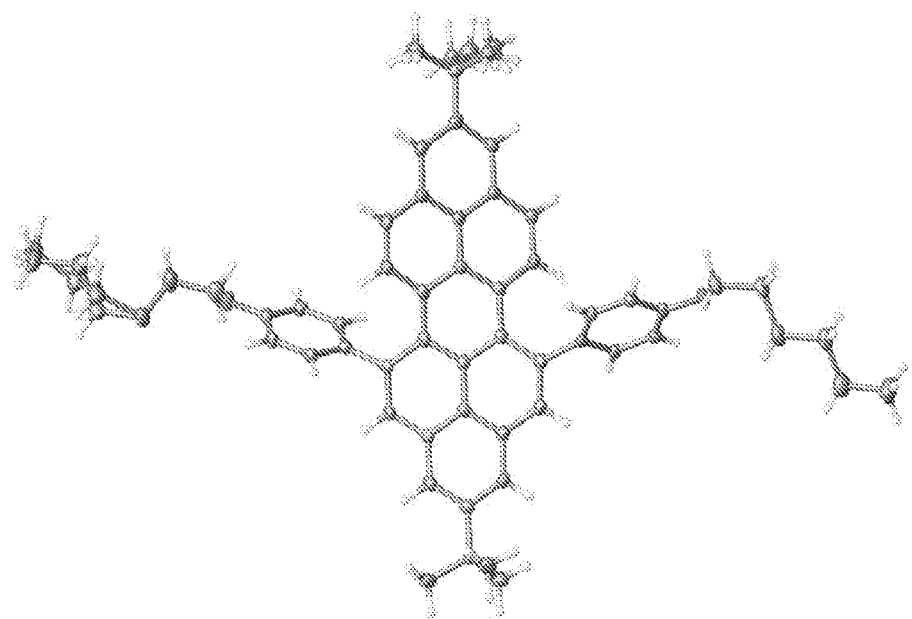
FIG. 53 is an X-ray image of a representative compound.

In a 100 mL flame-dried flask, compound 1100b (0.1 mmol) was dissolved in 80 mL of anhydrous $CH_2Cl_2$. Trifluoroacetic acid (570 mg, 5 mmol) was added and the reaction stirred under nitrogen. After stirring for 1 h at room temperature, the reaction was quenched with saturated $NaHCO_3$ solution (15 mL). The solution was then washed with $H_2O$ (2×50 mL) and dried ($Na_2SO_4$). After removal of the solvent under reduced pressure, the residue was purified by column chromatography ($SiO_2$, DCM) to afford the mixture of compound 1102b and 1104b (148 mg, 99%) as yellow oil. $^1H$ NMR (500 MHz, cdcl$_3$) δ 11.03 (s, 1H), 11.00 (s, 2H), 8.21 (d, J=9.4 Hz, 1H), 8.13 (s, 2H), 8.09 (d, J=2.1 Hz, 2H), 8.06 (d, J=2.1 Hz, 1H), 7.95-7.92 (m, 3H), 7.89 (s, 2H), 7.79 (d, J=5.6 Hz, 3H), 7.71-7.68 (m, 3H), 7.61-7.57 (m, 2H), 7.43 (d, J=8.7 Hz, 2H), 7.38-7.33 (m, 3H), 7.03-6.89 (m, 11H), 4.07 (t, J=6.6 Hz, 5H), 4.00-3.94 (m, 5H), 1.93-1.75 (m, 13H), 1.56-1.26 (m, 110H), 0.95-0.88 (m, 24H). $^{13}C$ NMR (101 MHz, cdcl$_3$) δ 159.58, 159.55, 158.59, 158.51, 149.11, 148.99, 138.72, 137.93, 137.48, 133.05, 133.00, 132.84, 132.68, 132.53, 131.22, 131.01, 130.24, 130.21, 130.14, 129.46, 128.98, 128.58, 128.47, 127.97, 127.38, 127.32, 126.34, 126.27, 125.67, 125.34, 124.57, 124.51, 123.60, 119.90, 119.78, 115.86, 115.74, 114.99, 114.95, 94.57, 94.52, 91.87, 91.75, 68.33, 34.81, 32.10, 32.08, 31.49, 31.47, 29.85, 29.81, 29.77, 29.75, 29.68, 29.65, 29.61, 29.58, 29.54, 29.51, 29.44, 26.34, 26.31, 26.24, 26.23, 22.86, 14.29 (see FIG. 53 for an X-ray image of compound 1102b).

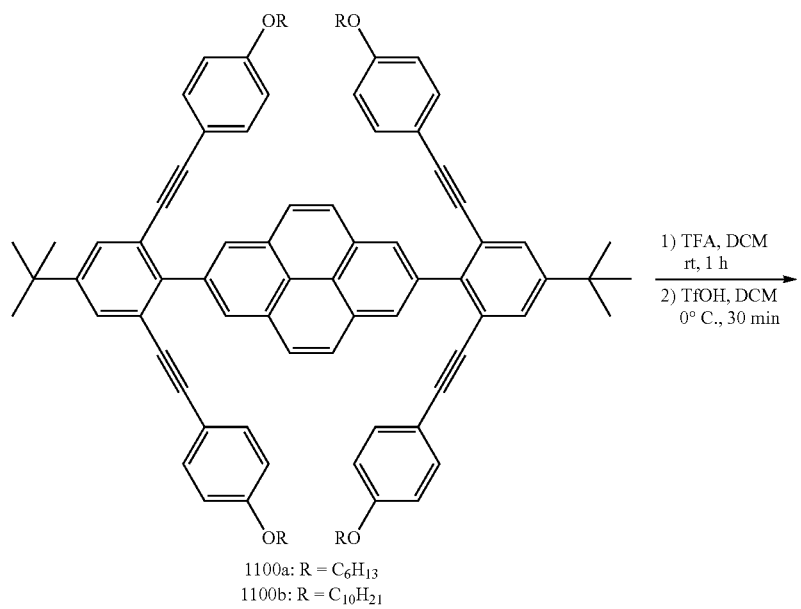

1100a: R = C₆H₁₃
1100b: R = C₁₀H₂₁

1) TFA, DCM
rt, 1 h
2) TfOH, DCM
0° C., 30 min

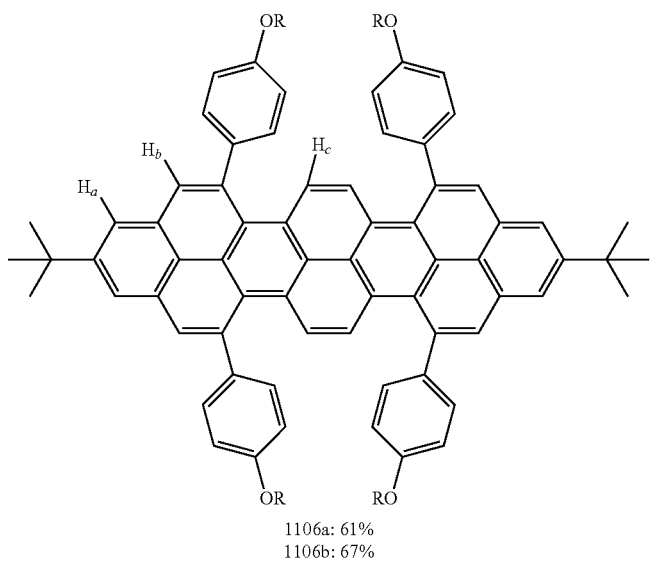

1106a: 61%
1106b: 67%

In a 100 mL flame-dried flask, compound 1100 (0.1 mmol) was dissolved in 80 mL of anhydrous CH$_2$Cl$_2$. Trifluoroacetic acid (570 mg, 5 mmol) was added and the reaction stirred under nitrogen for 1 h at room temperature. The solution was slowly added into the precooled triflic acid (2 equiv.) of CH$_2$Cl$_2$ (50 mL) solution at 0° C. After stirring for 30 min at 0° C., the reaction was quenched with saturated NaHCO$_3$ solution (20 mL), washed with H$_2$O (2×50 mL) and dried (Na$_2$SO$_4$). After removal of the solvent under reduced pressure, the residue was purified by column chromatography to afford the compound 1106 as deep red solid.

1106a: $^1$H NMR (400 MHz, cdcl$_3$) δ 8.30 (s, 4H), 8.14 (s, 4H), 8.10 (s, 4H), 7.41 (d, J=8.7 Hz, 8H), 6.95 (d, J=8.8 Hz, 8H), 4.05 (t, J=6.6 Hz, 8H), 1.91-1.79 (m, 8H), 1.62 (s, 18H), 1.56-1.48 (m, 8H), 1.39 (m, 16H), 0.94 (t, J=7.1 Hz, 12H). $^{13}$C NMR (100 MHz, cdcl$_3$) δ 158.38, 149.75, 139.35, 138.19, 131.36, 131.19, 130.07, 126.05, 125.73, 125.46, 124.75, 124.51, 122.52, 121.47, 115.09, 68.28, 35.36, 32.05, 31.86, 29.56, 25.97, 22.82, 14.24.

Figure 54:
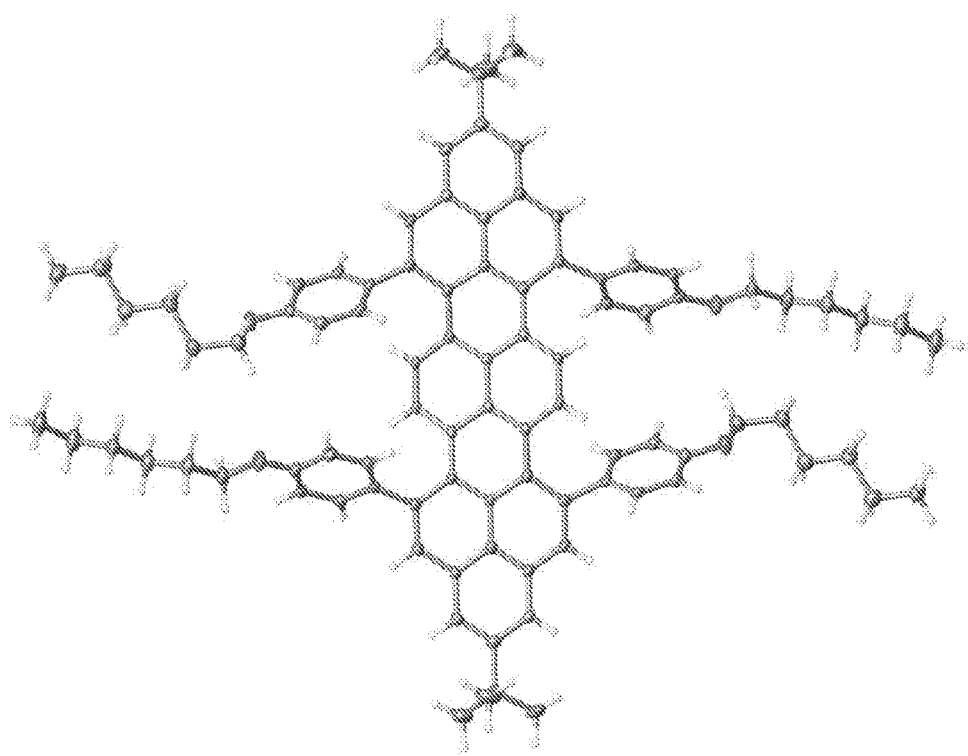
FIG. 54 is an X-ray image of a representative compound.

1106b: $^1$H NMR (400 MHz, toluene) δ 8.59 (s, 4H), 8.25 (s, 4H), 8.12 (s, 4H), 7.27 (d, J=8.6 Hz, 8H), 6.82 (d, J=8.7 Hz, 8H), 3.67 (t, J=6.5 Hz, 8H), 1.74-1.48 (m, 26H), 1.43-1.18 (m, 56H), 0.92 (t, J=6.8 Hz, 12H). $^{13}$C NMR (100 MHz, toluene) δ 159.01, 149.75, 140.10, 138.60, 132.09, 131.90, 130.55, 126.95, 126.49, 126.27, 125.95, 125.40, 122.94, 122.36, 115.34, 68.05, 53.40, 35.45, 32.58, 32.18, 30.35, 30.31, 30.21, 30.07, 30.05, 26.74, 23.34, 14.54 (see FIG. 54).
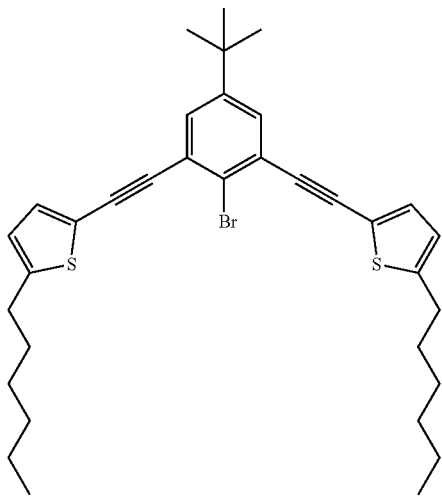
1202
¹H NMR (400 MHz, cdcl₃) δ 7.50 (s, 2H), 7.19 (d, J=3.6 Hz, 2H), 6.71 (dt, J=3.5, 0.8 Hz, 2H), 2.82 (t, J=7.6 Hz, 4H), 1.70 (dt, J=15.2, 7.4 Hz, 4H), 1.54-1.17 (m, 21H), 1.01-0.83 (m, 6H). ¹³C NMR (100 MHz, cdcl₃) δ 150.19, 149.22, 132.65, 129.85, 125.89, 124.60, 124.46, 120.09, 91.59, 87.46, 34.66, 31.66, 31.64, 31.09, 30.39, 28.84, 22.70, 14.21.
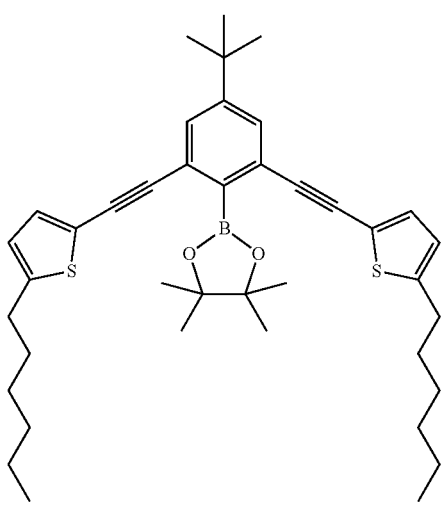
1204
¹H NMR (400 MHz, cdcl₃) δ 7.49 (s, 2H), 7.10 (d, J=3.6 Hz, 2H), 6.67 (d, J=3.6 Hz, 2H), 2.80 (t, J=7.5 Hz, 4H), 1.74-1.64 (m, 4H), 1.57-1.17 (m, 33H), 0.91 (t, J=6.9 Hz, 6H). ¹³C NMR (100 MHz, cdcl₃) δ 152.29, 148.21, 131.88, 128.75, 126.55, 124.19, 120.86, 93.05, 84.36, 83.89, 34.71, 31.61, 31.55, 31.03, 30.28, 28.76, 25.14, 22.65, 14.15.
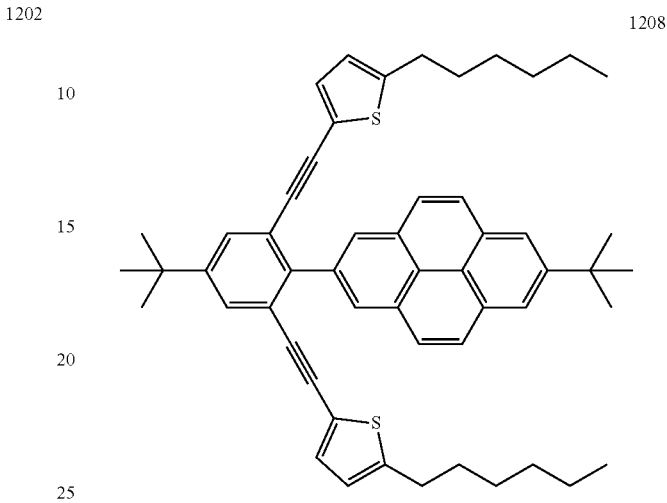
1208
¹H NMR (400 MHz, cdcl₃) δ 8.51 (s, 2H), 8.27 (s, 2H), 8.13 (m, 4H), 7.71 (s, 2H), 6.66 (d, J=3.6 Hz, 2H), 6.46 (d, J=3.6 Hz, 2H), 2.64 (t, J=7.6 Hz, 4H), 1.64 (s, 9H), 1.36 (d, J=83.2 Hz, 34H), 0.88 (t, J=6.8 Hz, 6H). ¹³C NMR (100 MHz, cdcl₃) δ 150.37, 149.04, 148.49, 142.51, 135.87, 131.87, 131.42, 130.37, 129.34, 127.97, 127.41, 127.35, 124.20, 124.15, 123.33, 123.16, 122.08, 120.41, 92.87, 86.35, 35.40, 34.79, 32.14, 31.61, 31.48, 31.32, 30.23, 28.74, 22.65, 14.19.
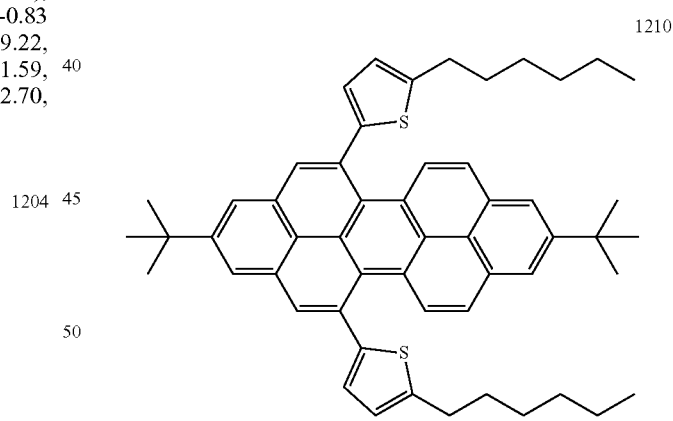
1210
¹H NMR (400 MHz, cdcl₃) δ 8.57 (d, J=9.4 Hz, 2H), 8.43 (s, 2H), 8.40 (s, 2H), 8.32 (s, 2H), 7.94 (d, J=9.4 Hz, 2H), 7.06 (d, J=3.4 Hz, 2H), 6.91 (d, J=3.4 Hz, 2H), 2.98 (t, J=7.4 Hz, 4H), 1.83 (m, 4H), 1.75-1.59 (m, 18H), 1.57-1.40 (m, 12H), 1.02 (t, J=6.9 Hz, 6H). ¹³C NMR (100 MHz, cdcl₃) δ 149.81, 149.27, 146.50, 145.17, 132.39, 131.90, 130.98, 130.75, 127.65, 126.17, 125.85, 125.25, 125.01, 124.89, 124.65, 124.49, 123.07, 122.62, 122.58, 122.39, 35.33, 35.30, 32.07, 32.01, 31.97, 31.87, 30.46, 28.89, 22.88, 14.37.

Figure 52:
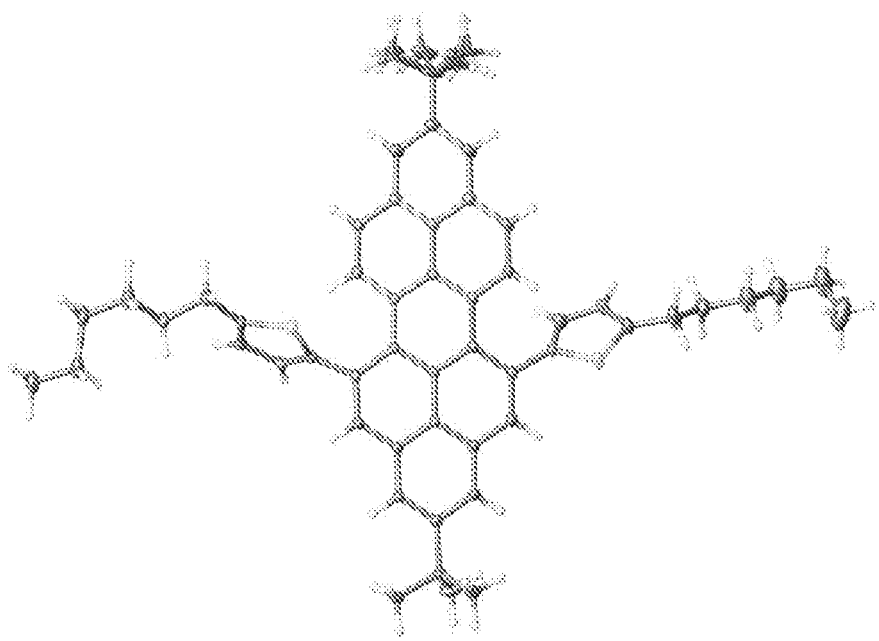
FIG. 52 is an X-ray image of a representative compound.

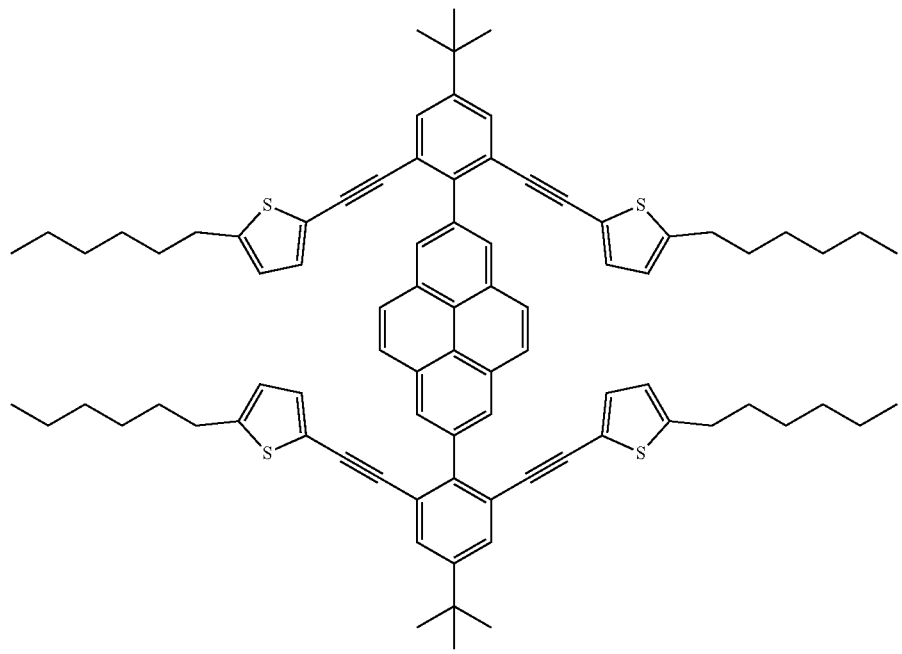
¹H NMR (400 MHz, cdcl₃) δ 8.54 (s, 4H), 8.18 (s, 4H), 7.70 (s, 4H), 6.67 (d, J=3.6 Hz, 4H), 6.43 (d, J=3.6 Hz, 4H), 2.59 (t, J=7.5 Hz, 8H), 1.46 (s, 18H), 1.24 (m, 32H), 0.87-0.80 (m, 12H). ¹³C NMR (100 MHz, cdcl₃) δ 150.39, 148.57, 142.42, 136.12, 131.95, 130.84, 129.37, 127.78, 127.33, 124.36, 124.17, 124.15, 123.35, 120.39, 92.93, 86.47, 34.81, 31.62, 31.49, 31.34, 30.24, 28.79, 22.67, 14.17.
¹H NMR (400 MHz, cdcl₃) δ 8.35 (s, 4H), 8.33 (s, 4H), 8.31 (s, 4H), 6.90 (d, J=3.4 Hz, 4H), 6.81 (d, J=3.4 Hz, 4H), 2.94 (t, J=7.6 Hz, 8H), 1.81-1.75 (m, 8H), 1.64-1.61 (m, 18H), 1.50-1.37 (m, 24H), 0.91 (m, 12H). ¹³C NMR (100 MHz, cdcl₃) δ 149.95, 145.93, 144.68, 132.51, 132.00, 130.84, 126.21, 126.01, 125.50, 124.99, 124.87, 124.74, 124.45, 123.04, 122.09, 35.37, 32.01, 32.00, 31.83, 30.59, 29.06, 22.82, 14.30 (see FIG. 52).
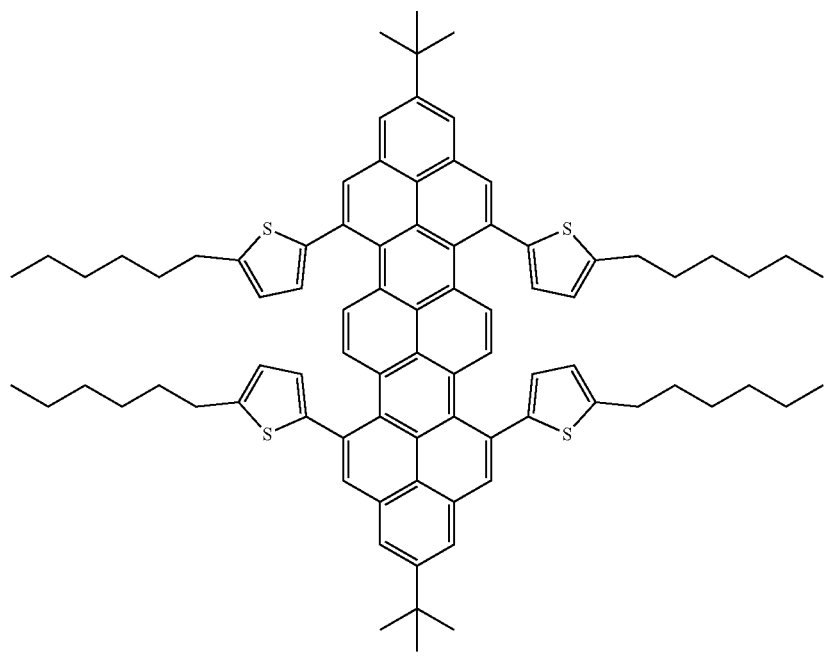

In view of the many possible embodiments to which the principles of the present disclosure may be applied, it should be recognized that the illustrated embodiments are only preferred examples of the disclosure and should not be taken as limiting the scope of the claimed invention. Rather, the scope of is defined by the following claims. We therefore claim as our invention all that comes within the scope and spirit of these claims.

We claim:

1. A compound having a structure satisfying Formula 1

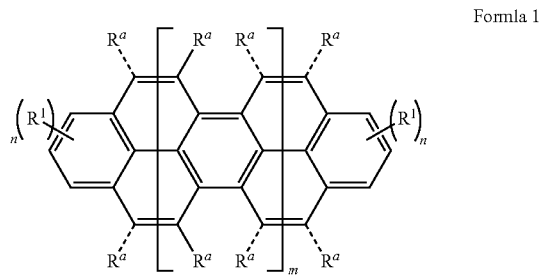

Formula 1 wherein each $R^1$ independently is hydrogen, halogen, aliphatic, aryl, heteroaliphatic, or heteroaryl; each $R^a$ independently is aryl; aryl substituted with one or more functional groups selected from aliphatic, alkoxy, amide amine, thioether, haloalkyl, nitro, halo, silyl, cycloaliphatic, or aryl; or an electron-donating group; each n independently is 1, 2, or 3; and m ranges from 1 to 1000.

2. The compound of claim 1, having a structure satisfying any one or more of Formulas 3-5:

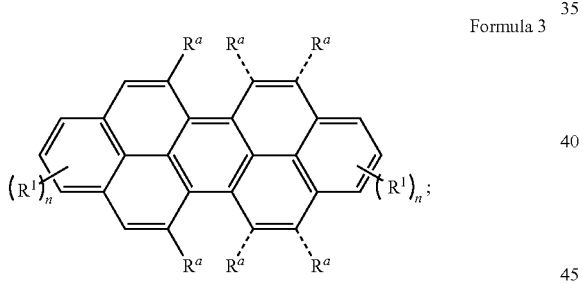

Formula 3

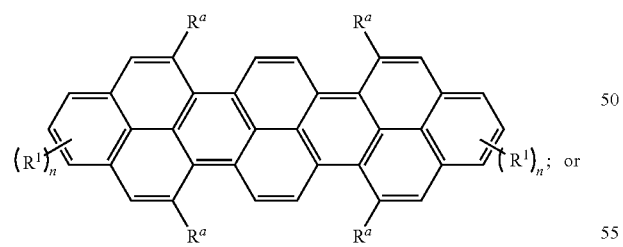

Formula 4

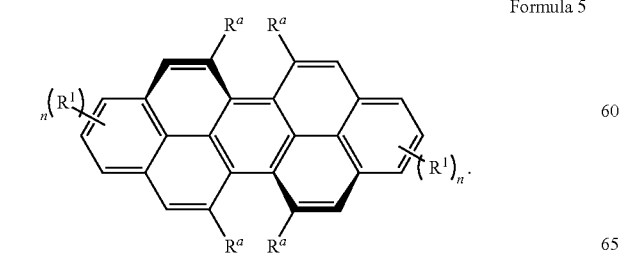

Formula 5

3. The compound of claim 1, wherein the $R^a$ group is substituted with one or more functional groups selected from aliphatic, alkoxy, amine, thioether, haloalkyl, nitro, halo, silyl, cycloaliphatic, or aryl, wherein the one or more functional groups are located meta, ortho, para, or combinations thereof, relative to a position at which the $R^a$ group is attached.

4. The compound of claim 1, wherein each $R^a$ group independently is substituted with a functional group that is para relative to a position at which the $R^a$ group is attached.

5. The compound of claim 1, wherein each $R^a$ group is

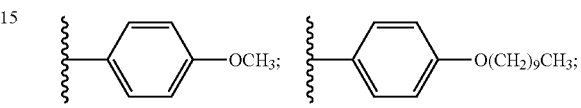

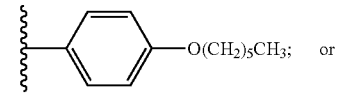

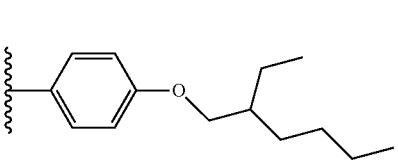

6. The compound of claim 1, wherein each $R^1$ independently is hydrogen, alkyl, or a combination thereof.

7. The compound of claim 6, wherein alkyl is methyl, ethyl, propyl, iso-propyl, butyl, iso-butyl, tert-butyl, or combinations thereof.

8. The compound of claim 1, wherein the compound is

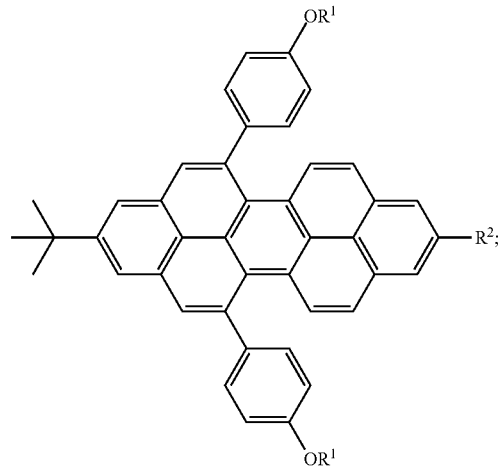

$R^1 = CH_3$, $R^2 =$ tert-butyl
$R^1 = C_6H_{13}$, $R^2 =$ tert-butyl
$R^1 = C_{10}H_{21}$, $R^2 =$ H -continued
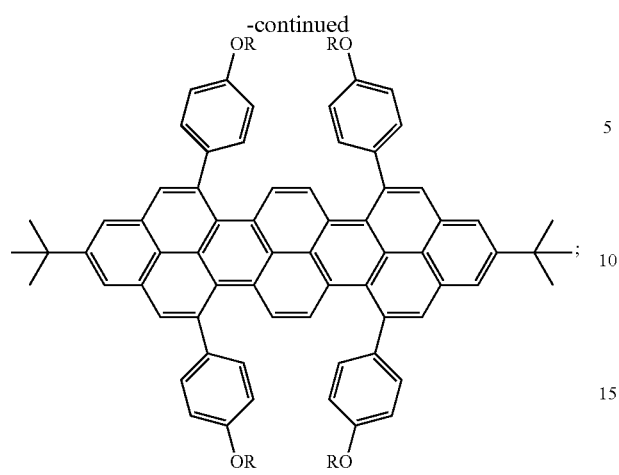
R = CH₃
R = C₆H₁₃
R = C₁₀H₂₁
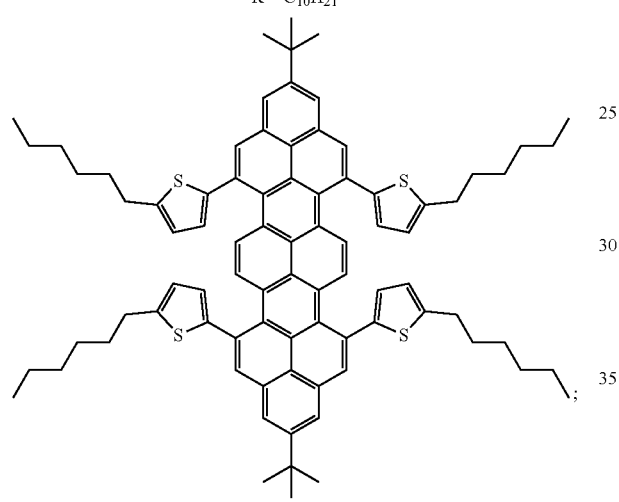
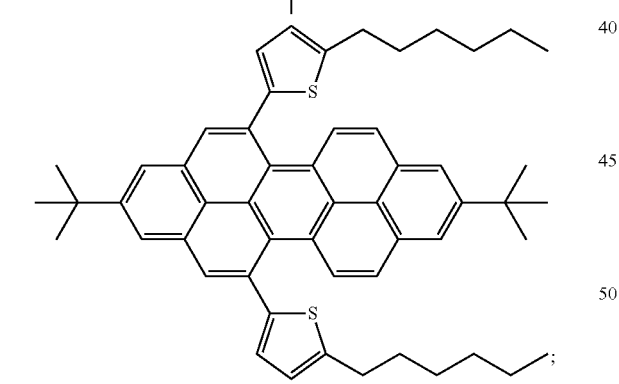
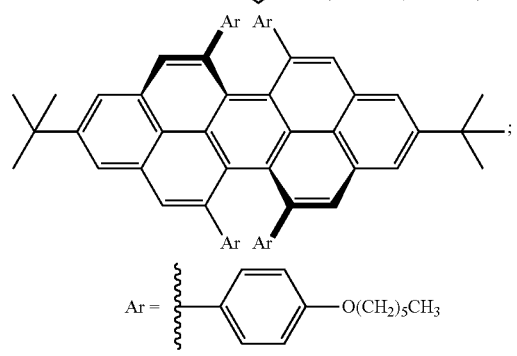
-continued
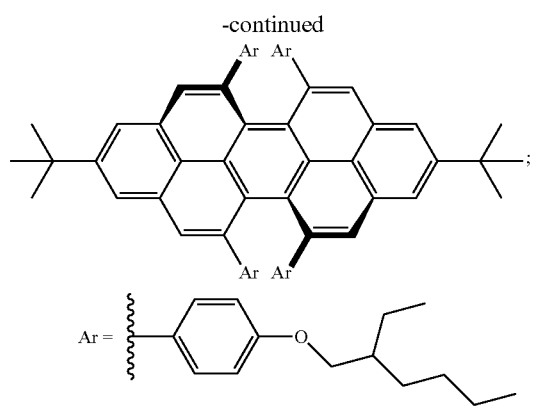
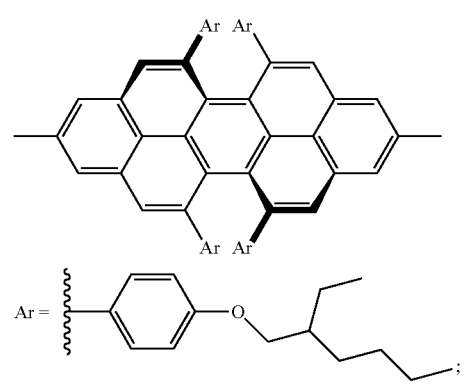
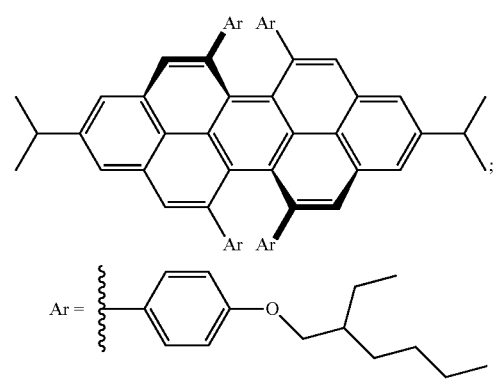
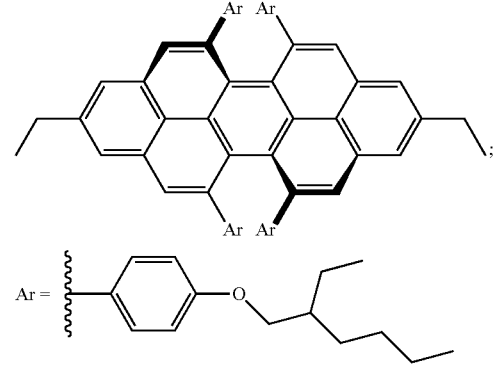

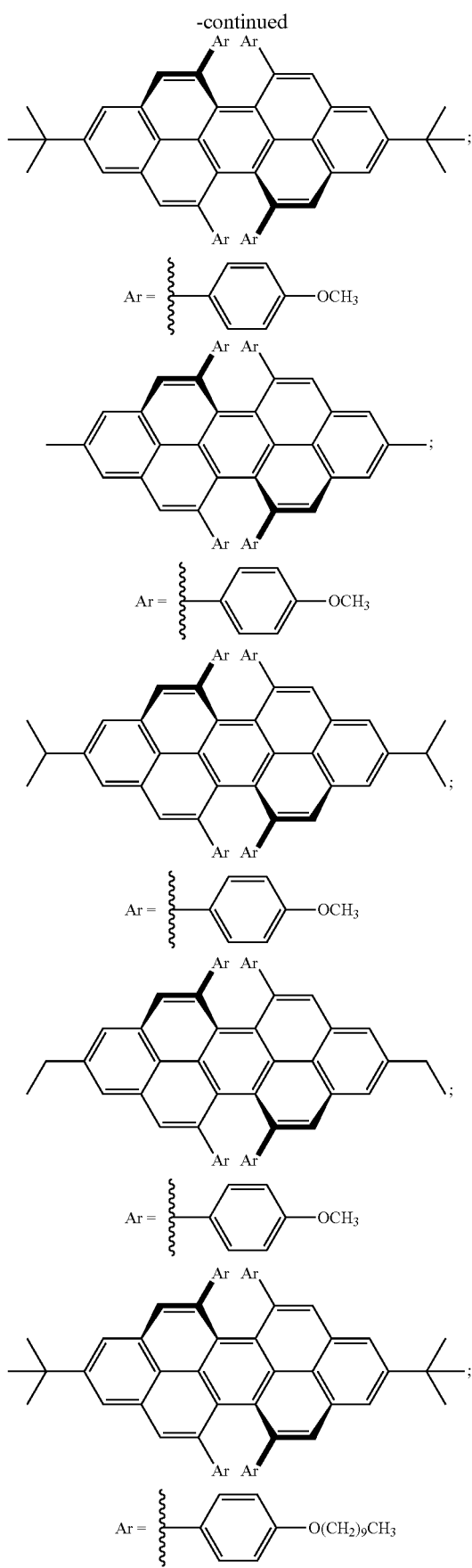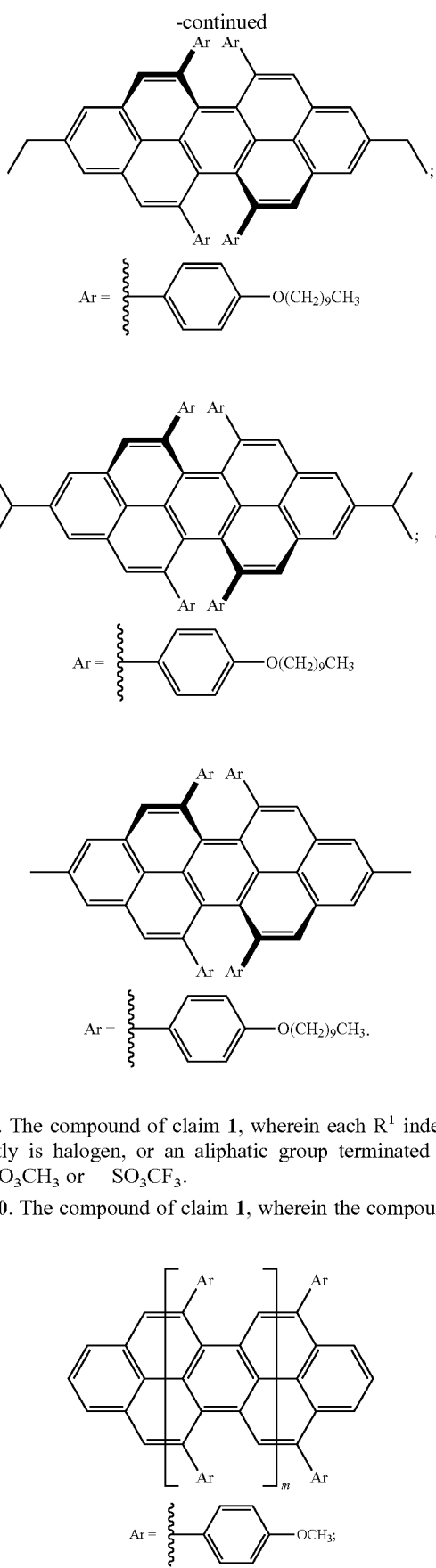
9. The compound of claim 1, wherein each $R^1$ independently is halogen, or an aliphatic group terminated with —$SO_3CH_3$ or —$SO_3CF_3$.
10. The compound of claim 1, wherein the compound is
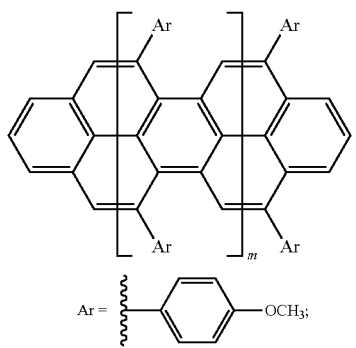

-continued

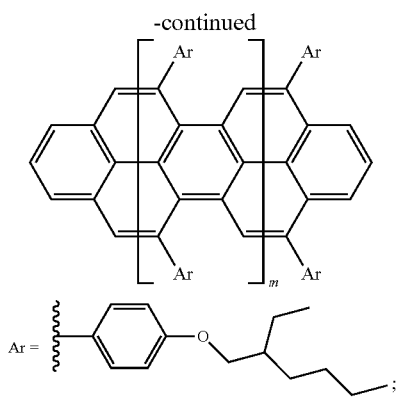

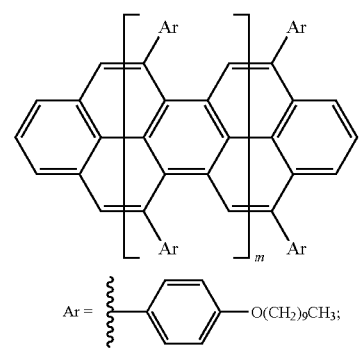

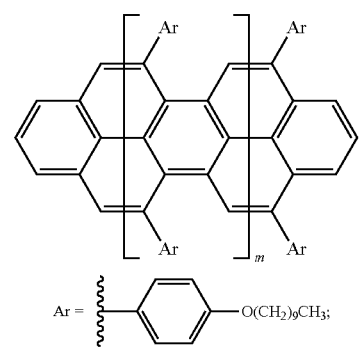

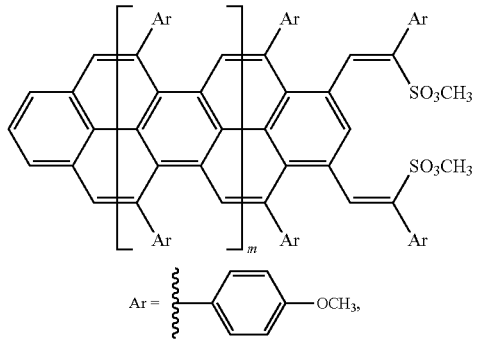

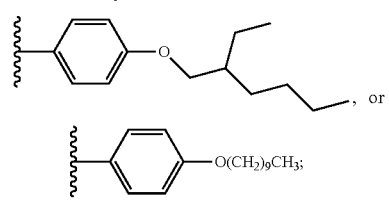

-continued

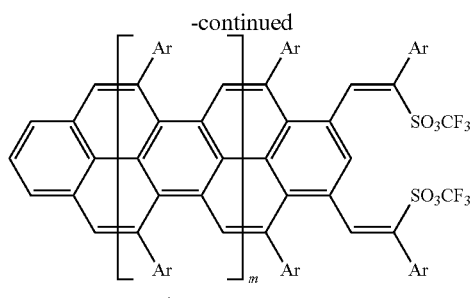

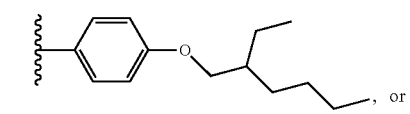

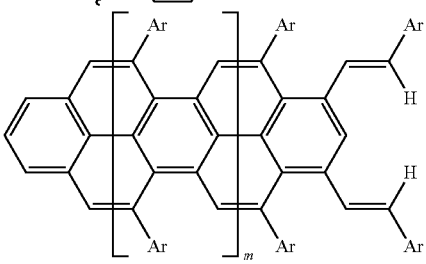

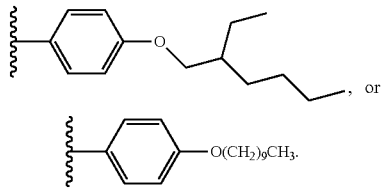

11. The compound of claim 1, wherein the compound is axially chiral.

12. A compound having a structure satisfying Formula 7

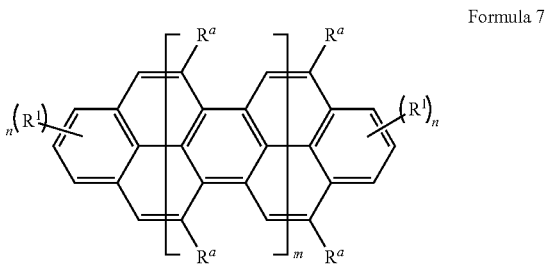

Formula 7 wherein each $R^1$ independently is hydrogen, halogen, aliphatic, aryl, heteroaliphatic, or heteroaryl; each $R^a$ independently is aryl; aryl substituted with one or more functional groups selected from aliphatic, alkoxy, amide amine, thioether, haloalkyl, nitro, halo, silyl, cycloaliphatic, or aryl; or an electron-donating group; each n independently is 1, 2, or 3; and m ranges from 1 to 1000.

13. A method for making the compound of claim 12, comprising exposing a diyne precursor to an acid at a temperature sufficient to cause the diyne precursor to cyclize to form a polymer; and wherein the diyne precursor has a formula

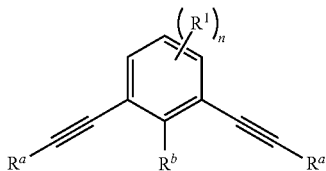

wherein each $R^1$ independently is hydrogen, halogen, aliphatic, aryl, heteroaliphatic, or heteroaryl; each $R^a$ independently is aryl; aryl substituted with one or more functional groups selected from aliphatic, alkoxy, amide amine, thioether, haloalkyl, nitro, halo, silyl, cycloaliphatic, or aryl; or an electron-donating group; each n independently is 1, 2, or 3; and m is 0 to 1000; and $R^b$ is a boron-containing moiety.

14. A method, comprising exposing a diyne precursor to an acid at a temperature sufficient to cause the diyne precursor to cyclize to form a polymer; and wherein the diyne precursor has a formula

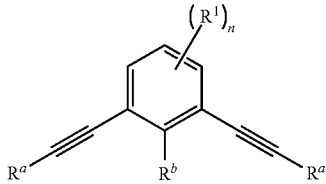

wherein each $R^1$ independently is hydrogen, halogen, aliphatic, aryl, heteroaliphatic, or heteroaryl; each $R^a$ independently is aryl; aryl substituted with one or more functional groups selected from aliphatic, alkoxy, amide amine, thioether, haloalkyl, nitro, halo, silyl, cycloaliphatic, or aryl; or an electron-donating group; each n independently is 1, 2, or 3; and m is 0 to 1000; and $R^b$ is a boron-containing moiety; and wherein the compound has a formula

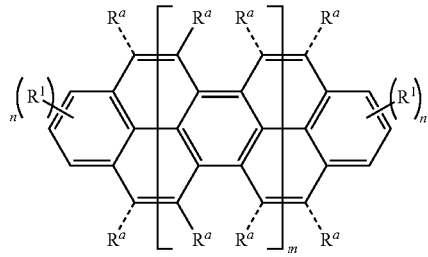

wherein m ranges from 0 to 1,000.

15. The method of claim 14, wherein the boron-containing moiety is a boronic acid or $B[-OC(R^6)_2C(R^6)_2O-]$, wherein each $R^6$ independently is aliphatic.

16. The method of claim 14, wherein the acid is $CF_3SO_3H$, $CH_3SO_3H$, or a combination thereof.

17. The method of claim 14, wherein the temperature ranges from −40° C. to ambient temperature.

18. The method of claim 14, wherein the temperature ranges from 0° C. to ambient temperature.

19. The method of claim 14, further comprising making the diyne precursor by halogen-metal exchange between a metal-containing compound and a compound having a formula

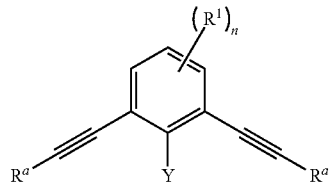

wherein Y is Br, Cl, F, or I.

20. The method of claim 19, wherein the metal-containing compound is selected from BuLi, or t-BuLi.

* * * * *